US007368284B2

(12) United States Patent
Koike

(10) Patent No.: US 7,368,284 B2
(45) Date of Patent: May 6, 2008

(54) PORCINE CMP-N-ACETYLNEURAMINIC ACID HYDROXYLASE GENE

(75) Inventor: Chihiro Koike, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 164 days.

(21) Appl. No.: 10/863,116

(22) Filed: Jun. 7, 2004

(65) Prior Publication Data

US 2005/0223418 A1    Oct. 6, 2005

Related U.S. Application Data

(60) Provisional application No. 60/476,396, filed on Jun. 6, 2003.

(51) Int. Cl.
*C12N 15/00* (2006.01)
*C07H 21/04* (2006.01)

(52) U.S. Cl. ............... 435/320.1; 435/191; 435/252.3; 536/23.2

(58) Field of Classification Search ............. 435/191, 435/252.3, 320.1; 536/23.2
See application file for complete search history.

(56) References Cited

U.S. PATENT DOCUMENTS 5,525,488 A * 6/1996 Mason et al. .............. 435/69.4
6,166,288 A  12/2000 Diamond et al.

FOREIGN PATENT DOCUMENTS

| JP | 06 113838 A2 | 4/1994 |
| WO | WO 97/03200 A1 | 1/1997 |
| WO | WO 00/51424 A2 | 9/2000 |
| WO | WO 02/088351 A1 | 11/2002 |
| WO | WO 2004/016742 A2 | 2/2004 |
| WO | WO 2004/028243 A2 | 4/2004 |

OTHER PUBLICATIONS

Zhu, A., Acc. No. ABZ68218 (2003).*
Schauer, R., et al., Acc. No. AAT78596 (1997).*
Bach, F.H., et al., "Delayed xenograft rejection," *Immunol. Today*, 17(8):379-84 (Aug. 1996).
Chou, H. H., et al., "A mutation in human CMP-sialic acid hydroxylase occurred after the Homo-Pan divergence," *Proc. Natl. Acad. Sci.* (USA), 95(20):11751-11756 (Sep. 29, 1998).
Cooper, D.K., et al., "Oligosaccharides and discordant xenotransplantation," *Immunol. Rev.*, 141:31-58 (Oct. 1994).
Dai, Y., et al., "Targeted disruption of the α1,3-galactosyltransferase gene in cloned pigs," *Nature Biotechnology*, 20:251-255 (Mar. 2002).
Deicher, H., "Über die Erzeugung heterospezifischer Hämagglutinine durch Injektion artfremden Serums. I. Mitteilung," *Zeitshrift für Hygiene*, 106:561-579 (1926).
Galili, U., et al., "Human natural anti-alpha-galactosyl IgG. II. The specific recognition of alpha (1----3)-linked galactose residues," *J. Exp. Med.*, 162(2):573-582 (Aug. 1, 1985).

Galili, U., et al., "Evolutionary relationship between the natural anti-Gal antibody and the Gal alpha 1----3Gal epitope in primates," *Proc. Nat. Acad. Sci.*, (USA), 84(5):1369-73 (Mar. 1987).
Galili, U., et al., "Evolution and pathophysiology of the human natural anti-alpha-galactosyl IgG (anti-Gal) antibody," *Springer Sem. Immunopathol*, 15(2-3):155-171 (1993).
Hanganutziu, M., "Hémagglutinines hétérogénétiques aprés injection de sérum de Cheval," *Comptes Rendus Soc. Biol.* (Paris), 91:1457-1459 (Nov. 22, 1924).
Higashi, H., et al., "Characterization of N-glycolylneuraminic acid-containing gangliosides as tumor-associated Hanganutziu-Deicher antigen in human colon cancer," *Cancer Res.*, 45(8):3796-3802 (Aug. 1985).
Higashihara, T., et al., "Survey of Hanganutziu and Deicher antibodies in operated patients," *Int Arch Allergy Appl Immunol.*, 95(2-3):231-235 (1991).
Irie, A., et al. "The molecular basis for the absence of N-glycolylneuraminic acid in humans," *J. Biol. Chem.*, 273(25): 15866-15871 (Jun. 19, 1998).
Isobe, T., et al., "A simple assay method for bacterial binding to glycosphingolipids on a polyvinylidene difluoride membrane after thin-layer chromatography blotting and in situ mass spectrometric analysis of the ligands," *Anal. Biochem.*, 236(1):35-40 (Aug. 5, 1996).
Joziasse, D.H., et al., "Bovine α1→3-galactosyltransferase: Isolation and characterization of a cDNA clone: Identification of homologous sequences in human genomic DNA," *J. Biol. Chem.* ,264(24):14290-14297 (Aug. 25, 1989).
Kawano, T., et al., "Biosynthesis of N-glycolylneuraminic acid-containing glycoconjugates. Purification and characterization of the key enzyme of the cytidine monophospho-N-acetylneuraminic acid hydroxylation system," *J. Biol. Chem.*, 269(12) 9024-9029 (Mar. 25, 1994).
Kelm, S. and Schauer, R., "Sialic acids in molecular and cellular interactions," *Int. Rev. Cytol*, 179:137-240 (1997).
King, T.P., et al., *Proceedings of the 6th International Symposium on Digestive Physiology in Pigs*, pp. 290-293, (1994).
Kozutsumi, Y., et al., "Participation of cytochrome b5 in CMP-N-acetylneuraminic acid hydroxylation in mouse liver cytosol," *J. Biochem.* (Tokyo), 108(5):704-706 (Nov. 1990).
Kyogashima, M., et al., "*Escherichia coli* K99 binds to *N*-glycolyllysialoparagloboside and *N*-glycolyl-GM3 found in piglet small intestine," *Arch. Biochem. Biophys.*, 270(1):391-397 (Apr. 1989).
Lai, L., et al., "Production of α-1,3-galactosyltransferase knockout pigs by nuclear transfer cloning," *Science* 295:1089-1092 (Feb. 8, 2002) and supplementary data, *Science Express*, Jan. 3, 2002.

(Continued)

*Primary Examiner*—Tekchand Saidha
(74) *Attorney, Agent, or Firm*—King & Spalding, LLP

(57) ABSTRACT

The present invention provides porcine CMP-N-Acetyl-neuraminic-Acid Hydroxylase (CMP-Neu5Ac hydroxylase) protein, cDNA, and genomic DNA regulatory sequences. Furthermore, the present invention includes porcine animals, tissues, and organs, as well as cells and cell lines derived from such animals, tissues, and organs, which lack expression of functional CMP-Neu5Ac hydroxylase. Such animals, tissues, organs, and cells can be used in research and in medical therapy, including in xenotransplantation, and in industrial livestock farming operations.

4 Claims, 13 Drawing Sheets

OTHER PUBLICATIONS

Lindahl, M. and Carlstedt, I., "Binding of K99 fimbriae of enterotoxigenic *Escherichia coli* to pig small intestinal mucin glycopeptides," *J. Gen. Microbiol.*, 136(Part 8):1609-1614 (Aug. 1990).

Lublin, D.M., et al., "Molecular cloning and chromosomal localization of human membrane cofactor protein (MCP). Evidence for inclusion in the multigene family of complement-regulatory proteins," *J. Exp. Med.*, 168(1):181-194 (Jul. 1, 1988).

Malykh, Y.N., et al., "Distribution and localization of CMP-N-acetylneuraminic acid hydroxylase and N-glycolylneuraminic acid-containing glycoconjugates in porcine lymph node and peripheral blood lymphocytes," *European Journal of Cell Biology*, 80(1):48-58 (Jan. 2001).

Malykh, Y.N., et al., "The role of CMP-N-acetylneuraminic acid hydroxylase in determining the level of N-glycolylneuraminic acid in porcine tissues," *Glycoconjugate J.*, 15(9):885-893 (Sep. 1998).

Malykh, Y., et al., "Regulation of N-glycolylneuraminic acid biosynthesis in developing pig small intestine," *Biochem. J.*, 370(part 2): 601-607 (Mar. 1, 2003).

Martensen, I., et al., "Cloning and expression of a membrane-bound CMP-N-acetylneuraminic acid hydroxylase from the starfish Asterias rubens," *Eur. J. Biochem.*, 268(19):5157-5166 (Oct. 2001).

McCurry, K.R., et al., "Human complement regulatory proteins protect swine-to-primate cardiac xenografts from humoral injury," *Nat. Med.*, 1(5), 423-427 (May 1995).

Medof, M.E., et al., "Cloning and characterization of cDNAs encoding the complete sequence of decay-accelerating factor of human complement," *Proc. Natl. Acad. Sci. USA*, 84(7):2007-2011 (Apr. 1987).

Phelps, C.J., et al., "Production of α1,3-galactosyltransferase-deficient pigs," *Science*, 299:411-414 (Jan. 17, 2003).

Philbrick, W.M., et al., "The CD59 antigen is a structural homologue of murine Ly-6 antigens but lacks interferon inducibility," *Eur. J. Immunol.*, 20(1):87-92 (Jan. 1990).

Polejaeva, I.A., et al., "Cloned pigs produced by nuclear transfer from adult somatic cells," *Nature*, 407:86-90 (Sep. 7, 2000).

Sandrin, M.S., et al., "Identification of gal(a1,3)gal as the major epitope for pig-to-human vascularised xenografts," *Transplant Rev.*, 8(3):134-139 (Jul. 1994).

Schlenzka, W., et al., "Purification and characterization of CMP-N-acetylneuraminic acid hydroxylase from pig submandibular glands," *Glycobiology*, 4(5):675-683 (Oct. 1994).

Schneckenburger, P., et al., "Purification, characterization and reconstitution of CMP-N- acetylneuraminate hydroxylase from mouse liver," *Glycoconj. J.*, 11(3):194-203 (Jun. 1994).

Schultze, B., et al., "Transmissible gastroenteritis coronavirus, but not the related porcine respiratory coronavirus, has a sialic acid (N-glycolylneuraminic acid) binding activity," *J. Virol.*, 70(8), pp. 5634-5637 (Aug. 1996).

Sharma, A., et al., "Pig cells that lack the gene for α1,3-galactosyltransferase express low levels of the gal antigen," *Transplantation*, 75(4):430-436 (Feb. 7, 2003).

Shaw, L., et al., "CMP-N-acetylneuraminic acid hydroxylase from mouse liver and pig submandibular glands. Interaction with membrane-bound and soluble cytochrome b5-dependent electron transport chains," *Eur. J. Biochem.*, 219(3):1001-1011 (Feb. 1, 1994).

Starzl, T.E., et al. "The biological basis of and strategies for clinical xenotransplantation," *Immunol. Rev.*, 141:213-244 (Oct. 1994).

Strahan, K., et al., "Pig alpha1,3galactosyltransferase: A major target for genetic manipulation in xenotransplantation," *Frontiers in Bioscience*, 1:e34-41 (Jul. 1, 1996) [www.bioscience.org/1996/v1/e/strahan1/htmls/34-41.htm].

Teneberg, S., et al., "Receptor-active glycolipids of epithelial cells of the small intestine of young and adult pigs in relation to susceptibility to infection with *Escherichia coli* K99," *FEBS Letters*, 263(1):10-14 (Apr. 9, 1990).

Varki, A., "Diversity in the sialic acids," *Glycobiology*, 2(1):25-40 (Feb. 1992). Erratum in: *Glycobiology*;2(2):following 168.(Apr. 1992).

\* cited by examiner ctgccagcctaagccacacagccacagcaacgctggtctgagctgtctgagcctatgccagagctcccgcagcgccgatgcttaac
                                                                                ETSF
                                                                    MZF1 ccactgagcaaggccagggattgaaccctcgtcctcatggatagcagttgagttgttccacggaactcctgagggaactcctgattatt
      SF1                                                                       MEF2
              TATA                                          CMYB tttattaaattatattcctgacttttgtgtgtctcatcagccactgactgtgtatctccattagtcatggtttgttaactctgt
          MEF2               NMP4              CAAT                  AP1       BRN2 cattcaaaccctcttcatcctctgctacgcagataacatcattatataataaatcgtgcctgaagaccagtgacgccccaagctaagttac
                                    SATB1                             ATF
                                        GAT1                          USF       WHN tgcttccctgggggaaaaagaagcaccgcgctgacacgaagtcgggcgcagaggaagacggggcagaggaagacgggggagca
      NMP4                              ZF5 gtgggagcagcagggcgcggggaagcactggggatgttccgcgttggcaggaggggtgttgggcgagctcccgtgatgcaggggga
                                                                                ZBP89
                                                                NFKB            MZF1

ZBP89
ggagccttttccgaagtagcgggacaagagccacggaagaactgttctgagttcccagtCCCGACGTCCTGGCAGCGCCCAGGCACTG
     MOK2                                                                       MOK2
                                                                      ZF5

TTATTGGTGCCTCCTGTGTCCACGCGCTTCCCGGCCAGCCCTGGCGCAGCCCCTATTTTCTGTTCCCCGATTCTGGTACCTCTCCCT
         NFY                    MYCMAX

CCCGCCCTCGGTGCGCAGCCGTCCTGCAGTGCCTGCTCCTCCAGGGGCGAAACCGATCAGGCCACCCGCCTCCTGAACAT
                                                                           ZF5

CCCTCCTTAGTTCCCACAG

Figure 4 pDH1:   5'-ACCACCCAAGTCTGGAATCTTCTTACACT-3'
pDH2:   5'-GACTCTCATACAAAGCTAAGCTGGGTAAG-3'
pDH2a:  5'-GACTCTCATACAAAACCTAAGCTGGGTAAG-3'
pDH2b:  5'-GACTCTCATACAAAACCTAGGCTGGGTAAG-3'
pDH2c:  5'-GACTCTCATACAAAACCTAGGCTAGGTAAG-3'
pDH3:   5'-CTCCTGGAAGCTTCTGTCAAGACGAAC-3'
pDH4:   5'-GCCTGATACACAGTGCTGTGCAATGGT-3'

Figure 5 pDH5: 5'-CCTTATACTGGCCCCAATTGGATCTTAC-3';

pDH6: 5'-CAGGAGGATTGATATCCTTCATGCTGCT-3';

pDH7: 5'-CTTACCTAGCCTAGGTTTTGTATGAGAGTC-3';

pDH8: 5'-GACAAAACCACAATTGGAATGCACTCGAG-3'.

Figure 9

SEQUENCE LISTING

```
<160> NUMBER OF SEQ ID NOS: 65

<210> SEQ ID NO 1
<211> LENGTH: 2728
<212> TYPE: DNA
<213> ORGANISM: Porcine

<400> SEQUENCE: 1
cccgacgtcc tggcagcgcc caggcactgt tattggtgcc tcctgtgtcc acgcgcttcc      60
cggccaggca gccctggcgg atcctatttt ctgttccccc gattctggta cctctccctc     120
ccgccctcgg tgcgcagccg tcctcctgca gtgcctgctc ctcaggggc gaaaccgatc      180 agggatcagg ccacccgcct cctgaacatc cctccttagt tcccacagtc taatgccttg     240
tggaagcaaa tgaccacag aagctgaagg aaaaaccacc attctttctt aatacctgga     300
gagaggcaac gacagactat gagcagcatc gaacaaacga cggagatcct gttgtgcctc     360
tcacctgccg aagctgccaa tctcaaggaa ggaatcaatt ttgttcgaaa taagagcact     420
ggcaaggatt acatcttatt taagaataag agccgcctga aggcatgtaa gaacatgtgc     480
aagcaccaag gaggcctctt cattaaagac attgaggatc taaatggaag gtctgttaaa     540
tgcacaaaac acaactggaa gttagatgta agcagcatga agtatatcaa tcctcctgga     600
agcttctgtc aagacgaact ggttgtagaa aaggatgaag aaaatggagt tttgcttcta     660
gaactaaatc ctcctaaccc gtgggattca gaacccagat ctcctgaaga tttggcattt     720
ggggaagtgc agatcacgta ccttactcac gcctgcatgg acctcaagct gggggacaag     780
agaatggtgt tcgacccttg gttaatcggt cctgcttttg cgcgaggatg gtggttacta     840
cacgagcctc catctgattg gctggagagg ctgagccgcg cagacttaat ttacatcagt     900
cacatgcact cagaccacct gagttaccca acactgaaga agcttgctga gagaagacca     960
gatgttccca tttatgttgg caacacggaa agacctgtat tttggaatct gaatcagagt    1020
ggcgtccagt tgactaatat caatgtagtg ccatttggaa tatggcagca ggtagacaaa    1080
```

```
aatcttcgat tcatgatctt gatggatggc gttcatcctg agatggacac ttgcattatt    1140
gtggaataca aaggtcataa atactcaat acagtggatt gcaccagacc caatggagga     1200
aggctgccta tgaaggttgc attaatgatg agtgattttg ctggaggagc ttcaggcttt    1260
ccaatgactt tcagtggtgg aaaatttact gaggaatgga agcccaatt cattaaaaca     1320 gaaaggaaga aactcctgaa ctacaaggct cggctggtga aggacctaca acccagaatt    1380
tactgcccct ttcctgggta tttcgtggaa tcccacccag cagacaagta tattaaggaa    1440
acaaacatca aaatgaccc aaatgaactc aacaatctta tcaagaagaa ttctgaggtg     1500
gtaacctgga ccccaagacc tggagccact cttgatctgg gtaggatgct aaaggaccca    1560
acagacagca agggcatcgt agagcctcca aagggacta agatttacaa ggattcctgg     1620
gattttggcc catatttgaa tatcttgaat gctgctatag agatgaaat atttcgtcac     1680 tcatcctgga taaagaaata cttcacttgg gctggattta aggattataa cctggtggtc    1740
aggatgattg agacagatga ggacttcagc cctttgcctg gaggatatga ctatttggtt    1800
gactttctgg atttatcctt tccaaaagaa agaccaagcc gggaacatcc atatgaggaa    1860
attcggagcc gggttgatgt catcagacac gtggtaaaga atggtctgct ctgggatgac    1920
ttgtacatag gattccaaac ccggcttcag cgggatcctg atatatacca tcatctgttt    1980
tggaatcatt ttcaaataaa actcccctc acaccacctg actggaagtc cttcctgatg     2040
tgctctgggt agagaggacc tgagctgtcc caggggtgcc caacaacatg aaaaaatcaa    2100
gaatttattg ctgctacgtc aaagcttata ccagagatta tgccttatag acattagcaa    2160
tggataatta tatgttgcac ttgtgaaatg tgcacatatc ctgtttatga atcaccacat    2220
agccagatta tcaatatttt acttatttcg taaaaaatcc acaatttttcc ataacagaat   2280 caacgtgtgc aataggaaca agattgctat ggaaaacgag ggtaacagga ggagatatta    2340
atccaagcat agaagaaata gacaaatgag gggccataag gggaatatag ggaagagaaa    2400
aaaattaaga tggaatttta aaaggagaat gtaaaaaata gatatttgtt ccttaatagg    2460
ttgattcctc aaatagagcc catgaatata atcaaatagg aagggttcat gactgttttc    2520 aattttttcaa aaagctttgt tgaaatcata gacttgcaaa acaaggctgt agaggccacc   2580
ctaaaatgga aaatttcact gggactgaaa ttattttgat tcaatgacaa aatttgttat    2640
ttactgcgga ttataaactc taacaaatag cgatctcttt gcttcataaa aacataaaca    2700
ctagctagta ataaaatgag ttctgcag                                       2728
```

<210> SEQ ID NO 2
<211> LENGTH: 577
<212> TYPE: PRT
<213> ORGANISM: Porcine

<400> SEQUENCE: 2

```
Met Ser Ser Ile Glu Gln Thr Thr Glu Ile Leu Leu Cys Leu Ser Pro
1               5                   10                  15

Ala Glu Ala Ala Asn Leu Lys Glu Gly Ile Asn Phe Val Arg Asn Lys
            20                  25                  30

Ser Thr Gly Lys Asp Tyr Ile Leu Phe Lys Asn Lys Ser Arg Leu Lys
        35                  40                  45

Ala Cys Lys Asn Met Cys Lys His Gln Gly Gly Leu Phe Ile Lys Asp
    50                  55                  60

Ile Glu Asp Leu Asn Gly Arg Ser Val Lys Cys Thr Lys His Asn Trp
65                  70                  75                  80
```

-continued

```
Lys Leu Asp Val Ser Ser Met Lys Tyr Ile Asn Pro Gly Ser Phe
                85                  90                  95
Cys Gln Asp Glu Leu Val Val Glu Lys Asp Glu Asn Gly Val Leu
                100                 105                 110
Leu Leu Glu Leu Asn Pro Pro Asn Pro Trp Asp Ser Glu Pro Arg Ser
                115                 120                 125
Pro Glu Asp Leu Ala Phe Gly Val Gln Ile Thr Tyr Leu Thr His
    130                 135                 140
Ala Cys Met Asp Leu Lys Leu Gly Asp Lys Arg Met Val Phe Asp Pro
145                 150                 155                 160
Trp Leu Ile Gly Pro Ala Phe Ala Arg Gly Trp Trp Leu Leu His Glu
                165                 170                 175
Pro Pro Ser Asp Trp Leu Glu Arg Leu Ser Arg Ala Asp Leu Ile Tyr
                180                 185                 190
Ile Ser His Met His Ser Asp His Leu Ser Tyr Pro Thr Leu Lys Lys
                195                 200                 205
Leu Ala Glu Arg Arg Pro Asp Val Pro Ile Tyr Val Gly Asn Thr Glu
    210                 215                 220
Arg Pro Val Phe Trp Asn Leu Asn Gln Ser Gly Val Gln Leu Thr Asn
225                 230                 235                 240
Ile Asn Val Val Pro Phe Gly Ile Trp Gln Gln Val Asp Lys Asn Leu
                245                 250                 255
Arg Phe Met Ile Leu Met Asp Gly Val His Pro Glu Met Asp Thr Cys
                260                 265                 270
Ile Ile Val Glu Tyr Lys Gly His Lys Ile Leu Asn Thr Val Asp Cys
                275                 280                 285
Thr Arg Pro Asn Gly Gly Arg Leu Pro Met Lys Val Ala Leu Met Met
    290                 295                 300
Ser Asp Phe Ala Gly Gly Ala Ser Gly Phe Pro Met Thr Phe Ser Gly
305                 310                 315                 320
Gly Lys Phe Thr Glu Glu Trp Lys Ala Gln Phe Ile Lys Thr Glu Arg
                325                 330                 335
Lys Lys Leu Leu Asn Tyr Lys Ala Arg Leu Val Lys Asp Leu Gln Pro
                340                 345                 350
Arg Ile Tyr Cys Pro Phe Pro Gly Tyr Phe Val Glu Ser His Pro Ala
    355                 360                 365
Asp Lys Tyr Ile Lys Glu Thr Asn Ile Lys Asn Asp Pro Asn Glu Leu
    370                 375                 380
Asn Asn Leu Ile Lys Lys Asn Ser Glu Val Val Thr Trp Thr Pro Arg
385                 390                 395                 400
Pro Gly Ala Thr Leu Asp Leu Gly Arg Met Leu Lys Asp Pro Thr Asp
                405                 410                 415
Ser Lys Gly Ile Val Glu Pro Pro Glu Gly Thr Lys Ile Tyr Lys Asp
                420                 425                 430
Ser Trp Asp Phe Gly Pro Tyr Leu Asn Ile Leu Asn Ala Ala Ile Gly
                435                 440                 445
Asp Glu Ile Phe Arg His Ser Ser Trp Ile Lys Glu Tyr Phe Thr Trp
    450                 455                 460
Ala Gly Phe Lys Asp Tyr Asn Leu Val Val Arg Met Ile Glu Thr Asp
465                 470                 475                 480
Glu Asp Phe Ser Pro Leu Pro Gly Gly Tyr Asp Tyr Leu Val Asp Phe
                485                 490                 495
```

-continued

```
Leu Asp Leu Ser Phe Pro Lys Glu Arg Pro Ser Arg Glu His Pro Tyr
                500                 505                 510
Glu Glu Ile Arg Ser Arg Val Asp Val Ile Arg His Val Val Lys Asn
            515                 520                 525
Gly Leu Leu Trp Asp Asp Leu Tyr Ile Gly Phe Gln Thr Arg Leu Gln
        530                 535                 540
Arg Asp Pro Asp Ile Tyr His His Leu Phe Trp Asn His Phe Gln Ile
545                 550                 555                 560
Lys Leu Pro Leu Thr Pro Pro Asp Trp Lys Ser Phe Leu Met Cys Ser
                565                 570                 575
Gly
```

<210> SEQ ID NO 3
<211> LENGTH: 2467
<212> TYPE: DNA
<213> ORGANISM: Porcine

<400> SEQUENCE: 3

| | | | | | |
|---|---|---|---|---|---|
| cccgacgtcc | tggcagcgcc | caggcactgt | tattggtgcc | tcctgtgtcc | acgcgcttcc | 60 |
| cggccaggca | gccctggcgg | atcctatttt | ctgttccccc | gattctggta | cctctccctc | 120 |
| ccgcccctcgg | tgcgcagccg | tcctcctgca | gtgcctgctc | ctccaggggc | gaaaccgatc | 180 |
| agggatcagg | ccacccgcct | cctgaacatc | cctccttagt | tcccacagtc | taatgccttg | 240 |
| tggaagcaaa | tgagccacag | aagctgaagg | aaaaaccacc | attctttctt | aatacctgga | 300 |
| gagaggcaac | gacagactat | gagcagcatc | gaacaaacga | cggagatcct | gttgtgcctc | 360 |
| tcacctgccg | aagctgccaa | tctcaaggaa | ggaatcaatt | tgttcgaaaa | taagagcact | 420 |
| ggcaaggatt | acatcttatt | taagaataag | agccgcctga | aggcatgtaa | gaacatgtgc | 480 |
| aagcaccaag | gaggcctctt | cattaaagac | attgaggatc | taaatggaag | gtctgttaaa | 540 |
| tgcacaaaac | acaactggaa | gttagatgta | agcagcatga | agtatatcaa | tcctcctgga | 600 |
| agcttctgtc | aagacgaact | ggttgtagaa | aaggatgaag | aaaatggagt | tttgcttcta | 660 |
| gaactaaatc | ctcctaaccc | gtgggattca | gaacccagat | ctcctgaaga | tttggcattt | 720 |
| ggggaagtgc | agatcacgta | ccttactcac | gcctgcatgg | acctcaagct | ggggacaag | 780 |
| agaatggtgt | tcgacccttg | gttaatcggt | cctgcttttg | cgcgaggatg | gtggttacta | 840 |
| cacgagcctc | catctgattg | gctggagagg | ctgagccgcg | cagacttaat | ttacatcagt | 900 |
| cacatgcact | cagaccacct | gagttaccca | acactgaaga | agcttgctga | gagaagacca | 960 |
| gatgttccca | tttatgttgg | caacacggaa | agacctgtat | tttggaatct | gaatcagagt | 1020 |
| ggcgtccagt | tgactaatat | caatgtagtg | ccatttggaa | tatggcagca | ggtagacaaa | 1080 |
| aatcttcgat | tcatgatctt | gatggatggc | gttcatcctg | agatggacac | ttgcattatt | 1140 |
| gtggaataca | aggtcataa | aatactcaat | acagtggatt | gcaccagacc | caatggagga | 1200 |
| aggctgccta | tgaaggttgc | attaatgatg | agtgattttg | ctggaggagc | ttcaggcttt | 1260 |
| ccaatgactt | tcagtggtgg | aaaatttact | gaggaatgga | agcccaatt | cattaaaaca | 1320 |
| gaaaggaaga | aactcctgaa | ctacaaggct | cggctggtga | aggacctaca | acccagaatt | 1380 |
| tactgcccct | ttcctgggta | tttcgtggaa | tcccacccag | cagacaagta | tattaaggaa | 1440 |
| acaaacatca | aaaatgaccc | aaatgaactc | aacaatctta | tcaagaagaa | ttctgaggtg | 1500 |
| gtaacctgga | ccccaagacc | tggagccact | cttgatctgg | taggatgct | aaaggaccca | 1560 |
| acagacagat | cctgtgtcag | gagttgggat | tctttgaaga | ttcggagccg | ggttgatgtc | 1620 |

-continued

```
atcagacacg tggtaaagaa tggtctgctc tgggatgact tgtacatagg attccaaacc    1680
cggcttcagc gggatcctga tatataccat catctgtttt ggaatcattt tcaaataaaa    1740
ctccccctca caccacctga ctggaagtcc ttcctgatgt gctctgggta gagaggacct    1800
gagctgtccc aggggtgccc aacaacatga aaaaatcaag aatttattgc tgctacgtca    1860
aagcttatac cagagattat gccttataga cattagcaat ggataattat atgttgcact    1920
tgtgaaatgt gcacatatcc tgtttatgaa tcaccacata gccagattat caatatttta    1980
cttatttcgt aaaaaatcca caattttcca taacagaatc aacgtgtgca ataggaacaa    2040
gattgctatg gaaaacgagg gtaacaggag gagatattaa tccaagcata gaagaaatag    2100
acaaatgagg ggccataagg ggaatatagg gaagagaaaa aaattaagat ggaattttaa    2160
aaggagaatg taaaaatag atatttgttc cttaataggt tgattcctca aatagagccc    2220
atgaatataa tcaaatagga agggttcatg actgttttca attttttcaaa aagctttgtt    2280 gaaatcatag acttgcaaaa caaggctgta gaggccaccc taaatggaa aatttcactg    2340 ggactgaaat tattttgatt caatgacaaa atttgttatt tactgcggat tataaactct    2400
aacaaatagc gatctctttg cttcataaaa acataaacac tagctagtaa taaaatgagt    2460
tctgcag                                                              2467
```

<210> SEQ ID NO 4
<211> LENGTH: 490
<212> TYPE: PRT
<213> ORGANISM: Porcine
<400> SEQUENCE: 4

```
Met Ser Ser Ile Glu Gln Thr Thr Glu Ile Leu Leu Cys Leu Ser Pro
1               5                   10                  15

Ala Glu Ala Ala Asn Leu Lys Glu Gly Ile Asn Phe Val Arg Asn Lys
            20                  25                  30

Ser Thr Gly Lys Asp Tyr Ile Leu Phe Lys Asn Lys Ser Arg Leu Lys
        35                  40                  45

Ala Cys Lys Asn Met Cys Lys His Gln Gly Gly Leu Phe Ile Lys Asp
    50                  55                  60

Ile Glu Asp Leu Asn Gly Arg Ser Val Lys Cys Thr Lys His Asn Trp
65                  70                  75                  80

Lys Leu Asp Val Ser Ser Met Lys Tyr Ile Asn Pro Pro Gly Ser Phe
                85                  90                  95

Cys Gln Asp Glu Leu Val Val Glu Lys Asp Glu Asn Gly Val Leu
            100                 105                 110

Leu Leu Glu Leu Asn Pro Pro Asn Pro Trp Asp Ser Glu Pro Arg Ser
        115                 120                 125

Pro Glu Asp Leu Ala Phe Gly Glu Val Gln Ile Thr Tyr Leu Thr His
    130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Trp Leu Leu His Glu
                165                 170                 175

Pro Pro Ser Asp Trp Leu Glu Arg Leu Ser Arg Ala Asp Leu Ile Tyr
            180                 185                 190

Ile Ser His Met His Ser Asp His Leu Ser Tyr Pro Thr Leu Lys Lys
        195                 200                 205

Leu Ala Glu Arg Arg Pro Asp Val Pro Ile Tyr Val Gly Asn Thr Glu
    210                 215                 220
```

```
Arg Pro Val Phe Trp Asn Leu Asn Gln Ser Gly Val Gln Leu Thr Asn
225                 230                 235                 240

Ile Asn Val Val Pro Phe Gly Ile Trp Gln Gln Val Asp Lys Asn Leu
            245                 250                 255

Arg Phe Met Ile Leu Met Asp Gly Val His Pro Glu Met Asp Thr Cys
        260                 265                 270

Ile Ile Val Glu Tyr Lys Gly His Lys Ile Leu Asn Thr Val Asp Cys
    275                 280                 285

Thr Arg Pro Asn Gly Arg Leu Pro Met Lys Val Ala Leu Met Met
290                 295                 300

Ser Asp Phe Ala Gly Gly Ala Ser Gly Phe Pro Met Thr Phe Ser Gly
305                 310                 315                 320

Gly Lys Phe Thr Glu Glu Trp Lys Ala Gln Phe Ile Lys Thr Glu Arg
                325                 330                 335

Lys Lys Leu Leu Asn Tyr Lys Ala Arg Leu Val Lys Asp Leu Gln Pro
            340                 345                 350

Arg Ile Tyr Cys Pro Phe Pro Gly Tyr Phe Val Glu Ser His Pro Ala
        355                 360                 365

Asp Lys Tyr Ile Lys Glu Thr Asn Ile Lys Asn Asp Pro Asn Glu Leu
    370                 375                 380

Asn Asn Leu Ile Lys Lys Asn Ser Glu Val Val Thr Trp Thr Pro Arg
385                 390                 395                 400

Pro Gly Ala Thr Leu Asp Leu Gly Arg Met Leu Lys Asp Pro Thr Asp
                405                 410                 415

Arg Ser Cys Val Arg Ser Trp Asp Ser Leu Lys Ile Arg Ser Arg Val
            420                 425                 430

Asp Val Ile Arg His Val Val Lys Asn Gly Leu Leu Trp Asp Asp Leu
        435                 440                 445

Tyr Ile Gly Phe Gln Thr Arg Leu Gln Arg Asp Pro Asp Ile Tyr His
    450                 455                 460

His Leu Phe Trp Asn His Phe Gln Ile Lys Leu Pro Leu Thr Pro Pro
465                 470                 475                 480

Asp Trp Lys Ser Phe Leu Met Cys Ser Gly
                485                 490

<210> SEQ ID NO 5
<211> LENGTH: 1624
<212> TYPE: DNA
<213> ORGANISM: Porcine

<400> SEQUENCE: 5
cccgacgtcc tggcagcgcc caggcactgt tattggtgcc tcctgtgtcc acgcgcttcc      60
cggccaggca gccctggcgg atcctatttt ctgttccccc gattctggta cctctccctc     120
ccgccctcgg tgcgcagccg tcctcctgca gtgcctgctc ctccaggggc gaaaccgatc     180
agggatcagg ccacccgcct cctgaacatc cctccttagt cccacagtc taatgccttg      240 tggaagcaaa tgagccacag aagctgaagg aaaaaccacc attctttctt aatacctgga     300
gagaggcaac gacagactat gagcagcatc gaacaaacga cggagatcct gttgtgcctc     360
tcacctgccg aagctgccaa tctcaaggaa ggaatcaatt ttgttcgaaa taagagcact     420
ggcaaggatt acatcttatt taagaataag agccgcctga aggcatgtaa gaacatgtgc     480
aagcaccaag gaggcctctt cattaaagac attgaggatc taaatggaag gtctgttaaa     540
tgcacaaaac acaactggaa gttagatgta agcagcatga agtatatcaa tcctcctgga     600
```

-continued

```
agcttctgtc aagacgaact ggttgtagaa aaggatgaag aaaatggagt tttgcttcta    660
gaactaaatc ctcctaaccc gtgggattca gaacccagat ctcctgaaga tttggcattt    720
ggggaagtgc agatcacgta ccttactcac gcctgcatgg acctcaagct ggggacaag     780
agaatggtgt tcgacccttg gttaatcggt cctgcttttg cgcgaggatg gtggttacta    840
cacgagcctc catctgattg gctggagagg ctgagccgcg cagacttaat ttacatcagt    900
cacatgcact cagaccacct gagttaccca acactgaaga agcttgctga gagaagacca    960
gatgttccca tttatgttgg caacacgaaa agacctgtat tttggaatct gaatcagagt   1020
ggcgtccagt tgactaatat caatgtagtg ccatttggaa tatggcagca ggtagacaaa   1080
aatcttcgat tcatgatctt gatggatggc gttcatcctg agatggacac ttgcattatt   1140
gtggaataca aaggtcataa atactcaat acagtggatt gcaccagacc caatggagga    1200
aggctgccta tgaaggttgc attaatgatg agtgattttg ctggaggagc ttcaggcttt   1260
ccaatgactt tcagtggtgg aaaatttact gaggaatgga agcccaatt cattaaaaca    1320
gaaaggaaga aactcctgaa ctacaaggct cggctggtga aggacctaca acccagaatt   1380
tactgcccct ttcctgggta tttcgtggaa tcccacccag cagacaagta tggctggata   1440
tttatataa cgtgtttacg cataagttaa tatatgctga atgagtgatt tagctgtgaa   1500
acaacatgaa atgagaaaga atgattagta ggggtctgga gcttatttta acaagcagcc   1560
tgaaaacaga agtatgaat aaaaaaaatt aaatgcaaaa aaaaaaaaaa aaaaaaaaa    1620
aaaa                                                                1624
```

<210> SEQ ID NO 6
<211> LENGTH: 383
<212> TYPE: PRT
<213> ORGANISM: Porcine

<400> SEQUENCE: 6

```
Met Ser Ser Ile Glu Gln Thr Thr Glu Ile Leu Leu Cys Leu Ser Pro
1               5                   10                  15

Ala Glu Ala Ala Asn Leu Lys Glu Gly Ile Asn Phe Val Arg Asn Lys
            20                  25                  30

Ser Thr Gly Lys Asp Tyr Ile Leu Phe Lys Asn Lys Ser Arg Leu Lys
        35                  40                  45

Ala Cys Lys Asn Met Cys Lys His Gln Gly Gly Leu Phe Ile Lys Asp
    50                  55                  60

Ile Glu Asp Leu Asn Gly Arg Ser Val Lys Cys Thr Lys His Asn Trp
65                  70                  75                  80

Lys Leu Asp Val Ser Ser Met Lys Tyr Ile Asn Pro Pro Gly Ser Phe
                85                  90                  95

Cys Gln Asp Glu Leu Val Val Glu Lys Asp Glu Glu Asn Gly Val Leu
            100                 105                 110

Leu Leu Glu Leu Asn Pro Pro Asn Pro Trp Asp Ser Glu Pro Arg Ser
        115                 120                 125

Pro Glu Asp Leu Ala Phe Gly Glu Val Gln Ile Thr Tyr Leu Thr His
    130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Trp Leu Leu His Glu
                165                 170                 175

Pro Pro Ser Asp Trp Leu Glu Arg Leu Ser Arg Ala Asp Leu Ile Tyr
```

```
                    180                 185                 190
Ile Ser His Met His Ser Asp His Leu Ser Tyr Pro Thr Leu Lys Lys
            195                 200                 205
Leu Ala Glu Arg Arg Pro Asp Val Pro Ile Tyr Val Gly Asn Thr Glu
        210                 215                 220
Arg Pro Val Phe Trp Asn Leu Asn Gln Ser Gly Val Gln Leu Thr Asn
225                 230                 235                 240
Ile Asn Val Val Pro Phe Gly Ile Trp Gln Gln Val Asp Lys Asn Leu
                245                 250                 255
Arg Phe Met Ile Leu Met Asp Gly Val His Pro Glu Met Asp Thr Cys
            260                 265                 270
Ile Ile Val Glu Tyr Lys Gly His Lys Ile Leu Asn Thr Val Asp Cys
        275                 280                 285
Thr Arg Pro Asn Gly Gly Arg Leu Pro Met Lys Val Ala Leu Met Met
    290                 295                 300
Ser Asp Phe Ala Gly Gly Ala Ser Gly Phe Pro Met Thr Phe Ser Gly
305                 310                 315                 320
Gly Lys Phe Thr Glu Glu Trp Lys Ala Gln Phe Ile Lys Thr Glu Arg
                325                 330                 335
Lys Lys Leu Leu Asn Tyr Lys Ala Arg Leu Val Lys Asp Leu Gln Pro
            340                 345                 350
Arg Ile Tyr Cys Pro Phe Pro Gly Tyr Phe Val Glu Ser His Pro Ala
        355                 360                 365
Asp Lys Tyr Gly Trp Ile Phe Tyr Ile Thr Cys Leu Arg Ile Ser
    370                 375                 380

<210> SEQ ID NO 7
<211> LENGTH: 2293
<212> TYPE: DNA
<213> ORGANISM: Porcine

<400> SEQUENCE: 7
cccgacgtcc tggcagcgcc caggcactgt tattggtgcc tcctgtgtcc acgcgcttcc      60
cggccaggca gccctggcgg atcctatttt ctgttccccc gattctggta cctctccctc     120
ccgccctcgg tgcgcagccg tcctcctgca gtgcctgctc ctccaggggc gaaaccgatc     180
agggatcagg ccaccgcct cctgaacatc cctccttagt tcccacagtc taatgccttg     240
tggaagcaaa tgagccacag aagctgaagg aaaaaccacc attctttctt aatacctgga     300
gagaggcaac gacagactat gagcagcatc gaacaaacga cggagatcct gttgtgcctc     360
tcacctgccg aagctgccaa tctcaaggaa ggaatcaatt tgttcgaaa taagagcact     420 ggcaaggatt acatcttatt taagaataag agccgcctga aggcatgtaa aacatgtgc     480 aagcaccaag gaggcctctt cattaaagac attgaggatc taaatggaag gtctgttaaa     540
tgcacaaaac acaactggaa gttagatgta agcagcatga agtatatcaa tcctcctgga     600
agcttctgtc aagacgaact ggttgtagaa aaggatgaag aaaatggagt tttgcttcta     660
gaactaaatc ctcctaaccc gtgggattca gaacccagat ctcctgaaga tttggcattt     720
ggggaagtgc agatcacgta ccttactcac gcctgcatgg acctcaagct gggggacaag     780
agaatggtgt cgacccttg gttaatcggt cctgcttttg cgcgaggatg gtggttacta     840
cacgagcctc catctgattg gctggagagg ctgagccgcg cagacttaat ttacatcagt     900
cacatgcact cagaccacct gagttaccca acactgaaga agcttgctga gagaagacca     960
gatgttccca tttatgttgg caacacggaa agacctgtat tttggaatct gaatcagagt    1020
```

-continued

```
ggcgtccagt tgactaatat caatgtagtg ccatttggaa tatggcagca ggtagacaaa    1080
aatcttcgat tcatgatctt gatggatggc gttcatcctg agatggacac ttgcattatt    1140
gtggaataca aggtcataa aatactcaat acagtggatt gcaccagacc caatggagga     1200
aggctgccta tgaaggttgc attaatgatg agtgattttg ctggaggagc ttcaggcttt    1260
ccaatgactt tcagtggtgg aaaatttact ggtaattctt tatatcaaaa tgatgccaag    1320
gagttggcat ggcactttgc taaatgctgt gtgaatcaat acaaagataa ttaggacatg    1380
gttcttcctc acaagaggtg tgcaatctta ttgggaaatc atacttgcaa gtcacaaata    1440
tagactaaag tttccagctg agaatatgct gatggagcat gaaacactaa ggagacaggg    1500
agaatctcag gaaaaatcaa gaataatttg gatcaaatgg attcctgaca tagaacatag    1560
agctgatcag aaagagtctg acattggtaa tccaggctta agtgctcttt gtatgtggtt    1620
cagaacagag tgtgggcagc ctgagggga tacataccct tgacctcgtg aaagctcat     1680 acggggagg gatgaggcta aggaagcccc tctaaagtgt gggattacga gaggttgggg     1740
gggtggtagg gaaatagtg gtcaaagagt ataaacttcc agttacaaga tgaataaatt     1800 ctagggtat aataacagca tggcactata gatagcatat tgtactatat actggaagtg     1860
ctgagagtag atcttacatg ttctaaccac acacacacac acacacacac acaccaca      1920 cacacacacc acacacacac acgtgcacac aaacagaaat ggtaattatg tgaggtgatg    1980
gcggtgttaa ctaactttat tgtggtcatc atttagccat acatgcatgt catgaaatca    2040
ccatgttgta caccttaaag ttatgtaata ctagatgtca gttatatctc aaagctagaa    2100
aaaatgtggg gaccaaggca gaagctcttc tgctctgtgt ctaagggtgg ttctggggct    2160
gggatgggga ggatggttaa gtggtatatt tttttcatac ctttgctcag tactatcatt    2220
gtaagtgttc aatatatgtc tgcttaataa attaatgttt ttagtaaaaa aaaaaaaaa     2280 aaaaaaaaaa aaa                                                       2293
```

<210> SEQ ID NO 8
<211> LENGTH: 351
<212> TYPE: PRT
<213> ORGANISM: Porcine

<400> SEQUENCE: 8

```
Met Ser Ser Ile Glu Gln Thr Thr Glu Ile Leu Leu Cys Leu Ser Pro
1               5                   10                  15

Ala Glu Ala Ala Asn Leu Lys Glu Gly Ile Asn Phe Val Arg Asn Lys
            20                  25                  30

Ser Thr Gly Lys Asp Tyr Ile Leu Phe Lys Asn Lys Ser Arg Leu Lys
        35                  40                  45

Ala Cys Lys Asn Met Cys Lys His Gln Gly Gly Leu Phe Ile Lys Asp
    50                  55                  60

Ile Glu Asp Leu Asn Gly Arg Ser Val Lys Cys Thr Lys His Asn Trp
65                  70                  75                  80

Lys Leu Asp Val Ser Ser Met Lys Tyr Ile Asn Pro Pro Gly Ser Phe
                85                  90                  95

Cys Gln Asp Glu Leu Val Val Glu Lys Asp Glu Glu Asn Gly Val Leu
            100                 105                 110

Leu Leu Glu Leu Asn Pro Pro Asn Pro Trp Asp Ser Glu Pro Arg Ser
        115                 120                 125

Pro Glu Asp Leu Ala Phe Gly Glu Val Gln Ile Thr Tyr Leu Thr His
    130                 135                 140
```

```
Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Leu Leu His Glu
            165                 170                 175

Pro Pro Ser Asp Trp Leu Glu Arg Leu Ser Arg Ala Asp Leu Ile Tyr
            180                 185                 190

Ile Ser His Met His Ser Asp His Leu Ser Tyr Pro Thr Leu Lys Lys
            195                 200                 205

Leu Ala Glu Arg Arg Pro Asp Val Pro Ile Tyr Val Gly Asn Thr Glu
        210                 215                 220

Arg Pro Val Phe Trp Asn Leu Asn Gln Ser Gly Val Gln Leu Thr Asn
225                 230                 235                 240

Ile Asn Val Val Pro Phe Gly Ile Trp Gln Gln Val Asp Lys Asn Leu
            245                 250                 255

Arg Phe Met Ile Leu Met Asp Gly Val His Pro Glu Met Asp Thr Cys
            260                 265                 270

Ile Ile Val Glu Tyr Lys Gly His Lys Ile Leu Asn Thr Val Asp Cys
        275                 280                 285

Thr Arg Pro Asn Gly Gly Arg Leu Pro Met Lys Val Ala Leu Met Met
290                 295                 300

Ser Asp Phe Ala Gly Gly Ala Ser Gly Phe Pro Met Thr Phe Ser Gly
305                 310                 315                 320

Gly Lys Phe Thr Gly Asn Ser Leu Tyr Gln Asn Asp Ala Lys Glu Leu
            325                 330                 335

Ala Trp His Phe Ala Lys Cys Cys Val Asn Gln Tyr Lys Asp Asn
            340                 345                 350

<210> SEQ ID NO 9
<211> LENGTH: 601
<212> TYPE: DNA
<213> ORGANISM: Porcine

<400> SEQUENCE: 9
ctgccagcct aagccacagc cacagcaacg ctgggtctga gccatgtctg cagcctatgc      60
cagagctccc cgcagcgccg gatgcttaac ccactgagca aggccaggga ttgaaccctc     120
gtcctcatgg atagcagttg agttgtttcc acggaactct taggggaact cctgattatt     180
ttttatttaa atttatattt ctctgacttt ttcgtgtgct catcagccac tgactgtgta     240
tctccattag tcatggtttg ttaactctgt cattcaaacc ctcttcatcc ttgctacgca     300
gataacatca ttataataaa atcgtgcctg aagaccagtg acgcccccaa gctaagttac     360
tgcttcccct gggggaaaaa agaagcaccg cgcgggcgct gacacgaagt ccgggcagag     420
gaagacgggg cagaggaaga cgggggagca gtgggagcag cggcagggc gcgggaagca     480 ctggggatgt tccgcgttgg caggagggtg ttgggcgagc tcccggtgat gcagggggga     540
ggagcctttt ccgaagtagc gggacaagag ccacgggaag gaactgttct gagttcccag     600
t                                                                     601

<210> SEQ ID NO 10
<211> LENGTH: 228
<212> TYPE: DNA
<213> ORGANISM: Porcine

<400> SEQUENCE: 10
cccgacgtcc tggcagcgcc caggcactgt tattggtgcc tcctgtgtcc acgcgcttcc      60
```

```
cggccaggca gccctggcgg atcctatttt ctgttccccc gattctggta cctctccctc    120
ccgccctcgg tgcgcagccg tcctcctgca gtgcctgctc ctccaggggc gaaaccgatc    180
agggatcagg ccacccgcct cctgaacatc cctccttagt tcccacag                228

<210> SEQ ID NO 11
<211> LENGTH: 98
<212> TYPE: DNA
<213> ORGANISM: Porcine

<400> SEQUENCE: 11
tctaatgcct tgtggaagca aatgagccac agaagctgaa ggaaaaacca ccattctttc    60
ttaatacctg gagagaggca acgacagact atgagcag                            98

<210> SEQ ID NO 12
<211> LENGTH: 204
<212> TYPE: DNA
<213> ORGANISM: Porcine

<400> SEQUENCE: 12
catcgaacaa acgacggaga tcctgttgtg cctctcacct gccgaagctg ccaatctcaa    60
ggaaggaatc aatttttgttc gaaataagag cactggcaag gattacatct tatttaagaa   120
taagagccgc ctgaaggcat gtaagaacat gtgcaagcac caaggaggcc tcttcattaa    180
agacattgag gatctaaatg gaag                                          204

<210> SEQ ID NO 13
<211> LENGTH: 92
<212> TYPE: DNA
<213> ORGANISM: Porcine

<400> SEQUENCE: 13
gtctgttaaa tgcacaaaac acaactggaa gttagatgta agcagcatga agtatatcaa    60
tcctcctgga agcttctgtc aagacgaact gg                                 92

<210> SEQ ID NO 14
<211> LENGTH: 110
<212> TYPE: DNA
<213> ORGANISM: Porcine

<400> SEQUENCE: 14
ttgtagaaaa ggatgaagaa aatggagttt tgcttctaga actaaatcct cctaacccgt    60
gggattcaga acccagatct cctgaagatt tggcatttgg ggaagtgcag               110

<210> SEQ ID NO 15
<211> LENGTH: 191
<212> TYPE: DNA
<213> ORGANISM: Porcine

<400> SEQUENCE: 15
atcacgtacc ttactcacgc ctgcatggac ctcaagctgg gggacaagag aatggtgttc    60
gacccttggt taatcggtcc tgcttttgcg cgaggatggt ggttactaca cgagcctcca    120
tctgattggc tggagaggct gagccgcgca gacttaattt acatcagtca catgcactca    180
gaccacctga g                                                        191

<210> SEQ ID NO 16
<211> LENGTH: 148
<212> TYPE: DNA
```

<210> SEQ ID NO 16
<211> LENGTH: 148
<212> TYPE: DNA
<213> ORGANISM: Porcine

<400> SEQUENCE: 16

```
ttacccaaca ctgaagaagc ttgctgagag aagaccagat gttcccattt atgttggcaa      60
cacggaaaga cctgtatttt ggaatctgaa tcagagtggc gtccagttga ctaatatcaa     120
tgtagtgcca tttggaatat ggcagcag                                        148
```

<210> SEQ ID NO 17
<211> LENGTH: 82
<212> TYPE: DNA
<213> ORGANISM: Porcine

<400> SEQUENCE: 17

```
gtagacaaaa atcttcgatt catgatcttg atggatggcg ttcatcctga gatggacact      60
tgcattattg tggaatacaa ag                                               82
```

<210> SEQ ID NO 18
<211> LENGTH: 138
<212> TYPE: DNA
<213> ORGANISM: Porcine

<400> SEQUENCE: 18

```
gtcataaaat actcaataca gtggattgca ccagacccaa tggaggaagg ctgcctatga      60
aggttgcatt aatgatgagt gattttgctg gaggagcttc aggctttcca atgactttca     120
gtggtggaaa atttactg                                                   138
```

<210> SEQ ID NO 19
<211> LENGTH: 1014
<212> TYPE: DNA
<213> ORGANISM: Porcine

<400> SEQUENCE: 19

```
gtaattcttt atatcaaaat gatgccaagg agttggcatg cactttgct aaatgctgtg       60
tgaatcaata caaagataat taggacatgg ttcttcctca caagaggtgt gcaatcttat     120
tgggaaatca tacttgcaag tcacaaatat agactaaagt ttccagctga atatgctg       180
atggagcatg aaacactaag gagacaggga gaatctcagg aaaaatcaag aataatttgg     240
atcaaatgga ttcctgacat agaacataga gctgatcaga aagagtctga cattggtaat     300
ccaggcttaa gtgctctttg tatgtggttc agaacagagt gtgggcagcc tgaggggat      360
acatacccttt gacctcgtgg aaagctcata cgggggaggg atgaggctaa ggaagcccct    420
ctaaagtgtg ggattacgag aggttggggg ggtggtaggg aaaatagtgg tcaaagagta     480
taaacttcca gttacaagat gaataaattc taggggtata ataacagcat ggcactatag     540
atagcatatt gtactatata ctggaagtgc tgagagtaga tcttacatgt tctaaccaca     600
cacacacaca cacacacaca cacaccacac acacacacca cacacacaca cgtgcacaca     660
aacagaaatg gtaattatgt gaggtgatgg cggtgttaac taactttatt gtggtcatca     720
tttagccata catgcatgtc atgaaatcac catgttgtac accttaaagt tatgtaatac     780
tagatgtcag ttatatctca aagctagaaa aaatgtgggg accaaggcag aagctcttct     840
gctctgtgtc taagggtggt tctggggctg ggatggggag gatggttaag tggtatattt     900
ttttcatacc tttgctcagt actatcattg taagtgttca atatatgtct gcttaataaa     960
ttaatgtttt tagtaaaaaa aaaaaaaaaa aaaaaaaaaa aaaa                     1014
```

<210> SEQ ID NO 20
<211> LENGTH: 136
<212> TYPE: DNA
<213> ORGANISM: Porcine

<400> SEQUENCE: 20
aggaatggaa agcccaattc attaaaacag aaaggaagaa actcctgaac tacaaggctc    60
ggctggtgaa ggacctacaa cccagaattt actgcccctt tcctgggtat ttcgtggaat   120
cccacccagc agacaa                                                  136

<210> SEQ ID NO 21
<211> LENGTH: 169
<212> TYPE: DNA
<213> ORGANISM: Porcine

<400> SEQUENCE: 21
gtatggctgg atattttata taacgtgttt acgcataagt taatatatgc tgaatgagtg    60
atttagctgt gaaacaacat gaaatgagaa agaatgatta gtagggtct ggagcttatt    120 ttaacaagca gcctgaaaac agagagtatg aataaaaaaa attaaatac              169

<210> SEQ ID NO 22
<211> LENGTH: 141
<212> TYPE: DNA
<213> ORGANISM: Porcine

<400> SEQUENCE: 22
gtatattaag gaaacaaaca tcaaaaatga cccaaatgaa ctcaacaatc ttatcaagaa    60
gaattctgag gtggtaacct ggaccccaag acctggagcc actcttgatc tgggtaggat   120
gctaaaggac ccaacagaca g                                            141

<210> SEQ ID NO 23
<211> LENGTH: 175
<212> TYPE: DNA
<213> ORGANISM: Porcine

<400> SEQUENCE: 23
caagggcatc gtagagcctc cagaagggac taagatttac aaggattcct gggattttgg    60
cccatatttg aatatcttga atgctgctat aggagatgaa atatttcgtc actcatcctg   120
gataaaagaa tacttcactt gggctggatt taaggattat aacctggtgg tcagg        175

<210> SEQ ID NO 24
<211> LENGTH: 117
<212> TYPE: DNA
<213> ORGANISM: Porcine

<400> SEQUENCE: 24
atgattgaga cagatgagga cttcagccct tgcctggag gatatgacta tttggttgac    60
tttctggatt tatcctttcc aaaagaaaga ccaagccggg aacatccata tgaggaa     117

<210> SEQ ID NO 25
<211> LENGTH: 31
<212> TYPE: DNA
<213> ORGANISM: Porcine

<400> SEQUENCE: 25
atcctgtgtc aggagttggg attctttgaa g                                  31

<210> SEQ ID NO 26

```
<211> LENGTH: 116
<212> TYPE: DNA
<213> ORGANISM: Porcine

<400> SEQUENCE: 26
attcggagcc gggttgatgt catcagacac gtggtaaaga atggtctgct ctgggatgac      60
ttgtacatag gattccaaac ccggcttcag cgggatcctg atatatacca tcatct         116

<210> SEQ ID NO 27
<211> LENGTH: 97
<212> TYPE: DNA
<213> ORGANISM: Porcine

<400> SEQUENCE: 27
gttttggaat cattttcaaa taaaactccc cctcacacca cctgactgga agtccttcct      60
gatgtgctct gggtagagag gacctgagct gtcccag                              97

<210> SEQ ID NO 28
<211> LENGTH: 655
<212> TYPE: DNA
<213> ORGANISM: Porcine

<400> SEQUENCE: 28
gggtgcccaa caacatgaaa aaatcaagaa tttattgctg ctacgtcaaa gcttatacca      60
gagattatgc cttatagaca ttagcaatgg ataattatat gttgcacttg tgaaatgtgc     120
acatatcctg tttatgaatc accacatagc cagattatca atattttact tatttcgtaa     180
aaaatccaca attttccata acagaatcaa cgtgtgcaat aggaacaaga ttgctatgga     240
aaacgagggt aacaggagga gatattaatc caagcataga agaaatagac aaatgagggg     300
ccataagggg aatataggga agagaaaaaa attaagatgg aattttaaaa ggagaatgta     360
aaaaatagat atttgttcct taataggttg attcctcaaa tagagcccat gaatataatc     420
aaataggaag ggttcatgac tgttttcaat ttttcaaaaa gctttgttga aatcatagac     480
ttgcaaaaca aggctgtaga ggccacccta aaatggaaaa tttcactggg actgaaatta     540
ttttgattca atgacaaaat ttgttattta ctgcggatta taaactctaa caaatagcga     600
tctctttgct tcataaaaac ataaacacta gctagtaata aaatgagttc tgcag          655

<210> SEQ ID NO 29
<211> LENGTH: 363
<212> TYPE: DNA
<213> ORGANISM: Porcine

<400> SEQUENCE: 29
gtgagaaggc ttcgccgctg ctgccgctgg cgccggcagc gccctccacg cacttcgtag      60
tgggcgcgcg ccctcctgca ttgtttctaa aagatttttt tttatccgct tatgctatca     120
gttactgagg aagtatttac aaatctacta ttattttgaa tttgcctttt tctccttata     180
gtttatcagt atctcttgag actgttattg gtgcctgcaa atttaaaatg attggggttt     240
tatgaggaag tgaacctttt atctttatga aacgcctaac tgaggcaatg ttaattgctt     300
aaaatacttt ctttattatc agtgtggcca tgccagtgtc ctcttggtta gaatttgcct     360
gat                                                                    363

<210> SEQ ID NO 30
<211> LENGTH: 143
<212> TYPE: DNA
<213> ORGANISM: Porcine
```

<400> SEQUENCE: 30

| | | | | | |
|---|---|---|---|---|---|
| ctgccaaagc | tgggagatgg | gggaaagtag | agtgggttat | tgaaactgaa | tatagagttc | 60 |
| agcatctaaa | agcgaggtag | tagaggagga | agctgtgtca | acggaaatac | tgagctgggt | 120 |
| tcacatcctc | tttctccaca | cag | | | | 143 |

<210> SEQ ID NO 31
<211> LENGTH: 237
<212> TYPE: DNA
<213> ORGANISM: Porcine

<400> SEQUENCE: 31

| | | | | | |
|---|---|---|---|---|---|
| gcaagtgaga | gggggcttta | gctgtcaggg | aaggcggaga | taaacccttg | atgggtagga | 60 |
| tggccattga | aaggagggga | gaaatttgcc | ccagcaggta | gccaccaagc | ttggggactt | 120 |
| ggagggaggg | ctttcaaacg | tattttcata | aaaaagacct | gtggagctgt | caatgctcag | 180 |
| ggattctctc | ttaaaatcta | acagtattaa | tctgctaaaa | catttgcctt | ttcatag | 237 |

<210> SEQ ID NO 32
<211> LENGTH: 4229
<212> TYPE: DNA
<213> ORGANISM: Porcine

<400> SEQUENCE: 32

| | | | | | |
|---|---|---|---|---|---|
| gtactgagaa | tcctttgctt | tctccctggc | gatcctttct | cccaattagg | tttggcagga | 60 |
| aatgtgctca | ttgagaaatt | ttaaatgatc | caatcaacat | gctatttccc | ccagcacatg | 120 |
| cctaactttt | tcttaagctc | ctttacggca | gctctctgat | tttgatttat | gaccttgact | 180 |
| taatttccca | tcctctctga | agaactattg | tttaaaatgt | attcctagtt | gataaacagt | 240 |
| gaaacttcta | aggcacatgt | gtgtgtgtgt | gtgtgtgtgt | gtgtgtttac | cagcttttat | 300 |
| attcaaagac | tcaagcctct | tttggatttc | cttcctgct | ctctcagaag | tgtgtgtgtg | 360 |
| aggtgagtgc | ttgtccaaac | actgccctag | aacagagaga | ctttccctga | tgaaaacccg | 420 |
| aaaaatggca | gagctctagc | tgcacctggc | tcaacagcg | gctcttctga | tcatttcttg | 480 |
| gaagaacgag | tgctggtacc | ccttttcccc | agcccttga | ttaaacctgc | atatcgcttg | 540 |
| cctcccatc | tcaggagcaa | ttctaggagg | gagggtgggc | tttcttttca | ggattgacaa | 600 |
| agctacccag | cttgcaaacc | aggggggatct | ggggggggg | tttgcacctg | atgctccccc | 660 |
| actgataatg | aatgagggat | tgaccccatc | tttttcaagct | ttgcttcagc | ctaacttgac | 720 |
| tctcgtagtg | tttcagccgt | ttccatatta | ggcttgtctt | ccaccgtgtc | gtgtcgtcaa | 780 |
| tcttatttct | caggtcatct | gtgggcagtt | tagtgcgaat | ggactcagag | gtaactggta | 840 |
| gctgtccaag | agctccctgc | tctaactgta | tagaagatca | ccacccaagt | ctggaatctt | 900 |
| cttacactgg | cccacagact | tgcatcactg | catacttagc | ttcagggccc | agctcccagg | 960 |
| ttaagtgctg | tcatacctgt | agcttgcttg | gctctgcaga | tagggttgct | agattaggca | 1020 |
| aatagagggt | gcccagtcaa | atttgcattt | cagataaaca | acgaatatat | ttttagttag | 1080 |
| atatgtttca | ggcactgcat | gggacatact | tttggtaggc | agcctactct | ggaagaacct | 1140 |
| cttggttgtt | tgctgacaga | ctgctttga | gtccccttgca | tcttctgggt | ggtttcaagt | 1200 |
| tagggagacc | tcagccatag | gttgttctgt | caccaagaag | cttctgcaag | cacgtgcagg | 1260 |
| ccttgaggtc | ttccgacttg | tggcccgggg | actctgcttt | ttctctgtcc | tttttctcc | 1320 |
| ttagtgggcc | atgtcctgtg | gtgttgtctt | agccagttgt | ttaagggagt | gttgcagctt | 1380 |

| | |
|---|---|
| tatgattaag agcatggtct ttccttgcaa actgcttggt ttagaagcct ggctccacca | 1440 |
| cttagcggct ctgtgacctc ggacacattt cttagccttt ctgggcctcg ctcttcttcc | 1500 |
| tcataaagtg aaaatgaaag tagacaaagc cttctctgtc tggctactga gaggatggag | 1560 |
| tgatttcata cacataaagc acttaaaata atgtctggca tatgatacat gctcaataaa | 1620 |
| tgtcacttac atttgctatt attattactc tgccatgatc ttgtgtagct taagaacaga | 1680 |
| ggtctttaca ggaattcagg ctgttcttga atctggcttg ctcagcttaa tatggtaatt | 1740 |
| gctttgccac agactggtct tcctctcctt cacccaaagc cttaggggt gaacgatccc | 1800 |
| agtttcaacc tattctgttg gcaggctaac atggagatgg caccatctta gctctgctgc | 1860 |
| aggtggggag ccagattcac ccagctttgc tcccagatac agctccccaa gcatttatat | 1920 |
| gctgaaactc catcccaaga gcagtctaca tggtacactc ccccatccat ctctccaaat | 1980 |
| ttggctgctt ctacttaggc tctctgtgca gcaattcacc tgaaatatct cttccacgat | 2040 |
| acagtcaagg gcagtgacct acctgttcca ccttcccttc ctcagccatt tttcttcttt | 2100 |
| gtacataatc aagatcagga actctcataa gctgtggtcc tcattttgtc aatctaattt | 2160 |
| cacagcctct tggcacatga agctgtcctc tctctccttt ctgcctactg cccatgagca | 2220 |
| gttgtgacac tgccacattt ctcctttaac gacccagcct gctgaatagc tgcatttgga | 2280 |
| atgttttcaa ttttttgttaa tttatttatt tcatcttttt tttttttttt tttttttttt | 2340 |
| tttttagggg ccgcacccat gggatatgga ggttcccagg ctagggatcc aatgggagct | 2400 |
| gtagctgctg gcctacacca cagccacagc aatgcacaat tcgagccaat ctttgaccta | 2460 |
| caccagagct cacggcaaca ctggattctt aacccactga ttgaggccag ggatcaaact | 2520 |
| ctcgtcctca tagatacgag tcagattcgt taacctctga gccatgatag ttgttagtta | 2580 |
| ctcattgatg agaaaggaag tgtcacaaaa tatcctccat aagtcgaagt ttgaatatgt | 2640 |
| tttctgcctt gttactagaa aagagcatta aaaattcttg attggaatga gcttggaaaa | 2700 |
| aaatcagcat agtttactga tatataagtg aaaatagacc ttgttagttt aaaccatctg | 2760 |
| atatttctgg tggaagacat atttgtctgt aaaaaaaaaa aatcttgaac ctgtttaaaa | 2820 |
| aaaaaacttg actggaaaca ctaccaaaat atgggagttc ctactgggac acagcagaaa | 2880 |
| tgaatctaac tagtatccat gaggacacag gtttgatgcc tggcctcgct aagtgggtta | 2940 |
| aggatatggt gttgctgcag ctccaattca accccctatcc tgggaacccc catatgccac | 3000 |
| cctaaaaagc aaaagaaag gtgctgccct aaaaagcaaa aagaaagaaa gaaagacagc | 3060 |
| cagacagact accaaatatg gagaggaaat ggaacttttca ggcccctatct ccaactatca | 3120 |
| catccctatc accgtctggt aagaaatgga aaaatatta ctaagcctcc tttgttgcta | 3180 |
| caattaatct gattctcatt ctgaagcagt gttgccagag ttaacaaata aaaatgcaaa | 3240 |
| gctgggtagt taaatttgaa ttacagataa acaaattttc agtatatgtt caatatcgtg | 3300 |
| taagacgttt taaaataatt ttttatttat ctgaaattta tattttcct gtatttatc | 3360 |
| tggcaaccat gatcagaaat ctttaaacaa tcaggaagtc ttttttctta gacaaatgaa | 3420 |
| aatttgagtt gatcttaggt ttagtacact atactagggg ccaagggtta tagtgtgact | 3480 |
| attaaatcac agataatctt tattactaca ttatttcctt atactggccc cacttggatc | 3540 |
| ttacccagct tagcttttgt atgagagtca tccttaaaga tgactttatt cttaaaaaa | 3600 |
| aaaaacaaat tttaagggct gcacccatag catatagaag ttcctaggct agcggtcaaa | 3660 |
| ttagagctgc agctgccagc ctatgccaca gccacagcaa tgccagatct gagctgcatc | 3720 |
| tgtgacctac actgcagctt gcagcaatgc tggatcctta acccattgaa caatgccagg | 3780 |

```
gattgaacac acatcctcat ggatactgct caggttccta acctgctgag ccacagttgg    3840
aactccaaag cagactttat tctgatggct ctgctgatct ctaacacgtt attttgtgcc    3900
atggtgttta tcttcacttt actcaagtca gggaaacacg aagagtctca tacaggataa    3960
acccaaggag aaatgtgcaa agtcacatac aaatcaaact gacaaaaatc aaatacaagg    4020
aaaaaatatc ttcactttca aaatcaccta ctgatgatga gtttatattt ccttggatat    4080
ttgaatatta gctattttt tcctttcatg agttttgtgt tcaaccaact acagtcgttt    4140
actttgatca cagaataatg catttaagcc ttaaatagat taatatttat tttcaccatt    4200
tcataaacct aagtacaatt tccatccag                                     4229

<210> SEQ ID NO 33
<211> LENGTH: 8164
<212> TYPE: DNA
<213> ORGANISM: Porcine

<400> SEQUENCE: 33
gtaaatacca tcaatactga tcaatgtttt ctgctgttac tgtcattggg gtccctcttg      60
tcaacttgtt tccaatctca ttagaagcct tggatgcatt ctgattttaa actgaggtat     120
tttaaaagta accatcactg aaaattctag gcaagttttc tctaaaaaat cccttcattc     180
attcatttgt tcagtaagta tttgatgaga ccttaccatg tgtaaacatt gcactaggta     240
ttaagaaata caaagatgga taagatagag tcggcgtaaa tgagatgata taatgagacg     300
ttataatgaa actcacaatt ccagtttggga aataaagtcc ttcaaattcc atgactcttt    360
ctggcacacg ttagaggcta cagcttctgt gtgattctca tgctggctcc acttccactt    420
tttccttctt cctactcaag aaagcctata gaaatatgag taagaagggc ttaatcatag    480
gaataaattt gtctctgttc taagtgatta aaaatgtctt tatcagtata aaaagttact    540
tgggaagatt cttaaaactg cttttacaca ctgttctaga atgactgtta tataaataaa    600
aaagtagatt tgatctaaca caattaaatg acctttggaa atattgacta attctcacct    660
tgcccctcaa agggatgcct gaaccatttc cttcttttgc cagaaagccc ccacccttg    720 tctgttgacc tagcctagga aatcttcaga tcacgttgtt agcacgaact ggttacatgt    780
gctgtacaaa tactatttaa ttcatctgat taaaaaaaaa gagataagaa gcaaagttt    840 gactatctta aactgtttgc gtaggtgaga ggacaattga ccatctactt tatgagtatg    900
taacccagaa acttaaagct ccttaaggga gctaagtctt ttggataaga cctatagtga    960 gacctttag caaaatggtt aagactgaat ggagctcact agcgtgggtt catatcctga   1020
tgctcaaaca cgcaattaaa tgactttagg tgggttagtc tctgttcctt agtttcctca   1080
atgggagata atattggtag tagcgatttt actgggttgt tgaaagaaca tctgttaaat   1140
gttcagaacg tgttacgaca gagtacagag taatgatttg cttgtatatg tatgactcaa   1200
atagtctgcc atatgccttg tgactgggtc ctgtggagca ggaaggaggg atttcccacc   1260
cagcagaaag ttgggtaaac tggaaaatag actgaggcca ggaaatgatg caaagcgttg   1320
atgttcactg ccacggcagg tgaagggcag ggccagagtt gtcagtaggg tcaggggagg   1380
actggaaata accaagaccc actgcacttt tcagcctttg ctccagtaag gtaatgttgt   1440
gagagtagaa aattttgtta acagaaccca cttttcagta cagtgctacc aatactgtag   1500
tgatttcata ccacatccca agaaagaaaa agatggctca atcccatgtg agctgagatt   1560
atttggtttt attgttaaat aaatagcatt gtgtggtcat cattaaaaaa ggtagatgtt   1620
```

```
aggaaagtag aaggaagaag actctcacct acattttcat cactgttttg gtatctgcca    1680
gttgtcacct tggtcccctt ccccgcctct cccctgcctc ctcttcctcc ttctccttt     1740 tttggaatac aattcaggta ccataaaatt tacccttta gagtgtttga ctcaatggtt     1800
tttagtattt tcacatgttg tgctattact atcactatat aattccaggt cattcacatc    1860 acccccaaa gaaaccttct aactattagc agtccattcc cttcttccct cagcccctgg     1920
caaccactaa tctacttact gtctccatgg atgttcctat attgaatcaa gctagcataa    1980 acccacttg ctcatggtca taattctttt ttatagtgct aaattacatt tgctaatatt     2040
caattaagga tttctatgtc catattcata aggaatattg gtgtgtagtt ttctctttgt    2100
gtgatatctt tgtctggttg ggggatcaga gtaataatta ctgctctcat agaatgaatt    2160
gagaagtgtt ccctcctttt ctatttattg aagagtttg tgaagtatat tggtattgat     2220
tcttctttaa acatttggtc agattcacca gtgaagccat ctgggccatg gctaatcttt    2280
gtgaaaagtt ttttgattac taattaaatc tctttaattt gttatgggtc tgctcctcag    2340
acgttctagt tcttcttgag tcagttttgt tcatttgttt cttcctagga cttctccct    2400 ttcatttgga ttatttagat tgatagtaat atccccttt taattcctgg ctgtagtaat    2460
ttgggtcttt tctcttttt cttggtcagt ttagctaaag gtttgtaatt gtattaatct    2520
tttcaaataa ctaaccttt tgttttgttt gttttttgtt ttttgttttt tgttttttgt    2580
ttttttttgc ttttaaggc tgcacctgag gcatatggaa gttctcaggc tagaggtcta    2640
atcggagcta cagctgctgg cctataccac aaccatagca atgccagatt caagctgcat    2700
ctgcgaccta caccacaact cggccaggga tcacacccgc aacctcatgg ttcctagtcg    2760
gatttgttaa ccactgtgcc acgacgggaa ctcccgccca tttttttaa cacctcatac    2820 tttaacataa agatgggctt cacatggact gatagctcaa atgaggaagg taagactatg    2880
aaagtaatgg aagaaatgta gactatttt gtgacctaga gattactgat acttcttgac    2940
ttttcaaaca atacttcaaa agtacagccc aagggaaaa aagaaagaaa aaagaaacac    3000
acatatacac aaacctagtg aataagatat catcgataca ctacagattt ctatgaactg    3060
gaagacccca tggacaaagt taaagaacat atgatagttt gagtgattat tttgcaatat    3120
ttacaaccaa tgagggaata ttatccagct tataggagga agtaatgcaa atcgacaaga    3180
aaaagatagg aaacccaata taaaaattaa gaaaatacaa aaattaagaa aggatatgaa    3240
ctagcatttt acaaaagaaa aatctccaaa agtcaatcag cacatgaaaa tatgctcaaa    3300
cctattaatt attagaaaac tacagactga agcaatgagg tgctttactt tacatctttt    3360
tgactgataa aaagttagaa acaaaggtga tatcaaatgt cagggataaa aggatataga    3420
aatcgtcatg cctgtggtgg gagtatggcc ggtgcagtca tgtgggaagg taatctgaca    3480
gtggttaggc agagcaggtt tatgaataca ctgtggccca tcaatcccac gcctgtttat    3540 gtaccaaga aatcctgttg tggcagaatc tatgggtcca ccctgggag catgaattaa    3600 taaaatgtgg caccagggtg tgtgaaactc cagctagaga tgagatgtcc acatggcaac    3660
atgaatgcat cttagaaaca tagatttgag tgaaaagag taagaaacag ccgggaaacc    3720
caataccatt tataaaaatt aaagatgcac acatacaatg tagtaaatat tttgcatgaa    3780 cttcaaatg gttgcctaca gggggggaga gtaaagaaga gtagaaaaca aagataaagg    3840
gagtaagtaa gtagctctgc ctggactgaa tataatgtgt catgaactga gaaatatggt    3900
taacataatc ctcttaactt gaggtcctaa atgaatgaat gagtccacta ttcatttacc    3960
cattctttaa tgtgtattgc attataatcc attttttag aaccaacgaa ttttgttccc    4020
```

```
ataactacta atcagcctgc cttttctccc tcattccctt atcagctcag gggcattcct    4080 agttttcaa  acgttcctca tttgaaccaa aaatagcatc attgtttaaa ttatacttgt    4140
tttcaaatac gatgcttata tattccaagt gtgtttgccc attttcttag gtggtagaaa    4200 ttttcattc  tacttttcta tctactcaga ttttcccgtt ggaattattt ccattgctat    4260
taaacttaga agtccccct  gtgatatgcc atttttttca acttttttaa gcacttggtt    4320
gcttttcttt gtgtctttaa gcacctagaa tacttataac cattgcacag cactgtgtat    4380
caggcagccc ttcctcttcc actaatttat ggtccttctc ttagactata ttaaactgtt    4440
atttaattag gatcctctct tcgtccttat gatttaatta ttatagtttt ctaatatgtt    4500
tttattataa ttcctcttca ttattcctcc ctattaaaaa ttttaatgaa ttccatttgt    4560
ttgttcttct agttaaatat taagtcataa tccaataac  ttagatgtca ttagtttatg    4620
tggtcaaagt aaggatacca catctttata gatgcaggca gttggcagat gtcatgattt    4680
tcttcagtgc ataaatgcaa tttatctttg agcaaggggc ataaaaactt ttatggtatt    4740
ggctttgaaa taatagttaa gaactgcaga ctcagttttt cctgcttttc ttgaaaaaga    4800
acacttctaa agaaggaaaa tccttaagca tggatatcga tgtaattttc tgaaagtctc    4860
ctgtaattcc ttgggatttt tgttgttgtt tgttggtcgg ttttttggg  ttttgtttg    4920 tttgttttgt tttgttttgt tttgctttta gggctgcacc tgtggcatat ggaagttccc    4980
aggctagggg tccaactgga gctacagctg ccagcctact ccacagccac agcaacatgg    5040
gatcctagct gcatctgtga cctaaccaca gctcttggta atgccagatt gttaacccac    5100
tgagcaatgc cagagatcga atctgcctcc tcatggacac tagtcagatt agtttctgct    5160
gagccacaat gggaattccc aattccttgt atttttgaac tggttatgtg ctagcatata    5220
attttgtttc ttgaatcttt gtgggttttt ttttttttttt tttttttgtct cttgtctttt    5280 taaggctgca cccacagcat atggaggttc ccaggctaga ggtcaaattg gagctacagc    5340
tgccagccta cacaacaact gcagcaaagt ggggcccaac ttatatgaca gttcgtggca    5400
atgccggatt cctaacccac tgagcagggc cagggatcga acctgagttt ccagtcagtt    5460
tcgttaacca ctgagccatg atagtaactc ctgtttgttc agtcttgaac ctccttttta    5520
attctttatt ccttgagggt gaaataattg ccataataat actatcatt  attacatgcc    5580 ttctctgtgc taggcatagt gacactttag gatttattat atcacttaat ccctacaaca    5640
actctgcaaa gtatgtatca taatcctatt tgacagatca ggaaattgca gcccaggatg    5700
cagataatat gcatccatca caagtgacta gatatagtcc ctctgctatt cagcagggtc    5760
tcattgcctt tccattccaa atgcaatagt ttgcatctat tgtatatgtg ttttgggggtt    5820 tttttgtctt ttttttttttt tttgtcttt  ctggggcctc acccttggca taggtaggtt    5880
cccaggctag gggtcaaatt gaagctgcag ctgccagcct acaccacagc cacagcaact    5940
cgggatctga gcctcatctg caacctacac caaagctcac ggcaacaccg gatccttaac    6000
ccactgagtg aggccagaga tcaaaccggc aacctcatgg ttcctagtcg gattcattaa    6060
ccactgagcc acgatgggaa ctccctaaat gcaatagttt gctctattaa ccccaaactc    6120
ccagtccatc ccactccctc ctcctccctc ttggcaacca caagtctgtt ctccatgtcc    6180
atgattttct ttctggggaa agtttcatt  tgtgccattt tcatttttac gggtaatttt    6240
tacttcagtt tcttccacta gcagttgtct taaagtgagt ataattaata ttcatttgga    6300
aaatgtaagc aaaacatttt ttaaagggcc atgcccacag catatgaaag tttctgggcc    6360
```

```
agggggttgaa tccaggctcc aagttgcagc tgtgccctac actgcagctg ggcaatgctg    6420
gatcctttaa cccactgtgc ccggctaggg atcaaacctg catttccaca gctacccgag    6480
ccattgcagt tggattctta acccactgca ctacagtggg aactcccaca aaacattttt    6540
taatgtcctt tgaataaagt aggaaagtgc tcgtctttga gggcagggcg gcaatgccat    6600
ttccacaagg tttgctttgg cttgggacct catctgctgt catttagtaa tgaataaaat    6660
tgctgacagt aataggatta actgtgtgtg agatagccca gggttagaga taaaaacact    6720
ggagaagtca ataagttgc tcgaggtcct ctagctaata agctattaag tgggagagtg    6780
agggctagaa acaggccatc tgtctcccaa gcacatgtcc attagtggtt tgctgatagc    6840
cttccagaac aacagagagg actctcaaac atggtcttgc ctccctccaa ttgatcccct    6900
ccatgtgcct cacagcgggt cttcctaaaa ttaagtctg atttttaattc tcccttgcta    6960 tagcacttag gtatggcttt cagccgtgca ataaaaagca ggcaagagtg gctcaatcat    7020
ataggaggtt gtttttctta gatcccaagc aggtaatcct gggcattatg gttgttctgc    7080
gtttatcaag gagccaaatt ctctatcacc tcctgttcta tcctcctcag tatctggctc    7140
tattcttcag catctcaaga tggcttgtgc tcctccaagc atggcagtca aattccacac    7200
aagaggggga aatatgaagg gcagacagtg ctggtctcct gagctgtccc tctttgtcgg    7260
ggaaataaat gtattccttc aagtcccgtg agacttctga agtagacgtc tgcttacgtc    7320
tcacccacca gaactatgta aactgcacat agtgctaggt ctacatagcc actcataact    7380
gccagggggt gggaaatctt taaataggtg taccaccaca caattaggat gctaatagta    7440
agggagaagg agagaatagg ttttgcgcaa gccaccagca tgcctgccac aattgcttaa    7500
aattcttcat tgaccctca ttgccacagg atgaaatcca aacgccttct tagttgggaa    7560
tctgacctac ctgtctctcc cacctggttc agacaccatt ctccttggtc ataaaattcc    7620
agtcatttgt gaacatccag ctcccccatg cctccatgcc tttgcacatg ctgttctttt    7680
atcttttatg ttgtccttt atcttttatc caaaagagat atcccatcat cacatctctt    7740
ttgtcagccc ccaaatactt tgtctttcaa gttcagctgg aggattacct cctatttgaa    7800
atcagctttg tctcttacaa ccaaacaagg ttttccttcc gagacactcc cacagcacct    7860
tgaactcatc tctatcaatc attcatttga ttgtaatgaa gttgttggtg gtatgcctgt    7920
gtctctgaca catctgcgat ctcatgagtt ccttaagtgg aatgtgaata gcgggatgaa    7980
cagtattggt cttcagccct catctctgca gatgttgctt gacccaaatg agcgttgcct    8040
tttattttga ttttgctttg atttgtctac tccatgtact tgagccatgc atttctgtct    8100
tagcgatgct ttttaaaagt cattttttgg ttgattatcc agatttgtcc acctttgctt    8160
ctag                                                                 8164
```

<210> SEQ ID NO 34
<211> LENGTH: 1604
<212> TYPE: DNA
<213> ORGANISM: Porcine

<400> SEQUENCE: 34

```
gtaaggaaat gttaaattgc aatattctta aaaacacaaa taaagctaac atatcaattt     60
atatatatat atatatatat attttttttt tttttacat cttatattac cttgagtatt    120
cttggaagtg gctagttagg acatataata aagttattct gaagtctttt ttttcttttt    180
tccatggtga gcagtggctt gatgtggatc tcagctccca gacgaggcac tgaacctgag    240
ccgcagtggt gaaagcacca agttctagcc actagaccac cagggaactc cctattctaa    300
```

```
attcttgagc acattattta ggaacctcag gaacttggca ggattacagg aaatatatct      360
agatttaaaa aaaaatcttt taacagaggt cccaaaggag agtcatgcac agctatggga      420
ggaagttcag aaactgccct tgctaccaga tcactgtcag ataaaatggc cagctacatg      480
tttctgcaca ttgccctaag atctttacaa acttttctgt gcattttcc acttttaaaa       540 gaaaatttcg gggttcctgt tgttgctcag tggttaacga acccaactag tatccatggg      600
gacaggggtt cgagccctgg cctcactcag tgggttaaga atctggcatt gctgtggctg      660
tggcgtaggc tggcggctac agctcagatt ggacccctag cctgagaacc tccatatgcc      720
gcaggtatgg ccctaaaaaa aaaaaaaag agagagagag aatttcctcc agaaaaaaca       780
ctttggtagt tgggagaag taaacaacca aaaattaatt tttctggagt attcgggaag       840
cttgtaaaaa tgggctctta ctttttgag gagacaaatg ggaacctacc cagaagaggc      900
acaatcacct gcatttgatt tcttgacctc tccctacctt ctttgctggc tttccacatt      960
tggatttctg tgaccttatc tctgctcctt ggtgttttca ttttcctgt ggacgtgcca      1020 gactatggga agggagtaag gcgttgattt agaatcctgt agtctctgcc tgtctctagt      1080
cattgttttc acccttctca aaggaccttg acatcctgag tgagtccgca agtaatttag      1140
gggagaagcc ttagaagcca gtgcagccag gctacatgac tgtgtccacc cactggaacc      1200
agtcattttt ataccctattc acagccccc taccatttaa atccccagag gtctgccata      1260
acatctgtaa ctccctttcc tggtaaattg tgttctaaaa gactggtaac aaaagatatt      1320
ctgtggtaca gagcataatt aaatacctgg gagctgattt gagtggggta aatcaactgg      1380 tttgaccct aaaacccacc atgagcattt ctgttctaat aaagtaatgc ccgtgctggg      1440
aattgtgttc tacggaaatg ctcctgctgt gtctttcttg agtcctgtgt cattgaacat      1500
gcttaggagc aaaggtcccc catgtggctt gtctgctaac cagcccagtt ccttgttctg      1560
gctggtaatg atccgatcat ctgaatctca ctgtcttcca acag                      1604
```

```
<210> SEQ ID NO 35
<211> LENGTH: 3628
<212> TYPE: DNA
<213> ORGANISM: Porcine
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
```

```
<221> NAME/KEY: misc_feature
<222> LOCATION: (2026)..(2026)
<223> OTHER INFORMATION: n is a, c, g, or t
<220> FEATURE:
<221> NAME/KEY: misc_feature
<222> LOCATION: (2136)..(2136)
<223> OTHER INFORMATION: n is a, c, g, or t

<400> SEQUENCE: 35
```

| | | | | | |
|---|---|---|---|---|---|
| gtaaggaagg | gtgagccctc | aactccgaag | aaaatgctgc | aataaaagca | ctgttggttt | 60 |
| tcagctttt | ttgtaatcac | tgctcattct | gaggtagatt | cgcttgggct | gataaaaaga | 120 |
| gaactaattc | agataaatgc | ttgcatttgc | atagcctctt | tttttaaaaa | cttttttttt | 180 |
| ttttttttt | ttttggcttt | tcagggctga | acctgtggca | tatggaggtt | cccaggctag | 240 |
| gggtcgaatc | agagctgtag | cccccgggcct | atgccactgc | catagcaaca | tgcatagcct | 300 |
| ccttttaaa | gtgccttcct | gttttatacc | attgggatgt | gagaagagct | attgtggaaa | 360 |
| ngagcatggg | gtataaccc | tggacctctc | acgtcctacc | ctcaggntag | tgggaaaact | 420 |
| ctgagtttaa | ggacatcaaa | gtgactcctt | tttagttaca | ttatggngga | atcagcncat | 480 |
| attttacaa | ggggcggagn | gtaanctgtt | ggagtttaca | agacatatgg | tggcattgca | 540 |
| actacttaac | cctactatta | tagcacaaaa | gcagccatag | tcggtcctga | aggagcctga | 600 |
| tgccttcagc | tttataggca | atgacgtgtg | aatatcacaa | acagtttcct | gtgtcaccaa | 660 |
| acatgattgc | cttttgattt | ccctttcaac | cctttaaaaa | aaggtaaaag | cccttcttag | 720 |
| cattcagcag | caggtcgctg | tgttttgcca | actcctgatc | tgtagcattt | cgacaacact | 780 |
| gagctctcaa | cttttgaacc | ctgagtccac | cacatccttc | agtgaaacca | gagccatgtg | 840 |
| atactaagga | tagaaacgga | aacttcctga | atccaggcga | tcaaatagga | gggagaaaga | 900 |
| ggaactttca | ttgacaaaac | cacaaatatt | gtgaatggac | tgttacaaat | attgtgaatg | 960 |
| ctcctattcc | caaccccctg | gcttcattac | agggtcctat | gtgttcatcc | ttattgagaa | 1020 |
| atttgtattg | ctactgccag | gttgccaata | cccagcggtg | cccatggtgt | tctaaaatga | 1080 |
| agcaatttca | actttatttt | tttttcctgt | gactttacat | gacaagttca | catgaaggat | 1140 |
| atactttgat | agtaatgtcc | atggttaggg | aatatacatt | gtttgctggt | tgactggccc | 1200 |
| ctggattttt | ctattgaaag | tccatgagat | ctcgaaggca | caggtgtgtt | ctctcgcttt | 1260 |
| ttaaggaaag | ggtttaaaaa | cttaagtaat | taacagcttt | agtaacaaat | tacctataac | 1320 |
| acacttaaaa | accgaatacc | acccactgga | gtattgtgct | acgattaaaa | atctacttgt | 1380 |
| ctactacatg | atatctttgt | cccacagaag | gttctggaac | caaacttgta | atttcaggat | 1440 |
| tatgagagcc | ctgagttcac | gcattgtgta | ataactatgt | tgtgtggtag | tcaatttgta | 1500 |
| cagcttgctt | agagagaaca | atgtcaagtt | aaggaggcga | ttgctttata | gtgcctgtca | 1560 |
| caagatgcca | ttgccattgt | cctagcaaga | gatattctat | gggagtatac | tacatttag | 1620 |
| tgaggataag | aacttttat | ggcatttagt | ccggtcattt | cccaaccact | gtcctgaaaa | 1680 |
| ccaatttcat | tttgatttca | ggggcttgtg | tgggcaaagt | tgccaggcat | taaaaagcca | 1740 |
| cttctcaact | gtagtatcac | aatgctttag | ttgggtagtg | tattgcagat | agcttatggc | 1800 |
| tgaaaagtta | ccaagccttg | cagttttcac | tcctttgagt | ttatttcctt | gacagaattg | 1860 |
| accctgagtt | ttttgactct | tacctgctca | actaataaac | accagagtca | tttatctcca | 1920 |
| ttgctcttgt | ctgacctta | tttaccgaat | aatgccttat | gggttcacaa | aaacaagggg | 1980 |
| ggagggggcc | agcatgcctt | agaaactgtc | tttagtcaag | aaatgngatt | ttattatgta | 2040 |
| aatatatgag | tattataata | gatagtgtta | ttaatagaca | ccagcaagaa | ttgtcaataa | 2100 |

```
tttaaaaatc acaaattaaa atacatccat gttagnatca tttatcctaa ctcccaaagc    2160
cctttaaagt ggaagattta gatgttaacc cagagattaa agacatgttc aaagaatcct    2220
tgattttttt ttgaatccct tgtttttaga gaagaaaacc taatgatttt ccccctctgg    2280
attctacata ttaaatatag ttttggaact tgaatattag tatggttaat aagtgctgat    2340
atgctgattt tgtttatatt tttcttatga gtaaatatcc tatatcacca gacattatag    2400
tctatgtaca aatatgattc ttaaacctga tagcacattc attagagttg gaattgcctt    2460 ttttttttt ttttttacag ttgcacctgc aacatatgaa agttcccagg ctagggttg      2520 aatccaagct gcagctgcca ccctacatta cagccgtagt aacagcagat ccgagctgca    2580
tctgcaacct atgctgcagc tcagggcaat gccagatcca ctgagtgaag ccagggatgg    2640
aacttgcatc ctcatagaga caacgtcgtg tccttaaccc actgagccag aacaggaact    2700
ccagaatttc ctttcaatag aagaagcacc aagtttagga tcagaaagcc tgaatttgaa    2760
taccaattta ctatttgtta gtcatatatt tctgagtgtg tttcctcatt tattaaaagc    2820
agactaaaag atgagagggt cttttgttga gaatcaaata caataacatg tgaaagtgtg    2880
taacactatg attgaaatat acctacacag ccatttattt gtttattgtt catgttttgc    2940
cacccacaca gtagtatata atccttttat gtaataaatg ctaataatga aagttggcaa    3000
cttatgtaag tactcaaaat gctggaggtc atgggatact gactgggata ctacagaggt    3060
aatgtcattt cctctgcgct aaacttattg tcttgtagtt agggactgac tctcttttagg    3120 acaaggagtt cattctgtat accatgtgtg gctatcaccc ttcgaagttg aaaaactgcc    3180
ccagggtggg cacccatccg ttctcttaga tatatggccg agacctttct ctcactggga    3240
gggaaccaca ctgaggaatg agaaaaaaaa aggaaaatc aagatgaaac cagaaacctc    3300
tttggcataa cttctccact ctgtactttt tgttagaact acccttgcac aaagcagcat    3360
cagtgtggaa gacagaattt gcacacctgg tttgatatac atgccgtggt atatgggatg    3420
ttctaacaat aaagaggact ctcccaggaa atctcctcac tgttatagtc agccttgagg    3480
aaagagctct tcttttggac tctggggaga gtctagtttt tcagttcctt gcttctcggt    3540
caacgtgttg gtgtaaggat cacactctct cttatactag ataattctat tttttcacct    3600
ttcaacctgt ctatccttct gaccctag                                      3628

<210> SEQ ID NO 36
<211> LENGTH: 300
<212> TYPE: DNA
<213> ORGANISM: Porcine

<400> SEQUENCE: 36
gtctgtgttc tttccacatg tttgggttat cctttctggg ataaatttga ggcgagatag     60
aaactttaag actaaagaaa caatggccta cttttttttgt acatggtcct gtgtaaatct   120
ctatttgagc tgaaataaga tggtcttcct ctccaattat ccatggtatg actctgatgg   180
ataacaaatc cagttctgaa aaagggggat ttctttccag aagagaggac agtttcttca   240
aatattgaat taaaagcaaa atagatgtaa accgttgttg gttttattgt tgaattccag   300

<210> SEQ ID NO 37
<211> LENGTH: 734
<212> TYPE: DNA
<213> ORGANISM: Porcine
<220> FEATURE:
<221> NAME/KEY: misc_feature
<222> LOCATION: (705)..(705)
```

```
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t

<400> SEQUENCE: 37
gtattttctt gccctcatca gcatgaaatt gctcttggta gaaaggataa taatagttat      60
ccaaaacatc atcctatgtt catctgtttc ttccctcttc attttccata gagtacagta     120
tattctatct ctgtcttagg aaaatggact gtcattcata taatcttaca gagaatcaat     180
tagtaatgta ctctatgccg tgacaggtgc gaaggttttt tttgaaggca acagataaaa     240
atatcctata tttcacctat tgtaatttcc ttaaaactga cattattgaa taaatgtttt     300
actttcatct tgaatattat tatgttatgg aatcatacac tttaccccaa taatcatcga     360
aaagaatttc caaaggttg agagagttgt gttgatctga ttactttcct ctgcatcctt      420
tgagcttaac ctttgaatat agtttgctaa ggaaagtagt ctgtttatga tcctggagtg     480
gaatcaggct aagtgtcctc attcagaacc cactgaatca gacagaatga atttatttcc     540
ttgaaagttc aaaatgtgtc actcaagagt ataaattttc aaatcttact ctctctttc      600 cttggatgtg agcaattctt cgataattga atgaggcaga ttatatagac ttacatggaa     660
gactgttggc ctgagaattc aaactatggt gttcaagact tcacngngag tccgatgcca     720
tttgtttccc acag                                                        734

<210> SEQ ID NO 38
<211> LENGTH: 2421
<212> TYPE: DNA
<213> ORGANISM: Porcine
<220> FEATURE:
<221> NAME/KEY: misc_feature
<222> LOCATION: (1387)..(1387)
<223> OTHER INFORMATION: n is a, c, g, or t
<220> FEATURE:
<221> NAME/KEY: misc_feature
<222> LOCATION: (1390)..(1390)
<223> OTHER INFORMATION: n is a, c, g, or t
<220> FEATURE:
<221> NAME/KEY: misc_feature
<222> LOCATION: (1406)..(1406)
<223> OTHER INFORMATION: n is a, c, g, or t
<220> FEATURE:
<221> NAME/KEY: misc_feature
<222> LOCATION: (1972)..(1972)
<223> OTHER INFORMATION: n is a, c, g, or t
<220> FEATURE:
<221> NAME/KEY: misc_feature
<222> LOCATION: (1983)..(1983)
<223> OTHER INFORMATION: n is a, c, g, or t

<400> SEQUENCE: 38
gtaattcttt atatcaaaat gatgccaagg agttggcatg gcactttgct aaatgctgtg      60
tgaatcaata caaagataat taggacatgg ttcttcctca caagaggtgt gcaatcttat     120
tgggaaatca tacttgcaag tcacaaatat agactaaagt ttccagctga gaatatgctg     180
atggagcatg aaacactaag gagacaggga gaatctcagg aaaaatcaag ataatttgg      240 atcaaatgga ttcctgacat agaacataga gctgatcaga aagagtctga cattggtaat     300
ccaggcttaa gtgctctttg tatgtggttc agaacagagt gtgggcagcc tgaggggat      360 acataccctt gacctcgtgg aaagctcata cgggggaggg atgaggctaa ggaagcccct     420
ctaaagtgtg ggattacgag aggttggggg ggtggtaggg aaaatagtgg tcaaagagta     480
taaacttcca gttacaagat gaataaattc taggggtata ataacagcat ggcactatag     540
```

| | |
|---|---|
| atagcatatt gtactatata ctggaagtgc tgagagtaga tcttacatgt tctaaccaca | 600 |
| cacacacaca cacacacaca cacaccacac acacacacca cacacacaca cgtgcacaca | 660 |
| aacagaaatg gtaattatgt gaggtgatgg cggtgttaac taactttatt gtggtcatca | 720 |
| tttagccata catgcatgtc atgaaatcac catgttgtac accttaaagt tatgtaatac | 780 |
| tagatgtcag ttatatctca aagctagaaa aaatgtgggg accaaggcag aagctcttct | 840 |
| gctctgtgtc taagggtggt tctggggctg ggatggggag gatggttaag tggtatattt | 900 |
| ttttcatacc tttgctcagt actatcattg taagtgttca atatatgtct gcttaataaa | 960 |
| ttaatgtttt tagtaagtaa tctctgttta gtaatgtgtc agaaatgccc tacttgcaat | 1020 |
| aggaagaaaa cctgtccagt cccttccttt tttctgtaag tctgatttca ttgcctccca | 1080 |
| gaatgcatca ccatgtgaga gatagaggga aggtgctgtc cttatggggt taacagtgtg | 1140 |
| actagggagg caaatatatac ctactaaagg gtggtagcat aattcagttc ttatgtgagt | 1200 |
| atgtgtatgt gtgtgagtat gtgcacatgc acatacattt taaaaggtct gtaatatact | 1260 |
| aacatgttca tagtggttac acctagctta taggtaacat ttttttcccct gtatccttgt | 1320 |
| ttgtgtttat caaattttca taacagtaat ggtagaagga gtacctgaca tggtaccata | 1380 |
| catgctnggn cctgcctaat ttctcnattt cctttattgc ccatacccccc attgcttgac | 1440 |
| aagcataagt ccatactggc ttgttttcgt tcctcagact cagtacacca tgtagctcca | 1500 |
| tgccctgggt ctttgtatgt gctatttcta ctgcttagag tgctattgcc cctgaccacc | 1560 |
| acgtggtcag caacttctct tctgcgtctg tgtctatggt ctatgattcc agatgtcatc | 1620 |
| ttcactaact acccttctaa tatgcccttc catcccaccc gtcctcatcc ttacccccagc | 1680 |
| cactctctat ttggtggctc tgtttttattt tcttcctagc tcatcactct ttgaaatgaa | 1740 |
| cttatttact tattcaatat ttgcttcttt cactagaatg aatgctccat gagagcaggg | 1800 |
| acctgcttta tcttgctcgc cactgtattc acagtgccta gaactacgtc tggcacatag | 1860 |
| taggtgctca ataaatatcg atcaaatgaa agaatgagca aacgaacaaa tgaacaacac | 1920 |
| gtgaggtagg catcatgatt ccatcaacag aggagaaaac cagacttaaa gnaatgaagt | 1980 |
| ggnggagctg catttgatct tgactgactc caacatccat gctcttgacc actgtgcatc | 2040 |
| tccagagtgt aatgaacata ctttacttt atattccacc aaaataacaa agccatgccc | 2100 |
| atgttagtag agagttaatc gacagtgccc ttaaaatatg catgcaccca gggtacaact | 2160 |
| atgcatgctg ccctgtgttt tcagttggat ccaaatgaat tgccgtaaac aaagagggga | 2220 |
| ttcaatgtct ttgactagtt tgggatattt tcctagtaac caactttgca aaataaagcc | 2280 |
| actaatgaca aggagctttg ttctacttct gcatcactca actgtcaatt tttatctctt | 2340 |
| gcaagacttc taatctacta gaactttttgt ttttctgtga tttctgaaca gagaagacta | 2400 |
| atccaaaccc tgtcattcca g | 2421 |

<210> SEQ ID NO 39
<211> LENGTH: 457
<212> TYPE: DNA
<213> ORGANISM: Porcine

<400> SEQUENCE: 39

| | |
|---|---|
| gtatggctgg atattttata taacgtgttt acgcataagt taatatatgc tgaatgagtg | 60 |
| atttagctgt gaaacaacat gaaatgagaa agaatgatta gtagggtctg ggagcttatt | 120 |
| ttaacaagca gcctgaaaac agagagtatg aataaaaaaa attaaataca agagtgtgct | 180 |

-continued

| | |
|---|---|
| attaccaatt atgtataata gtcttgtaca tctaacttca attccaatca ctatatgctt | 240 |
| atactaaaaa acgaagtata gagtcaacct tctttgacta acagctcttc cctagtcagg | 300 |
| gacattagct caagtatagt ctttatttt cctggggtaa gaaagaagg attgggaagt | 360 |
| aggaatgcaa agaaataaaa aataattctg tcattgttca aataagaatg tcatctgaaa | 420 |
| ataaactgcc ttacatggga atgctcttat ttgtcag | 457 |

<210> SEQ ID NO 40
<211> LENGTH: 4012
<212> TYPE: DNA
<213> ORGANISM: Porcine

<400> SEQUENCE: 40

| | |
|---|---|
| gtttgacttg aatatttaca gggaacaaaa atgatttctg aattttttca tgtttatgag | 60 |
| aaaataaagg gcatacctat ggcctcttgg caggtccctg tttgtaggaa tattaagttt | 120 |
| ttcttgacta gcatcctgag cttgtcatgc attaagatct acacaccacc ctttaaagtg | 180 |
| ggagtcttac tgtataaaat aaactattaa ataagtatct ttcaactctg ggtgggggg | 240 |
| ggagactgag ttttttcaca gtcctatata ataattttct tatcctataa aataattagg | 300 |
| agttcccgta gtggctcagc aatagcaaac ccgactagta tcgatgagga tgcgggttcg | 360 |
| attcctggcc cccctcagtg ggttaaggat ctggcattgc cgtgagctgt ggtgtaggtg | 420 |
| gcagacacgg ctcagatccc acgttactgt ggctgtggca taggccagca gctccagctc | 480 |
| tgattagacc cttagcctgg gaacttccat atgctgtggg tgtggccttg aaaaaaaata | 540 |
| aataaataag ataattactc aaatgttttc cttgtctcag aaccttactt caggataaag | 600 |
| agtgagaaag ttttttttat gaagggccat tattacagct caaaaataag ttgtcttcag | 660 |
| caagtagaaa gcaataagcc tgagagttag tgttcctatc agtgtaaata ttacctcctc | 720 |
| gccaatcccc agacagtcca tttgaacaat taacggtgcc ctgggagtac agttcagaaa | 780 |
| cattaatgtg gatgttccag acctgtattt ttataagtac ttgtcttgag ccggatggaa | 840 |
| ccatcattcc tcaccattat ttagaagtgg actgtgactc tgttggagat cagggcacac | 900 |
| ggttaccaaa agcacaccct ctcctggcc ttaccttgc aaagctgggg tctgggacac | 960 |
| agtcagctga ttatacccctt ttactaactt cccacagctc aaatctggtc aattctcctt | 1020 |
| cacaaatctc ttaaaaatcc atcactcacc tccagcctct tctgctgtgg ccttgattca | 1080 |
| gcctctcaca atttttttt aaccagaatt ctggcagtgg ccctgactt gcctctgtgc | 1140 |
| tcccagcccc gctgtcctct gatccatcct ccatgccagc cttttcaat ctgctggtca | 1200 |
| cgattcattg atgggttagg aaatcaatgg catcacaact agcatttaga aaaaggaaat | 1260 |
| aggcgttccc gccgtggcac agcagaaata atccgacta ggaaccataa ggttgcgggt | 1320 |
| tcaaccctg gccttgttca gtgggttaag gatccggcat tgccgtgggc tgttttgtaa | 1380 |
| gtcacagaca tggctctgat ccggcattgc tgtggctctg gcgtaggcct gcagcatcag | 1440 |
| ctccaattag accccctatcc tgggagcctc catatgctgc aagtgcagcc ctaaaaaaaa | 1500 |
| taaaaaata aaaaaaata aataaaagaa gtagacaaat tgtatagaac aaccctgagt | 1560 |
| atgttgcctg agcacatata acaagggtaa gtattatttc aggaaactct ggttcacag | 1620 |
| atactcttgg catatggacc cctagagtcc tgatgtaaaa tatattcttc ctgggatctt | 1680 |
| aggcaagaag tttgaaagct ccaactctgc actgctgcca agaaatgat ttttaagtgc | 1740 |
| aaaactcttc ccgttccctt ccctgtataa aattccatag gatctctcca gtgcctctag | 1800 |
| gataaaggca gttttcattc tctagttcaa ggtgagagaa gatttaatt atttcacgtt | 1860 |

-continued

```
ttagtgggga attcaagagt ctggcacctg acatttgctg aactctctcc attatccctc    1920
tctagttccc cagacgcatc ctatggtaga aattcgcaaa ctagagtgag cgtcagagta    1980
acccaaggaa actgggtaaa tgcagctccc tgggctctac cccctgagat tctgattcag    2040
tagatctgaa gcagagccct ggaatatgca tatgcatcat tgtgtcacac caagcattct    2100
gggtaatgag agttgatgtt aggttctcag tagtaagaca agtatagaga ttccggggga    2160
ctgagtgctc agctctgcct tggggaggag ggagagggct aaagagaaca ggagatgggg    2220
acagggaatg ctcaacctcc aatcttaggc atttgagcta tgtcttaggg gtcaggagga    2280
ggttaccaat atagtgatta agagattgag gttccagtca gagggatatg ctggagaagg    2340
ggggtgaaaa taatgtcata ggtttggtga gtgcagatac tttgagtttt ttaatatttt    2400
tattgaaata tagttgattt acaatgctct tagtgagtac aattactttg aataagtgca    2460
tagatgtatg ccattcttcc agaaatgatt tattgagctc ctttgggcat catgctaagt    2520 acagggaaa cagctgtgaa gaggtccttc ccttatgaag tcattcatcc ccttcagtaa    2580
atgaaggtaa aggaaaagga tgagacaggg acgccgtgtt ggaccagggt cagaaaggcc    2640
ttataagacc ttgcctggag ggcaaggaac ttgcctgtga gtaaggagag cttgagaaag    2700
cgataaagca aagaaggaac attactgcat tgtgttttag aaaaaccatg tcctggggaa    2760
gaactcctag agtcaggggg gccagttggg agactgtgct tttttccagg aggagataag    2820
tgaggctgct ggctgagatg gagcaaggat ttagagaagc agatatgaga ttcatttaga    2880
agttagacat tttaggatct gacacataat ttatcaccaa aaccagtgca tctctggctt    2940
tgggccacca gttttggaga agtggaatgt agggacctac cattacctgc caatctttac    3000
tacacagatg cctatttccc tcctcatatt tcctttctcc agatcacgtc ctattctatt    3060
gccaggactc aagattccac cttgcatgca gtgatccatc ttcacactgg atggacagct    3120
ctagggatgt cagagcacac tcttgtccat actgctgact gggtctcctg tcagcccatc    3180
tgtctatcag ctgtggtatt attagtataa taagagggct gtatatgaga gacacaaaat    3240
tctaggtgta gctcaaagat aggctagagt tattcctatg tacaacaaat atttatggga    3300 cccccttctgt gtactgtcat ggttgctgct ttcatcatac ttgtagtcta atggaggtgg    3360
gggcagggca ggaataagcg gatgtccaca aaatcagtaa gaccacttat attcaacatt    3420
ttcataattt agttatttga gcccaaaggg tccacatccg tggtattcca acttttttt    3480 ccccggacat ggatctttat ctttttttt ttttcttttt tgcggccaga cctgcggcat    3540
atggaagttc ccaggccagg ggttgaatgg gagttgcagc tgcctggtct acaccacagc    3600
cacagcaagg tgggatctga gctgcatctg tgacatacac cgcagctgag gtaacaccag    3660
attctgaacc cactgaatga ggccagggat ggaacccgtc tccttatgaa cactatgtca    3720
tgttcttcac cctctgagcc acaacggaa ctccagactt cgtctttaaa tgtattctga    3780
cttggagagc tatcacacta agcaattaac aggagctgac ctggtttagg ctggggtggg    3840
gccctactcc tcaatgttcc ctgaggcaca tctgtgggac ccctgggcat catctatctg    3900
agcagcctta gagctgctca tccagttgac tgttgatgta gaagtgcaaa cttctgcctt    3960
ccttatttgt tgctttcttt tttcattgtt ctctcccctt tgtgtctta ag    4012
```

<210> SEQ ID NO 41
<211> LENGTH: 2281
<212> TYPE: DNA
<213> ORGANISM: Porcine

```
<400> SEQUENCE: 41
gtatgctatg aagttattat ttgttttgt tttcttgtat tacagagcta tatgaaaacc      60
tcttagtatt ccagttggtt tctcaataag cattcattga gccttactga ctgtcagacg    120
gagggcgtat tggactatgt gctgaaacaa tcctttgttg aaaatgtagg gaatgttgaa    180
aatgtaggga atgaaatgta gatccagctc tgtttctctt ttggaggatt cttttttcctc   240 catcaccgtg tcttggttct tgtttgtttt gggttttgt gggtgttgta ttgtgttgtg     300
ttggttatgg cagtgacagc tatttaaact gtgaaacggg ggagttcccg tcgtggcgca    360
gtggttaacg aatccgactg ggaaccatga ggttgcgggt tcggtccctg cccttgctca    420
gtgggttaac gatccggcgt tgccgtgagc tgtggtgtag gttgcagaca cggctcggat    480
cccgcgttgc tgtggctcta gcgtaggcca gcggctacag ctccgattgg acccctagcc    540
tgggaacctc catatgccgc aggagcggcc caaagaaata gcaaaagac aaaataaata    600 aataaataaa taagtaagta aaataaactg tgaaacgggg agttcccttc atggctcagc    660
agttaacaaa cccagctagg atccatgagg atgtaggttc gatccctggc cttgctcagt    720
gggttaagaa tccagcgttg ctgtgagctg tgatgtaggt cgcagatgca gcccagatcc    780
tgcattgctg tggctgtggc gtaggctggc agctgaagct ccgattcaac ccctagcctg    840
ggaacatcca tatgctgcag gtgtggcctt aagaggcaaa aaaataaaaa aataaaaaat    900
aaataaattg tgggacagac aggtggctcc actgcagagc tggtgtcctg tagcagcctg    960
gaagcaggta aggtaaggac tgcagctggg taaggactga attgcaccaa ctgggaagta   1020
agcctagatc tagaacttaa gttagccctg acatagacac acagagctca ccagctaagt   1080
ggttcagctt ataagctggt cactgaaact gaggatgtcc acaaaagcaa ataagtagc    1140 aacaggcagc gggatgcaag agaaagagga ggcctaaaat ggtctgggaa tccctgccat   1200
acctatattt tatcctactt atatttagtg cctgaatgtg tgcctggaga gcaaagttta   1260
gggaaagcat cgggaaatgc acagtattca tacccttagg aacaaagatc agttacctcc   1320
agggtaaaga ctatttccaa gtttaaattt caacccctga acattagtac tgggtaccag   1380
gcaacacttg ccatcctcaa aatcaatgaa tcctaaaatt caacctgggg gtcagtgaca   1440
gtctgtgaca aagttttgc tggtcagtaa cgaaataagt atgagcacca tctgagtatg   1500
gtcaccaaga tgtcaactct cttcctttg gacgaattgt cattattcca agattaggtc    1560 cttctctattt ttgaggtgtg aaaacatctt cctttcata aaataaaagg atagtaggtg   1620
gaagaatttt ttttgttttt tggtcttttt gctatttctt tgggccgctt ctgcagcata   1680
tggaggttcc caggccaggg gtcgaatcgg agctttagcc accggcccac gccagagcca   1740
cagcaacacg ggatccaagc cgcatctgca gcctacacca cagctcacgg caatgccgga   1800
tcgttaaccc actgagcaag ggcagggacc gaacccgcaa cctcatggtt cctagtcgga   1860
ttcgttaacc actgcgccac gacgggaact cctaatgata ctctttttata tttagctact   1920 atgtgatgat gagaaacagt ccacattta ttattttta gccaatttga tatctcatta    1980
ctaagataat gataattttc tctataaatt ttatttaagt tagtgttatg aagtggtttt   2040
gctagtgtag aaggctagga tttgaattca gttcaagaaa gaagagaggg agggaggga    2100 agggatgggt agagggatgg ggcagtggga gagagcaaag aggagagaca gtttttgtat   2160
taattctgct tcattgctat catttaaggg cacttgggtc ttgcacattc tagaatttc    2220 taaggacctt gaccgccaga ttgatatgct tcttcccttt accatgttgt catttgaaca   2280
g                                                                  2281
```

<210> SEQ ID NO 42
<211> LENGTH: 4559
<212> TYPE: DNA
<213> ORGANISM: Porcine

<400> SEQUENCE: 42

```
gtaagcagga ataccagtgg aagtgcccct ttcttccttc cttcctaaat aaactttttt      60
attttggaac aactttagag ttacagaaaa gttgcaaaga tattatagac agtagtgttt     120
atatatatat ataaatttt ttttgctttt tatgaccaca cctgtggcat atggaggttc     180
ccagtctagg ggttgaattg gagctacagc tgccagtctg tgccataacc acagcaatgc     240
aggatctggg ccacgtctgt gacctacacc aaagctcaca gctggattct taacccactg     300
agcaaggcca gggattgaac ctgcatcctc gtggttccta gttggattcg tttccgcttt     360
gccgcaatgg gaactccaaa ttattgttaa tatcttactt tactgggta catttgttac      420
aaccaatact ctgatactga acattactg ttaactccgt acttgcttct ttttgagtca      480
tttgcaaaga ctggcttctt gacctgcttc cttccaaaca gctggcctgc ctatgctgtt     540
ctcagacctg caagcactga tctctgcccc ccttgccttc tctccagtgg tgtctccttc     600
cccaaacaaa cccagtgtgg ctctggaaag ggagttaagt caacataaac caacacatat     660
tttgttgagc tccaattttg agcaaatccc tcacctacgg cagacaggca tgatgttaag     720
aactagggct ttggacacaa ggtcaagacc aagaagggtt cctcaccct actgattcag      780
ataaccaata atgaggcttt gaatccctgt ccaaaggttg ttttttttcc cttctattga     840
gcttcttgcc accttatcag ttttttttat gacagtcaaa tgacatgata tatgtgagca     900
tacatggtaa ttttttaattc tatataaatg aatcactaaa taaattagga ggatatatag     960
tccaccttta agcgtattac acgtgtcaca tgaatgtgtg gcgacttaat tgtagaggtt    1020
taaatgtagc ttcctataat agatgtgttc ctaaactaca ttttaatcat tggacttgta    1080
tttttatgtt agcacttgct gttgaagaaa agcctatgcc aaaagttcag tgaaaccaat    1140
aatccactgc cagcttttctg agttaaaaaa atccctggg ttttcacaca caggaacacc     1200
ctgtgtgaaa cactcattta gagcaaaatg catctgataa ggagttcctg ttgtgcctca    1260
actggttaag gacctgacat tctccatgag aatgtgagtt tgatccccgg ccccactcga    1320
tgggttaagg atctggtgtt gccacaaact gcagctccga ttcatctcct agcctagaaa    1380
cttccacagc ccagaatatg ccacagaatt cggctgttta aaaaaaaaaa gaaaaaaaaa    1440
agaatcataa atgtgttggt ttgttcacca aatacatgat aacttgctct tgccaagctc    1500
agcttcataa atattaagtc atttaataca gcagccacct tatgaacaga tattactata    1560
cttcccattt acagataagg aaaatgccat atttaaccaa gagattaaat aactttcccg    1620
aggtcttata gcaagtaaat catggtgcag gggtttgacc acacgcagtc tatctccaga    1680
gtctgtgtat ttagccactg ttttactttc aaatttaaat ttataaaact tctaaattat    1740
ctgttaacca taatctttgg aatttttaaa accacgagtt cctataaaat gtttcattga    1800
aagtaagtca cttttccata gcttttgata atacatctgt aggataaagt aagccacagc    1860
tctcttgcag acttggtaca ccctgggca aagcatcatg cctgtcacgt acatggtggt    1920
ccttactttg actctcagtg cttttattgc ccaggaattt tgtgagattt ctagttgttg    1980
aggtttgttt aaagaggtta tgccggtact tggaagagct ctttcttgc tacctggagc    2040
cttctcatat ttccttttg aggagggaca tgaattgcct ttcaaactca taaatatatt    2100
```

```
ttctagtaca caagtctcca tcttccttag acgcatggct cctggagttc tccatcctcc    2160
tgctccactt tgggtgggct cctctctggg tctgccacca atctgccacc cagagacatc    2220
cttgacccac ttccagaccc caccatggct tcactttctt cgctttcctc ctttgtggaa    2280
ccttctgctt aagaatctga ggaagaaaat ttgcacgtga gctaaactgg aggtactttc    2340
ctgcctggtc ttgcacgata gcttggctga gcccatgatg ctgggtggct gttactttcc    2400
atggacaccc gaaggcgttg ctcctttggc ttctagttgc atgcagtgtt gcttatccca    2460
ggctgatctt tcttccactg taggtgactt ttaagaatta agggattaat ctatatctac    2520
aacaacaaca acaaagacct tttcaagctg aggtagggct ttctgtatat gtttggagtg    2580
gttatccagc agactttact tgaaggcagg ggtcatatcc tcaagtgctc ataaacggac    2640
cacagaaaga tctcataatt gggtggagct gggtggggac cgtgtcatgt ggccaggaaa    2700
tgccagatgg gaagggagtg gcccttactg agctccagct gaactctgaa ttttctagaa    2760
aactcagaaa tctggatttt tcatgtgtaa tacccagatt tatagatgtg aaagctaat     2820 tctttttttt tttaagggac tataggcaat gaactaagat ctaggttgta tttggacaag    2880
gggtcatcag tttaagctgt gtagttgagc gctcagctat tgggctgagg gaccccctaaa   2940 tactgagacg gggaggtcct tgctctgggg catcacaagt acactccctg gtctcattca    3000 aacactttc ctacaaaatt gatcccattt cttcagtgca ctgtctgaat gcatttggcc     3060
cagagccgtg ctgaggcata gggaaggggt ccacggtttc atggcatcgt tttgtgctgt    3120
gtgtccctgc tgtcgtccag gatacctacc tctcctcctc ctgcatctga atgtccccc     3180 acagactctc tgggattcta cagcctctgg cctgttcctc agacacctct tacctgccag    3240 cttttccagat tcacattagt tagtccaaat ctactgccgt cagtgactca cttcatttct   3300
tcttctccga ggcagttcag cccggtacag ttgttttgtc aacacttcag ttgagtctgg    3360
aagatgtgca tgggttatgc acgagagcgg tccatcattt tgagctagaa gtcctttctc    3420
agcccagaga caagtcctca tctcctttac ttcctgactc ttcttcctct gcatccttcc    3480
aagatatctc tttctccagc caccacctaa atctcttctt ttcccggggt tccgtgctca    3540
acccactctt cttcttaaat ctgtggctgg gtgaacgcat ctgctggcac cacttctctg    3600
ctaaagactc caaaaatcca taggtcctgc ccggcctttg cccacctctc tccaacactg    3660 tccagctta gatgtagagc taatcccccc agagatatca ttccctggat gtctaagtcc     3720
tttggtatct cactttcagc gtgttcaaaa tcctcttaca actgttcttt ctcctttcc     3780 atcttgatta ttggcaacat gccagccttt cccctacccc cagcagtgag ccaagctaga    3840
aacaagggct taatcttcaa tctttccttc tccatcccta aacctaatga gtctccaagc    3900
ccttcccagt ttacacccta aatgttgctc aaaacatccc ctagttcttc cacgtgctct    3960
cctctatatt gaaaggtcaa gaaaggccat cttccctcca ctgtgaggaa atagatcttg    4020
atactgcccc tgagctgggc agtcctcgac ctgacaaact gtgcagtgtt ctaaatctc     4080 tactggcaaa atgagagtgc ctttgacctg tgttgcgatc tcagatcaca gtggatgtaa    4140
ttgttttata ggaatggtga acgaaaaaga agtaaatccc taatgccaaa ctcctgatca    4200
ttctatgtca tttaatagcc tgtcatttat gataaagttt cctctactgg cattagcaca    4260
atacttctca ggaaaaaaaa atatgatgcc agatactgaa aagctcctgg gtaaacatga    4320
acatgggtac cgataaaatg gtgaagccag tccaatctta gagtgacttc ccttcatgct    4380
acttcatgct ctttttttt ttttttttta agaaaacccc cttttttttt tctcacacca     4440
gtcacagagg agaccgaggc ttagcaaggt taaggtcaca tgattagtaa gtgctgggct    4500
```

```
gaaactcaaa accatctctg cttgtctcct aaccctgtgc acctctgact attcaacag    4559

<210> SEQ ID NO 43
<211> LENGTH: 458
<212> TYPE: DNA
<213> ORGANISM: Porcine

<400> SEQUENCE: 43
gtaagggcct tgaccaccga attaaggtaa tcttgctctg tggcaggcct tgttttcagt     60
attttaagta cactggctca ggtaatcctc acaacagccc caggaggaat gttctattac    120
ctccactgta tagatgagga acttgaggca cagaatggtt gccaaggtca cacagctata    180
ttgggggttc atacccagcc atccaactct gtctgtactc tctgccactc tgcaccccca    240
gctcctgatc cacttcctgt ttccatccct cgatttctgc tgcactcagg ggccctctc     300 cccctcggcc tgtgagatct gcttcagtag gcttttctcc ctgactcctc catccctgtc    360
cttacaggca gctgcttctc tccgggacac gaggggtcca tacggacact ctctactggc    420
tgggttgcgc taactcgtg attcctcctc tgtttcag                             458

<210> SEQ ID NO 44
<211> LENGTH: 2482
<212> TYPE: DNA
<213> ORGANISM: Porcine

<400> SEQUENCE: 44
gtaagtccga aaatgcctgt cgtgtgtgcc ttaggctgct gcggaggagg ccagggctat     60
ataagcagag tcagtgactg actgtgccct gcagtgttga tggccatgga gattccaccg    120
ttagagcttt tttctttgtt aaccttgaag gcaaatctgg ttaggaagat aactttcaaa    180
gagtcaccat ctggacattc atgcccatgt gcttcaatcc tgtatacaag cagtttagag    240
tacagggaag ggaaggacat tatgaaaggg agagggtgtg tttggatcca gcagctccat    300
cctcagaatt tatctgaaga cactgcaaaa ttactaagaa tcactatgac aagaatgagg    360
atggggtgat atggcaaagt tgtgatcctg gaagaccttc atctcccatg ttgcccaact    420
ctgaacatga atttggtgaa ctagttggtt aaggggatga tcctccaagt ttctccctgg    480
ttgagctcca aaaaccatgt aagtttctca tagcaaaacc gtataggtcc ttagggcttt    540
agttggaata tttgtgctga aatgctggaa agccccattt gccattttg tatttgcaaa     600 ataatcatca agaggggaga atgcattctt tcatgaccac tgaccctctg aaaaggtcag    660
gaatttagtc tgaagtaggc aagcctccta ccccgcttct gccatgagct tgcacgcaca    720
ggcctgtctt gacatttctt ctttatagat ttcttttga atatcttgaa attgcttaa      780 aaatatttaa agaatgtaga attatataaa ataaaaagga ataaccca cacctcccac      840 aaaaccctgt ttcctgcctt tctccaccca ctctccaggg taacacttgg taacagcata    900
gttgtatcac cccaggccta tttttgagca tatcagcatt tcaagaaatg tatttttct     960 caataaaaca tcccttatag ttgaggaggg gaggttatca ttcctgggtt ttgtttttt    1020 tttttttta atgtaatcct ggtacatcgg taatttgcat ttttattca ttaatatctt    1080 tggtatttct agtgttggga cacacaggtc aacctcagtt tttgggtttt tttttttgtc    1140 ttttttgtctt tctagggcca cacctgcagc atatggacgt tcccaagcta ggagtctaat    1200
cagagctgta gccaccagcc tacgtcatag ccatagcaac gtcagatcca agccgtgtct    1260
gtgacctaca agcacagctc atggcaacac cggatcctta accactgaac gaggccaggg    1320
```

```
gatcgaacac acatcctcat ggatcctagt catgttcatt aaccactgag tcatgatggg    1380
aactccaact tcaactattt taatgtctgt aaaacattcc atttggaaac catttcattt    1440
gtaaagcaaa atgaaaacat tttgttcatt ttcaacagag ttcgtagctg acttctgttc    1500
tggaaaaaag gaaatggagc aaatttgagt gagaaagatt caaagataac ttttctttta    1560
aaaaaaatta tatcttggaa acttctgggc tattgattct gaagactatt tttctatata    1620
ctgttttgat agcaaagttc ataaatgtga aaggatcctg cgatgaatct tgggaagcag    1680
tcatagccca atatatcttt gttgctttta aaatgagatt tagtttacta aatatttttc    1740
tgatcataaa ataacacag atctaccgca gaaaatttgg aaaaaaaaaa acttttaaat    1800
tcaaaaaaca gttaaaccac aaatgatccc accatccaga gagcaatttg tactttggtg    1860
tctagttcat ctttcttttt ctgtttacaa gcacatatac cacaagcatt ttttcaaaaa    1920
atgaaaatgg ataatacta tacatacgtc tgtacacctg catagttact gaacagtctt    1980
tgatctaccc tgtaagtttc taacttttca ttatttgaaa tgatgttttg gcaaagaaat    2040
atgtaggtgt gtctcgcaca ctttcataat gatttcttag gataaatttc ttaggataaa    2100
ttcataatga tttcttataa taatccatac tctgccaact gatcttcagg gaagccaact    2160
cgccttctca gaaataacat ataacccatt tacttgccct ctcaccaata ctaggtccta    2220 atgttttgt gtacagattc tatattttta catacaagaa ttccttaaag caaggcatgt    2280
cacagaaaaa tagaaggaag acacaattgt catgtttaag gactgcattc tgtaccaaaa    2340
atgctaagtt aaatgaacat ctgaaacagt acagaaacgc tatctttcag ggaaagctga    2400
gtaccaggta ctgaacagat tttggcaaat acagcaggca tggatgtttc caaaacatgt    2460
ttttctactt tatctcttac ag                                             2482

<210> SEQ ID NO 45
<211> LENGTH: 1335
<212> TYPE: DNA
<213> ORGANISM: Porcine

<400> SEQUENCE: 45
gtaaagcatc ctgcaggtct gggagacact cttattctcc agcccatcac actgtgtttg     60
gcatcagaat taagcaggca ctatgcctat cagaaaacct gacttttggg ggaatgaaag    120
aagctaacat tacaagaatg tctgtgttta aaaataagtc aataagggag ttcccatcgt    180
ggctcagtgg taacgaaccc tactagtatc cattgaggac acaggttcaa tatctggcct    240
cactcagtcg gctaaggatc cagtgatgcc gtgagctgca gtgtaggcca cagacgtggc    300
tcagatctgg tgctgctgtg gctatggtgt aggccggccc cctgtaactc caattcgacc    360
cctaggctgg gaacctaaaa agaccccaaa aaagtcgctt taatgaatag tgaatacatc    420
cagcccaaag tccacagact ctttggtctg gttgtggcaa acatacagcc agttaacaaa    480
caagacaaaa attatcctag gtggtcagtg ggggttcaga gctgaatcct gaacactgga    540
aggaaaacag caaccaaatc caaatactgt atggttttgc ttatatgtag aatctaaatt    600
caaagcaaat gagcaaacca attgaaacag ttatggaaga caagcaggtg ttgtcaggg    660 gggagataag gggaggcagg aaagacctgg gcgagggaga ttaagaggta ccaactttca    720
gttgcaaaac aaatgagtca ccagtatgaa atgtgcaatg tgggaaatac aggccataac    780
tttataatct ctttttttttt tttgtctttt ttgccttttc taaggctgct cccgtggcat    840
atggaggttc ccaggctagg agtccaaaca gagctgtagc tgccagccta caccagagcc    900
acagcaacac gggaacctta acccgctgag caaggccagg gatcgaaccc gagtcctcac    960
```

-continued

```
agatgccagt agggttcatt aaccactgag ccacgacagg aattccaggg tctgttgtgt    1020
tcttaaaaca cttccaggag agtgagtggt atgtcataag taaacaataa atgttaacca    1080
caacaagctt atgaaataaa caggaaagcc atatgaccta caatcagtca ttgggagaat    1140
ccacaaaagg ttgagcagag gatcaattcc agctcacact ccagttttag attctcccct    1200
gccttaaagc atcacagact acataatctg agctgaagaa taaaaattaa aactcacccc    1260
agtgcaaaac agaaatgaaa aagtattaaa acgaggttca tactgttgtt cattagcaat    1320
atcttttatt cacag                                                    1335

<210> SEQ ID NO 46
<211> LENGTH: 40431
<212> TYPE: DNA
<213> ORGANISM: Porcine
<220> FEATURE:
<221> NAME/KEY: misc_feature
<222> LOCATION: (16625)..(16625)
<223> OTHER INFORMATION: n is a, c, g, or t
<220> FEATURE:
<221> NAME/KEY: misc_feature
<222> LOCATION: (16637)..(16637)
<223> OTHER INFORMATION: n is a, c, g, or t
<220> FEATURE:
<221> NAME/KEY: misc_feature
<222> LOCATION: (16671)..(16671)
<223> OTHER INFORMATION: n is a, c, g, or t
<220> FEATURE:
<221> NAME/KEY: misc_feature
<222> LOCATION: (16731)..(16731)
<223> OTHER INFORMATION: n is a, c, g, or t
<220> FEATURE:
<221> NAME/KEY: misc_feature
<222> LOCATION: (16741)..(16741)
<223> OTHER INFORMATION: n is a, c, g, or t
<220> FEATURE:
<221> NAME/KEY: misc_feature
<222> LOCATION: (16764)..(16764)
<223> OTHER INFORMATION: n is a, c, g, or t
<220> FEATURE:
<221> NAME/KEY: misc_feature
<222> LOCATION: (16769)..(16769)
<223> OTHER INFORMATION: n is a, c, g, or t
<220> FEATURE:
<221> NAME/KEY: misc_feature
<222> LOCATION: (18290)..(18290)
<223> OTHER INFORMATION: n is a, c, g, or t
<220> FEATURE:
<221> NAME/KEY: misc_feature
<222> LOCATION: (18400)..(18400)
<223> OTHER INFORMATION: n is a, c, g, or t
<220> FEATURE:
<221> NAME/KEY: misc_feature
<222> LOCATION: (21127)..(21127)
<223> OTHER INFORMATION: n is a, c, g, or t
<220> FEATURE:
<221> NAME/KEY: misc_feature
<222> LOCATION: (21129)..(21129)
<223> OTHER INFORMATION: n is a, c, g, or t
<220> FEATURE:
<221> NAME/KEY: misc_feature
<222> LOCATION: (22681)..(22681)
<223> OTHER INFORMATION: n is a, c, g, or t
<220> FEATURE:
<221> NAME/KEY: misc_feature
<222> LOCATION: (22684)..(22684)
<223> OTHER INFORMATION: n is a, c, g, or t
<220> FEATURE:
<221> NAME/KEY: misc_feature
<222> LOCATION: (22700)..(22700)
<223> OTHER INFORMATION: n is a, c, g, or t
<220> FEATURE:
<221> NAME/KEY: misc_feature
<222> LOCATION: (23266)..(23266)
```

<223> OTHER INFORMATION: n is a, c, g, or t
<220> FEATURE:
<221> NAME/KEY: misc_feature
<222> LOCATION: (23277)..(23277)
<223> OTHER INFORMATION: n is a, c, g, or t

<400> SEQUENCE: 46

| | | | | | | |
|---|---|---|---|---|---|---|
| ctgccagcct | aagccacagc | cacagcaacg | ctgggtctga | gccatgtctg | cagcctatgc | 60 |
| cagagctccc | cgcagcgccg | gatgcttaac | ccactgagca | aggccaggga | ttgaaccctc | 120 |
| gtcctcatgg | atagcagttg | agttgtttcc | acggaactct | taggggaact | cctgattatt | 180 |
| ttttatttaa | atttatattt | ctctgacttt | ttcgtgtgct | catcagccac | tgactgtgta | 240 |
| tctccattag | tcatggtttg | ttaactctgt | cattcaaacc | ctcttcatcc | ttgctacgca | 300 |
| gataacatca | ttataataaa | atcgtgcctg | aagaccagtg | acgccccaa | gctaagttac | 360 |
| tgcttcccct | gggggaaaa | agaagcaccg | cgcgggcgct | gacacgaagt | ccgggcagag | 420 |
| gaagacgggg | cagaggaaga | cggggagca | gtgggagcag | cgggcagggc | gcggaagca | 480 |
| ctggggatgt | tccgcgttgg | caggagggtg | ttgggcgagc | tcccggtgat | gcaggggga | 540 |
| ggagcctttt | ccgaagtagc | gggacaagag | ccacgggaag | gaactgttct | gagttcccag | 600 |
| tcccgacgtc | ctgcagcgc | ccaggcactg | ttattggtgc | ctcctgtgtc | cacgcgcttc | 660 |
| ccggccagge | agccctggcg | gatcctattt | tctgttcccc | cgattctggt | acctctccct | 720 |
| cccgccctcg | gtgcgcagcc | gtcctcctgc | agtgcctgct | cctccagggg | cgaaaccgat | 780 |
| cagggatcag | gccacccgcc | tcctgaacat | ccctccttag | ttcccacagg | tgagaaggct | 840 |
| tcgccgctgc | tgccgctggc | gccggcagcg | ccctccacgc | acttcgtagt | gggcgcgcgc | 900 |
| cctcctgcat | tgtttctaaa | agatttttt | ttatccgctt | atgctatcag | ttactgagga | 960 |
| agtatttaca | aatctactat | tattttgaat | ttgccttttt | ctccttatag | tttatcagta | 1020 |
| tctcttgaga | ctgttattgg | tgcctgcaaa | tttaaaatga | ttggggtttt | atgaggaagt | 1080 |
| gaacctttta | tctttatgaa | acgcctaact | gaggcaatgt | taattgctta | aaatactttc | 1140 |
| tttattatca | gtgtggccat | gccagtgtcc | tcttggttag | aatttgcctg | atctgccaaa | 1200 |
| gctgggagat | ggggaaagt | agagtgggtt | attgaaactg | aatatagagt | tcagcatcta | 1260 |
| aaagcgaggt | agtagaggag | gaagctgtgt | caacggaaat | actgagctgg | gttcacatcc | 1320 |
| tctttctcca | cacagtctaa | tgccttgtgg | aagcaaatga | gccacagaag | ctgaaggaaa | 1380 |
| aaccaccatt | ctttcttaat | acctggagag | aggcaacgac | agactatgag | caggcaagtg | 1440 |
| agaggggct | ttagctgtca | gggaaggcgg | agataaaccc | ttgatgggta | ggatggccat | 1500 |
| tgaaaggagg | ggagaaattt | gccccagcag | gtagccacca | agcttgggga | cttggaggga | 1560 |
| gggctttcaa | acgtattttc | ataaaaaaga | cctgtggagc | tgtcaatgct | cagggattct | 1620 |
| ctcttaaaat | ctaacagtat | taatctgcta | aaacatttgc | cttttcatag | catcgaacaa | 1680 |
| acgacggaga | tcctgttgtg | cctctcacct | gccgaagctg | ccaatctcaa | ggaaggaatc | 1740 |
| aattttgttc | gaaataagag | cactggcaag | gattacatct | tatttaagaa | taagagccgc | 1800 |
| ctgaaggcat | gtaagaacat | gtgcaagcac | caaggaggcc | tcttcattaa | agacattgag | 1860 |
| gatctaaatg | gaaggtactg | agaatccttt | gctttctccc | tggcgatcct | ttctcccaat | 1920 |
| taggtttggc | aggaaatgtg | ctcattgaga | aatttttaaat | gatccaatca | acatgctatt | 1980 |
| tccccagca | catgcctaac | ttttttcttaa | gctcctttac | ggcagctctc | tgattttgat | 2040 |
| ttatgacctt | gacttaattt | cccatcctct | ctgaagaact | attgtttaaa | atgtattcct | 2100 |
| agttgataaa | cagtgaaact | tctaaggcac | atgtgtgtgt | gtgtgtgtgt | gtgtgtgtgt | 2160 |

```
ttaccagctt ttatattcaa agactcaagc ctcttttgga tttcctttcc tgctctctca    2220
gaagtgtgtg tgtgaggtga gtgcttgtcc aaacactgcc ctagaacaga gagactttcc    2280
ctgatgaaaa cccgaaaaat ggcagagctc tagctgcacc tggcctcaac agcggctctt    2340
ctgatcattt cttggaagaa cgagtgctgg tacccctttt ccccagcccc ttgattaaac    2400
ctgcatatcg cttgcctccc catctcagga gcaattctag agggagggt gggctttctt     2460 ttcaggattg acaaagctac ccagcttgca aaccaggggg atctggggg ggggtttgca     2520 cctgatgctc ccccactgat aatgaatgag ggattgaccc catcttttca agctttgctt    2580
cagcctaact tgactctcgt agtgtttcag ccgtttccat attaggcttg tcttccaccg    2640
tgtcgtgtcg tcaatcttat ttctcaggtc atctgtgggc agtttagtgc gaatggactc    2700
agaggtaact ggtagctgtc caagagctcc ctgctctaac tgtatagaag atcaccaccc    2760
aagtctggaa tcttcttaca ctggcccaca gacttgcatc actgcatact tagcttcagg    2820
gcccagctcc caggttaagt gctgtcatac ctgtagcttg cttggctctg cagatagggt    2880
tgctagatta ggcaaataga gggtgcccag tcaaatttgc atttcagata aacaacgaat    2940 atattttag ttagatatgt ttcaggcact gcatgggaca tacttttggt aggcagccta     3000
ctctggaaga acctcttggt tgtttgctga cagactgctt ttgagtccct tgcatcttct    3060
gggtggtttc aagttaggga gacctcagcc ataggttgtt ctgtcaccaa gaagcttctg    3120
caagcacgtg caggccttga ggtcttccga cttgtggccc ggggactctg ctttttctct    3180 gtccttttt ctccttagtg ggccatgtcc tgtggtgttg tcttagccag ttgtttaagg     3240
gagtgttgca gctttatgat taagagcatg gtctttcctt gcaaactgct tggtttagaa    3300
gcctggctcc accacttagc ggctctgtga cctcggacac atttcttagc cttttctgggc   3360 ctcgctcttc ttcctcataa agtgaaaatg aaagtagaca agccttctc tgtctggcta     3420 ctgagaggat ggagtgattt catacacata agcacttaa aataatgtct ggcatatgat     3480
acatgctcaa taaatgtcac ttacatttgc tattattatt actctgccat gatcttgtgt    3540
agcttaagaa cagaggtctt tacaggaatt caggctgttc ttgaatctgg cttgctcagc    3600
ttaatatggt aattgctttg ccacagactg gtcttcctct ccttcaccca aagccttagg    3660
gggtgaacga tcccagtttc aacctattct gttggcaggc taacatggag atggcaccat    3720
cttagctctg ctgcaggtgg ggagccagat tcacccagct ttgctcccag atacagctcc    3780
ccaagcattt atatgctgaa actccatccc aagagcagtc tacatggtac actcccccat    3840
ccatctctcc aaatttggct gcttctactt aggctctctg tgcagcaatt cacctgaaat    3900
atctcttcca cgatacagtc aagggcagtg acctacctgt tccaccttcc cttcctcagc    3960
cattttcctt cttttgtacat aatcaagatc aggaactctc ataagctgtg gtcctcattt    4020
tgtcaatcta atttcacagc ctcttggcac atgaagctgt cctctctctc ctttctgcct    4080
actgcccatg agcagttgtg acactgccac atttctcctt taacgaccca gcctgctgaa    4140
tagctgcatt tggaatgttt tcaattttg ttaatttatt tatttcatct ttttttttttt    4200 tttttttttt ttttttttt agggccgcac ccatgggata tggaggttcc caggctaggg    4260
atccaatggg agctgtagct gctggcctac accacagcca cagcaatgca caattcgagc    4320
caatctttga cctacaccag agctcacggc aacactggat tcttaaccca ctgattgagg    4380
ccagggatca aactctcgtc ctcatagata cgagtcagat tcgttaacct ctgagccatg    4440
atagttgtta gttactcatt gatgagaaag gaagtgtcac aaaatatcct ccataagtcg    4500
```

```
aagtttgaat atgttttctg ccttgttact agaaaagagc attaaaaatt cttgattgga    4560
atgaagcttg gaaaaaatca gcatagttta ctgatatata agtgaaaata gaccttgtta    4620
gtttaaacca tctgatattt ctggtggaag acatatttgt ctgtaaaaaa aaaaaatctt    4680
gaacctgttt aaaaaaaaaa cttgactgga aacactacca aaatatggga gttcctactg    4740
ggacacagca gaaatgaatc taactagtat ccatgaggac acaggtttga tgcctggcct    4800
cgctaagtgg gttaaggata tggtgttgct gcagctccaa ttcaacccct atcctgggaa    4860
cccccatatg ccaccctaaa aagcaaaaag aaggtgctg ccctaaaaag caaaagaaa      4920
gaaagaaaga cagccagaca gactaccaaa tatggagagg aaatgaact tttaggccct    4980
atctccaact atcacatccc tatcaccgtc tggtaagaaa tggaaaaaat attactaagc    5040
ctcctttgtt gctacaatta atctgattct cattctgaag cagtgttgcc agagttaaca    5100
aataaaaatg caaagctggg tagttaaatt tgaattacag ataaacaaat tttcagtata    5160
tgttcaatat cgtgtaagac gttttaaaat aattttttat ttatctgaaa tttatatttt    5220
tcctgtattt tatctggcaa ccatgatcag aaatctttaa acaatcagga agtcttttt     5280
cttagacaaa tgaaaatttg agttgatctt aggtttagta cactatacta ggggccaagg    5340
gttatagtgt gactattaaa tcacagataa tctttattac tacattattt ccttatactg    5400
gccccacttg gatcttaccc agcttagctt ttgtatgaga gtcatcctta aagatgactt    5460
tattctttaa aaaaaaaaac aaattttaag ggctgcaccc atagcatata gaagttccta    5520
ggctagcggt caaattagag ctgcagctgc cagcctatgc cacagccaca gcaatgccag    5580
atctgagctg catctgtgac ctacactgca gcttgcagca atgctggatc cttaacccat    5640
tgaacaatgc cagggattga acacacatcc tcatggatac tgctcaggtt cctaacctgc    5700
tgagccacag ttggaactcc aaagcagact ttattctgat ggctctgctg atctctaaca    5760
cgttattttg tgccatggtg tttatcttca ctttactcaa gtcagggaaa cacgaagagt    5820
ctcatacagg ataaacccaa ggagaaatgt gcaaagtcac atacaaatca aactgacaaa    5880
aatcaaatac aaggaaaaaa tatcttcact ttcaaaatca cctactgatg atgagtttat    5940
atttccttgg atatttgaat attagctatt ttttccttt catgagtttt gtgttcaacc     6000
aactacagtc gtttactttg atcacagaat aatgcattta agccttaaat agattaatat    6060
ttatttcac catttcataa acctaagtac aatttccatc caggtctgtt aaatgcacaa     6120
aacacaactg gaagttagat gtaagcagca tgaagtatat caatcctcct ggaagcttct    6180
gtcaagacga actgggtaaa taccatcaat actgatcaat gttttctgct gttactgtca    6240
ttggggtccc tcttgtcaac ttgtttccaa tctcattaga agccttggat gcattctgat    6300
tttaaactga ggtattttaa aagtaaccat cactgaaaat tctaggcaag ttttctctaa    6360
aaaatcccctt cattcattca tttgttcagt aagtatttga tgagaccttta ccatgtgtaa   6420
acattgcact aggtattaag aaatacaaag atggataaga tagagtcggc gtaaatgaga    6480
tgatataatg agacgttata atgaaactca caattccagt tgggaaataa agtccttcaa    6540
attccatgac tctttctggc acacgttaga ggctacagct tctgtgtgat tctcatgctg    6600
gctccacttc cacttttcc ttcttcctac tcaagaaagc ctatagaaat atgagtaaga    6660
agggcttaat cataggaata aatttgtctc tgttctaagt gattaaaaat gtctttatca    6720
gtataaaaag ttacttggga agattcttaa aactgctttt acacactgtt ctagaatgac    6780
tgttatataa ataaaaaagt agatttgatc taacacaatt aaatgacctt tggaaatatt    6840
gactaattct caccttgccc ctcaaaggga tgcctgaacc atttccttct tttgccagaa    6900
```

```
agcccccacc ctttgtctgt tgacctagcc taggaaatct tcagatcacg ttgttagcac    6960
gaactggtta catgtgctgt acaaatacta tttaattcat ctgattaaaa aaaagagat    7020 aagaagcaaa agtttgacta tcttaaactg tttgcgtagg tgagaggaca attgaccatc    7080
tactttatga gtatgtaacc cagaaactta aagctcctta agggagctaa gtcttttgga    7140
taagacctat agtgagacct tttagcaaaa tggttaagac tgaatggagc tcactagcgt    7200
gggttcatat cctgatgctc aaacacgcaa ttaaatgact ttaggtgggt tagtctctgt    7260
tccttagttt cctcaatggg agataatatt ggtagtagcg attttactgg gttgttgaaa    7320
gaacatctgt taaatgttca gaacgtgtta cgacagagta cagagtaatg atttgcttgt    7380
atatgtatga ctcaaatagt ctgccatatg ccttgtgact gggtcctgtg gagcaggaag    7440
gagggatttc ccacccagca gaaagttggg taaactggaa aatagactga ggccaggaaa    7500
tgatgcaaag cgttgatgtt cactgccacg gcaggtgaag ggcagggcca gagttgtcag    7560
tagggtcagg ggaggactgg aaataaccaa gacccactgc acttttcagc ctttgctcca    7620
gtaaggtaat gttgtgagag tagaaaattt tgttaacaga acccacttt cagtacagtg    7680 ctaccaatac tgtagtgatt tcataccaca tcccaagaaa gaaaagatg gctcaatccc    7740 atgtgagctg agattatttg gttttattgt taaataaata gcattgtgtg gtcatcatta    7800
aaaaaggtag atgttaggaa agtagaagga agaagactct cacctacatt ttcatcactg    7860
ttttggtatc tgccagttgt caccttggtc cccttcccg cctctccct gcctcctctt    7920 cctccttctc ctttttttgg aatacaattc aggtaccata aaatttaccc ttttagagtg    7980
tttgactcaa tggtttttag tattttcaca tgttgtgcta ttactatcac tatataattc    8040
caggtcattc acatcacccc ccaaagaaac cttctaacta ttagcagtcc attcccttct    8100
tccctcagcc cctggcaacc actaatctac ttactgtctc catggatgtt cctatattga    8160
atcaagctag cataaacccc acttgctcat ggtcataatt ctttttata gtgctaaatt    8220 acatttgcta atattcaatt aaggatttct atgtccatat tcataaggaa tattggtgtg    8280
tagttttctc tttgtgtgat atctttgtct ggttggggga tcagagtaat aattactgct    8340
ctcatagaat gaattgagaa gtgttccctc cttttctatt tattggaaga gtttgtgaag    8400
tatattggta ttgattcttc tttaaacatt tggtcagatt caccagtgaa gccatctggg    8460
ccatggctaa tctttgtgaa aagttttttg attactaatt aaatctcttt aatttgttat    8520
gggtctgctc ctcagacgtt ctagttcttc ttgagtcagt tttgttcatt tgtttcttcc    8580
taggactttc tccctttcat ttggattatt tagattgata gtaatatccc ccttttaatt    8640
cctggctgta gtaatttggg tcttttctct tttttcttgg tcagtttagc taaaggtttg    8700
taattgtatt aatcttttca ataactaac tttttgttt tgtttgtttt tgttttttg    8760 ttttttgttt tttgttttt tttgctttt aaggctgcac ctgaggcata tggaagttct    8820
caggctagag gtctaatcgg agctacagct gctggcctat accacaacca tagcaatgcc    8880
agattcaagc tgcatctgcg acctacacca caactcggcc agggatcaca cccgcaacct    8940
catggttcct agtcggattt gttaaccact gtgccacgac gggaactccc gcccattttt    9000
tttaacacct catactttaa cataaagatg ggcttacat ggactgatag ctcaaatgag    9060
gaaggtaaga ctatgaaagt aatggaagaa atgtagacta ttttgtgac ctagagatta    9120 ctgatacttc ttgactttc aaacaatact tcaaaagtac agcccaaagg gaaaaagaa    9180 agaaaaaga aacacacata tacacaaacc tagtgaataa gatatcatcg atacactaca    9240
```

```
gatttctatg aactggaaga ccccatggac aaagttaaag aacatatgat agtttgagtg    9300
attattttgc aatatttaca accaatgagg gaatattatc cagcttatag gaggaagtaa    9360
tgcaaatcga caagaaaaag ataggaaacc caatataaaa attaagaaaa tacaaaaatt    9420
aagaaaggat atgaactagc attttacaaa agaaaaatct ccaaaagtca atcagcacat    9480
gaaaatatgc tcaaacctat taattattag aaaactacag actgaagcaa tgaggtgctt    9540
tactttacat cttttttgact gataaaaagt tagaaacaaa ggtgatatca aatgtcaggg    9600
ataaaaggat atagaaatcg tcatgcctgt ggtgggagta tggccggtgc agtcatgtgg    9660
gaaggtaatc tgacagtggt taggcagagc aggtttatga atacactgtg cccatcaat    9720 cccacgcctg tttatgtacc aaagaaatcc tgttgtggca gaatctatgg gtccacccct    9780
gggagcatga attaataaaa tgtggcacca gggtgtgtga aactccagct agagatgaga    9840
tgtccacatg gcaacatgaa tgcatcttag aaacatagat ttgagtgaaa aagagtaaga    9900
aacagccggg aaacccaata ccatttataa aaattaaaga tgcacacata caatgtagta    9960
aatattttgc atgaactttc aaatggttgc ctacaggggg ggagagtaaa aagagtaga    10020 aaacaaagat aaagggagta agtaagtagc tctgcctgga ctgaatataa tgtgtcatga    10080
actgagaaat atggttaaca taatcctctt aacttgaggt cctaaatgaa tgaatgagtc    10140
cactattcat ttacccattc tttaatgtgt attgcattat aatccatttt tttagaacca    10200
acgaattttg ttcccataac tactaatcag cctgcctttt ctccctcatt cccttatcag    10260
ctcaggggca ttcctagttt ttcaaacgtt cctcatttga accaaaaata gcatcattgt    10320
ttaaattata cttgttttca aatacgatgc ttatatattc caagtgtgtt tgcccatttt    10380
cttaggtggt agaaattttt cattctactt ttctatctac tcagatttttc ccgttggaat    10440 tatttccatt gctattaaac ttagaagtcc cccctgtgat atgccatttt tttcatactt    10500
tttaagcact tggttgcttt tcttttgtgtc tttaagcacc tagaatactt ataaccattg    10560
cacagcactg tgtatcaggc agcccttcct cttccactaa tttatggtcc ttctcttaga    10620
ctatattaaa ctgttattta attaggatcc tctcttcgtc cttatgattt aattattata    10680
gttttctaat atgttttttat tataattcct cttcattatt cctccctatt aaaaatttta    10740
atgaattcca tttgtttgtt cttctagtta aatattaagt cataatccaa ataacttaga    10800
tgtcattagt ttatgtggtc aaagtaagga taccacatct ttatagatgc aggcagttgg    10860
cagatgtcat gattttcttc agtgcataaa tgcaatttat cttttgagcaa ggggcataaa    10920 aactttttatg gtattggctt tgaaataata gttaagaact gcagactcag ttttttcctgc    10980 ttttcttgaa aaagaacact tctaaagaag gaaaatcctt aagcatggat atcgatgtaa    11040
ttttctgaaa gtctcctgta attccttggg attttttgttg ttgtttgttg gtcggttttt    11100
ttgggttttt gtttgtttgt tttgtttttgt tttgtttttgc ttttagggct gcacctgtgg    11160
catatggaag ttcccaggct aggggtccaa ctggagctac agctgccagc ctactccaca    11220
gccacagcaa catgggatcc tagctgcatc tgtgacctaa ccacagctct tggtaatgcc    11280
agattgttaa cccactgagc aatgccagag atcgaatctg cctcctcatg gacactagtc    11340
agattagttt ctgctgagcc acaatgggaa ttcccaattc cttgtatttt tgaactggtt    11400
atgtgctagc atataatttt gtttcttgaa tctttgtggg tttttttttt ttttttttttt    11460 tgtctcttgt cttttttaagg ctgcacccac agcatatgga ggttcccagg ctagaggtca    11520
aattggagct acagctgcca gcctacacaa caactgcagc aaagtggggc ccaacttata    11580
tgacagttcg tggcaatgcc ggattcctaa cccactgagc agggccaggg atcgaacctg    11640
```

```
agtttccagt cagtttcgtt aaccactgag ccatgatagt aactcctgtt tgttcagtct    11700
tgaacctcct ttttaattct ttattccttg agggtgaaat aattgccata ataatactat    11760
catttattac atgccttctc tgtgctaggc atagtgacac tttaggattt attatatcac    11820
ttaatcccta caacaactct gcaaagtatg tatcataatc ctatttgaca gatcaggaaa    11880
ttgcagccca ggatgcagat aatatgcatc catcacaagt gactagatat agtccctctg    11940
ctattcagca gggtctcatt gcctttccat tccaaatgca atagtttgca tctattgtat    12000
atgtgttttg gggtttttttt gtcttttttt ttttttttgt cttttctggg gcctcaccct    12060
tggcataggt aggttcccag gctaggggtc aaattgaagc tgcagctgcc agcctacacc    12120
acagccacag caactcggga tctgagcctc atctgcaacc tacaccaaag ctcacggcaa    12180
caccggatcc ttaacccact gagtgaggcc agagatcaaa ccggcaacct catggttcct    12240
agtcggattc attaaccact gagccacgat gggaactccc taaatgcaat agtttgctct    12300
attaacccca aactcccagt ccatcccact ccctcctcct ccctcttggc aaccacaagt    12360
ctgttctcca tgtccatgat tttcttttct ggggaaagtt tcatttgtgc cattttcat     12420 tttacgggta attttactt cagtttcttc cactagcagt tgtcttaaag tgagtataat     12480
taatattcat ttggaaaatg taagcaaaac attttttaaa gggccatgcc cacagcatat    12540
gaaagtttct gggccagggg ttgaatccag gctccaagtt gcagctgtgc cctacactgc    12600
agctgggcaa tgctggatcc tttaacccac tgtgcccggc tagggatcaa acctgcattt    12660
ccacagctac ccgagccatt gcagttggat tcttaaccca ctgcactaca gtgggaactc    12720
ccacaaaaca ttttttaatg tcctttgaat aaagtaggaa agtgctcgtc tttgagggca    12780
gggcggcaat gccatttcca caaggttttgc tttggcttgg gacctcatct gctgtcattt    12840
agtaatgaat aaaattgctg acagtaatag gattaactgt gtgtggagat agccagggtt    12900
agagataaaa acactggaga agtcaaataa gttgctcgag gtcctctagc taataagcta    12960
ttaagtggga gagtgagggc tagaaacagg ccatctgtct cccaagcaca tgtccattag    13020
tggtttgctg atagccttcc agaacaacag agaggactct caaacatggt cttgcctccc    13080
tccaattgat cccctccatg tgcctcacag cgggtctttc taaaattaag ttctgatttt    13140
aattctccct tgctatagca cttaggtatg gctttcagcc gtgcaataaa aagcaggcaa    13200
gagtggctca atcatatagg aggttgtttt tcttagatcc caagcaggta atcctgggca    13260
ttatggttgt tctgcgtta tcaaggagcc aaattctcta tcacctcctg ttctatcctc     13320
ctcagtatct ggctctattc ttcagcatct caagatggct tgtgctcctc caagcatggc    13380
agtcaaattc cacacaagag ggggaaatat gaagggcaga cagtgctggt ctcctgagct    13440
gtccctcttt gtcggggaaa taaatgtatt ccttcaagtc ccgtgagact tctgaagtag    13500
acgtctgctt acgtctcacc caccagaact atgtaaactg cacatagtgc taggtctaca    13560
tagccactca taactgccag ggggtgggaa atctttaaat aggtgtacca ccacacaatt    13620
aggatgctaa tagtaaggga gaaggagaga ataggttttg cgcaagccac cagcatgcct    13680
gccacaattg cttaaaattc ttcattgacc cctcattgcc acaggatgaa atccaaacgc    13740
cttcttagtt gggaatctga cctacctgtc tctcccacct ggttcagaca ccattctcct    13800
tggtcataaa attccagtca tttgtgaaca tccagctccc ccatgcctcc atgcctttgc    13860
acatgctgtt cttttatctt ttatgttgtc cttttatctt ttatccaaaa gagatatccc    13920
atcatcacat ctcttttgtc agccccccaaa tactttgtct ttcaagttca gctggaggat   13980
```

```
tacctcctat ttgaaatcag ctttgtctct tacaaccaaa caaggttttc cttccgagac   14040
actcccacag caccttgaac tcatctctat caatcattca tttgattgta atgaagttgt   14100
tggtggtatg cctgtgtctc tgacacatct gcgatctcat gagttcctta agtggaatgt   14160
gaatagcggg atgaacagta ttggtcttca gccctcatct ctgcagatgt tgcttgaccc   14220
aaatgagcgt tgccttttat tttgattttg ctttgatttg tctactccat gtacttgagc   14280
catgcatttc tgtcttagcg atgctttttta aaagtcattt tttggttgat tatccagatt   14340
tgtccacctt tgcttctagt tgtagaaaag gatgaagaaa atggagtttt gcttctagaa   14400
ctaaatcctc ctaacccgtg ggattcagaa cccagatctc ctgaagattt ggcatttggg   14460
gaagtgcagg taaggaaatg ttaaattgca atattcttaa aaacacaaat aaagctaaca   14520
tatcaattta tatatatata tatatatata ttttttttttt ttttttacatc ttatattacc   14580 ttgagtattc ttggaagtgg ctagttagga catataataa agttattctg aagtctttttt   14640 tttcttttt ccatggtgag cagtggcttg atgtggatct cagctcccag acgaggcact   14700
gaacctgagc cgcagtggtg aaagcaccaa gttctagcca ctagaccacc agggaactcc   14760
ctattctaaa ttcttgagca cattatttag gaacctcagg aacttggcag gattacagga   14820
aatatatcta gatttaaaaa aaaatctttt aacagaggtc ccaaaggaga gtcatgcaca   14880
gctatgggag gaagttcaga aactgcccct gctaccagat cactgtcaga taaaatggcc   14940
agctacatgt ttctgcacat tgccctaaga tctttacaaa cttttctgtg cattttttcca   15000 cttttaaaag aaaatttcgg ggttcctgtt gttgctcagt ggttaacgaa cccaactagt   15060
atccatgggg acaggggttc gagccctggc ctcactcagt gggttaagaa tctggcattg   15120
ctgtggctgt ggcgtaggct ggcggctaca gctcagattg gaccccctagc ctgagaacct   15180 ccatatgccg caggtatggc cctaaaaaaa aaaaaaaaga gagagagaga atttcctcca   15240
gaaaaaacac tttggtagtt tgggagaagt aaacaaccaa aaattaattt ttctggagta   15300
ttcgggaagc ttgtaaaaat gggctcttac ttttttgagg agacaaatgg gaacctaccc   15360
agaagaggca caatcacctg catttgattt cttgacctct ccctaccttc tttgctggct   15420
ttccacattt ggatttctgt gaccttatct ctgctccttg gtgttttcat ttttcctgtg   15480
gacgtgccag actatgggaa gggagtaagg cgttgattta gaatcctgta gtctctgcct   15540
gtctctagtc attgttttca cccttctcaa aggaccttga catcctgagt gagtccgcaa   15600
gtaatttagg ggagaagcct tagaagccag tgcagccagg ctacatgact gtgtccaccc   15660
actggaacca gtcattttta tacctattca cagccccct accatttaaa tccccagagg   15720
tctgccataa catctgtaac tccctttcct ggtaaattgt gttctaaaag actggtaaca   15780
aaagatattc tgtggtacag agcataatta aatcctggg gctgatttg agtggggtaa   15840 atcaactggt ttgaccccta aaacccacca tgagcatttc tgttctaata agtaatgcc   15900 cgtgctggga attgtgttct acggaaatgc tcctgctgtg tctttcttga gtcctgtgtc   15960
attgaacatg cttaggagca aaggtccccc atgtggcttg tctgctaacc agcccagttc   16020
cttgttctgg ctggtaatga tccgatcatc tgaatctcac tgtcttccaa cagatcacgt   16080
accttactca cgcctgcatg gacctcaagc tggggacaa gagaatggtg ttcgacccttt   16140 ggttaatcgg tcctgctttt gcgcgaggat ggtggttact acacgagcct ccatctgatt   16200
ggctggagag gctgagccgc gcagacttaa tttacatcag tcacatgcac tcagaccacc   16260
tgaggtaagg aaggggtgagc cctcaactcc gaagaaaatg ctgcaataaa agcactgttg   16320
gttttcagct ttttttgtaa tcactgctca ttctgaggta gattcgcttg ggctgataaa   16380
```

```
aagagaacta attcagataa atgcttgcat ttgcatagcc tctttttta aaaactttt    16440
ttttttttt ttttttttgg cttttcaggg ctgaacctgt ggcatatgga ggttcccagg   16500
ctaggggtcg aatcagagct gtagccccgg gcctatgcca ctgccatagc aacatgcata   16560
gcctcctttt taaagtgcct tcctgtttta taccattggg atgtgagaag agctattgtg   16620
gaaangagca tggggtnata accctggacc tctcacgtcc taccctcagg ntagtgggaa   16680
aactctgagt ttaaggacat caaagtgact ccttttagt tacattatgg nggaatcagc    16740
ncatatttt acaaggggcg gagngtaanc tgttggagtt tacaagacat atggtggcat    16800
tgcaactact taaccctact attatagcac aaaagcagcc atagtcggtc ctgaaggagc   16860
ctgatgcctt cagctttata ggcaatgacg tgtgaatatc acaaacagtt tcctgtgtca   16920
ccaaacatga ttgccttttg atttcccttt caacccttta aaaaaggta aaagcccttc    16980
ttagcattca gcagcaggtc gctgtgtttt gccaactcct gatctgtagc atttcgacaa   17040
cactgagctc tcaacttttg aaccctgagt ccaccacatc cttcagtgaa accagagcca   17100
tgtgatacta aggatagaaa cggaaacttc ctgaatccag gcgatcaaat aggagggaga   17160
aagaggaact ttcattgaca aaaccacaaa tattgtgaat ggactgttac aaatattgtg   17220
aatgctccta ttcccaaccc cctggcttca ttacagggtc ctatgtgttc atccttattg    17280
agaaatttgt attgctactg ccaggttgcc aatacccagc ggtgcccatg gtgttctaaa    17340
atgaagcaat ttcaacttta tttttttc ctgtgacttt acatgacaag ttcacatgaa     17400
ggatatactt tgatagtaat gtccatggtt agggaatata cattgtttgc tggttgactg    17460
gccctggat ttttctattg aaagtccatg agatctcgaa ggcacaggtg tgttctctcg    17520
cttttaagg aaagggttta aaacttaag taattaacag ctttagtaac aaattaccta    17580
taacacactt aaaaaccgaa taccacccac tggagtattg tgctacgatt aaaaatctac    17640
ttgtctacta catgatatct ttgtcccaca gaaggttctg gaaccaaact tgtaatttca   17700
ggattatgag agccctgagt tcacgcattg tgtaataact atgttgtgtg gtagtcaatt   17760
tgtacagctt gcttagagag aacaatgtca agttaaggag gcgattgctt tatagtgcct   17820
gtcacaagat gccattgcca ttgtcctagc aagagatatt ctatgggagt atactacatt    17880
ttagtgagga taagaacttt ttatggcatt tagtccggtc atttcccaac cactgtcctg   17940
aaaaccaatt tcattttgat ttcaggggct tgtgtgggca aagttgccag gcattaaaaa    18000
gccacttctc aactgtagta tcacaatgct ttagttgggt agtgtattgc agatagctta    18060
tggctgaaaa gttaccaagc cttgcagttt tcactccttt gagtttattt ccttgacaga    18120
attgaccctg agttttttga ctcttacctg ctcaactaat aaacaccaga gtcatttatc    18180
tccattgctc ttgtctgacc tttatttacc gaataatgcc ttatggttc acaaaaacaa    18240
ggggggaggg ggccagcatg ccttagaaac tgtctttagt caagaaatgn gattttatta    18300
tgtaaatata tgagtattat aatagatagt gttattaata gacaccagca agaattgtca    18360
ataatttaaa aatcacaaat taaaatacat ccatgttagn atcatttatc ctaactccca    18420
aagcccttta aagtggaaga tttagatgtt aacccagaga ttaaagacat gttcaaagaa   18480
tccttgattt ttttttgaat cccttgtttt tagagaagaa aacctaatga ttttccccct    18540
ctggattcta catattaaat atagttttgg aacttgaata ttagtatggt taataagtgc   18600
tgatatgctg attttgttta tattttctt atgagtaaat atcctatatc accagacatt   18660
atagtctatg tacaaatatg attcttaaac ctgatagcac attcattaga gttggaattg   18720
```

```
cctttttttt tttttttttt acagttgcac ctgcaacata tgaaagttcc caggctaggg    18780
gttgaatcca agctgcagct gccaccctac attacagccg tagtaacagc agatccgagc    18840
tgcatctgca acctatgctg cagctcaggg caatgccaga tccactgagt gaagccaggg    18900
atggaacttg catcctcata gagacaacgt cgtgtcctta acccactgag ccagaacagg    18960
aactccagaa tttcctttca atagaagaag caccaagttt aggatcagaa agcctgaatt    19020
tgaataccaa tttactattt gttagtcata tatttctgag tgtgtttcct catttattaa    19080
aagcagacta aaagatgaga gggtcttttg ttgagaatca aatacaataa catgtgaaag    19140
tgtgtaacac tatgattgaa atatacctac acagccattt atttgtttat tgttcatgtt    19200
ttgccaccca cacagtagta tataatcctt ttatgtaata aatgctaata atgaaagttg    19260
gcaacttatg taagtactca aaatgctgga ggtcatggga tactgactgg gatactacag    19320
aggtaatgtc atttcctctg cgctaaactt attgtcttgt agttagggac tgactctctt    19380
taggacaagg agttcattct gtataccatg tgtggctatc acccttcgaa gttgaaaaac    19440
tgccccaggg tgggcaccca tccgttctct tagatatatg gccgagacct ttctctcact    19500
gggagggaac cacactgagg aatgagaaaa aaaaaaggaa aatcaagatg aaaccagaaa    19560
cctctttggc ataacttctc cactctgtac ttttttgttag aactacccctt gcacaaagca    19620 gcatcagtgt ggaagacaga atttgcacac ctggtttgat atacatgccg tggtatatgg    19680
gatgttctaa caataaagag gactctccca ggaaatctcc tcactgttat agtcagcctt    19740
gaggaaagag ctcttctttt ggactctggg gagagtctag tttttcagtt ccttgcttct    19800
cggtcaacgt gttggtgtaa ggatcacact ctctcttata ctagataatt ctatttttc    19860 accttcaac ctgtctatcc ttctgaccct agttacccaa cactgaagaa gcttgctgag    19920
agaagaccag atgttcccat ttatgttggc aacacggaaa gacctgtatt ttggaatctg    19980
aatcagagtg gcgtccagtt gactaatatc aatgtagtgc catttggaat atggcagcag    20040
gtctgtgttc tttccacatg tttgggttat cctttctggg ataaatttga ggcgagatag    20100 aaacttaag actaaagaaa caatggccta ctttttttgt acatggtcct gtgtaaatct    20160
ctatttgagc tgaaataaga tggtcttcct ctccaattat ccatggtatg actctgatgg    20220
ataacaaatc cagttctgaa aaagggggat ttctttccag aagagaggac agtttcttca    20280
aatattgaat taaaagcaaa atagatgtaa accgttgttg gttttattgt tgaattccag    20340
gtagacaaaa atcttcgatt catgatcttg atggatggcg ttcatcctga gatggacact    20400
tgcattattg tggaatacaa aggtattttc ttgccctcat cagcatgaaa ttgctcttgg    20460
tagaaaggat aataatagtt atccaaaaca tcatcctatg ttcatctgtt tcttccctct    20520
tcattttcca tagagtacag tatattctat ctctgtctta ggaaaatgga ctgtcattca    20580
tataatctta cagagaatca attagtaatg tactctatgc cgtgacaggt gcgaaggttt    20640
tttttgaagg caacagataa aaatatccta tatttcacct attgtaattt ccttaaaact    20700
gacattattg aataaatgtt ttactttcat cttgaatatt attatgttat ggaatcatac    20760
actttacccc aataatcatc gaaaagaatt tccaaaaggt tgagagagtt gtgttgatct    20820
gattactttc ctctgcatcc tttgagctta accttttgaat atagtttgct aaggaaagta    20880
gtctgtttat gatcctggag tggaatcagg ctaagtgtcc tcattcagaa cccactgaat    20940
cagacagaat gaatttattt ccttgaaagt tcaaaatgtg tcactcaaga gtataaattt    21000
tcaaatctta ctctctcttt tccttggatg tgagcaattc ttcgtaaatt gaatgaggca    21060
gattatatag acttacatgg aagactgttg gcctgagaat tcaaactatg gtgttcaaga    21120
```

```
cttcacngng agtccgatgc catttgtttc ccacaggtca taaaatactc aatacagtgg    21180
attgcaccag acccaatgga ggaaggctgc ctatgaaggt tgcattaatg atgagtgatt    21240
ttgctggagg agcttcaggc tttccaatga ctttcagtgg tggaaaattt actggtaatt    21300
ctttatatca aaatgatgcc aaggagttgg catggcactt tgctaaatgc tgtgtgaatc    21360
aatacaaaga taattaggac atggttcttc ctcacaagag gtgtgcaatc ttattgggaa    21420
atcatacttg caagtcacaa atatagacta aagtttccag ctgagaatat gctgatggag    21480
catgaaacac taaggagaca gggagaatct caggaaaaat caagaataat ttggatcaaa    21540
tggattcctg acatagaaca tagagctgat cagaaagagt ctgacattgg taatccaggc    21600
ttaagtgctc tttgtatgtg gttcagaaca gagtgtgggc agcctgaggg ggatacatac    21660
ccttgacctc gtggaaagct catacggggg agggatgagg ctaaggaagc ccctctaaag    21720
tgtgggatta cgagaggttg ggggggtggt agggaaaata gtggtcaaag agtataaact    21780
tccagttaca agatgaataa attctagggg tataataaca gcatggcact atagatagca    21840
tattgtacta tatactggaa gtgctgagag tagatcttac atgttctaac cacacacaca    21900
cacacacaca cacacacacc acacacacac accacacaca cacacgtgca cacaaacaga    21960
aatggtaatt atgtgaggtg atggcggtgt taactaactt tattgtggtc atcatttagc    22020
catacatgca tgtcatgaaa tcaccatgtt gtacaccta aagttatgta atactagatg    22080
tcagttatat ctcaaagcta gaaaaaatgt ggggaccaag gcagaagctc ttctgctctg    22140
tgtctaaggg tggttctggg gctgggatgg ggaggatggt taagtggtat attttttca    22200 taccttgct cagtactatc attgtaagtg ttcaatatat gtctgcttaa taaattaatg    22260
tttttagtaa gtaatctctg tttagtaatg tgtcagaaat gccctacttg caataggaag    22320
aaaacctgtc cagtcccttc ctttttctg taagtctgat ttcattgcct cccagaatgc    22380
atcaccatgt gagagataga gggaaggtgc tgtccttatg gggttaacag tgtgactagg    22440
gaggcaaaat ataccactac aagggtggta gcataattca gttcttatgt gagtatgtgt    22500
atgtgtgtga gtatgtgcac atgcacatac attttaaaag gtctgtaata tactaacatg    22560
ttcatagtgg ttacacctag cttataggta acatttttc ccctgtatcc ttgtttgtgt    22620
ttatcaaatt tcataacag taatggtaga aggagtacct gacatggtac catacatgct    22680
nggncctgcc taatttctcn atttccttta ttgcccatac ccccattgct tgacaagcat    22740
aagtccatac tggcttgttt tcgttcctca gactcagtac accatgtagc tccatgccct    22800
gggtctttgt atgtgctatt tctactgctt agagtgctat tgcccctgac caccacgtgg    22860
tcagcaactt ctcttctgcg tctgtgtcta tggtctatga ttccagatgt catcttcact    22920 aactacccctt ctaatatgcc cttccatccc accgtcctc atccttaccc cagccactct    22980
ctatttggtg gctctgtttt atttcttcc tagctcatca ctctttgaaa tgaacttatt    23040
tacttattca atatttgctt ctttcactag aatgaatgct ccatgagagc agggacctgc    23100
tttatcttgc tcgccactgt attcacagtg cctagaacta cgtctggcac atagtaggtg    23160
ctcaataaat atcgatcaaa tgaaagaatg agcaaacgaa caaatgaaca acacgtgagg    23220
taggcatcat gattccatca acagaggaga aaaccagact taaagnaatg aagtggngga    23280
gctgcatttg atcttgactg actccaacat ccatgctctt gaccactgtg catctccaga    23340
gtgtaatgaa catactttac ttttatattc caccaaaata acaaagccat gcccatgtta    23400
gtagagagtt aatcgacagt gcccttaaaa tatgcatgca cccagggtac aactatgcat    23460
```

-continued

```
gctgccctgt gttttcagtt ggatccaaat gaattgccgt aaacaaagag gggattcaat    23520
gtctttgact agtttgggat attttcctag taaccaactt tgcaaaataa agccactaat    23580
gacaaggagc tttgttctac ttctgcatca ctcaactgtc aattttttatc tcttgcaaga   23640 cttctaatct actagaactt ttgttttttct gtgattctg aacagagaag actaatccaa   23700
accctgtcat tccagaggaa tggaaagccc aattcattaa aacagaaagg aagaaactcc   23760
tgaactacaa ggctcggctg gtgaaggacc tacaacccag aatttactgc cccttttcctg  23820 ggtatttcgt ggaatcccac ccagcagaca agtatggctg gatattttat ataacgtgtt   23880
tacgcataag ttaatatatg ctgaatgagt gatttagctg tgaaacaaca tgaaatgaga   23940
aagaatgatt agtaggggtc tggagcttat tttaacaagc agcctgaaaa cagagagtat   24000
gaataaaaaa aattaaatac aagagtgtgc tattaccaat tatgtataat agtcttgtac   24060
atctaacttc aattccaatc actatatgct tatactaaaa aacgaagtat agagtcaacc   24120
ttctttgact aacagctctt ccctagtcag ggacattagc tcaagtatag tctttattt    24180 tcctggggta agaaaagaag gattgggaag taggaatgca aagaaataaa aaataattct   24240
gtcattgttc aaataagaat gtcatctgaa aataaactgc cttacatggg aatgctctta   24300
tttgtcaggt atattaagga aacaaacatc aaaaatgacc caaatgaact caacaatctt   24360
atcaagaaga attctgaggt ggtaacctgg accccaagac ctggagccac tcttgatctg   24420
ggtaggatgc taaaggaccc aacagacagg tttgacttga atatttacag ggaacaaaaa   24480
tgatttctga attttttcat gtttatgaga aaataaaggg catacctatg gcctcttggc    24540
aggtccctgt ttgtaggaat attaagtttt tcttgactag catcctgagc ttgtcatgca   24600
ttaagatcta cacccacccc tttaaagtgg gagtcttact gtataaaata aactattaaa   24660
taagtatctt tcaactctgg ggtgggggggg gagactgagt ttttcacag tcctatataa   24720 taattttctt atcctataaa ataattagga gttcccgtag tggctcagca atagcaaacc   24780
cgactagtat cgatgaggat gcgggttcga ttcctggccc ccctcagtgg gttaaggatc    24840
tggcattgcc gtgagctgtg gtgtaggtgg cagacacggc tcagatccca cgttactgtg   24900
gctgtggcat aggccagcag ctccagctct gattagaccc ttagcctggg aacttccata   24960
tgctgtgggt gtggccttga aaaaaaataa ataaataaga taattactca aatgttttcc    25020
ttgtctcaga accttacttc aggataaaga gtgagaaagt tttttttatg aagggccatt   25080
attacagctc aaaaataagt tgtcttcagc aagtagaaag caataagcct gagagttagt   25140
gttcctatca gtgtaaatat tacctcctcg ccaatcccca gacagtccat ttgaacaatt   25200
aacggtgccc tgggagtaca gttcagaaac attaatgtgg atgttccaga cctgtatttt   25260
tataagtact tgtcttgagc cggatggaac catcattcct caccattatt tagaagtgga   25320
ctgtgactct gttggagatc agggcacacg gttaccaaaa gcacacccctt ctcctggcct  25380 tacctttgca aagctggggt ctgggacaca gtcagctgat tataccctt tactaacttc    25440 ccacagctca aatctggtca attctccttc acaaatctct taaaaatcca tcactcacct   25500
ccagcctctt ctgctgtggc cttgattcag cctctcacaa ttttttttta accagaattc   25560
tggcagtggc ccctgacttg cctctgtgct cccagccccg ctgtcctctg atccatcctc   25620
catgccagcc tttttcaatc tgctggtcac gattcattga tgggttagga aatcaatggc   25680
atcacaacta gcatttagaa aaaggaaata ggcgttcccg ccgtggcaca gcagaaataa   25740
atccgactag gaaccataag gttgcgggtt caaccccctgg ccttgttcag tgggttaagg   25800
atccggcatt gccgtgggct gttttgtaag tcacagacat ggctctgatc cggcattgct   25860
```

```
gtggctctgg cgtaggcctg cagcatcagc tccaattaga cccctatcct gggagcctcc    25920
atatgctgca agtgcagccc taaaaaaaat aaaaaaataa aaaaaaataa ataaaagaag    25980
tagacaaatt gtatagaaca accctgagta tgttgcctga gcacatataa caagggtaag    26040
tattatttca ggaaactctg gtttcacaga tactcttggc atatggaccc ctagagtcct    26100
gatgtaaaat atattcttcc tgggatctta ggcaagaagt tgaaagctc caactctgca    26160 ctgctgccaa agaaatgatt tttaagtgca aaactcttcc cgttcccttc cctgtataaa    26220
attccatagg atctctccag tgcctctagg ataaaggcag ttttcattct ctagttcaag    26280
gtgagagaag attttaatta tttcacgttt tagtggggaa ttcaagagtc tggcacctga    26340
catttgctga actctctcca ttatccctct ctagttcccc agacgcatcc tatggtagaa    26400
attcgcaaac tagagtgagc gtcagagtaa cccaaggaaa ctgggtaaat gcagctccct    26460
gggctctacc ccctgagatt ctgattcagt agatctgaag cagagccctg gaatatgcat    26520
atgcatcatt gtgtcacacc aagcattctg gtaatgaga gttgatgtta ggttctcagt    26580
agtaagacaa gtatagagat tccgggggac tgagtgctca gctctgcctt ggggaggagg    26640
gagagggcta aagagaacag gagatgggga cagggaatgc tcaacctcca atcttaggca    26700
tttgagctat gtcttagggg tcaggaggag gttaccaata tagtgattaa gagattgagg    26760
ttccagtcag agggatatgc tggagaaggg gggtgaaaat aatgtcatag gtttggtgag    26820
tgcagatact ttgagttttt taatatttt attgaaatat agttgattta caatgctctt    26880
agtgagtaca attactttga ataagtgcat agatgtatgc cattcttcca gaaatgattt    26940
attgagctcc tttgggcatc atgctaagta caggggaaac agctgtgaag aggtccttcc    27000
cttatgaagt cattcatccc cttcagtaaa tgaaggtaaa ggaaaaggat gagacaggga    27060
cgccgtgttg gaccagggtc agaaaggcct tataagacct tgcctggagg gcaaggaact    27120
tgcctgtgag taaggagagc ttgagaaagc gataaagcaa agaaggaaca ttactgcatt    27180 gtgtttaga aaaccatgt cctggggaag aactcctaga gtcagggggg ccagttggga    27240
gactgtgctt ttttccagga ggagataagt gaggctgctg gctgagatgg agcaaggatt    27300
tagagaagca gatatgagat tcatttagaa gttagacatt ttaggatctg acacataatt    27360
tatcaccaaa accagtgcat ctctggcttt gggccaccag ttttggagaa gtggaatgta    27420
gggacctacc attacctgcc aatctttact acacagatgc ctatttccct cctcatattt    27480
cctttctcca gatcacgtcc tattctattg ccaggactca agattccacc ttgcatgcag    27540
tgatccatct tcacactgga tggacagctc tagggatgtc agagcacact cttgtccata    27600
ctgctgactg ggtctcctgt cagcccatct gtctatcagc tgtggtatta ttagtataat    27660
aagagggctg tatatgagag acacaaaatt ctaggtgtag ctcaaagata ggctagagtt    27720
attcctatgt acaacaaata tttatgggac cccttctgtg tactgtcatg gttgctgctt    27780
tcatcatact tgtagtctaa tggaggtggg ggcagggcag gaataagcgg atgtccacaa    27840
aatcagtaag accacttata ttcaacattt tcataattta gttatttgag cccaaagggt    27900
ccacatccgt ggtattccaa ctttttttc cccggacatg gatctttatc ttttttttt    27960 tttcttttt gcggccagac ctgcggcata tggaagttcc caggccaggg gttgaatggg    28020
agttgcagct gcctggtcta caccacagcc acagcaaggt gggatctgag ctgcatctgt    28080
gacatacacc gcagctgagg taacaccaga ttctgaaccc actgaatgag gccagggatg    28140
gaacccgtct ccttatgaac actatgtcat gttcttcacc ctctgagcca caacgggaac    28200
```

```
tccagacttc gtctttaaat gtattctgac ttggagagct atcacactaa gcaattaaca    28260
ggagctgacc tggtttaggc tggggtgggg ccctactcct caatgttccc tgaggcacat    28320
ctgtgggacc cctgggcatc atctatctga gcagccttag agctgctcat ccagttgact    28380
gttgatgtag aagtgcaaac ttctgccttc cttatttgtt gctttctttt ttcattgttc    28440
tctccccttt gtgtctttaa gcaagggcat cgtagagcct ccagaaggga ctaagattta    28500
caaggattcc tgggatttg gcccatattt gaatatcttg aatgctgcta taggagatga    28560
aatatttcgt cactcatcct ggataaaaga atacttcact tgggctggat ttaaggatta    28620
taacctggtg gtcagggtat gctatgaagt tattatttgt ttttgttttc ttgtattaca    28680
gagctatatg aaaacctctt agtattccag ttggtttctc aataagcatt cattgagcct    28740
tactgactgt cagacggagg gcgtattgga ctatgtgctg aaacaatcct ttgttgaaaa    28800
tgtagggaat gttgaaaatg tagggaatga aatgtagatc cagctctgtt tctcttttgg    28860
aggattcttt ttcctccatc accgtgtctt ggttcttgtt tgttttgggt ttttgtgggt    28920
gttgtattgt gttgtgttgg ttatggcagt gacagctatt taaactgtga acgggggag    28980 ttcccgtcgt ggcgcagtgg ttaacgaatc cgactgggaa ccatgaggtt gcgggttcgg    29040
tccctgccct tgctcagtgg gttaacgatc cggcgttgcc gtgagctgtg gtgtaggttg    29100
cagacacggc tcggatcccg cgttgctgtg gctctagcgt aggccagcgg ctacagctcc    29160
gattggaccc ctagcctggg aacctccata tgccgcagga gcggcccaaa gaaatagcaa    29220
aaagacaaaa taaataaata aataaataag taagtaaaat aaactgtgaa acggggagtt    29280
cccttcatgg ctcagcagtt aacaaaccca gctaggatcc atgaggatgt aggttcgatc    29340
cctggccttg ctcagtgggt taagaatcca gcgttgctgt gagctgtgat gtaggtcgca    29400
gatgcagccc agatcctgca ttgctgtggc tgtggcgtag gctggcagct gaagctccga    29460
ttcaacccct agcctgggaa catccсatatg ctgcaggtgt ggccttaaga ggcaaaaaaa    29520
taaaaaaata aaaaataaat aaattgtggg acagacaggt ggctccactg cagagctggt    29580
gtcctgtagc agcctggaag caggtaaggt aaggactgca gctgggtaag gactgaattg    29640
caccaactgg gaagtaagcc tagatctaga acttaagtta gccctgacat agacacacag    29700
agctcaccag ctaagtggtt cagcttataa gctggtcact gaaactgagg atgtccacaa    29760
aagcaaaata agtagcaaca ggcagcggga tgcaagagaa agaggaggcc taaaatggtc    29820
tgggaatccc tgccatacct atattttatc ctacttatat ttagtgcctg aatgtgtgcc    29880
tggagagcaa agtttaggga aagcatcggg aaatgcacag tattcatacc cttaggaaca    29940
aagatcagtt acctccaggg taaagactat ttccaagttt aaatttcaac ccctgaacat    30000
tagtactggg taccaggcaa cacttgccat cctcaaaatc aatgaatcct aaaattcaac    30060
ctgggggtca gtgacagtct gtgacaaagt ttttgctggt cagtaacgaa ataagtatga    30120
gcaccatctg agtatggtca ccaagatgtc aactctcttt cctttggacg aattgtcatt    30180
attccaagat taggtccttt ctattttga ggtgtgaaaa catctttcct ttcataaaat    30240
aaaaggatag taggtggaag aatttttttt gtttttggt cttttgcta tttctttggg    30300 ccgcttctgc agcatatgga ggttcccagg ccaggggtcg aatcggagct ttagccaccg    30360
gcccacgcca gagccacagc aacacgggat ccaagccgca tctgcagcct acaccacagc    30420
tcacggcaat gccggatcgt taacccactg agcaagggca gggaccgaac ccgcaacctc    30480
atggttccta gtcggattcg ttaaccactg cgccacgacg ggaactccta atgatactct    30540
tttatattta gctactatgt gatgatgaga aacagtccac atttttattat tttttagcca    30600
```

```
atttgatatc tcattactaa gataatgata attttctcta taaatttat ttaagttagt      30660
gttatgaagt ggttttgcta gtgtagaagg ctaggatttg aattcagttc aagaaagaag      30720
agagggaggg agggagaggg atgggtagag ggatggggca gtgggagaga gcaaagagga      30780
gagacagttt ttgtattaat tctgcttcat tgctatcatt taagggcact tgggtcttgc      30840
acattctaga attttctaag gaccttgacc gccagattga tatgcttctt ccctttacca      30900
tgttgtcatt tgaacagatg attgagacag atgaggactt cagcccttttg cctggaggat     30960
atgactattt ggttgacttt ctggatttat cctttccaaa agaaagacca agccgggaac      31020
atccatatga ggaagtaagc aggaatacca gtggaagtgc ccctttcttc cttccttcct      31080
aaataaactt ttttattttg gaacaacttt agagttacag aaaagttgca aagatattat      31140
agacagtagt gtttatatat atatataaat tttttttttgc tttttatgac cacacctgtg     31200
gcatatggag gttcccagtc taggggttga attggagcta cagctgccag tctgtgccat      31260
aaccacagca atgcaggatc tgggccacgt ctgtgaccta caccaaagct cacagctgga      31320
ttcttaaccc actgagcaag gccagggatt gaacctgcat cctcgtggtt cctagttgga      31380
ttcgtttccg cttttgccgca atgggaactc caaattattg ttaatatctt actttactgg     31440
ggtacatttg ttacaaccaa tactctgata ctgaaacatt actgttaact ccgtacttgc      31500
ttcttttttga gtcatttgca aagactggct tcttgacctg cttccttcca aacagctggc     31560
ctgcctatgc tgttctcaga cctgcaagca ctgatctctg ccccccttgc cttctctcca      31620
gtggtgtctc cttccccaaa caaacccagt gtggctctgg aaagggagtt aagtcaacat      31680
aaaccaacac atattttgtt gagctccaat tttgagcaaa tccctcacct acggcagaca      31740
ggcatgatgt taagaactag ggcttttggac acaaggtcaa gaccaagaag ggttcctcac     31800
ccctactgat tcagataacc aataatgagg ctttgaatcc ctgtccaaag gttgtttttt      31860
ttcccttcta ttgagcttct tgccaccttaa tcagtttttt ttatgacagt caaatgacat     31920
gatatatgtg agcatacatg gtaatttta attctatata aatgaatcac taaataaatt      31980
aggaggatat atagtccacc tttaagcgta ttacacgtgt cacatgaatg tgtggcgact      32040
taattgtaga ggtttaaatg tagcttccta taatagatgt gttcctaaac tacattttaa      32100
tcattggact tgtattttta tgttagcact tgctgttgaa gaaagcctta tgccaaaagt      32160
tcagtgaaac caataatcca ctgccagctt tctgagttaa aaaaaatccc tgggttttca     32220
cacacaggaa caccctgtgt gaaacactca tttagagcaa aatgcatctg ataaggagtt      32280
cctgttgtgc ctcaactggt taaggacctg acattctcca tgagaatgtg agtttgatcc      32340
ccggccccac tcgatgggtt aaggatctgg tgttgccaca aactgcagct ccgattcatc      32400
tcctagccta gaaacttcca cagcccagaa tatgccacag aattcggctg tttaaaaaaa     32460
aaagaaaaa aaaagaatc ataaatgtgt tggtttgttc accaaataca tgataacttg      32520
ctcttgccaa gctcagcttc ataaatatta agtcatttaa tacagcagcc accttatgaa      32580
cagatattac tatacttccc atttacagat aaggaaaatg ccatatttaa ccaagagatt      32640
aaataacttt cccgaggtct tatagcaagt aaatcatggt gcaggggttt gaccacacgc     32700
agtctatctc cagagtctgt gtatttagcc actgttttac tttcaaattt aaatttataa      32760
aacttctaaa ttatctgtta accataatct ttggaatttt taaaaccacg agttcctata      32820
aaatgtttca ttgaaagtaa gtcacttttc catagctttt gataatacat ctgtaggata      32880
aagtaagcca cagctctctt gcagacttgg tacaccctgg ggcaaagcat catgcctgtc      32940
```

```
acgtacatgg tggtccttac tttgactctc agtgctttta ttgcccagga attttgtgag   33000
atttctagtt gttgaggttt gtttaaagag gttatgccgg tacttggaag agctcttttc   33060
ttgctacctg gagccttctc atatttcctt tttgaggagg gacatgaatt gcctttcaaa   33120
ctcataaata tattttctag tacacaagtc tccatcttcc ttagacgcat ggctcctgga   33180
gttctccatc ctcctgctcc actttgggtg ggctcctctc tgggtctgcc accaatctgc   33240
cacccagaga catccttgac ccacttccag accccaccat ggcttcactt tcttcgcttt   33300
cctcctttgt ggaaccttct gcttaagaat ctgaggaaga aaatttgcac gtgagctaaa   33360
ctggaggtac tttcctgcct ggtcttgcac gatagcttgg ctgagcccat gatgctgggt   33420
ggctgttact ttccatggac acccgaaggc gttgctcctt tggcttctag ttgcatgcag   33480
tgttgcttat cccaggctga tctttcttcc actgtaggtg acttttaaga attaagggat   33540
taatctatat ctacaacaac aacaacaaag accttttcaa gctgaggtag ggctttctgt   33600
atatgtttgg agtggttatc cagcagactt tacttgaagg caggggtcat atcctcaagt   33660
gctcataaac ggaccacaga aagatctcat aattgggtgg agctgggtgg ggaccgtgtc   33720
atgtggccag gaaatgccag atgggaaggg agtggcccct actgagctcc agctgaactc   33780
tgaattttct agaaaactca gaaatctgga ttttcatgt gtaatacccca gatttataga   33840 tgtggaaagc taattctttt tttttttaag ggactatagg caatgaacta agatctaggt   33900
tgtatttgga caaggggtca tcagtttaag ctgtgtagtt gagcgctcag ctattgggct   33960
gagggacccc taaatactga gacggggagg tccttgctct ggggcatcac aagtacactc   34020
cctggtctca ttcaaacact tttcctacaa aattgatccc atttcttcag tgcactgtct   34080
gaatgcattt ggcccagagc cgtgctgagg catagggaag gggtccacgg tttcatggca   34140
tcgttttgtg ctgtgtgtcc ctgctgtcgt ccaggatacc tacctctcct cctcctgcat   34200
ctgaatgtcc ccccacagac tctctgggat tctacagcct ctggcctgtt cctcagacac   34260
ctcttacctg ccagctttcc agattcacat tagttagtcc aaatctactg ccgtcagtga   34320
ctcacttcat ttcttcttct ccgaggcagt tcagcccggt acagttgttt tgtcaacact   34380
tcagttgagt ctggaagatg tgcatgggtt atgcacgaga gcggtccatc attttgagct   34440
agaagtcctt tctcagccca gagacaagtc ctcatctcct ttacttcctg actcttcttc   34500
ctctgcatcc ttccaagata tctctttctc cagccaccac ctaaatctct tcttttcccg   34560
gggttccgtg ctcaacccac tcttcttctt aaatctgtgg ctgggtgaac gcatctgctg   34620
gcaccacttc tctgctaaag actccaaaaa tccataggtc ctgcccggcc tttgcccacc   34680
tctctccaac actgtccagc tttagatgta gagctaatcc ccccagagat atcattccct   34740
ggatgtctaa gtcctttggt atctcacttt cagcgtgttc aaaatcctct tacaactgtt   34800 cttttctcctt ttccatcttg attattggca acatgccagc cttttcccta ccccccagcag   34860 tgagccaagc tagaaacaag ggcttaatct tcaatctttc cttctccatc cctaaaccta   34920
atgagtctcc aagcccttcc cagtttacac cctaaatgtt gctcaaaaca tcccctagtt   34980
cttccacgtg ctctcctcta tattgaaagg tcaagaaagg ccatcttccc tccactgtga   35040
ggaaatagat cttgatactg cccctgagct gggcagtcct cgacctgaca aactgtgcag   35100
tgtttctaaa tctctactgg caaaatgaga gtgcctttga cctgtgttgc gatctcagat   35160
cacagtggat gtaattgttt tataggaatg gtgaacgaaa aagaagtaaa tccctaatgc   35220
caaactcctg atcattctat gtcatttaat agcctgtcat ttatgataaa gtttcctcta   35280
ctggcattag cacaatactt ctcaggaaaa aaaaatatga tgccagatac tgaaaagctc   35340
```

```
ctgggtaaac atgaacatgg gtaccgataa aatggtgaag ccagtccaat cttagagtga   35400
cttcccttca tgctacttca tgctcttttt tttttttttt tttaagaaaa accccttttt   35460
tttttctcac accagtcaca gaggagaccg aggcttagca aggttaaggt cacatgatta   35520
gtaagtgctg ggctgaaact caaaaccatc tctgcttgtc tcctaaccct gtgcacctct   35580
gactattcaa cagatcctgt gtcaggagtt gggattcttt gaaggtaagg ccttgacca   35640
ccgaattaag gtaatcttgc tctgtggcag gccttgtttt cagtattta agtacactgg   35700
ctcaggtaat cctcacaaca gccccaggag gaatgttcta ttacctccac tgtatagatg   35760
aggaacttga ggcacagaat ggttgccaag gtcacacagc tatattgggg gttcataccc   35820
agccatccaa ctctgtctgt actctctgcc actctgcacc cccagctcct gatccacttc   35880
ctgtttccat ccctcgattt ctgctgcact caggggcccc tctccccctc ggcctgtgag   35940
atctgcttca gtaggctttt ctccctgact cctccatccc tgtccttaca ggcagctgct   36000
tctctccggg acacgagggg tccatacgga cactctctac tggctgggtt gcgcctaact   36060
cgtgattcct cctctgtttc agattcggag ccggggttgat gtcatcagac acgtggtaaa   36120
gaatggtctg ctctgggatg acttgtacat aggattccaa acccggcttc agcgggatcc   36180
tgatatatac catcatctgt aagtccgaaa atgcctgtcg tgtgtgcctt aggctgctgc   36240
ggaggaggcc agggctatat aagcagagtc agtgactgac tgtgccctgc agtgttgatg   36300
gccatggaga ttccaccgtt agagcttttt tctttgttaa ccttgaaggc aaatctggtt   36360
aggaagataa ctttcaaaga gtcaccatct ggacattcat gcccatgtgc ttcaatcctg   36420
tatacaagca gtttagagta cagggaaggg aaggacatta tgaaagggag agggtgtgtt   36480
tggatccagc agctccatcc tcagaattta tctgaagaca ctgcaaaatt actaagaatc   36540
actatgacaa gaatgaggat ggggtgatat ggcaaagttg tgatcctgga agaccttcat   36600
ctcccatgtt gcccaactct gaacatgaat ttggtgaact agttggttaa ggggatgatc   36660
ctccaagttt ctccctggtt gagctccaaa aaccatgtaa gtttctcata gcaaaaccgt   36720
ataggtcctt agggctttag ttggaatatt tgtgctgaaa tgctggaaag ccccatttgc   36780
cattttgta tttgcaaaat aatcatcaag aggggagaat gcattctttc atgaccactg   36840
accctctgaa aaggtcagga atttagtctg aagtaggcaa gcctcctacc ccgcttctgc   36900
catgagcttg cacgcacagg cctgtcttga catttcttct ttatagattt cttttttgaat   36960
atcttgaaat tgctttaaaa atatttaaag aatgtagaat tatataaaat aaaaaggaaa   37020
taaccccaca cctcccacaa aaccctgttt cctgcctttc tccacccact ctccagggta   37080
acacttggta acagcatagt tgtatcaccc caggcctatt tttgagcata tcagcatttc   37140
aagaaatgta ttttttctca ataaaacatc ccttatagtt gaggagggga ggttatcatt   37200
cctgggtttt gttttttttt ttttttaat gtaatcctgg tacatcggta atttgcattt   37260
tttattcatt aatatctttg gtatttctag tgttgggaca cacaggtcaa cctcagtttt   37320
tgggtttttt tttttgtctt tttgtctttc tagggccaca cctgcagcat atggacgttc   37380
ccaagctagg agtctaatca gagctgtagc caccagccta cgtcatagcc atagcaacgt   37440
cagatccaag ccgtgtctgt gacctacaag cacagctcat ggcaacaccg gatccttaac   37500
cactgaacga ggcaggggga tcgaacacac atcctcatgg atcctagtca tgttcattaa   37560
ccactgagtc atgatgggaa ctccaacttc aactatttta atgtctgtaa aacattccat   37620
ttggaaacca tttcatttgt aaagcaaaat gaaaacattt tgttcatttt caacagagtt   37680
```

```
cgtagctgac ttctgttctg gaaaaaagga aatggagcaa atttgagtga gaaagattca    37740
aagataactt ttctttaaa aaaattata tcttggaaac ttctgggcta ttgattctga      37800
agactatttt tctatatact gttttgatag caaagttcat aaatgtgaaa ggatcctgcg    37860
atgaatcttg ggaagcagtc atagcccaat atatctttgt tgcttttaaa atgagattta   37920
gtttactaaa tattttctg atcataaaaa taacacagat ctaccgcaga aaatttggaa    37980
aaaaaaaaac ttttaaattc aaaaaacagt taaaccacaa atgatcccac catccagaga   38040
gcaatttgta ctttggtgtc tagttcatct ttcttttct gtttacaagc acatatacca    38100
caagcatttt ttcaaaaaat gaaatgggaa taatactata catacgtctg tacacctgca    38160
tagttactga acagtctttg atctaccctg taagtttcta acttttcatt atttgaaatg    38220
atgttttggc aaagaaatat gtaggtgtgt ctcgcacact ttcataatga tttcttagga    38280
taaatttctt aggataaatt cataatgatt tcttataata atccatactc tgccaactga    38340
tcttcaggga agccaactcg ccttctcaga ataacatat aacccattta cttgccctct     38400
caccaatact aggtcctaat gttttgtgt acagattcta tattttaca tacaagaatt      38460 ccttaaagca aggcatgtca cagaaaaata gaaggaagac acaattgtca tgtttaagga    38520
ctgcattctg taccaaaaat gctaagttaa atgaacatct gaaacagtac agaaacgcta    38580
tctttcaggg aaagctgagt accaggtact gaacagattt tggcaaatac agcaggcatg    38640 gatgttttcca aaacatgttt ttctactta tctcttacag gttttggaat cattttcaaa    38700
taaaactccc cctcacacca cctgactgga agtccttcct gatgtgctct gggtagagag    38760
gacctgagct gtcccaggta aagcatcctg caggtctggg agacactctt attctccagc    38820
ccatcacact gtgtttggca tcagaattaa gcaggcacta tgcctatcag aaaacctgac    38880
ttttggggga atgaaagaag ctaacattac aagaatgtct gtgtttaaaa ataagtcaat    38940
aagggagttc ccatcgtggc tcagtggtaa cgaaccctac tagtatccat tgaggacaca   39000
ggttcaatat ctggcctcac tcagtcggct aaggatccag tgatgccgtg agctgcagtg   39060
taggccacag acgtggctca gatcggtgc tgctgtggct atggtgtagg ccggcccct     39120 gtaactccaa ttcgacccct aggctgggaa cctaaaaaga ccccaaaaaa gtcgctttaa    39180
tgaatagtga atacatccag cccaaagtcc acagactctt tggtctggtt gtggcaaaca    39240
tacagccagt taacaaacaa gacaaaaatt atcctaggtg gtcagtgggg gttcagagct    39300
gaatcctgaa cactggaagg aaaacagcaa ccaaatccaa atactgtatg gttttgctta    39360
tatgtagaat ctaaattcaa agcaaatgag caaaccaatt gaaacagtta tggaagacaa    39420
gcaggtggtt gtcagggggg agataagggg aggcaggaaa gacctgggcg agggagatta   39480
agaggtacca actttcagtt gcaaaacaaa tgagtcacca gtatgaaatg tgcaatgtgg    39540
gaaatacagg ccataacttt ataatctctt ttttttttt gtcttttttg ccttttctaa    39600
ggctgctccc gtggcatatg gaggttccca ggctaggagt ccaaacagag ctgtagctgc    39660
cagcctacac cagagccaca gcaacacggg aaccttaacc cgctgagcaa ggccagggat    39720
cgaacccgag tcctcacaga tgccagtagg gttcattaac cactgagcca cgacaggaat    39780
tccagggtct gttgtgttct taaaacactt ccaggagagt gagtggtatg tcataagtaa    39840
acaataaatg ttaaccacaa caagcttatg aaataaacag gaaagccata tgacctacaa    39900
tcagtcattg ggagaatcca caaaggttg agcagaggat caattccagc tcacactcca    39960
gttttagatt ctcccctgcc ttaaagcatc acagactaca taatctgagc tgaagaataa    40020
aaattaaaac tcaccccagt gcaaaacaga aatgaaaaag tattaaaacg aggttcatac    40080
```

```
tgttgttcat tagcaatatc ttttattcac aggggtgccc aacaacatga aaaaatcaag    40140
aatttattgc tgctacgtca aagcttatac cagagattat gccttataga cattagcaat    40200 ggataaattat atgttgcact tgtgaaatgt gcacatatcc tgtttatgaa tcaccacata    40260
gccagattat caatatttta cttatttcgt aaaaaatcca caattttcca taacagaatc    40320
aacgtgtgca ataggaacaa gattgctatg gaaaacgagg gtaacaggag gagatattaa    40380
tccaagcata gaagaaatag acaaatgagg ggccataagg ggaatatagg g             40431
```

```
<210> SEQ ID NO 47
<211> LENGTH: 1192
<212> TYPE: DNA
<213> ORGANISM: Porcine

<400> SEQUENCE: 47
```

```
ctgccagcct aagccacagc cacagcaacg ctgggtctga gccatgtctg cagcctatgc     60
cagagctccc cgcagcgccg gatgcttaac ccactgagca aggccaggga ttgaaccctc    120
gtcctcatgg atagcagttg agttgtttcc acggaactct taggggaact cctgattatt    180
ttttatttaa atttatattt ctctgacttt ttcgtgtgct catcagccac tgactgtgta    240
tctccattag tcatggtttg ttaactctgt cattcaaacc ctcttcatcc ttgctacgca    300
gataacatca ttataataaa atcgtgcctg aagaccagtg acgcccccaa gctaagttac    360
tgcttcccct gggggggaaaa agaagcaccg cgcgggcgct gacacgaagt ccgggcagag    420
gaagacgggg cagaggaaga cggggggagca gtgggagcag cgggcagggc gcgggaagca    480
ctggggatgt tccgcgttgg caggagggtg ttgggcgagc tcccggtgat gcaggggggga    540 ggagcctttt ccgaagtagc gggacaagag ccacgggaag gaactgttct gagttcccag    600
tcccgacgtc ctggcagcgc ccaggcactg ttattggtgc ctcctgtgtc cacgcgcttc    660
ccggccaggc agccctggcg gatcctattt tctgttcccc cgattctggt acctctccct    720
cccgccctcg gtgcgcagcc gtcctcctgc agtgcctgct cctccagggg cgaaaccgat    780
cagggatcag gccacccgcc tcctgaacat ccctccttag ttcccacagg tgagaaggct    840
tcgccgctgc tgccgctggc gccggcagcg ccctccacgc acttcgtagt gggcgcgcgc    900
cctcctgcat tgtttctaaa agattttttt ttatccgctt atgctatcag ttactgagga    960
agtatttaca aatctactat tattttgaat ttgccttttt ctccttatag tttatcagta   1020
tctcttgaga ctgttattgg tgcctgcaaa tttaaaatga ttggggtttt atgaggaagt   1080 gaaccttta tctttatgaa acgcctaact gaggcaatgt taattgctta aaatactttc    1140
tttattatca gtgtggccat gccagtgtcc tcttggttag aatttgcctg at           1192
```

```
<210> SEQ ID NO 48
<211> LENGTH: 39239
<212> TYPE: DNA
<213> ORGANISM: Porcine
<220> FEATURE:
<221> NAME/KEY: misc_feature
<222> LOCATION: (15433)..(15433)
<223> OTHER INFORMATION: n is a, c, g, or t
<220> FEATURE:
<221> NAME/KEY: misc_feature
<222> LOCATION: (15445)..(15445)
<223> OTHER INFORMATION: n is a, c, g, or t
<220> FEATURE:
<221> NAME/KEY: misc_feature
<222> LOCATION: (15479)..(15479)
<223> OTHER INFORMATION: n is a, c, g, or t
<220> FEATURE:
```

```
<221> NAME/KEY: misc_feature
<222> LOCATION: (15539)..(15539)
<223> OTHER INFORMATION: n is a, c, g, or t
<220> FEATURE:
<221> NAME/KEY: misc_feature
<222> LOCATION: (15549)..(15549)
<223> OTHER INFORMATION: n is a, c, g, or t
<220> FEATURE:
<221> NAME/KEY: misc_feature
<222> LOCATION: (15572)..(15572)
<223> OTHER INFORMATION: n is a, c, g, or t
<220> FEATURE:
<221> NAME/KEY: misc_feature
<222> LOCATION: (15577)..(15577)
<223> OTHER INFORMATION: n is a, c, g, or t
<220> FEATURE:
<221> NAME/KEY: misc_feature
<222> LOCATION: (17098)..(17098)
<223> OTHER INFORMATION: n is a, c, g, or t
<220> FEATURE:
<221> NAME/KEY: misc_feature
<222> LOCATION: (17208)..(17208)
<223> OTHER INFORMATION: n is a, c, g, or t
<220> FEATURE:
<221> NAME/KEY: misc_feature
<222> LOCATION: (19935)..(19935)
<223> OTHER INFORMATION: n is a, c, g, or t
<220> FEATURE:
<221> NAME/KEY: misc_feature
<222> LOCATION: (19937)..(19937)
<223> OTHER INFORMATION: n is a, c, g, or t
<220> FEATURE:
<221> NAME/KEY: misc_feature
<222> LOCATION: (21489)..(21489)
<223> OTHER INFORMATION: n is a, c, g, or t
<220> FEATURE:
<221> NAME/KEY: misc_feature
<222> LOCATION: (21492)..(21492)
<223> OTHER INFORMATION: n is a, c, g, or t
<220> FEATURE:
<221> NAME/KEY: misc_feature
<222> LOCATION: (21508)..(21508)
<223> OTHER INFORMATION: n is a, c, g, or t
<220> FEATURE:
<221> NAME/KEY: misc_feature
<222> LOCATION: (22074)..(22074)
<223> OTHER INFORMATION: n is a, c, g, or t
<220> FEATURE:
<221> NAME/KEY: misc_feature
<222> LOCATION: (22085)..(22085)
<223> OTHER INFORMATION: n is a, c, g, or t

<400> SEQUENCE: 48
ctgccaaagc tgggagatgg gggaaagtag agtgggttat tgaaactgaa tatagagttc      60
agcatctaaa agcgaggtag tagaggagga agctgtgtca acggaaatac tgagctgggt     120
tcacatcctc tttctccaca cagtctaatg ccttgtggaa gcaaatgagc cacagaagct     180
gaaggaaaaa ccaccattct ttcttaatac ctggagagag gcaacgacag actatgagca     240
ggcaagtgag aggggcttt agctgtcagg gaaggcggag ataaacccctt gatgggtagg     300 atggccattg aaaggagggg agaaatttgc cccagcaggt agccaccaag cttgggact      360 tggagggagg gctttcaaac gtatttcat aaaaagacc tgtggagctg tcaatgctca       420
gggattctct cttaaaatct aacagtatta atctgctaaa acatttgcct tttcatagca     480
tcgaacaaac gacggagatc ctgttgtgcc tctcacctgc cgaagctgcc aatctcaagg     540
aaggaatcaa ttttgttcga aataagagca ctggcaagga ttcatctta tttaagaata     600 agagccgcct gaaggcatgt aagaacatgt gcaagcacca aggaggcctc ttcattaaag     660
acattgagga tctaaatgga aggtactgag aatccttgc tttctccctg gcgatccttt      720
ctcccaatta ggtttggcag gaaatgtgct cattgagaaa ttttaaatga tccaatcaac     780
```

```
atgctatttc ccccagcaca tgcctaactt tttcttaagc tcctttacgg cagctctctg    840
attttgattt atgaccttga cttaatttcc catcctctct gaagaactat tgtttaaaat    900
gtattcctag ttgataaaca gtgaaacttc taaggcacat gtgtgtgtgt gtgtgtgtgt    960
gtgtgtgttt accagctttt atattcaaag actcaagcct cttttggatt tcctttcctg   1020
ctctctcaga agtgtgtgtg tgaggtgagt gcttgtccaa acactgccct agaacagaga   1080
gactttccct gatgaaaacc cgaaaatgg cagagctcta gctgcacctg gcctcaacag    1140
cggctcttct gatcatttct tggaagaacg agtgctggta ccccttttcc ccagcccctt   1200
gattaaacct gcatatcgct tgcctcccca tctcaggagc aattctagga gggagggtgg   1260
gctttctttt caggattgac aaagctaccc agcttgcaaa ccaggggat ctggggggg    1320
ggtttgcacc tgatgctccc ccactgataa tgaatgaggg attgacccca tcttttcaag   1380
ctttgcttca gcctaacttg actctcgtag tgtttcagcc gtttccatat taggcttgtc   1440
ttccaccgtg tcgtgtcgtc aatcttattt ctcaggtcat ctgtgggcag tttagtgcga   1500
atggactcag aggtaactgg tagctgtcca agagctccct gctctaactg tatagaagat   1560
caccacccaa gtctggaatc ttcttacact ggcccacaga cttgcatcac tgcatactta   1620
gcttcagggc ccagctccca ggttaagtgc tgtcatacct gtagcttgct tggctctgca   1680
gatagggttg ctagattagg caaatagagg gtgcccagtc aaatttgcat ttcagataaa   1740
caacgaatat attttagtt agatatgttt caggcactgc atgggacata cttttggtag    1800
gcagcctact ctggaagaac ctcttggttg tttgctgaca gactgctttt gagtcccttg   1860
catcttctgg gtggtttcaa gttagggaga cctcagccat aggttgttct gtcaccaaga   1920
agcttctgca agcacgtgca ggccttgagg tcttccgact tgtggcccgg ggactctgct   1980
ttttctctgt cctttttct ccttagtggg ccatgtcctg tggtgttgtc ttagccagtt    2040
gtttaaggga gtgttgcagc tttatgatta agagcatggt ctttccttgc aaactgcttg   2100
gtttagaagc ctggctccac cacttagcgg ctctgtgacc tcggacacat tcttagcct    2160
ttctgggcct cgctcttctt cctcataaag tgaaaatgaa agtagacaaa gccttctctg   2220
tctggctact gagaggatgg agtgatttca tacacataaa gcacttaaaa taatgtctgg   2280
catatgatac atgctcaata aatgtcactt acatttgcta ttattattac tctgccatga   2340
tcttgtgtag cttaagaaca gaggtcttta caggaattca ggctgttctt gaatctggct   2400
tgctcagctt aatatggtaa ttgctttgcc acagactggt cttcctctcc ttcacccaaa   2460
gccttagggg gtgaacgatc ccagtttcaa cctattctgt tggcaggcta acatggagat   2520
ggcaccatct tagctctgct gcaggtgggg agccagattc acccagcttt gctcccagat   2580
acagctcccc aagcatttat atgctgaaac tccatcccaa gagcagtcta catggtacac   2640
tccccatcc atctctccaa atttggctgc ttctacttag gctctctgtg cagcaattca    2700
cctgaaatat ctcttccacg atacagtcaa gggcagtgac ctacctgttc caccttccct   2760
tcctcagcca ttttcttct tgtacataa tcaagatcag gaactctcat aagctgtggt     2820
cctcattttg tcaatctaat ttcacagcct cttggcacat gaagctgtcc tctctctcct   2880
ttctgcctac tgcccatgag cagttgtgac actgccacat ttctccttta acgacccagc   2940
ctgctgaata gctgcatttg gaatgttttc aattttgtt aatttattta tttcatcttt    3000
tttttttttt tttttttttt tttttttag gccgcaccc atgggatatg gaggttccca    3060
ggctagggat ccaatgggag ctgtagctgc tggcctacac cacagccaca gcaatgcaca   3120
```

```
attcgagcca atctttgacc tacaccagag ctcacggcaa cactggattc ttaaccccact    3180 gattgaggcc agggatcaaa ctctcgtcct catagatacg agtcagattc gttaacctct    3240
gagccatgat agttgttagt tactcattga tgagaaagga agtgtcacaa aatatcctcc    3300
ataagtcgaa gtttgaatat gttttctgcc ttgttactag aaaagagcat taaaaattct    3360
tgattggaat gaagcttgga aaaaatcagc atagtttact gatatataag tgaaaataga    3420
ccttgttagt ttaaaccatc tgatatttct ggtggaagac atatttgtct gtaaaaaaaa    3480
aaaatcttga acctgtttaa aaaaaaaact tgactggaaa cactaccaaa atatgggagt    3540
tcctactggg acacagcaga aatgaatcta actagtatcc atgaggacac aggtttgatg    3600
cctggcctcg ctaagtgggt taaggatatg gtgttgctgc agctccaatt caaccccctat    3660 cctgggaacc cccatatgcc accctaaaaa gcaaaagaa aggtgctgcc ctaaaaagca    3720 aaagaaaga aagaaagaca gccagacaga ctaccaaata tggagaggaa atggaacttt    3780
taggccctat ctccaactat cacatcccta tcaccgtctg gtaagaaatg gaaaaaatat    3840
tactaagcct cctttgttgc tacaattaat ctgattctca ttctgaagca gtgttgccag    3900
agttaacaaa taaaaatgca aagctgggta gttaaatttg aattacagat aaacaaattt    3960
tcagtatatg ttcaatatcg tgtaagacgt tttaaaataa ttttttattt atctgaaatt    4020 tatattttc ctgtattta tctggcaacc atgatcagaa atctttaaac aatcaggaag    4080
tcttttttct tagacaaatg aaaatttgag ttgatcttag gtttagtaca ctatactagg    4140
ggccaagggt tatagtgtga ctattaaatc acagataatc tttattacta cattatttcc    4200
ttatactggc cccacttgga tcttacccag cttagctttt gtatgagagt catccttaaa    4260
gatgacttta ttcttaaaa aaaaaaacaa attttaaggg ctgcacccat agcatataga    4320
agttcctagg ctagcggtca aattagagct gcagctgcca gcctatgcca cagccacagc    4380
aatgccagat ctgagctgca tctgtgacct acactcagc ttgcagcaat gctggatcct    4440
taacccattg aacaatgcca gggattgaac acacatcctc atggatactg ctcaggttcc    4500
taacctgctg agccacagtt ggaactccaa agcagacttt attctgatgg ctctgctgat    4560
ctctaacacg ttattttgtg ccatggtgtt tatcttcact ttactcaagt cagggaaaca    4620
cgaagagtct catacaggat aaacccaagg agaaatgtgc aaagtcacat acaaatcaaa    4680
ctgacaaaaa tcaaatacaa ggaaaaaata tcttcactt caaaatcacc tactgatgat    4740
gagtttatat ttccttggat atttgaatat tagctatttt tttcctttca tgagttttgt    4800
gttcaaccaa ctacagtcgt ttactttgat cacagaataa tgcatttaag ccttaaatag    4860
attaatattt attttcacca tttcataaac ctaagtacaa tttccatcca ggtctgttaa    4920
atgcacaaaa cacaactgga agttagatgt aagcagcatg aagtatatca atcctcctgg    4980
aagcttctgt caagacgaac tgggtaaata ccatcaatac tgatcaatgt tttctgctgt    5040
tactgtcatt ggggtccctc ttgtcaactt gtttccaatc tcattagaag ccttggatgc    5100
attctgattt taaactgagg tattttaaaa gtaaccatca ctgaaaattc taggcaagtt    5160
ttctctaaaa aatccctcca ttcattcatt tgttcagtaa gtatttgatg agaccttacc    5220
atgtgtaaac attgcactag gtattaagaa atacaaagat ggataagata gagtcggcgt    5280
aaatgagatg atataatgag acgttataat gaaactcaca attccagttg ggaaataaag    5340
tccttcaaat tccatgactc tttctggcac acgttagagg ctacagcttc tgtgtgattc    5400
tcatgctggc tccacttcca cttttccctt cttcctactc aagaaagcct atagaaatat    5460
gagtaagaag ggcttaatca taggaataaa tttgtctctg ttctaagtga ttaaaaatgt    5520
```

```
ctttatcagt ataaaaagtt acttgggaag attcttaaaa ctgcttttac acactgttct   5580
agaatgactg ttatataaat aaaaaagtag atttgatcta acacaattaa atgacctttg   5640
gaaatattga ctaattctca ccttgccoct caaagggatg cctgaaccat ttccttcttt   5700
tgccagaaag cccccaccct ttgtctgttg acctagccta ggaaatcttc agatcacgtt   5760
gttagcacga actggttaca tgtgctgtac aaatactatt taattcatct gattaaaaaa   5820
aaagagataa gaagcaaaag tttgactatc ttaaactgtt tgcgtaggtg agaggacaat   5880
tgaccatcta ctttatgagt atgtaaccca gaaacttaaa gctccttaag ggagctaagt   5940
cttttggata agacctatag tgagaccttt tagcaaaatg gttaagactg aatggagctc   6000
actagcgtgg gttcatatcc tgatgctcaa acacgcaatt aaatgacttt aggtgggtta   6060
gtctctgttc cttagtttcc tcaatgggag ataatattgg tagtagcgat tttactgggt   6120
tgttgaaaga acatctgtta aatgttcaga acgtgttacg acagagtaca gagtaatgat   6180
ttgcttgtat atgtatgact caaatagtct gccatatgcc ttgtgactgg gtcctgtgga   6240
gcaggaagga gggatttccc acccagcaga aagttgggta aactggaaaa tagactgagg   6300
ccaggaaatg atgcaaagcg ttgatgttca ctgccacggc aggtgaaggg cagggccaga   6360
gttgtcagta gggtcagggg aggactggaa ataaccaaga cccactgcac tttcagcct   6420 ttgctccagt aaggtaatgt tgtgagagta gaaaattttg ttaacagaac ccacttttca   6480
gtacagtgct accaatactg tagtgatttc ataccacatc ccaagaaaga aaaagatggc   6540
tcaatcccat gtgagctgag attatttggt tttattgtta aataaatagc attgtgtggt   6600
catcattaaa aaaggtagat gttaggaaag tagaaggaag aagactctca cctacatttt   6660
catcactgtt ttggtatctg ccagttgtca ccttggtccc cttccccgcc tctcccctgc   6720
ctcctcttcc tccttctcct ttttttggaa tacaattcag gtaccataaa atttacccttt  6780 ttagagtgtt tgactcaatg gttttttagta ttttcacatg ttgtgctatt actatcacta   6840
tataattcca ggtcattcac atcaccccccc aaagaaaccct tctaactatt agcagtccat  6900
tcccttcttc cctcagccccc tggcaaccac taatctactt actgtctcca tggatgttcc   6960
tatattgaat caagctagca taaacccccac ttgctcatgg tcataattct ttttttatagt  7020 gctaaattac atttgctaat attcaattaa ggatttctat gtccatattc ataaggaata   7080
ttggtgtgta gttttctctt tgtgtgatat cttttgtctgg ttgggggatc agagtaataa   7140
ttactgctct catagaatga attgagaagt gttccctcct tttctattta ttggaagagt   7200
ttgtgaagta tattggtatt gattcttctt taaacatttg gtcagattca ccagtgaagc   7260
catctgggcc atggctaatc tttgtgaaaa gttttttgat tactaattaa atctcttttaa  7320 tttgttatgg gtctgctcct cagacgttct agttcttctt gagtcagttt tgttcatttg   7380
tttcttccta ggactttctc cctttcattt ggattattta gattgatagt aatatccccc   7440
ttttaattcc tggctgtagt aatttgggtc ttttctcttt tttcttggtc agtttagcta   7500
aaggtttgta attgtattaa tcttttcaaa taactaactt ttttgttttg tttgttttt    7560 gttttttgtt ttttgttttt tgtttttttt tgcttttta ggctgcacct gaggcatatg   7620
gaagttctca ggctagaggt ctaatcggag ctacagctgc tggcctatac cacaaccata   7680
gcaatgccag attcaagctg catctgcgac ctacaccaca actcggccag ggatcacacc   7740 cgcaaccctca tggttcctag tcggatttgt taaccactgt gccacgacgg gaactcccgc   7800 ccatttttttt taacacctca tactttaaca taaagatggg cttcacatgg actgatagct   7860
```

```
caaatgagga aggtaagact atgaaagtaa tggaagaaat gtagactatt tttgtgacct    7920
agagattact gatacttctt gacttttcaa acaatacttc aaaagtacag cccaaaggga    7980
aaaaagaaag aaaaaagaaa cacacatata cacaaaccta gtgaataaga tatcatcgat    8040
acactacaga tttctatgaa ctggaagacc ccatggacaa agttaaagaa catatgatag    8100
tttgagtgat tattttgcaa tatttacaac caatgaggga atattatcca gcttatagga    8160
ggaagtaatg caaatcgaca agaaaaagat aggaaaccca atataaaaat taagaaaata    8220
caaaaattaa gaaaggatat gaactagcat tttacaaaag aaaaatctcc aaaagtcaat    8280
cagcacatga aaatatgctc aaacctatta attattagaa aactacagac tgaagcaatg    8340
aggtgcttta ctttacatct ttttgactga taaaaagtta gaaacaaagg tgatatcaaa    8400
tgtcagggat aaaaggatat agaaatcgtc atgcctgtgg tgggagtatg gccggtgcag    8460
tcatgtggga aggtaatctg acagtggtta ggcagagcag gtttatgaat acactgtggc    8520
ccatcaatcc cacgcctgtt tatgtaccaa agaaatcctg ttgtggcaga atctatgggt    8580
ccacccctgg gagcatgaat taataaaatg tggcaccagg gtgtgtgaaa ctccagctag    8640
agatgagatg tccacatggc aacatgaatg catcttagaa acatagattt gagtgaaaaa    8700
gagtaagaaa cagccgggaa acccaatacc atttataaaa attaaagatg cacacataca    8760
atgtagtaaa tattttgcat gaactttcaa atggttgcct acagggggg agagtaaaga    8820 agagtagaaa acaaagataa agggagtaag taagtagctc tgcctggact gaatataatg    8880
tgtcatgaac tgagaaatat ggttaacata atcctcttaa cttgaggtcc taaatgaatg    8940
aatgagtcca ctattcattt acccattctt taatgtgtat tgcattataa tccattttt    9000 tagaaccaac gaattttgtt cccataacta ctaatcagcc tgccttttct ccctcattcc    9060
cttatcagct caggggcatt cctagttttt caaacgttcc tcatttgaac caaaaatagc    9120
atcattgttt aaattatact tgttttcaaa tacgatgctt atatattcca agtgtgtttg    9180
cccatttcct taggtggtag aaatttttca ttctactttt ctatctactc agattttccc    9240
gttggaatta tttccattgc tattaaactt agaagtcccc cctgtgatat gccattttt    9300 tcatactttt taagcacttg gttgcttttc tttgtgtctt taagcaccta gaatacttat    9360
aaccattgca cagcactgtg tatcaggcag cccttcctct tccactaatt tatggtcctt    9420
ctcttagact atattaaact gttatttaat taggatcctc tcttcgtcct tatgatttaa    9480
ttattatagt tttctaatat gttttttatta taattcctct tcattattcc tccctattaa    9540
aaattttaat gaattccatt tgtttgttct tctagttaaa tattaagtca taatccaaat    9600
aacttagatg tcattagttt atgtggtcaa agtaaggata ccacatcttt atagatgcag    9660
gcagttggca gatgtcatga ttttcttcag tgcataaatg caatttatct ttgagcaagg    9720
ggcataaaaa cttttatggt attggctttg aaataatagt taagaactgc agactcagtt    9780
tttcctgctt tccttgaaaa agaacacttc taaagaagga aaatccttaa gcatggatat    9840
cgatgtaatt ttctgaaagt ctcctgtaat tccttgggat ttttgttgtt gtttgttggt    9900
cggttttttt gggttttttgt ttgtttgttt tgttttgttt tgtttttgctt ttagggctgc    9960 acctgtggca tatggaagtt cccaggctag gggtccaact ggagctacag ctgccagcct   10020
actccacagc cacagcaaca tgggatccta gctgcatctg tgacctaacc acagctcttg   10080
gtaatgccag attgttaacc cactgagcaa tgccagagat cgaatctgcc tcctcatgga   10140
cactagtcag attagtttct gctgagccac aatgggaatt cccaattcct tgtatttttg   10200
aactggttat gtgctagcat ataattttgt ttcttgaatc tttgtgggtt ttttttttt   10260
```

```
tttttttttg tctcttgtct ttttaaggct gcacccacag catatggagg ttcccaggct   10320
agaggtcaaa ttggagctac agctgccagc ctacacaaca actgcagcaa agtggggccc   10380
aacttatatg acagttcgtg gcaatgccgg attcctaacc cactgagcag ggccagggat   10440
cgaacctgag tttccagtca gtttcgttaa ccactgagcc atgatagtaa ctcctgtttg   10500
ttcagtcttg aacctccttt ttaattcttt attccttgag ggtgaaataa ttgccataat   10560
aatactatca tttattacat gccttctctg tgctaggcat agtgacactt taggatttat   10620
tatatcactt aatccctaca acaactctgc aaagtatgta tcataatcct atttgacaga   10680
tcaggaaatt gcagcccagg atgcagataa tatgcatcca tcacaagtga ctagatatag   10740
tccctctgct attcagcagg gtctcattgc ctttccattc caaatgcaat agtttgcatc   10800
tattgtatat gtgttttggg gttttttttgt ctttttttttt ttttttgtct tttctggggc   10860
ctcacccttg gcataggtag gttcccaggc taggggtcaa attgaagctg cagctgccag   10920
cctacaccac agccacagca actcgggatc tgagcctcat ctgcaaccta caccaaagct   10980
cacggcaaca ccggatcctt aacccactga gtgaggccag agatcaaacc ggcaaccctca  11040
tggttcctag tcggattcat taaccactga gccacgatgg gaactcccta aatgcaatag   11100
tttgctctat taaccccaaa ctcccagtcc atcccactcc ctcctcctcc ctcttggcaa   11160
ccacaagtct gttctccatg tccatgattt tctttttctgg ggaaagtttc atttgtgcca   11220
ttttttcattt tacgggtaat ttttacttca gtttcttcca ctagcagttg tcttaaagtg   11280
agtataatta atattcattt ggaaaatgta agcaaaacat ttttttaagg gccatgccca   11340
cagcatatga aagtttctgg gccagggggtt gaatccaggc tccaagttgc agctgtgccc   11400
tacactgcag ctgggcaatg ctggatcctt taacccactg tgcccggcta gggatcaaac   11460
ctgcatttcc acagctaccc gagccattgc agttggattc ttaacccact gcactacagt   11520
gggaactccc acaaaacatt ttttaatgtc ctttgaataa agtaggaaag tgctcgtctt   11580
tgagggcagg gcggcaatgc catttccaca aggtttgctt tggcttggga cctcatctgc   11640
tgtcatttag taatgaataa aattgctgac agtaatagga ttaactgtgt gtggagatag   11700
ccagggttag agataaaaac actggagaag tcaaataagt tgctcgaggt cctctagcta   11760
ataagctatt aagtgggaga gtgagggcta gaaacaggcc atctgtctcc caagcacatg   11820
tccattagtg gtttgctgat agccttccag aacaacagag aggactctca aacatggtct   11880
tgcctccctc caattgatcc cctccatgtg cctcacagcg ggtctttcta aaattaagtt   11940
ctgattttaa ttctcccttg ctatagcact taggtatggc tttcagccgt gcaataaaaa   12000
gcaggcaaga gtggctcaat catataggag gttgttttttc ttagatccca agcaggtaat   12060
cctgggcatt atggttgttc tgcgtttatc aaggagccaa attctctatc acctcctgtt   12120
ctatcctcct cagtatctgg ctctattctt cagcatctca agatggcttg tgctcctcca   12180
agcatggcag tcaaattcca cacaagaggg ggaaatatga agggcagaca gtgctggtct   12240
cctgagctgt ccctctttgt cggggaaata aatgtattcc ttcaagtccc gtgagacttc   12300
tgaagtagac gtctgcttac gtctcaccca ccagaactat gtaaactgca catagtgcta   12360
ggtctacata gccactcata actgccaggg ggtgggaaat cttttaaatag gtgtaccacc   12420
acacaattag gatgctaata gtaagggaga aggagagaat aggttttgcg caagccacca   12480
gcatgcctgc cacaattgct taaaattctt cattgacccc tcattgccac aggatgaaat   12540
ccaaacgcct tcttagttgg gaatctgacc tacctgtctc tcccacctgg ttcagacacc   12600
```

```
attctccttg gtcataaaat tccagtcatt tgtgaacatc cagctccccc atgcctccat    12660
gcctttgcac atgctgttct tttatctttt atgttgtcct tttatctttt atccaaaaga    12720
gatatcccat catcacatct cttttgtcag cccccaaata ctttgtcttt caagttcagc    12780
tggaggatta cctcctattt gaaatcagct ttgtctctta caaccaaaca aggttttcct    12840
tccgagacac tcccacagca ccttgaactc atctctatca atcattcatt tgattgtaat    12900
gaagttgttg gtggtatgcc tgtgtctctg acacatctgc gatctcatga gttccttaag    12960
tggaatgtga atagcgggat gaacagtatt ggtcttcagc cctcatctct gcagatgttg    13020
cttgacccaa atgagcgttg cctttatttt tgattttgct ttgatttgtc tactccatgt    13080
acttgagcca tgcatttctg tcttagcgat gctttttaaa agtcattttt tggttgatta    13140
tccagatttg tccacctttg cttctagttg tagaaaagga tgaagaaaat ggagttttgc    13200
ttctagaact aaatcctcct aacccgtggg attcagaacc cagatctcct gaagatttgg    13260
catttgggga agtgcaggta aggaaatgtt aaattgcaat attcttaaaa acacaaataa    13320
agctaacata tcaatttata tatatatata tatatatatt tttttttttt tttacatctt    13380
atattacctt gagtattctt ggaagtggct agttaggaca tataataaag ttattctgaa    13440 gtctttttt ttcttttcc atggtgagca gtggcttgat gtggatctca gctcccagac    13500
gaggcactga acctgagccg cagtggtgaa agcaccaagt tctagccact agaccaccag    13560
ggaactccct attctaaatt cttgagcaca ttatttagga acctcaggaa cttggcagga    13620
ttacaggaaa tatatctaga tttaaaaaaa aatcttttaa cagaggtccc aaaggagagt    13680
catgcacagc tatgggagga agttcagaaa ctgcccttgc taccagatca ctgtcagata    13740
aaatggccag ctacatgttt ctgcacattg ccctaagatc tttacaaact tttctgtgca    13800 ttttccact tttaaaagaa aatttcgggg ttcctgttgt tgctcagtgg ttaacgaacc    13860
caactagtat ccatggggac aggggttcga gccctggcct cactcagtgg gttaagaatc    13920
tggcattgct gtggctgtgg cgtaggctgg cggctacagc tcagattgga cccctagcct    13980
gagaacctcc atatgccgca ggtatggccc taaaaaaaaa aaaaagaga gagagagaat    14040 ttcctccaga aaaacactt tggtagtttg ggagaagtaa acaaccaaaa attaattttt    14100
ctggagtatt cgggaagctt gtaaaaatgg gctcttactt ttttgaggag acaaatggga    14160
acctacccag aagaggcaca atcacctgca tttgatttct tgacctctcc ctaccttctt    14220
tgctggcttt ccacatttgg atttctgtga ccttatctct gctccttggt gttttcattt    14280
ttcctgtgga cgtgccagac tatgggaagg gagtaaggcg ttgatttaga atcctgtagt    14340
ctctgcctgt ctctagtcat tgttttcacc cttctcaaag gaccttgaca tcctgagtga    14400
gtccgcaagt aatttagggg agaagcctta gaagccagtg cagccaggct acatgactgt    14460
gtccacccac tggaaccagt cattttata cctattcaca gcccccctac catttaaatc    14520
cccagaggtc tgccataaca tctgtaactc cctttcctgg taaattgtgt tctaaaagac    14580
tggtaacaaa agatattctg tggtacagag cataattaaa tacctgggag ctgatttgag    14640
tggggtaaat caactggttt gaccctaaa acccaccatg agcatttctg ttctaataaa    14700
gtaatgcccg tgctgggaat tgtgttctac ggaaatgctc ctgctgtgtc tttcttgagt    14760
cctgtgtcat tgaacatgct taggagcaaa ggtcccccat gtggcttgtc tgctaaccag    14820
cccagttcct tgttctggct ggtaatgatc cgatcatctg aatctcactg tcttccaaca    14880
gatcacgtac cttactcacg cctgcatgga cctcaagctg ggggacaaga gaatggtgtt    14940
cgacccttgg ttaatcggtc ctgctttgc gcgaggatgg tggttactac acgagcctcc    15000
```

```
atctgattgg ctggagaggc tgagccgcgc agacttaatt tacatcagtc acatgcactc   15060
agaccacctg aggtaaggaa gggtgagccc tcaactccga agaaaatgct gcaataaaag   15120
cactgttggt tttcagcttt ttttgtaatc actgctcatt ctgaggtaga ttcgcttggg   15180
ctgataaaaa gagaactaat tcagataaat gcttgcattt gcatagcctc ttttttaaa   15240 aactttttt ttttttttt tttttggct tttcagggct gaacctgtgg catatggagg   15300
ttcccaggct aggggtcgaa tcagagctgt agccccgggc ctatgccact gccatagcaa   15360
catgcatagc ctcctttta aagtgccttc ctgttttata ccattgggat gtgagaagag   15420
ctattgtgga aangagcatg gggtnataac cctggacctc tcacgtccta ccctcaggnt   15480
agtgggaaaa ctctgagttt aaggacatca aagtgactcc tttttagtta cattatgggng  15540 gaatcagcnc atattttac aagggcgga gngtaanctg ttggagttta caagacatat   15600
ggtggcattg caactactta accctactat tatagcacaa aagcagccat agtcggtcct   15660
gaaggagcct gatgccttca gctttatagg caatgacgtg tgaatatcac aaacagtttc   15720
ctgtgtcacc aaacatgatt gccttttgat ttcccttca accctttaaa aaaggtaaa   15780 agcccttctt agcattcagc agcaggtcgc tgtgttttgc caactcctga tctgtagcat   15840
ttcgacaaca ctgagctctc aactttgaa ccctgagtcc accacatcct tcagtgaaac   15900
cagagccatg tgatactaag gatagaaacg gaaacttcct gaatccaggc gatcaaatag   15960
gagggagaaa gaggaacttt cattgacaaa accacaaata ttgtgaatgg actgttacaa   16020
atattgtgaa tgctcctatt cccaaccccc tggcttcatt acagggtcct atgtgttcat   16080
ccttattgag aaatttgtat tgctactgcc aggttgccaa tacccagcgg tgcccatggt   16140
gttctaaaat gaagcaattt caactttatt tttttttcct gtgactttac atgacaagtt   16200
cacatgaagg atatactttg atagtaatgt ccatggttag ggaatataca ttgtttgctg   16260
gttgactggc ccctggattt ttctattgaa agtccatgag atctcgaagg cacaggtgtg   16320
ttctctcgct ttttaaggaa agggtttaaa aacttaagta attaacagct ttagtaacaa   16380
attacctata acacacttaa aaaccgaata ccacccactg gagtattgtg ctacgattaa   16440
aaatctactt gtctactaca tgatatcttt gtcccacaga aggttctgga accaaacttg   16500
taatttcagg attatgagag ccctgagttc acgcattgtg taataactat gttgtgtggt   16560
agtcaatttg tacagcttgc ttagagagaa caatgtcaag ttaaggaggc gattgcttta   16620
tagtgcctgt cacaagatgc cattgccatt gtcctagcaa gagatattct atgggagtat   16680
actacatttt agtgaggata agaactttt atggcattta gtccggtcat ttcccaacca   16740
ctgtcctgaa aaccaatttc attttgattt caggggcttg tgtgggcaaa gttgccaggc   16800
attaaaaagc cacttctcaa ctgtagtatc acaatgcttt agttgggtag tgtattgcag   16860
atagcttatg gctgaaaagt taccaagcct tgcagttttc actcctttga gtttatttcc   16920
ttgacagaat tgaccctgag ttttttgact cttacctgct caactaataa acaccagagt   16980
catttatctc cattgctctt gtctgacctt tatttaccga ataatgcctt atgggttcac   17040
aaaaacaagg ggggaggggg ccagcatgcc ttagaaactg tctttagtca agaaatgnga   17100
ttttattatg taaatatatg agtattataa tagatagtgt tattaataga caccagcaag   17160
aattgtcaat aatttaaaaa tcacaaatta aaatacatcc atgttagnat catttatcct   17220
aactcccaaa gcccttttaaa gtggaagatt tagatgttaa cccagagatt aaagacatgt   17280
tcaaagaatc cttgattttt ttttgaatcc cttgtttta gagaagaaaa cctaatgatt   17340
```

```
ttccccctct ggattctaca tattaaatat agttttggaa cttgaatatt agtatggtta    17400
ataagtgctg atatgctgat tttgtttata tttttcttat gagtaaatat cctatatcac    17460
cagacattat agtctatgta caaatatgat tcttaaacct gatagcacat tcattagagt    17520
tggaattgcc tttttttttt tttttttttac agttgcacct gcaacatatg aaagttccca    17580 ggctagggt tgaatccaag ctgcagctgc caccctacat tacagccgta gtaacagcag    17640
atccgagctg catctgcaac ctatgctgca gctcagggca atgccagatc cactgagtga    17700
agccagggat ggaacttgca tcctcataga gacaacgtcg tgtccttaac ccactgagcc    17760
agaacaggaa ctccagaatt tcctttcaat agaagaagca ccaagtttag gatcagaaag    17820
cctgaatttg aataccaatt tactatttgt tagtcatata tttctgagtg tgtttcctca    17880
tttattaaaa gcagactaaa agatgagagg gtcttttgtt gagaatcaaa tacaataaca    17940
tgtgaaagtg tgtaacacta tgattgaaat atacctacac agccatttat ttgtttattg    18000
ttcatgtttt gccacccaca cagtagtata taatcctttt atgtaataaa tgctaataat    18060
gaaagttggc aacttatgta agtactcaaa atgctggagg tcatgggata ctgactggga    18120
tactacagag gtaatgtcat ttcctctgcg ctaaacttat tgtcttgtag ttagggactg    18180
actctcttta ggacaaggag ttcattctgt ataccatgtg tggctatcac ccttcgaagt    18240
tgaaaaactg ccccagggtg ggcacccatc cgttctctta gatatatggc cgagaccttt    18300
ctctcactgg gagggaacca cactgaggaa tgagaaaaaa aaaggaaaa tcaagatgaa    18360 accagaaacc tctttggcat aacttctcca ctctgtactt tttgttagaa ctacccttgc    18420
acaaagcagc atcagtgtgg aagacagaat ttgcacacct ggtttgatat acatgccgtg    18480
gtatatggga tgttctaaca ataaagagga ctctcccagg aaatctcctc actgttatag    18540
tcagccttga ggaaagagct cttcttttgg actctgggga gagtctagtt tttcagttcc    18600
ttgcttctcg gtcaacgtgt tggtgtaagg atcacactct ctcttatact agataattct    18660 atttttttcac ctttcaacct gtctatcctt ctgaccctag ttacccaaca ctgaagaagc    18720
ttgctgagag aagaccagat gttcccattt atgttggcaa cacggaaaga cctgtatttt    18780
ggaatctgaa tcagagtggc gtccagttga ctaatatcaa tgtagtgcca tttggaatat    18840
ggcagcaggt ctgtgttctt tccacatgtt tgggttatcc tttctgggat aaatttgagg    18900
cgagatagaa actttaagac taaagaaaca atggcctact tttttttgtac atggtcctgt    18960 gtaaatctct atttgagctg aaataagatg gtcttcctct ccaattatcc atggtatgac    19020
tctgatggat aacaaatcca gttctgaaaa aaggggattt ctttccagaa gagaggacag    19080
tttcttcaaa tattgaatta aaagcaaaat agatgtaaac cgttgttggt tttattgttg    19140
aattccaggt agacaaaaat cttcgattca tgatcttgat ggatggcgtt catcctgaga    19200
tggacacttg cattattgtg gaatacaaag gtattttctt gccctcatca gcatgaaatt    19260
gctcttggta gaaaggataa taatagttat ccaaaacatc atcctatgtt catctgtttc    19320
ttccctcttc attttccata gagtacagta tattctatct ctgtcttagg aaaatggact    19380
gtcattcata taatcttaca gagaatcaat tagtaatgta ctctatgccg tgacaggtgc    19440
gaaggttttt tttgaaggca acagataaaa atatcctata tttcacctat tgtaatttcc    19500
ttaaaactga cattattgaa taaatgtttt actttcatct tgaatattat tatgttatgg    19560
aatcatacac tttaccccaa taatcatcga aaagaatttc caaaaggttg agagagttgt    19620
gttgatctga ttacttttcct ctgcatcctt tgagcttaac ctttgaatat agtttgctaa    19680
ggaaagtagt ctgtttatga tcctggagtg gaatcaggct aagtgtcctc attcagaacc    19740
```

```
cactgaatca gacagaatga atttatttcc ttgaaagttc aaaatgtgtc actcaagagt    19800
ataaattttc aaatcttact ctctcttttc cttggatgtg agcaattctt cgataattga    19860
atgaggcaga ttatatagac ttacatggaa gactgttggc ctgagaattc aaactatggt    19920
gttcaagact tcacngngag tccgatgcca tttgtttccc acaggtcata aaatactcaa    19980
tacagtggat tgcaccagac ccaatggagg aaggctgcct atgaaggttg cattaatgat    20040
gagtgatttt gctggaggag cttcaggctt tccaatgact ttcagtggtg gaaaatttac    20100
tggtaattct ttatatcaaa atgatgccaa ggagttggca tggcactttg ctaaatgctg    20160
tgtgaatcaa tacaaagata attaggacat ggttcttcct cacaagaggt gtgcaatctt    20220
attgggaaat catacttgca agtcacaaat atagactaaa gtttccagct gagaatatgc    20280
tgatggagca tgaaacacta aggagacagg gagaatctca ggaaaaatca agaataattt    20340
ggatcaaatg gattcctgac atagaacata gagctgatca gaaagagtct gacattggta    20400
atccaggctt aagtgctctt tgtatgtggt tcagaacaga gtgtgggcag cctgaggggg    20460
atacataccc ttgacctcgt ggaaagctca tacgggggag ggatgaggct aaggaagccc    20520
ctctaaagtg tgggattacg agaggttggg ggggtggtag ggaaaatagt ggtcaaagag    20580
tataaacttc cagttacaag atgaataaat tctaggggta taataacagc atggcactat    20640
agatagcata ttgtactata tactggaagt gctgagagta gatcttacat gttctaacca    20700
cacacacaca cacacacaca cacacaccac acacacacac cacacacaca cacgtgcaca    20760
caaacagaaa tggtaattat gtgaggtgat ggcggtgtta actaacttta ttgtggtcat    20820
catttagcca tacatgcatg tcatgaaatc accatgttgt acaccttaaa gttatgtaat    20880
actagatgtc agttatatct caaagctaga aaaaatgtgg ggaccaaggc agaagctctt    20940
ctgctctgtg tctaagggtg gttctggggc tgggatgggg aggatggtta agtggtatat    21000
ttttttcata cctttgctca gtactatcat tgtaagtgtt caatatatgt ctgcttaata    21060
aattaatgtt tttagtaagt aatctctgtt tagtaatgtg tcagaaatgc cctacttgca    21120
ataggaagaa aacctgtcca gtcccttcct ttttctgta agtctgatt cattgcctcc    21180 cagaatgcat caccatgtga gagatagagg gaaggtgctg tccttatggg gttaacagtg    21240
tgactaggga ggcaaaatat acctactaaa gggtggtagc ataattcagt tcttatgtga    21300
gtatgtgtat gtgtgtgagt atgtgcacat gcacatacat tttaaaaggt ctgtaatata    21360
ctaacatgtt catagtggtt acacctagct tataggtaac attttttccc ctgtatcctt    21420
gtttgtgttt atcaaatttt cataacagta atggtagaag gagtacctga catggtacca    21480
tacatgctng gncctgccta atttctcnat ttccttttatt gcccataccc ccattgcttg    21540
acaagcataa gtccatactg gcttgttttc gttcctcaga ctcagtacac catgtagctc    21600
catgccctgg gtctttgtat gtgctatttc tactgcttag agtgctattg ccctgaccca    21660
ccacgtggtc agcaacttct cttctgcgtc tgtgtctatg gtctatgatt ccagatgtca    21720
tcttcactaa ctaccttcct aatatgccct tccatcccac ccgtcctcat ccttaccca    21780 gccactctct atttggtggc tctgtttat tttcttccta gctcatcact ctttgaaatg    21840
aacttattta cttattcaat atttgcttct ttcactagaa tgaatgctcc atgagagcag    21900
ggacctgctt tatcttgctc gccactgtat tcacagtgcc tagaactacg tctggcacat    21960
agtaggtgct caataaatat cgatcaaatg aagaatgag caaacgaaca atgaacaac    22020 acgtgaggta ggcatcatga ttccatcaac agaggagaaa accagactta aagnaatgaa    22080
```

```
gtggnggagc tgcatttgat cttgactgac tccaacatcc atgctcttga ccactgtgca    22140
tctccagagt gtaatgaaca tactttactt ttatattcca ccaaaataac aaagccatgc    22200
ccatgttagt agagagttaa tcgacagtgc ccttaaaata tgcatgcacc cagggtacaa    22260
ctatgcatgc tgccctgtgt tttcagttgg atccaaatga attgccgtaa acaaagaggg    22320
gattcaatgt ctttgactag tttgggatat tttcctagta accaactttg caaaataaag    22380
ccactaatga caaggagctt tgttctactt ctgcatcact caactgtcaa tttttatctc    22440
ttgcaagact tctaatctac tagaactttt gtttttctgt gatttctgaa cagagaagac    22500
taatccaaac cctgtcattc cagaggaatg gaaagcccaa ttcattaaaa cagaaaggaa    22560
gaaactcctg aactacaagg ctcggctggt gaaggaccta caacccagaa tttactgccc    22620
ctttcctggg tatttcgtgg aatcccaccc agcagacaag tatggctgga tattttatat    22680
aacgtgttta cgcataagtt aatatatgct gaatgagtga tttagctgtg aaacaacatg    22740
aaatgagaaa gaatgattag taggggtctg gagcttattt taacaagcag cctgaaaaca    22800
gagagtatga ataaaaaaaa ttaaatacaa gagtgtgcta ttaccaatta tgtataatag    22860
tcttgtacat ctaacttcaa ttccaatcac tatatgctta tactaaaaaa cgaagtatag    22920
agtcaacctt ctttgactaa cagctcttcc ctagtcaggg acattagctc aagtatagtc    22980 tttattttc ctggggtaag aaaagaagga ttgggaagta ggaatgcaaa gaaataaaaa    23040
ataattctgt cattgttcaa ataagaatgt catctgaaaa taaactgcct tacatgggaa    23100
tgctcttatt tgtcaggtat attaaggaaa caaacatcaa aaatgaccca aatgaactca    23160
acaatcttat caagaagaat tctgaggtgg taacctggac cccaagacct ggagccactc    23220
ttgatctggg taggatgcta aaggacccaa cagacaggtt tgacttgaat atttacaggg    23280
aacaaaaatg atttctgaat ttttttcatgt ttatgagaaa ataaagggca tacctatggc    23340
ctcttggcag gtccctgttt gtaggaatat taagttttc ttgactagca tcctgagctt    23400
gtcatgcatt aagatctaca caccaccctt taaagtggga gtcttactgt ataaaataaa    23460
ctattaaata agtatctttc aactctgggg tgggggggga gactgagttt ttcacagtc    23520 ctatataata atttcttat cctataaaat aattaggagt tcccgtagtg gctcagcaat    23580
agcaaacccg actagtatcg atgaggatgc gggttcgatt cctggccccc ctcagtgggt    23640
taaggatctg gcattgccgt gagctgtggt gtaggtggca gacacggctc agatcccacg    23700
ttactgtggc tgtggcatag gccagcagct ccagctctga ttagaccctt agcctgggaa    23760
cttccatatg ctgtgggtgt ggccttgaaa aaaataaat aataagata attactcaaa    23820 tgttttcctt gtctcagaac cttacttcag gataaagagt gagaaagttt tttttatgaa    23880
gggccattat tacagctcaa aaataagttg tcttcagcaa gtagaaagca ataagcctga    23940
gagttagtgt tcctatcagt gtaaatatta cctcctcgcc aatccccaga cagtccattt    24000
gaacaattaa cggtgccctg ggagtacagt tcagaaacat taatgtggat gttccagacc    24060 tgtatttta taagtacttg tcttgagccg gatggaacca tcattcctca ccattattta    24120
gaagtggact gtgactctgt tggagatcag ggcacacggt taccaaaagc acacccttct    24180
cctggcctta cctttgcaaa gctggggtct gggacacagt cagctgatta taccctttta    24240
ctaacttccc acagctcaaa tctggtcaat ctccttcac aaatctctta aaatccatc    24300 actcacctcc agcctcttct gctgtggcct tgattcagcc tctcacaatt tttttttaac    24360
cagaattctg gcagtggccc ctgacttgcc tctgtgctcc cagccccgct gtcctctgat    24420
ccatcctcca tgccagcctt tttcaatctg ctggtcacga ttcattgatg ggttaggaaa    24480
```

```
tcaatggcat cacaactagc atttagaaaa aggaaatagg cgttcccgcc gtggcacagc   24540
agaaataaat ccgactagga accataaggt tgcgggttca acccctggcc ttgttcagtg   24600
ggttaaggat ccggcattgc cgtgggctgt tttgtaagtc acagacatgg ctctgatccg   24660
gcattgctgt ggctctggcg taggcctgca gcatcagctc caattagacc cctatcctgg   24720
gagcctccat atgctgcaag tgcagcccta aaaaaataa aaaataaaa aaaataaat      24780 aaagaagta gacaaattgt atagaacaac cctgagtatg ttgcctgagc acatataaca    24840
agggtaagta ttatttcagg aaactctggt ttcacagata ctcttggcat atggacccct   24900
agagtcctga tgtaaaatat attcttcctg ggatcttagg caagaagttt gaaagctcca   24960
actctgcact gctgccaaag aaatgatttt taagtgcaaa actcttcccg ttcccttccc   25020
tgtataaaat tccataggat ctctccagtg cctctaggat aaaggcagtt ttcattctct   25080
agttcaaggt gagagaagat tttaattatt tcacgtttta gtggggaatt caagagtctg   25140
gcacctgaca tttgctgaac tctctccatt atccctctct agttcccccag acgcatccta  25200 tggtagaaat tcgcaaacta gagtgagcgt cagagtaacc caaggaaact gggtaaatgc   25260
agctccctgg gctctacccc ctgagattct gattcagtag atctgaagca gagccctgga   25320
atatgcatat gcatcattgt gtcacaccaa gcattctggg taatgagagt tgatgttagg   25380
ttctcagtag taagacaagt atagagattc cgggggactg agtgctcagc tctgccttgg   25440
ggaggaggga gagggctaaa gagaacagga gatggggaca gggaatgctc aacctccaat   25500
cttaggcatt tgagctatgt cttaggggtc aggaggaggt taccaatata gtgattaaga   25560
gattgaggtt ccagtcagag ggatatgctg gagaagggggg gtgaaaataa tgtcataggt  25620
ttggtgagtg cagatacttt gagtttttta atatttttat tgaaatatag ttgatttaca   25680
atgctcttag tgagtacaat tactttgaat aagtgcatag atgtatgcca ttcttccaga   25740
aatgatttat tgagctcctt tgggcatcat gctaagtaca ggggaaacag ctgtgaagag   25800
gtccttccct tatgaagtca ttcatcccct tcagtaaatg aaggtaaagg aaaaggatga   25860
gacagggacg ccgtgttgga ccagggtcag aaaggcctta taagaccttg cctggagggc   25920
aaggaacttg cctgtgagta aggagagctt gagaaagcga taaagcaaag aaggaacatt   25980
actgcattgt gttttagaaa aaccatgtcc tggggaagaa ctcctagagt caggggggcc   26040
agttgggaga ctgtgctttt ttccaggagg agataagtga ggctgctggc tgagatggag   26100
caaggattta gagaagcaga tatgagattc atttagaagt tagacatttt aggatctgac   26160
acataattta tcaccaaaac cagtgcatct ctggctttgg gccaccagtt ttggagaagt   26220
ggaatgtagg gacctaccat tacctgccaa tctttactac acagatgcct atttccctcc   26280
tcatatttcc tttctccaga tcacgtccta ttctattgcc aggactcaag attccaccttt  26340 gcatgcagtg atccatcttc acactggatg gacagctcta gggatgtcag agcacactct   26400
tgtccatact gctgactggg tctcctgtca gcccatctgt ctatcagctg tggtattatt   26460
agtataataa gagggctgta tatgagagac acaaaattct aggtgtagct caaagatagg   26520
ctagagttat tcctatgtac aacaaatatt tatgggaccc cttctgtgta ctgtcatggt   26580
tgctgctttc atcatacttg tagtctaatg gaggtggggg cagggcagga ataagcggat   26640
gtccacaaaa tcagtaagac cacttatatt caacattttc ataatttagt tatttgagcc   26700
caaagggtcc acatccgtgg tattccaact ttttttccc cggacatgga tctttatctt    26760
tttttttttt tcttttttgc ggccagacct gcggcatatg gaagttccca ggccagggt    26820
```

```
tgaatgggag ttgcagctgc ctggtctaca ccacagccac agcaaggtgg gatctgagct   26880
gcatctgtga catacaccgc agctgaggta acaccagatt ctgaacccac tgaatgaggc   26940
cagggatgga acccgtctcc ttatgaacac tatgtcatgt tcttcaccct ctgagccaca   27000
acgggaactc cagacttcgt ctttaaatgt attctgactt ggagagctat cacactaagc   27060
aattaacagg agctgacctg gtttaggctg gggtggggcc ctactcctca atgttccctg   27120
aggcacatct gtgggacccc tgggcatcat ctatctgagc agccttagag ctgctcatcc   27180
agttgactgt tgatgtagaa gtgcaaactt ctgccttcct tatttgttgc tttctttttt   27240
cattgttctc tcccctttgt gtctttaagc aagggcatcg tagagcctcc agaagggact   27300
aagatttaca aggattcctg ggattttggc ccatatttga atatcttgaa tgctgctata   27360
ggagatgaaa tatttcgtca ctcatcctgg ataaaagaat acttcacttg ggctggattt   27420
aaggattata acctggtggt cagggtatgc tatgaagtta ttatttgttt ttgttttctt   27480
gtattacaga gctatatgaa aacctcttag tattccagtt ggtttctcaa taagcattca   27540
ttgagcctta ctgactgtca gacggagggc gtattggact atgtgctgaa acaatccttt   27600
gttgaaaatg tagggaatgt tgaaaatgta gggaatgaaa tgtagatcca gctctgtttc   27660
tcttttggag gattctttt cctccatcac cgtgtcttgg ttcttgtttg ttttgggttt    27720
ttgtgggtgt tgtattgtgt tgtgttggtt atggcagtga cagctattta aactgtgaaa   27780
cgggggagtt cccgtcgtgg cgcagtggtt aacgaatccg actgggaacc atgaggttgc   27840
gggttcggtc cctgcccttg ctcagtgggt taacgatccg cgttgccgt gagctgtggt     27900 gtaggttgca gacacggctc ggatcccgcg ttgctgtggc tctagcgtag gccagcggct   27960
acagctccga ttggaccct agcctgggaa cctccatatg ccgcaggagc ggcccaaaga    28020
aatagcaaaa agacaaaata aataaataaa taaataagta agtaaaataa actgtgaaac   28080
ggggagttcc cttcatggct cagcagttaa caaacccagc taggatccat gaggatgtag   28140
gttcgatccc tggccttgct cagtgggtta agaatccagc gttgctgtga gctgtgatgt   28200
aggtcgcaga tgcagcccag atcctgcatt gctgtggctg tggcgtaggc tggcagctga   28260
agctccgatt caaccctag cctgggaaca tccatatgct gcaggtgtgg ccttaagagg    28320
caaaaaaata aaaaaataaa aataaataaa attgtgggac agacaggtgg ctccactgca   28380
gagctggtgt cctgtagcag cctggaagca ggtaaggtaa ggactgcagc tgggtaagga   28440
ctgaattgca ccaactggga agtaagccta gatctagaac ttaagttagc cctgacatag   28500
acacacagag ctcaccagct aagtggttca gcttataagc tggtcactga aactgaggat   28560
gtccacaaaa gcaaaataag tagcaacagg cagcgggatg caagagaaag aggaggccta   28620
aaatggtctg ggaatccctg ccataccat attttatcct acttatattt agtgcctgaa     28680
tgtgtgcctg gagagcaaag tttagggaaa gcatcgggaa atgcacagta ttcataccct   28740
taggaacaaa gatcagttac ctccagggta aagactattt ccaagtttaa atttcaaccc   28800
ctgaacatta gtactgggta ccaggcaaca cttgccatcc tcaaaatcaa tgaatcctaa   28860
aattcaacct gggggtcagt gacagtctgt gacaaagttt ttgctggtca gtaacgaaat   28920
aagtatgagc accatctgag tatggtcacc aagatgtcaa ctctctttcc tttggacgaa   28980
ttgtcattat tccaagatta ggtccttct attttttgagg tgtgaaaaca tctttccttt   29040
cataaaataa aaggatagta ggtggaagaa tttttttgt ttttttggtct tttgctatt     29100 tctttgggcc gcttctgcag catatggagg ttcccaggcc aggggtcgaa tcggagcttt   29160
agccaccggc ccacgccaga gccacagcaa cacgggatcc aagccgcatc tgcagcctac   29220
```

```
accacagctc acggcaatgc cggatcgtta acccactgag caagggcagg gaccgaaccc   29280
gcaacctcat ggttcctagt cggattcgtt aaccactgcg ccacgacggg aactcctaat   29340
gatactcttt tatatttagc tactatgtga tgatgagaaa cagtccacat tttattattt   29400
tttagccaat ttgatatctc attactaaga taatgataat tttctctata aattttattt   29460
aagttagtgt tatgaagtgg ttttgctagt gtagaaggct aggatttgaa ttcagttcaa   29520
gaaagaagag agggagggag ggagagggat gggtagaggg atgggcagt gggagagagc   29580
aaagaggaga gacagttttt gtattaattc tgcttcattg ctatcattta agggcacttg   29640
ggtcttgcac attctagaat tttctaagga ccttgaccgc cagattgata tgcttcttcc   29700
ctttaccatg ttgtcatttg aacagatgat tgagacagat gaggacttca gcccttttgcc  29760
tggaggatat gactatttgg ttgactttct ggatttatcc tttccaaaag aaagaccaag   29820
ccgggaacat ccatatgagg aagtaagcag gaataccagt ggaagtgccc ctttcttcct   29880
tccttcctaa ataaactttt ttattttgga acaactttag agttacagaa aagttgcaaa   29940
gatattatag acagtagtgt ttatatatat atataaattt ttttttgctt tttatgacca   30000
cacctgtggc atatggaggt tcccagtcta ggggttgaat tggagctaca gctgccagtc   30060
tgtgccataa ccacagcaat gcaggatctg ggccacgtct gtgacctaca ccaaagctca   30120
cagctggatt cttaacccac tgagcaaggc cagggattga acctgcatcc tcgtggttcc   30180
tagttggatt cgtttccgct ttgccgcaat gggaactcca aattattgtt aatatcttac   30240
tttactgggg tacatttgtt acaaccaata ctctgatact gaaacattac tgttaactcc   30300
gtacttgctt cttttttgagt catttgcaaa gactggcttc ttgacctgct tccttccaaa   30360
cagctggcct gccatgctg ttctcagacc tgcaagcact gatctctgcc ccccttgcct   30420
tctctccagt ggtgtctcct tccccaaaca aacccagtgt ggctctggaa agggagttaa   30480
gtcaacataa accaacacat attttgttga gctccaattt tgagcaaatc cctcacctac   30540
ggcagacagg catgatgtta agaactaggg ctttggacac aaggtcaaga ccaagaaggg   30600
ttcctcaccc ctactgattc agataaccaa taatgaggct ttgaatccct gtccaaaggt   30660
tgtttttttt cccttctatt gagcttcttg ccaccttatc agttttttttt atgacagtca   30720
aatgacatga tatatgtgag catacatggt aattttttaat tctatataaa tgaatcacta   30780
aataaattag gaggatatat agtccacctt taagcgtatt acacgtgtca catgaatgtg   30840
tggcgactta attgtagagg tttaaatgta gcttcctata atagatgtgt tcctaaacta   30900
cattttaatc attggacttg tattttttatg ttagcacttg ctgttgaaga aaagcctatg   30960
ccaaaagttc agtgaaacca ataatccact gccagctttc tgagttaaaa aaaatccctg   31020
ggttttcaca cacaggaaca ccctgtgtga aacactcatt tagagcaaaa tgcatctgat   31080
aaggagttcc tgttgtgcct caactggtta aggacctgac attctccatg agaatgtgag   31140
tttgatcccc ggccccactc gatgggttaa ggatctggtg ttgccacaaa ctgcagctcc   31200
gattcatctc ctagcctaga aacttccaca gcccagaata tgccacagaa ttcggctgtt   31260
taaaaaaaaa aagaaaaaaa aaagaatcat aaatgtgttg gtttgttcac caaatacatg   31320
ataacttgct cttgccaagc tcagcttcat aaatattaag tcatttaata cagcagccac   31380
cttatgaaca gatattacta tacttcccat ttacagataa ggaaaatgcc atatttaacc   31440
aagagattaa ataactttcc cgaggtctta tagcaagtaa atcatggtgc aggggtttga   31500
ccacacgcag tctatctcca gagtctgtgt atttagccac tgttttactt tcaaatttaa   31560
```

```
atttataaaa cttctaaatt atctgttaac cataatcttt ggaattttta aaaccacgag  31620
ttcctataaa atgtttcatt gaaagtaagt cacttttcca tagcttttga taatacatct  31680
gtaggataaa gtaagccaca gctctcttgc agacttggta caccctgggg caaagcatca  31740
tgcctgtcac gtacatggtg gtccttactt tgactctcag tgcttttatt gcccaggaat  31800
tttgtgagat ttctagttgt tgaggtttgt ttaaagaggt tatgccggta cttggaagag  31860
ctcttttctt gctacctgga gccttctcat atttcctttt tgaggaggga catgaattgc  31920
ctttcaaact cataaatata ttttctagta cacaagtctc catcttcctt agacgcatgg  31980
ctcctggagt tctccatcct cctgctccac tttgggtggg ctcctctctg ggtctgccac  32040
caatctgcca cccagagaca tccttgaccc acttccagac ccaccatgg cttcactttc  32100
ttcgctttcc tcctttgtgg aaccttctgc ttaagaatct gaggaagaaa atttgcacgt  32160
gagctaaact ggaggtactt tcctgcctgg tcttgcacga tagcttggct gagcccatga  32220
tgctgggtgg ctgttacttt ccatggacac ccgaaggcgt tgctcctttg gcttctagtt  32280
gcatgcagtg ttgcttatcc caggctgatc tttcttccac tgtaggtgac ttttaagaat  32340
taagggatta atctatatct acaacaacaa caacaaagac ctttttcaagc tgaggtaggg  32400
ctttctgtat atgtttggag tggttatcca gcagacttta cttgaaggca ggggtcatat  32460
cctcaagtgc tcataaacgg accacagaaa gatctcataa ttgggtggag ctgggtgggg  32520
accgtgtcat gtggccagga aatgccagat gggaagggag tggcccttac tgagctccag  32580
ctgaactctg aattttctag aaaactcaga aatctggatt tttcatgtgt aatacccaga  32640
tttatagatg tggaaagcta attctttttt tttttaaggg actataggca atgaactaag  32700
atctaggttg tatttggaca aggggtcatc agtttaagct gtgtagttga gcgctcagct  32760
attgggctga gggacccta aatactgaga cggggaggtc cttgctctgg ggcatcacaa  32820
gtacactccc tggtctcatt caaacacttt tcctacaaaa ttgatcccat ttcttcagtg  32880
cactgtctga atgcatttgg cccagagccg tgctgaggca tagggaaggg gtccacggtt  32940
tcatggcatc gttttgtgct gtgtgtccct gctgtcgtcc aggataccta cctctcctcc  33000
tcctgcatct gaatgtcccc ccacagactc tctgggattc tacagcctct ggcctgttcc  33060
tcagacacct cttacctgcc agcttttccag attcacatta gttagtccaa atctactgcc  33120
gtcagtgact cacttcattt cttcttctcc gaggcagttc agcccggtac agttgttttg  33180
tcaacacttc agttgagtct ggaagatgtg catgggttat gcacgagagc ggtccatcat  33240
tttgagctag aagtcctttc tcagcccaga gacaagtcct catctccttt acttcctgac  33300
tcttcttcct ctgcatcctt ccaagatatc tctttctcca gccaccacct aaatctcttc  33360
ttttcccggg gttccgtgct caaccccactc ttcttcttaa atctgtggct gggtgaacgc  33420
atctgctggc accacttctc tgctaaagac tccaaaaatc cataggtcct gcccggcctt  33480
tgcccacctc tctccaacac tgtccagctt tagatgtaga gctaatcccc ccagagatat  33540
cattccctgg atgtctaagt cctttggtat ctcactttca gcgtgttcaa atcctcttat  33600
caactgttct ttctccttt ccatcttgat tattggcaac atgccagcct ttcccctacc  33660
cccagcagtg agccaagcta gaaacaaggg cttaatcttc aatctttcct tctccatccc  33720
taaacctaat gagtctccaa gcccttccca gtttacaccc taaatgttgc tcaaaacatc  33780
ccctagttct tccacgtgct ctcctctata ttgaaaggtc aagaaaggcc atcttccctc  33840
cactgtgagg aaatagatct tgatactgcc cctgagctgg gcagtcctcg acctgacaaa  33900
ctgtgcagtg tttctaaatc tctactggca aaatgagagt gcctttgacc tgtgttgcga  33960
```

```
tctcagatca cagtggatgt aattgtttta taggaatggt gaacgaaaaa gaagtaaatc   34020
cctaatgcca aactcctgat cattctatgt catttaatag cctgtcattt atgataaagt   34080
ttcctctact ggcattagca caatacttct caggaaaaaa aaatatgatg ccagatactg   34140
aaaagctcct gggtaaacat gaacatgggt accgataaaa tggtgaagcc agtccaatct   34200
tagagtgact tcccttcatg ctacttcatg ctcttttttt ttttttttttt taagaaaaac   34260 ccctttttt tttctcacac cagtcacaga ggagaccgag gcttagcaag gttaaggtca   34320
catgattagt aagtgctggg ctgaaactca aaccatctc tgcttgtctc ctaaccctgt   34380
gcacctctga ctattcaaca gatcctgtgt caggagttgg gattctttga aggtaagggc   34440
cttgaccacc gaattaaggt aatcttgctc tgtggcaggc cttgttttca gtattttaag   34500
tacactggct caggtaatcc tcacaacagc cccaggagga atgttctatt acctccactg   34560
tatagatgag gaacttgagg cacagaatgg ttgccaaggt cacacagcta tattgggggt   34620
tcatacccag ccatccaact ctgtctgtac tctctgccac tctgcacccc cagctcctga   34680
tccacttcct gtttccatcc ctcgatttct gctgcactca ggggcccctc tcccctcgg   34740 cctgtgagat ctgcttcagt aggcttttct ccctgactcc tccatccctg tccttacagg   34800
cagctgcttc tctccgggac acgagggggtc catacggaca ctctctactg gctgggttgc   34860
gcctaactcg tgattcctcc tctgtttcag attcggagcc gggttgatgt catcagacac   34920
gtggtaaaga atggtctgct ctgggatgac ttgtacatag gattccaaac ccggcttcag   34980
cgggatcctg atatatacca tcatctgtaa gtccgaaaat gcctgtcgtg tgtgccttag   35040
gctgctgcgg aggaggccag ggctatataa gcagagtcag tgactgactg tgccctgcag   35100
tgttgatggc catggagatt ccaccgttag agctttttc tttgttaacc ttgaaggcaa   35160
atctggttag gaagataact ttcaaagagt caccatctgg acattcatgc ccatgtgctt   35220
caatcctgta tacaagcagt ttagagtaca gggaagggaa ggacattatg aaagggagag   35280
ggtgtgtttg gatccagcag ctccatcctc agaatttatc tgaagacact gcaaaattac   35340
taagaatcac tatgacaaga atgaggatgg ggtgatatgg caaagttgtg atcctggaag   35400
accttcatct cccatgttgc ccaactctga acatgaattt ggtgaactag ttggttaagg   35460
ggatgatcct ccaagtttct ccctggttga gctccaaaaa ccatgtaagt ttctcatagc   35520
aaaaccgtat aggtccttag ggctttagtt ggaatatttg tgctgaaatg ctggaaagcc   35580
ccatttgcca ttttttgtatt tgcaaaataa tcatcaagag gggagaatgc attctttcat   35640
gaccactgac cctctgaaaa ggtcaggaat ttagtctgaa gtaggcaagc ctcctacccc   35700
gcttctgcca tgagcttgca cgcacaggcc tgtcttgaca tttcttcttt atagatttct   35760
ttttgaatat cttgaaattg ctttaaaaat atttaaagaa tgtagaatta tataaaataa   35820
aaaggaaata accccacacc tcccacaaaa ccctgtttcc tgcctttctc cacccactct   35880
ccagggtaac acttggtaac agcatagttg tatcacccca ggcctatttt tgagcatatc   35940
agcatttcaa gaaatgtatt ttttctcaat aaaacatccc ttatagttga ggagggagg   36000 ttatcattcc tgggttttgt ttttttttt tttttaatgt aatcctggta catcggtaat   36060
ttgcattttt tattcattaa tatctttggt atttctagtg ttgggacaca caggtcaacc   36120 tcagttttttg ggtttttttt tttgtctttt tgtctttcta gggccacacc tgcagcatat   36180
ggacgttccc aagctaggag tctaatcaga gctgtagcca ccagcctacg tcatagccat   36240
agcaacgtca gatccaagcc gtgtctgtga cctacaagca cagctcatgg caacaccgga   36300
```

```
tccttaacca ctgaacgagg ccaggggatc gaacacacat cctcatggat cctagtcatg   36360
ttcattaacc actgagtcat gatgggaact ccaacttcaa ctatttaat gtctgtaaaa    36420 cattccattt ggaaaccatt tcatttgtaa agcaaaatga aaacattttg ttcattttca   36480
acagagttcg tagctgactt ctgttctgga aaaaggaaa tggagcaaat ttgagtgaga    36540
aagattcaaa gataactttt cttttaaaaa aaattatatc ttggaaactt ctgggctatt   36600
gattctgaag actattttc tatatactgt tttgatagca aagttcataa atgtgaaagg    36660
atcctgcgat gaatcttggg aagcagtcat agcccaatat atctttgttg cttttaaaat   36720
gagatttagt ttactaaata tttttctgat cataaaaata acacgatct accgcagaaa    36780 atttggaaaa aaaaaaactt ttaaattcaa aaaacagtta aaccacaaat gatcccacca   36840
tccagagagc aatttgtact ttggtgtcta gttcatcttt cttttctgt ttacaagcac    36900 atataccaca agcatttttt caaaaatga aatgggata atactataca tacgtctgta    36960
cacctgcata gttactgaac agtctttgat ctaccctgta agtttctaac ttttcattat   37020
ttgaaatgat gttttggcaa agaaatatgt aggtgtgtct cgcacactt cataatgatt    37080 tcttaggata aatttcttag gataaattca taatgatttc ttataataat ccatactctg   37140
ccaactgatc ttcagggaag ccaactcgcc ttctcagaaa taacatataa cccatttact   37200
tgccctctca ccaatactag gtcctaatgt ttttgtgtac agattctata ttttacata    37260 caagaattcc ttaaagcaag gcatgtcaca gaaaaataga aggaagacac aattgtcatg   37320
tttaaggact gcattctgta ccaaaaatgc taagttaaat gaacatctga acagtacag    37380 aaacgctatc tttcagggaa agctgagtac caggtactga acagattttg gcaaatacag   37440
caggcatgga tgtttccaaa acatgttttt ctactttatc tcttacaggt tttggaatca   37500
ttttcaaata aaactccccc tcacaccacc tgactggaag tccttcctga tgtgctctgg   37560
gtagagagga cctgagctgt cccaggtaaa gcatcctgca ggtctgggag acactcttat   37620
tctccagccc atcacactgt gtttggcatc agaattaagc aggcactatg cctatcagaa   37680
aacctgactt tgggggaat gaaagaagct aacattacaa gaatgtctgt gttaaaaat     37740 aagtcaataa gggagttccc atcgtggctc agtggtaacg aaccctacta gtatccattg   37800
aggacacagg ttcaatatct ggcctcactc agtcggctaa ggatccagtg atgccgtgag   37860
ctgcagtgta ggccacagac gtggctcaga tctggtgctg ctgtggctat ggtgtaggcc   37920 ggcccctgt aactccaatt cgaccccctag gctgggaacc taaaagacc ccaaaaaagt    37980 cgctttaatg aatagtgaat acatccagcc caaagtccac agactctttg gtctggttgt   38040
ggcaaacata cagccagtta acaaacaaga caaaaattat cctaggtggt cagtggggt    38100 tcagagctga atcctgaaca ctggaaggaa acagcaacc aaatccaaat actgtatggt    38160
tttgcttata tgtagaatct aaattcaaag caaatgagca aaccaattga aacagttatg   38220
gaagacaagc aggtggttgt cagggggag ataaggggag gcaggaaaga cctgggcgag    38280
ggagattaag aggtaccaac tttcagttgc aaaacaaatg agtcaccagt atgaaatgtg   38340
caatgtggga aatacaggcc ataactttat aatctctttt ttttttttgt ctttttgcc    38400 ttttctaagg ctgctcccgt ggcatatgga ggttcccagg ctaggagtcc aaacagagct   38460
gtagctgcca gcctacacca gagccacagc aacacgggaa ccttaacccg ctgagcaagg   38520
ccagggatcg aacccgagtc ctcacagatg ccagtagggt tcattaacca ctgagccacg   38580
acaggaattc cagggtctgt tgtgttctta aaacacttcc aggagagtga gtggtatgtc   38640
ataagtaaac aataaatgtt aaccacaaca agcttatgaa ataaacagga aagccatatg   38700
```

| | |
|---|---|
| acctacaatc agtcattggg agaatccaca aaaggttgag cagaggatca attccagctc | 38760 |
| acactccagt tttagattct cccctgcctt aaagcatcac agactacata atctgagctg | 38820 |
| aagaataaaa attaaaactc accccagtgc aaaacagaaa tgaaaaagta ttaaaacgag | 38880 |
| gttcatactg ttgttcatta gcaatatctt ttattcacag gggtgcccaa caacatgaaa | 38940 |
| aaatcaagaa tttattgctg ctacgtcaaa gcttatacca gagattatgc cttatagaca | 39000 |
| ttagcaatgg ataattatat gttgcacttg tgaaatgtgc acatatcctg tttatgaatc | 39060 |
| accacatagc cagattatca atattttact tatttcgtaa aaaatccaca attttccata | 39120 |
| acagaatcaa cgtgtgcaat aggaacaaga ttgctatgga aaacgagggt aacaggagga | 39180 |
| gatattaatc caagcataga agaaatagac aaatgagggg ccataagggg aatataggg | 39239 |

<210> SEQ ID NO 49
<211> LENGTH: 14929
<212> TYPE: DNA
<213> ORGANISM: Porcine

<400> SEQUENCE: 49

| | |
|---|---|
| tctaatgcct tgtggaagca aatgagccac agaagctgaa ggaaaaacca ccattctttc | 60 |
| ttaatacctg gagagaggca acgacagact atgagcaggc aagtgagagg gggctttagc | 120 |
| tgtcagggaa ggcggagata aaccctttgat gggtaggatg ccattgaaa ggaggggaga | 180 |
| aatttgcccc agcaggtagc caccaagctt ggggacttgg agggagggct ttcaaacgta | 240 |
| ttttcataaa aaagacctgt ggagctgtca atgctcaggg attctctctt aaaatctaac | 300 |
| agtattaatc tgctaaaaca tttgcctttt catagcatcg aacaaacgac ggagatcctg | 360 |
| ttgtgcctct cacctgccga agctgccaat ctcaaggaag gaatcaattt tgttcgaaat | 420 |
| aagagcactg gcaaggatta catcttattt aagaataaga gccgcctgaa ggcatgtaag | 480 |
| aacatgtgca agcaccaagg aggcctcttc attaaagaca ttgaggatct aaatggaagg | 540 |
| tactgagaat cctttgcttt ctccctggcg atcctttctc ccaattaggt ttggcaggaa | 600 |
| atgtgctcat tgagaaattt taaatgatcc aatcaacatg ctatttcccc cagcacatgc | 660 |
| ctaacttttt cttaagctcc tttacggcag ctctctgatt ttgatttatg accttgactt | 720 |
| aatttcccat cctctctgaa gaactattgt ttaaaatgta ttcctagttg ataaacagtg | 780 |
| aaacttctaa ggcacatgtg tgtgtgtgtg tgtgtgtgtg tgtgtttacc agcttttata | 840 |
| ttcaaagact caagcctctt ttggatttcc tttcctgctc tctcagaagt gtgtgtgtga | 900 |
| ggtgagtgct tgtccaaaca ctgccctaga acagagagac tttccctgat gaaaacccga | 960 |
| aaaatggcag agctctagct gcacctggcc tcaacagcgg ctcttctgat catttcttgg | 1020 |
| aagaacgagt gctggtaccc cttttcccca gccccttgat taaacctgca tatcgcttgc | 1080 |
| ctccccatct caggagcaat tctaggaggg agggtgggct ttcttttcag gattgacaaa | 1140 |
| gctacccagc ttgcaaacca gggggatctg gggggggggt ttgcacctga tgctccccca | 1200 |
| ctgataatga atgagggatt gaccccatct ttttcaagctt tgcttcagcc taacttgact | 1260 |
| ctcgtagtgt ttcagccgtt tccatattag gcttgtcttc caccgtgtcg tgtcgtcaat | 1320 |
| cttatttctc aggtcatctg tgggcagttt agtgcgaatg gactcagagg taactggtag | 1380 |
| ctgtccaaga gctccctgct ctaactgtat agaagatcac cacccaagtc tggaatcttc | 1440 |
| ttacactggc ccacagactt gcatcactgc atacttagct tcagggccca gctcccaggt | 1500 |
| ttacactggc ccacagactt gcatcactgc atacttagct tcagggccca gctcccaggt | 1500 |
| taagtgctgt catacctgta gcttgcttgg ctctgcagat agggttgcta gattaggcaa | 1560 |

```
atagagggtg cccagtcaaa tttgcatttc agataaacaa cgaatatatt tttagttaga    1620
tatgtttcag gcactgcatg ggacatactt ttggtaggca gcctactctg gaagaacctc    1680
ttggttgttt gctgacagac tgcttttgag tcccttgcat cttctgggtg gtttcaagtt    1740
agggagacct cagccatagg ttgttctgtc accaagaagc ttctgcaagc acgtgcaggc    1800
cttgaggtct tccgacttgt ggcccgggga ctctgctttt tctctgtcct ttttctcct    1860 tagtgggcca tgtcctgtgg tgttgtctta gccagttgtt taagggagtg ttgcagcttt    1920
atgattaaga gcatggtctt tccttgcaaa ctgcttggtt tagaagcctg gctccaccac    1980
ttagcggctc tgtgacctcg gacacatttc ttagcctttc tgggcctcgc tcttcttcct    2040
cataaagtga aaatgaaagt agacaaagcc ttctctgtct ggctactgag aggatggagt    2100
gatttcatac acataaagca cttaaaataa tgtctggcat atgatacatg ctcaataaat    2160
gtcacttaca tttgctatta ttattactct gccatgatct tgtgtagctt aagaacagag    2220
gtctttacag gaattcaggc tgttcttgaa tctggcttgc tcagcttaat atggtaattg    2280
ctttgccaca gactggtctt cctctccttc acccaaagcc ttaggggggtg aacgatccca    2340 gtttcaacct attctgttgg caggctaaca tggagatggc accatcttag ctctgctgca    2400
ggtggggagc cagattcacc cagctttgct cccagataca gctccccaag catttatatg    2460
ctgaaactcc atcccaagag cagtctacat ggtacactcc cccatccatc tctccaaatt    2520
tggctgcttc tacttaggct ctctgtgcag caattcacct gaaatatctc ttccacgata    2580
cagtcaaggg cagtgaccta cctgttccac cttcccttcc tcagccattt ttcttctttg    2640
tacataatca agatcaggaa ctctcataag ctgtggtcct cattttgtca atctaatttc    2700
acagcctctt ggcacatgaa gctgtcctct ctctcctttc tgcctactgc ccatgagcag    2760
ttgtgacact gccacatttc tcctttaacg acccagcctg ctgaatagct gcatttggaa    2820
tgttttcaat ttttgttaat ttatttattt catcttttt ttttttttt ttttttttt    2880 tttttagggc cgcacccatg ggatatggag gttcccaggc tagggatcca atgggagctg    2940
tagctgctgg cctacaccac agccacagca atgcacaatt cgagccaatc tttgacctac    3000
accagagctc acggcaacac tggattctta acccactgat tgaggccagg gatcaaactc    3060
tcgtcctcat agatacgagt cagattcgtt aacctctgag ccatgatagt tgttagttac    3120
tcattgatga gaaggaagt gtcacaaaat atcctccata agtcgaagtt tgaatatgtt     3180
ttctgccttg ttactagaaa agagcattaa aaattcttga ttggaatgaa gcttggaaaa    3240
aatcagcata gtttactgat atataagtga aaatagacct tgttagttta aaccatctga    3300
tatttctggt ggaagacata tttgtctgta aaaaaaaaa atcttgaacc tgtttaaaaa    3360
aaaaacttga ctggaaacac taccaaaata tgggagttcc tactgggaca cagcagaaat    3420
gaatctaact agtatccatg aggacacagg tttgatgcct ggcctcgcta agtgggttaa    3480
ggatatggtt ttgctgcagc tccaattcaa cccctatcct gggaaccccc atatgccacc    3540
ctaaaaagca aaagaaagg tgctgcccta aaagcaaaa agaaagaaag aaagacagcc     3600
agacagacta ccaaatatgg agaggaaatg gaacttttag gccctatctc caactatcac    3660
atccctatca ccgtctggta agaaatggaa aaatattac taagcctcct ttgttgctac     3720
aattaatctg attctcattc tgaagcagtg ttgccagagt taacaaataa aaatgcaaag    3780
ctgggtagtt aaatttgaat tacagataaa caaattttca gtatatgttc aatatcgtgt    3840
aagacgtttt aaaataattt tttatttatc tgaaatttat attttcctg tattttatct     3900 ggcaaccatg atcagaaatc tttaaacaat caggaagtct ttttcttag acaaatgaaa     3960
```

```
atttgagttg atcttaggtt tagtacacta tactaggggc caagggttat agtgtgacta    4020
ttaaatcaca gataatcttt attactacat tatttcctta tactggcccc acttggatct    4080
tacccagctt agcttttgta tgagagtcat ccttaaagat gactttattc tttaaaaaaa    4140
aaaacaaatt ttaagggctg cacccatagc atatagaagt tcctaggcta gcggtcaaat    4200
tagagctgca gctgccagcc tatgccacag ccacagcaat gccagatctg agctgcatct    4260
gtgacctaca ctgcagcttg cagcaatgct ggatccttaa cccattgaac aatgccaggg    4320
attgaacaca catcctcatg gatactgctc aggttcctaa cctgctgagc cacagttgga    4380
actccaaagc agactttatt ctgatggctc tgctgatctc taacacgtta ttttgtgcca    4440
tggtgtttat cttcacttta ctcaagtcag ggaaacacga agagtctcat acaggataaa    4500
cccaaggaga aatgtgcaaa gtcacataca aatcaaactg acaaaaatca aatacaagga    4560
aaaaatatct tcactttcaa aatcacctac tgatgatgag tttatatttc cttggatatt    4620
tgaatattag ctattttttt cctttcatga gttttgtgtt caaccaacta cagtcgttta    4680
ctttgatcac agaataatgc atttaagcct taaatagatt aatatttatt ttcaccattt    4740
cataaaccta agtacaattt ccatccaggt ctgttaaatg cacaaaacac aactggaagt    4800
tagatgtaag cagcatgaag tatatcaatc ctcctggaag cttctgtcaa gacgaactgg    4860
gtaaatacca tcaatactga tcaatgtttt ctgctgttac tgtcattggg gtccctcttg    4920
tcaacttgtt tccaatctca ttagaagcct tggatgcatt ctgattttaa actgaggtat    4980
tttaaaagta accatcactg aaaattctag gcaagttttc tctaaaaaat cccttcattc    5040
attcatttgt tcagtaagta tttgatgaga ccttaccatg tgtaaacatt gcactaggta    5100
ttaagaaata caaagatgga taagatagag tcggcgtaaa tgagtgata taatgagacg    5160
ttataatgaa actcacaatt ccagttggga aataaagtcc ttcaaattcc atgactcttt    5220
ctggcacacg ttagaggcta cagcttctgt gtgattctca tgctggctcc acttccactt    5280
tttccttctt cctactcaag aaagcctata gaaatatgag taagaagggc ttaatcatag    5340
gaataaattt gtctctgttc taagtgatta aaaatgtctt tatcagtata aaagttact    5400
tgggaagatt cttaaaactg cttttacaca ctgttctaga atgactgtta tataaataaa    5460
aaagtagatt tgatctaaca caattaaatg acctttggaa atattgacta attctcacct    5520
tgcccctcaa agggatgcct gaaccatttc cttcttttgc cagaaagccc ccacccttg    5580
tctgttgacc tagcctagga aatcttcaga tcacgttgtt agcacgaact ggttacatgt    5640
gctgtacaaa tactatttaa ttcatctgat taaaaaaaaa gagataagaa gcaaagttt    5700
gactatctta aactgtttgc gtaggtgaga ggacaattga ccatctactt tatgagtatg    5760
taacccagaa acttaaagct ccttaaggga gctaagtctt ttggataaga cctatagtga    5820
gaccttttag caaaatggtt aagactgaat ggagctcact agcgtgggtt catatcctga    5880
tgctcaaaca cgcaattaaa tgactttagg tgggttagtc tctgttcctt agtttcctca    5940
atggagata atattggtag tagcgatttt actgggttgt tgaaagaaca tctgttaaat    6000
gttcagaacg tgttacgaca gagtacagag taatgatttg cttgtatatg tatgactcaa    6060
atagtctgcc atatgccttg tgactgggtc ctgtggagca ggaaggaggg atttcccacc    6120
cagcagaaag ttgggtaaac tggaaaatag actgaggcca ggaaatgatg caaagcgttg    6180
atgttcactg ccacggcagg tgaagggcag ggccagagtt gtcagtaggg tcaggggagg    6240
actggaaata accaagaccc actgcacttt tcagcctttg ctccagtaag gtaatgttgt    6300
```

```
gagagtagaa aattttgtta acagaaccca cttttcagta cagtgctacc aatactgtag    6360
tgatttcata ccacatccca agaaagaaaa agatggctca atcccatgtg agctgagatt    6420
atttggtttt attgttaaat aaatagcatt gtgtggtcat cattaaaaaa ggtagatgtt    6480
aggaaagtag aaggaagaag actctcacct acattttcat cactgttttg gtatctgcca    6540
gttgtcacct tggtccccctt ccccgcctct cccctgcctc ctcttcctcc ttctcctttt    6600
tttggaatac aattcaggta ccataaaatt tacccttttta gagtgtttga ctcaatggtt    6660
tttagtattt tcacatgttg tgctattact atcactatat aattccaggt cattcacatc    6720
accccccaaa gaaaccttct aactattagc agtccattcc cttcttccct cagcccctgg    6780
caaccactaa tctacttact gtctccatgg atgttcctat attgaatcaa gctagcataa    6840
accccacttg ctcatggtca taattctttt ttatagtgct aaattacatt tgctaatatt    6900
caattaagga tttctatgtc catattcata aggaatattg gtgtgtagtt ttctctttgt    6960
gtgatatctt tgtctggttg ggggatcaga gtaataatta ctgctctcat agaatgaatt    7020
gagaagtgtt ccctccttttt ctatttattg gaagagtttg tgaagtatat tggtattgat    7080
tcttctttaa acatttggtc agattcacca gtgaagccat ctgggccatg gctaatcttt    7140
gtgaaaagtt ttttgattac taattaaatc tctttaattt gttatgggtc tgctcctcag    7200
acgttctagt tcttcttgag tcagttttgt tcatttgttt cttcctagga ctttctccct    7260
ttcatttgga ttatttagat tgatagtaat atccccctttt taattcctgg ctgtagtaat    7320
ttgggtcttt tctctttttt cttggtcagt ttagctaaag gtttgtaatt gtattaatct    7380
tttcaaataa ctaacttttt tgttttgttt gttttttgtt ttttgttttt tgttttttgt    7440
ttttttttgc tttttaaggc tgcacctgag gcatatggaa gttctcaggc tagaggtcta    7500
atcggagcta cagctgctgg cctataccac aaccatagca atgccagatt caagctgcat    7560
ctgcgaccta caccacaact cggccaggga tcacacccgc aacctcatgg ttcctagtcg    7620
gatttgttaa ccactgtgcc acgacgggaa ctcccgccca tttttttttaa cacctcatac    7680 tttaacataa agatgggctt cacatggact gatagctcaa atgaggaagg taagactatg    7740
aaagtaatgg aagaaatgta gactatttttt gtgacctaga gattactgat acttcttgac    7800
ttttcaaaca atacttcaaa agtacagccc aaagggaaaa aagaaagaaa aagaaacac    7860 acatatacac aaacctagtg aataagatat catcgataca ctacagattt ctatgaactg    7920
gaagacccca tggacaaagt taaagaacat atgatagttt gagtgattat tttgcaatat    7980
ttacaaccaa tgagggaata ttatccagct tataggagga agtaatgcaa atcgacaaga    8040 aaagatagg aaacccaata taaaaattaa gaaaatacaa aaattaagaa aggatatgaa    8100
ctagcatttt acaaaagaaa aatctccaaa agtcaatcag cacatgaaaa tatgctcaaa    8160
cctattaatt attagaaaac tacagactga agcaatgagg tgctttactt tacatctttt    8220
tgactgataa aaagttagaa acaaaggtga tatcaaatgt cagggataaa aggatataga    8280
aatcgtcatg cctgtggtgg gagtatggcc ggtgcagtca tgtgggaagg taatctgaca    8340
gtggttaggc agagcaggtt tatgaataca ctgtggccca tcaatcccac gcctgtttat    8400
gtaccaaaga aatcctgttg tggcagaatc tatgggtcca cccctgggag catgaattaa    8460
taaaatgtgg caccagggtg tgtgaaactc cagctagaga tgagatgtcc acatggcaac    8520
atgaatgcat cttagaaaca tagatttgag tgaaaaagag taagaaacag ccgggaaacc    8580
caataccatt tataaaaatt aaagatgcac acatacaatg tagtaaatat tttgcatgaa    8640 cttttcaaatg gttgcctaca gggggggaga gtaaagaaga gtagaaaaca aagataaagg    8700
```

```
gagtaagtaa gtagctctgc ctggactgaa tataatgtgt catgaactga gaaatatggt    8760
taacataatc ctcttaactt gaggtcctaa atgaatgaat gagtccacta ttcatttacc    8820
cattctttaa tgtgtattgc attataatcc attttttag aaccaacgaa ttttgttccc    8880
ataactacta atcagcctgc cttttctccc tcattccctt atcagctcag gggcattcct    8940 agttttcaa acgttcctca tttgaaccaa aaatagcatc attgtttaaa ttatacttgt    9000
tttcaaatac gatgcttata tattccaagt gtgtttgccc attttcttag gtggtagaaa    9060
tttttcattc tacttttcta tctactcaga ttttcccgtt ggaattattt ccattgctat    9120
taaacttaga agtcccccct gtgatatgcc attttttca acttttaa gcacttggtt    9180 gcttttcttt gtgtcttaa gcacctagaa tacttataac cattgcacag cactgtgtat    9240
caggcagccc ttcctcttcc actaatttat ggtccttctc ttagactata ttaaactgtt    9300
atttaattag gatcctctct tcgtccttat gatttaatta ttatagtttt ctaatatgtt    9360
tttattataa ttcctcttca ttattcctcc ctattaaaaa ttttaatgaa ttccattgt    9420 ttgttcttct agttaaatat taagtcataa tccaaataac ttagatgtca ttagtttatg    9480
tggtcaaagt aaggatacca catctttata gatgcaggca gttggcagat gtcatgattt    9540
tcttcagtgc ataaatgcaa tttatctttg agcaaggggc ataaaaactt ttatggtatt    9600
ggctttgaaa taatagttaa gaactgcaga ctcagttttt cctgcttttc ttgaaaaaga    9660
acacttctaa agaaggaaaa tccttaagca tggatatcga tgtaatttc tgaaagtctc    9720 ctgtaattcc ttgggatttt tgttgttgtt tgttggtcgg ttttttggg ttttgtttg    9780 tttgttttgt tttgttttgt tttgctttta gggctgcacc tgtggcatat ggaagttccc    9840
aggctagggg tccaactgga gctacagctg ccagcctact ccacagccac agcaacatgg    9900
gatcctagct gcatctgtga cctaaccaca gctcttggta atgccagatt gttaacccac    9960
tgagcaatgc cagagatcga atctgcctcc tcatggacac tagtcagatt agtttctgct   10020
gagccacaat gggaattccc aattccttgt attttgaac tggttatgtg ctagcatata   10080
attttgtttc ttgaatcttt gtgggttttt ttttttttt ttttttgtct cttgtctttt   10140
taaggctgca cccacagcat atggaggttc ccaggctaga ggtcaaattg gagctacagc   10200
tgccagccta cacaacaact gcagcaaagt ggggcccaac ttatatgaca gttcgtggca   10260
atgccggatt cctaacccac tgagcagggc cagggatcga acctgagttt ccagtcagtt   10320
tcgttaacca ctgagccatg atagtaactc ctgtttgttc agtcttgaac ctcctttta   10380 attctttatt ccttgagggt gaaataattg ccataataat actatcattt attacatgcc   10440
ttctctgtgc taggcatagt gacactttag gatttattat atcacttaat ccctacaaca   10500
actctgcaaa gtatgtatca taatcctatt tgacagatca ggaaattgca gcccaggatg   10560
cagataatat gcatccatca caagtgacta gatatagtcc ctctgctatt cagcagggtc   10620
tcattgcctt tccattccaa atgcaatagt ttgcatctat tgtatatgtg ttttggggtt   10680
tttttgtctt ttttttttt tttgtctttt ctggggcctc accttggca taggtaggtt   10740 cccaggctag gggtcaaatt gaagctgcag ctgccagcct acaccacagc cacagcaact   10800
cgggatctga gcctcatctg caacctacac caaagctcac ggcaacaccg gatccttaac   10860
ccactgagtg aggccagaga tcaaaccggc aacctcatgg ttcctagtcg gattcattaa   10920
ccactgagcc acgatgggaa ctccctaaat gcaatagttt gctctattaa ccccaaactc   10980
ccagtccatc ccactccctc ctcctccctc ttggcaacca caagtctgtt ctccatgtcc   11040
```

```
atgattttct tttctgggga aagtttcatt tgtgccattt ttcattttac gggtaatttt   11100
tacttcagtt tcttccacta gcagttgtct taaagtgagt ataattaata ttcatttgga   11160
aaatgtaagc aaaacatttt ttaaagggcc atgcccacag catatgaaag tttctgggcc   11220
aggggttgaa tccaggctcc aagttgcagc tgtgccctac actgcagctg ggcaatgctg   11280
gatcctttaa cccactgtgc ccggctaggg atcaaacctg catttccaca gctacccgag   11340
ccattgcagt tggattctta acccactgca ctacagtggg aactcccaca aaacattttt   11400
taatgtcctt tgaataaagt aggaaagtgc tcgtctttga gggcagggcg gcaatgccat   11460
ttccacaagg tttgctttgg cttgggacct catctgctgt catttagtaa tgaataaaat   11520
tgctgacagt aataggatta actgtgtgtg gagatagcca gggttagaga taaaaacact   11580
ggagaagtca ataagttgc tcgaggtcct ctagctaata agctattaag tgggagagtg   11640
agggctagaa acaggccatc tgtctcccaa gcacatgtcc attagtggtt tgctgatagc   11700
cttccagaac aacagagagg actctcaaac atggtcttgc ctccctccaa ttgatcccct   11760
ccatgtgcct cacagcgggt cttttctaaaa ttaagttctg attttaattc tcccttgcta   11820
tagcacttag gtatggcttt cagccgtgca ataaaaagca ggcaagagtg gctcaatcat   11880
ataggaggtt gttttttctta gatcccaagc aggtaatcct gggcattatg gttgttctgc   11940
gtttatcaag gagccaaatt ctctatcacc tcctgttcta tcctcctcag tatctggctc   12000
tattcttcag catctcaaga tggcttgtgc tcctccaagc atggcagtca aattccacac   12060
aagaggggga aatatgaagg gcagacagtg ctggtctcct gagctgtccc tctttgtcgg   12120
ggaaataaat gtattccttc aagtcccgtg agacttctga agtagacgtc tgcttacgtc   12180
tcacccacca gaactatgta aactgcacat agtgctaggt ctacatagcc actcataact   12240
gccaggggt gggaaatctt taaataggtg taccaccaca caattaggat gctaatagta   12300
agggagaagg agagaatagg ttttgcgcaa gccaccagca tgcctgccac aattgcttaa   12360
aattcttcat tgacccctca ttgccacagg atgaaatcca aacgccttct tagttgggaa   12420
tctgacctac ctgtctctcc cacctggttc agacaccatt ctccttggtc ataaaattcc   12480
agtcatttgt gaacatccag ctccccatg cctccatgcc tttgcacatg ctgttctttt   12540
atcttttatg ttgtccttt atcttttatc caaaagagat atcccatcat cacatctctt   12600
ttgtcagccc ccaaatactt tgtctttcaa gttcagctgg aggattacct cctatttgaa   12660
atcagctttg tctcttacaa ccaaacaagg ttttccttcc gagacactcc cacagcacct   12720
tgaactcatc tctatcaatc attcatttga ttgtaatgaa gttgttggtg gtatgcctgt   12780
gtctctgaca catctgcgat tcatgagtt ccttaagtgg aatgtgaata gcgggatgaa   12840
cagtattggt cttcagccct catctctgca gatgttgctt gacccaaatg agcgttgcct   12900
tttattttga ttttgctttg atttgtctac tccatgtact tgagccatgc atttctgtct   12960
tagcgatgct ttttaaaagt cattttttgg ttgattatcc agatttgtcc acctttgctt   13020
ctagttgtag aaaaggatga agaaaatgga gttttgcttc tagaactaaa tcctcctaac   13080
ccgtgggatt cagaacccag atctcctgaa gatttggcat tgggggaagt gcaggtaagg   13140
aaatgttaaa ttgcaatatt cttaaaaaca caaataaagc taacatatca atttatatat   13200
atatatatat atatatttt ttttttttt acatcttata ttaccttgag tattcttgga   13260
agtggctagt taggacatat aataaagtta ttctgaagtc ttttttttc ttttttccatg   13320
gtgagcagtg gcttgatgtg gatctcagct cccagacgag gcactgaacc tgagccgcag   13380
tggtgaaagc accaagttct agccactaga ccaccaggga actccctatt ctaaattctt   13440
```

```
gagcacatta tttaggaacc tcaggaactt ggcaggatta caggaaatat atctagattt   13500
aaaaaaaaat cttttaacag aggtcccaaa ggagagtcat gcacagctat gggaggaagt   13560
tcagaaactg cccttgctac cagatcactg tcagataaaa tggccagcta catgtttctg   13620
cacattgccc taagatcttt acaaacttttt ctgtgcattt ttccacttttt aaaagaaaat   13680 ttcggggttc ctgttgttgc tcagtggtta acgaacccaa ctagtatcca tggggacagg   13740
ggttcgagcc ctggcctcac tcagtgggtt aagaatctgg cattgctgtg gctgtggcgt   13800
aggctggcgg ctacagctca gattggaccc ctagcctgag aacctccata tgccgcaggt   13860
atggccctaa aaaaaaaaaa aagagagag agagaatttc ctccagaaaa aacactttgg   13920
tagtttggga gaagtaaaca accaaaaatt aattttctg gagtattcgg gaagcttgta    13980
aaaatgggct cttactttt tgaggagaca atgggaacc tacccagaag aggcacaatc     14040
acctgcattt gatttcttga cctctcccta ccttctttgc tggctttcca catttggatt   14100
tctgtgacct tatctctgct ccttggtgtt ttcattttc ctgtggacgt gccagactat    14160
gggaagggag taaggcgttg atttagaatc ctgtagtctc tgcctgtctc tagtcattgt   14220 tttcacccctt ctcaaaggac cttgacatcc tgagtgagtc cgcaagtaat ttaggggaga  14280
agccttagaa gccagtgcag ccaggctaca tgactgtgtc cacccactgg aaccagtcat   14340 ttttataccct attcacagcc ccctaccat ttaaatcccc agaggtctgc cataacatct   14400
gtaactccct ttcctggtaa attgtgttct aaaagactgg taacaaaga tattctgtgg    14460 tacagagcat aattaaatac ctgggagctg atttgagtgg ggtaaatcaa ctggtttgac   14520
ccctaaaacc caccatgagc atttctgttc taataaagta atgcccgtgc tgggaattgt   14580
gttctacgga aatgctcctg ctgtgtcttt cttgagtcct gtgtcattga acatgcttag   14640
gagcaaaggt cccccatgtg gcttgtctgc taaccagccc agttccttgt tctggctggt   14700
aatgatccga tcatctgaat ctcactgtct tccaacagat cacgtacctt actcacgcct   14760
gcatggacct caagctgggg gacaagagaa tggtgttcga cccttggtta atcggtcctg   14820
cttttgcgcg aggatggtgg ttactacacg agcctccatc tgattggctg gagaggctga   14880
gccgcgcaga cttaatttac atcagtcaca tgcactcaga ccacctgag                14929

<210> SEQ ID NO 50
<211> LENGTH: 17221
<212> TYPE: DNA
<213> ORGANISM: Porcine

<400> SEQUENCE: 50
aggaatggaa agcccaattc attaaaacag aaaggaagaa actcctgaac tacaaggctc      60
ggctggtgaa ggacctacaa cccagaattt actgccccctt tcctgggtat ttcgtggaat    120
cccacccagc agacaagtat ggctggatat tttatataac gtgtttacgc ataagttaat    180
atatgctgaa tgagtgattt agctgtgaaa caacatgaaa tgagaaagaa tgattagtag    240
gggtctggag cttatttaa caagcagcct gaaaacagag agtatgaata aaaaaaatta     300
aatacgtatg gctggatatt ttatataacg tgtttacgca taagttaata tatgctgaat    360
gagtgattta gctgtgaaac aacatgaaat gagaaagaat gattagtagg ggtctggagc    420
ttattttaac aagcagcctg aaaacagaga gtatgaataa aaaaaattaa atacaagagt    480
gtgctattac caattatgta taatagtctt gtacatctaa cttcaattcc aatcactata    540
tgcttatact aaaaaacgaa gtatagagtc aaccttcttt gactaacagc tcttccctag    600
```

```
tcagggacat tagctcaagt atagtcttta tttttcctgg ggtaagaaaa aaggattgg      660 gaagtaggaa tgcaaagaaa taaaaaataa ttctgtcatt gttcaaataa aatgtcatc      720 tgaaaataaa ctgccttaca tgggaatgct cttatttgtc aggtatatta aggaaacaaa    780
catcaaaaat gacccaaatg aactcaacaa tcttatcaag aagaattctg aggtggtaac    840
ctggacccca agacctggag ccactcttga tctgggtagg atgctaaagg acccaacaga    900
caggtttgac ttgaatattt acagggaaca aaaatgattt ctgaattttt tcatgtttat    960
gagaaaataa agggcatacc tatggcctct tggcaggtcc ctgtttgtag aatattaag    1020 tttttcttga ctagcatcct gagcttgtca tgcattaaga tctacacacc cccttttaaa   1080
gtgggagtct tactgtataa aataaactat taaataagta tctttcaact ctggggtggg    1140
gggggagact gagttttttc acagtcctat ataataattt tcttatccta taaaataatt    1200
aggagttccc gtagtggctc agcaatagca aacccgacta gtatcgatga ggatgcgggt    1260
tcgattcctg gcccccctca gtgggttaag gatctggcat tgccgtgagc tgtggtgtag    1320
gtggcagaca cggctcagat cccacgttac tgtggctgtg cataggcca gcagctccag     1380 ctctgattag acccttagcc tgggaacttc catatgctgt gggtgtggcc ttgaaaaaaa    1440
ataaataaat aagataatta ctcaaatgtt ttccttgtct cagaacctta cttcaggata    1500
aagagtgaga aagttttttt tatgaagggc cattattaca gctcaaaaat aagttgtctt    1560
cagcaagtag aaagcaataa gcctgagagt tagtgttcct atcagtgtaa atattacctc    1620
ctcgccaatc cccagacagt ccatttgaac aattaacggt gccctgggag tacagttcag    1680
aaacattaat gtggatgttc cagacctgta ttttt ataag tacttgtctt gagccggatg    1740
gaaccatcat tcctcaccat tatttagaag tggactgtga ctctgttgga gatcagggca    1800
cacggttacc aaaagcacac ccttctcctg gccttacctt tgcaaagctg gggtctggga    1860
cacagtcagc tgattatacc cttttactaa cttcccacag ctcaaatctg gtcaattctc    1920
cttcacaaat ctcttaaaaa tccatcactc acctccagcc tcttctgctg tggccttgat    1980
tcagcctctc acaatttttt tttaaccaga attctggcag tggcccctga cttgcctctg    2040
tgctcccagc cccgctgtcc tctgatccat cctccatgcc agccttttc aatctgctgg     2100 tcacgattca ttgatgggtt aggaaatcaa tggcatcaca actagcattt agaaaaagga    2160
aataggcgtt cccgccgtgg cacagcagaa ataaatccga ctaggaacca taaggttgcg    2220
ggttcaaccc ctggccttgt tcagtgggtt aaggatccgg cattgccgtg ggctgttttg    2280
taagtcacag acatggctct gatccggcat tgctgtggct ctggcgtagg cctgcagcat    2340
cagctccaat tagaccccta tcctgggagc ctccatatgc tgcaagtgca gccctaaaaa    2400
aaataaaaaa ataaaaaaaa ataaataaaa gaagtagaca aattgtatag aacaaccctg    2460
agtatgttgc ctgagcacat ataacaaggg taagtattat ttcaggaaac tctggtttca    2520
cagatactct tggcatatgg acccctagag tcctgatgta aaatatattc ttcctgggat    2580
cttaggcaag aagtttgaaa gctccaactc tgcactgctg ccaaagaaat gatttttaag    2640
tgcaaaactc ttcccgttcc cttccctgta taaaattcca taggatctct ccagtgcctc    2700
taggataaag gcagttttca ttctctagtt caaggtgaga aagatttta attatttcac     2760 gttttagtgg ggaattcaag agtctggcac ctgacatttg ctgaactctc tccattatcc    2820
ctctctagtt ccccagacgc atcctatggt agaaattcgc aaactagagt gagcgtcaga    2880
gtaacccaag gaaactgggt aaatgcagct ccctgggctc taccccctga gattctgatt    2940
cagtagatct gaagcagagc cctggaatat gcatatgcat cattgtgtca caccaagcat    3000
```

```
tctgggtaat gagagttgat gttaggttct cagtagtaag acaagtatag agattccggg    3060
ggactgagtg ctcagctctg ccttggggag gagggagagg gctaaagaga acaggagatg    3120
gggacaggga atgctcaacc tccaatctta ggcatttgag ctatgtctta ggggtcagga    3180
ggaggttacc aatatagtga ttaagagatt gaggttccag tcagagggat atgctggaga    3240
aggggggtga aaataatgtc ataggttttgg tgagtgcaga tactttgagt tttttaatat    3300
ttttattgaa atatagttga tttacaatgc tcttagtgag tacaattact ttgaataagt    3360
gcatagatgt atgccattct tccagaaatg atttattgag ctccttttggg catcatgcta    3420
agtacagggg aaacagctgt gaagaggtcc ttcccttatg aagtcattca tccccttcag    3480
taaatgaagg taaaggaaaa ggatgagaca gggacgccgt gttggaccag ggtcagaaag    3540
gccttataag accttgcctg gagggcaagg aacttgcctg tgagtaagga gagcttgaga    3600
aagcgataaa gcaaagaagg aacattactg cattgtgttt tagaaaaacc atgtcctggg    3660
gaagaactcc tagagtcagg ggggccagtt gggagactgt gcttttttcc aggaggagat    3720
aagtgaggct gctggctgag atggagcaag gatttagaga agcagatatg agattcattt    3780
agaagttaga catttttagga tctgacacat aatttatcac caaaaccagt gcatctctgg    3840
ctttgggcca ccagttttgg agaagtggaa tgtagggacc taccattacc tgccaatctt    3900
tactacacag atgcctattt ccctcctcat atttcctttc tccagatcac gtcctattct    3960
attgccagga ctcaagattc caccttgcat gcagtgatcc atcttcacac tggatggaca    4020
gctctaggga tgtcagagca cactcttgtc catactgctg actgggtctc ctgtcagccc    4080
atctgtctat cagctgtggt attattagta taataagagg gctgtatatg agagacacaa    4140
aattctaggt gtagctcaaa gataggctag agttattcct atgtacaaca atatttatg    4200
ggacccttc tgtgtactgt catggttgct gctttcatca tacttgtagt ctaatggagg    4260
tgggggcagg gcaggaataa gcggatgtcc acaaaatcag taagaccact tatattcaac    4320
attttcataa tttagttatt tgagcccaaa gggtccacat ccgtggtatt ccaacttttt    4380
tttccccgga catggatctt tatctttttt ttttttttctt ttttgcggcc agacctgcgg    4440
catatggaag ttcccaggcc aggggttgaa tgggagttgc agctgcctgg tctacaccac    4500
agccacagca aggtgggatc tgagctgcat ctgtgacata caccgcagct gaggtaacac    4560
cagattctga acccactgaa tgaggccagg gatggaaccc gtctccttat gaacactatg    4620
tcatgttctt caccctctga gccacaacgg gaactccaga cttcgtcttt aaatgtattc    4680
tgacttggag agctatcaca ctaagcaatt aacaggagct gacctggttt aggctggggt    4740
ggggccctac tcctcaatgt tccctgaggc acatctgtgg gaccccctggg catcatctat    4800
ctgagcagcc ttagagctgc tcatccagtt gactgttgat gtagaagtgc aaacttctgc    4860
cttccttatt tgttgctttc ttttttcatt gttctctccc ctttgtgtct ttaagcaagg    4920
gcatcgtaga gcctccagaa gggactaaga tttacaagga ttcctgggat tttggcccat    4980
atttgaatat cttgaatgct gctataggag atgaaatatt tcgtcactca tcctggataa    5040
aagaatactt cacttgggct ggatttaagg attataacct ggtggtcagg gtatgctatg    5100
aagttattat ttgttttttgt tttcttgtat tacagagcta tatgaaaacc tcttagtatt    5160
ccagttggtt tctcaataag cattcattga gccttactga ctgtcagacg gagggcgtat    5220
tggactatgt gctgaaacaa tcctttgttg aaaatgtagg gaatgttgaa aatgtaggga    5280
atgaaatgta gatccagctc tgtttctctt ttggaggatt ctttttcctc catcaccgtg    5340
```

```
tcttggttct tgtttgtttt gggttttttgt gggtgttgta ttgtgttgtg ttggttatgg    5400
cagtgacagc tatttaaact gtgaaacggg ggagttcccg tcgtggcgca gtggttaacg    5460
aatccgactg ggaaccatga ggttgcgggt tcggtccctg cccttgctca gtgggttaac    5520
gatccggcgt tgccgtgagc tgtggtgtag gttgcagaca cggctcggat cccgcgttgc    5580
tgtggctcta gcgtaggcca gcggctacag ctccgattgg acccctagcc tgggaacctc    5640
catatgccgc aggagcggcc caagaaaata gcaaaaagac aaaataaata aataaataaa    5700
taagtaagta aaataaactg tgaaacgggg agttcccttc atggctcagc agttaacaaa    5760
cccagctagg atccatgagg atgtaggttc gatccctggc cttgctcagt gggttaagaa    5820
tccagcgttg ctgtgagctg tgatgtaggt cgcagatgca gcccagatcc tgcattgctg    5880
tggctgtggc gtaggctggc agctgaagct ccgattcaac ccctagcctg gaacatcca    5940 tatgctgcag gtgtggcctt aagaggcaaa aaataaaaa ataaaaaat aaataaattg    6000 tgggacagac aggtggctcc actgcagagc tggtgtcctg tagcagcctg gaagcaggta    6060
aggtaaggac tgcagctggg taaggactga attgcaccaa ctgggaagta agcctagatc    6120
tagaacttaa gttagccctg acatagacac acagagctca ccagctaagt ggttcagctt    6180
ataagctggt cactgaaact gaggatgtcc acaaaagcaa aataagtagc aacaggcagc    6240
gggatgcaag agaagagga ggcctaaaat ggtctgggaa tccctgccat acctatattt    6300
tatcctactt atatttagtg cctgaatgtg tgcctggaga gcaaagttta gggaaagcat    6360
cgggaaatgc acagtattca taccctttagg aacaaagatc agttacctcc agggtaaaga    6420
ctatttccaa gtttaaattt caaccctga acattagtac tgggtaccag gcaacacttg    6480
ccatcctcaa aatcaatgaa tcctaaaatt caacctgggg gtcagtgaca gtctgtgaca    6540 aagttttgc tggtcagtaa cgaaataagt atgagcacca tctgagtatg gtcaccaaga    6600
tgtcaactct ctttcctttg gacgaattgt cattattcca agattaggtc ctttctattt    6660
ttgaggtgtg aaacatctt tcctttcata aaataaaagg atagtaggtg aagaattttt    6720
ttttgttttt tggtcttttt gctatttctt tgggccgctt ctgcagcata tggaggttcc    6780
caggccaggg gtcgaatcgg agctttagcc accggcccac gccagagcca cagcaacacg    6840
ggatccaagc cgcatctgca gcctacacca cagctcacgg caatgccgga tcgttaaccc    6900
actgagcaag ggcagggacc gaaccgcaa cctcatggtt cctagtcgga ttcgttaacc    6960
actgcgccac gacgggaact cctaatgata ctctttata tttagctact atgtgatgat    7020
gagaaacagt ccacattta ttattttta gccaatttga tatctcatta ctaagataat    7080 gataatttc tctataaatt ttatttaagt tagtgttatg aagtggtttt gctagtgtag    7140
aaggctagga tttgaattca gttcaagaaa gaagagaggg agggagggag agggatgggt    7200
agagggatgg ggcagtggga gagagcaaag aggagagaca gttttgtat taattctgct    7260 tcattgctat catttaaggg cacttgggtc ttgcacattc tagaattttc taaggacctt    7320
gaccgccaga ttgatatgct tcttcccttt accatgttgt catttgaaca gatgattgag    7380
acagatgagg acttcagccc tttgcctgga ggatatgact atttggttga ctttctggat    7440
ttatcctttc caaaagaaag accagccgg gaacatccat atgaggaagt aagcaggaat    7500
accagtggaa gtgccccttt cttccttcct tcctaaataa acttttttat tttgaacaa    7560 ctttagagtt acagaaaagt tgcaaagata ttatagacag tagtgtttat atatatatat    7620
aaattttttt ttgctttta tgaccacacc tgtggcatat ggaggttccc agtctagggg    7680
ttgaattgga gctacagctg ccagtctgtg ccataaccac agcaatgcag gatctgggcc    7740
```

```
acgtctgtga cctacaccaa agctcacagc tggattctta acccactgag caaggccagg   7800
gattgaacct gcatcctcgt ggttcctagt tggattcgtt ccgctttgc cgcaatggga    7860
actccaaatt attgttaata tcttacttta ctggggtaca tttgttacaa ccaatactct   7920
gatactgaaa cattactgtt aactccgtac ttgcttcttt ttgagtcatt tgcaaagact   7980
ggcttcttga cctgcttcct tccaaacagc tggcctgcct atgctgttct cagacctgca   8040
agcactgatc tctgcccccc ttgccttctc tccagtggtg tctccttccc caaacaaacc   8100
cagtgtggct ctggaaaggg agttaagtca acataaacca acacatattt tgttgagctc   8160
caattttgag caaatccctc acctacggca gacaggcatg atgttaagaa ctagggcttt   8220
ggacacaagg tcaagaccaa gaagggttcc tcacccctac tgattcagat aaccaataat   8280
gaggctttga atccctgtcc aaaggttgtt tttttttccct tctattgagc ttcttgccac   8340
cttatcagtt tttttatga cagtcaaatg acatgatata tgtgagcata catggtaatt   8400
tttaattcta tataaatgaa tcactaaata aattaggagg atatatagtc caccttaag   8460
cgtattacac gtgtcacatg aatgtgtggc gacttaattg tagaggttta atgtagctt    8520
cctataatag atgtgttcct aaactacatt ttaatcattg gacttgtatt tttatgttag   8580
cacttgctgt tgaagaaaag cctatgccaa aagttcagtg aaaccaataa tccactgcca   8640
gctttctgag ttaaaaaaaa tccctgggtt ttcacacaca ggaacaccct gtgtgaaaca   8700
ctcatttaga gcaaaatgca tctgataagg agttcctgtt gtgcctcaac tggttaagga   8760
cctgacattc tccatgagaa tgtgagtttg atccccggcc ccactcgatg ggttaaggat   8820
ctggtgttgc cacaaactgc agctccgatt catctcctag cctagaaact tccacagccc   8880
agaatatgcc acagaattcg gctgtttaaa aaaaaaaga aaaaaaaag aatcataaat     8940
gtgttggttt gttcaccaaa tacatgataa cttgctcttg ccaagctcag cttcataaat   9000
attaagtcat ttaatacagc agccaccttc tgaacagata ttactatact tcccatttac   9060
agataaggaa aatgccatat ttaaccaaga gattaaataa ctttcccgag gtcttatagc   9120
aagtaaatca tggtgcaggg gtttgaccac acgcagtcta tctccagagt ctgtgtattt   9180
agccactgtt ttactttcaa atttaaattt ataaaacttc taaattatct gttaaccata   9240
atctttggaa ttttaaaac cacgagttcc tataaaatgt ttcattgaaa gtaagtcact    9300
tttccatagc ttttgataat acatctgtag gataaagtaa gccacagctc tcttgcagac   9360
ttggtacacc ctggggcaaa gcatcatgcc tgtcacgtac atggtggtcc ttactttgac   9420
tctcagtgct tttattgccc aggaattttg tgagatttct agttgttgag gtttgtttaa   9480
agaggttatg ccggtacttg gaagagctct tttcttgcta cctggagcct tctcatattt   9540
ccttttttgag gagggacatg aattgccttt caaactcata aatatatttt ctagtacaca   9600
agtctccatc ttccttagac gcatggctcc tggagttctc catcctcctg ctccactttg   9660
ggtgggctcc tctctgggtc tgccaccaat ctgcacccca gagacatcct tgacccactt   9720
ccagacccca ccatggcttc actttcttcg ctttcctcct ttgtggaacc ttctgcttaa   9780
gaatctgagg aagaaaattt gcacgtgagc taaactggag gtactttcct gcctggtctt   9840
gcacgatagc ttggctgagc ccatgatgct gggtggctgt tacttccat ggacacccga    9900
aggcgttgct cctttggctt ctagttgcat gcagtgttgc ttatcccagg ctgatctttc   9960
ttccactgta ggtgactttt aagaattaag ggattaatct atatctacaa caacaacaac   10020
aaagaccttt tcaagctgag gtagggcttt ctgtatatgt ttggagtggt tatccagcag   10080
```

```
actttacttg aaggcagggg tcatatcctc aagtgctcat aaacggacca cagaaagatc    10140
tcataattgg gtggagctgg gtggggaccg tgtcatgtgg ccaggaaatg ccagatggga    10200
agggagtggc ccttactgag ctccagctga actctgaatt ttctagaaaa ctcagaaatc    10260
tggatttttc atgtgtaata cccagattta tagatgtgga aagctaattc ttttttttt    10320
taagggacta taggcaatga actaagatct aggttgtatt tggacaaggg gtcatcagtt    10380
taagctgtgt agttgagcgc tcagctattg ggctgaggga cccctaaata ctgagacggg    10440
gaggtccttg ctctggggca tcacaagtac actccctggt ctcattcaaa cacttttcct    10500
acaaaattga tcccatttct tcagtgcact gtctgaatgc atttggccca gagccgtgct    10560
gaggcatagg gaaggggtcc acggtttcat ggcatcgttt tgtgctgtgt gtccctgctg    10620
tcgtccagga tacctacctc tcctcctcct gcatctgaat gtcccccac agactctctg     10680
ggattctaca gcctctggcc tgttcctcag acacctctta cctgccagct ttccagattc    10740
acattagtta gtccaaatct actgccgtca gtgactcact tcatttcttc ttctccgagg    10800
cagttcagcc cggtacagtt gttttgtcaa cacttcagtt gagtctggaa gatgtgcatg    10860
ggttatgcac gagagcggtc catcattttg agctagaagt cctttctcag cccagagaca    10920
agtcctcatc tcctttactt cctgactctt cttcctctgc atccttccaa gatatctctt    10980
tctccagcca ccacctaaat ctcttctttt cccggggttc cgtgctcaac ccactcttct    11040
tcttaaatct gtggctgggt gaacgcatct gctggcacca cttctctgct aaagactcca    11100
aaaatccata ggtcctgccc ggcctttgcc cacctctctc caacactgtc cagctttaga    11160
tgtagagcta atccccccag agatatcatt ccctggatgt ctaagtcctt tggtatctca    11220
ctttcagcgt gttcaaaatc ctcttacaac tgttctttct cctttccat cttgattatt      11280
ggcaacatgc cagcctttcc cctaccccca gcagtgagcc aagctagaaa caagggctta    11340
atcttcaatc tttccttctc catccctaaa cctaatgagt ctccaagccc ttcccagttt    11400
acaccctaaa tgttgctcaa acatcccct agttcttcca cgtgctctcc tctatattga    11460
aaggtcaaga aaggccatct tccctccact gtgaggaaat agatcttgat actgcccctg    11520
agctgggcag tcctcgacct gacaaactgt gcagtgtttc taaatctcta ctggcaaaat    11580
gagagtgcct ttgacctgtg ttgcgatctc agatcacagt ggatgtaatt gttttatagg    11640
aatggtgaac gaaaagaag taatcccta atgccaaact cctgatcatt ctatgtcatt       11700
taatagcctg tcatttatga taaagttttcc tctactggca ttagcacaat acttctcagg    11760
aaaaaaaat atgatgccag atactgaaaa gctcctgggt aaacatgaac atgggtaccg     11820
ataaaatggt gaagccagtc caatcttaga gtgacttccc ttcatgctac ttcatgctct    11880
tttttttttt ttttttttaag aaaaacccct tttttttttc tcacaccagt cacagaggag    11940
accgaggctt agcaaggtta aggtcacatg attagtaagt gctgggctga aactcaaaac    12000
catctctgct tgtctcctaa ccctgtgcac ctctgactat tcaacagatc ctgtgtcagg    12060
agttgggatt ctttgaaggt aagggccttg accaccgaat taaggtaatc ttgctctgtg    12120
gcaggccttg ttttcagtat tttaagtaca ctggctcagg taatcctcac aacagcccca    12180
ggaggaatgt tctattacct ccactgtata gatgaggaac ttgaggcaca gaatggttgc    12240
caaggtcaca cagctatatt gggggttcat acccagccat ccaactctgt ctgtactctc    12300
tgccactctg caccccagc tcctgatcca cttcctgttt ccatccctcg atttctgctg     12360
cactcagggg cccctctccc cctcggcctg tgagatctgc ttcagtaggc ttttctccct    12420
gactcctcca tccctgtcct tacaggcagc tgcttctctc cgggacacga ggggtccata    12480
```

```
cggacactct ctactggctg ggttgcgcct aactcgtgat tcctcctctg tttcagattc   12540
ggagccgggt tgatgtcatc agacacgtgg taaagaatgg tctgctctgg gatgacttgt   12600
acataggatt ccaaacccgg cttcagcggg atcctgatat ataccatcat ctgtaagtcc   12660
gaaaatgcct gtcgtgtgtg ccttaggctg ctgcggagga ggccagggct atataagcag   12720
agtcagtgac tgactgtgcc ctgcagtgtt gatggccatg gagattccac cgttagagct   12780 ttttctttg ttaaccttga aggcaaatct ggttaggaag ataactttca aagagtcacc    12840
atctggacat tcatgcccat gtgcttcaat cctgtataca agcagtttag agtacaggga   12900
agggaaggac attatgaaag ggagagggtg tgtttggatc cagcagctcc atcctcagaa   12960
tttatctgaa gacactgcaa aattactaag aatcactatg acaagaatga ggatggggtg   13020
atatggcaaa gttgtgatcc tggaagacct tcatctccca tgttgcccaa ctctgaacat   13080
gaatttggtg aactagttgg ttaaggggat gatcctccaa gtttctccct ggttgagctc   13140 caaaaccat gtaagtttct catagcaaaa ccgtataggt ccttagggct ttagttggaa    13200
tatttgtgct gaaatgctgg aaagcccat ttgccatttt tgtatttgca aaataatcat    13260
caagagggga gaatgcattc tttcatgacc actgaccctc tgaaaaggtc aggaatttag   13320
tctgaagtag gcaagcctcc taccccgctt ctgccatgag cttgcacgca caggcctgtc   13380
ttgacatttc ttctttatag atttcttttt gaatatcttg aaattgcttt aaaaatattt   13440
aaagaatgta gaattatata aaataaaaag gaaataaccc cacacctccc acaaaaccct   13500
gtttcctgcc tttctccacc cactctccag ggtaacactt ggtaacagca tagttgtatc   13560
accccaggcc tattttgag catatcagca tttcaagaaa tgtatttttt ctcaataaaa    13620 catccttat agttgaggag gggaggttat cattcctggg ttttgttttt ttttttttt     13680 taatgtaatc ctggtacatc ggtaatttgc attttttatt cattaatatc tttggtattt   13740
ctagtgttgg gacacacagg tcaacctcag ttttgtggtt ttttttttg tcttttgtc     13800 tttctagggc cacacctgca gcatatggac gttcccaagc taggagtcta atcagagctg   13860
tagccaccag cctacgtcat agccatagca acgtcagatc caagccgtgt ctgtgaccta   13920
caagcacagc tcatggcaac accggatcct taaccactga acgaggccag gggatcgaac   13980
acacatcctc atggatccta gtcatgttca ttaccactg agtcatgatg ggaactccaa    14040
cttcaactat tttaatgtct gtaaaacatt ccatttggaa accatttcat ttgtaaagca   14100
aaatgaaaac attttgttca ttttcaacag agttcgtagc tgacttctgt tctggaaaaa   14160
aggaaatgga gcaaatttga gtgagaaaga ttcaaagata acttttcttt taaaaaaat    14220 tatatcttgg aaacttctgg gctattgatt ctgaagacta ttttctata tactgttttg    14280 atagcaaagt tcataaatgt gaaaggatcc tgcgatgaat cttgggaagc agtcatagcc   14340
caatatatct ttgttgcttt taaaatgaga tttagtttac taaatatttt tctgatcata   14400 aaataacac agatctaccg cagaaatttt ggaaaaaaa aaactttaa attcaaaaaa     14460 cagttaaacc acaaatgatc ccaccatcca gagagcaatt tgtactttgg tgtctagttc   14520
atctttcttt ttctgtttac aagcacatat accacaagca tttttcaaa aatgaaaat    14580 gggataatac tatacatacg tctgtacacc tgcatagtta ctgaacagtc tttgatctac   14640
cctgtaagtt tctaactttt cattatttga aatgatgttt tggcaaagaa atatgtaggt   14700
gtgtctcgca cactttcata atgatttctt aggataaatt tcttaggata aattcataat   14760
gatttcttat aataatccat actctgccaa ctgatcttca gggaagccaa ctcgccttct   14820
```

-continued

```
cagaaataac atataaccca tttacttgcc ctctcaccaa tactaggtcc taatgttttt   14880
gtgtacagat tctatatttt tacatacaag aattccttaa agcaaggcat gtcacagaaa   14940
aatagaagga agacacaatt gtcatgttta aggactgcat tctgtaccaa aaatgctaag   15000
ttaaatgaac atctgaaaca gtacagaaac gctatctttc agggaaagct gagtaccagg   15060
tactgaacag attttggcaa atacagcagg catggatgtt tccaaaacat gttttctac    15120 tttatctctt acaggttttg gaatcatttt caaataaaac tccccctcac accacctgac   15180
tggaagtcct tcctgatgtg ctctgggtag agaggacctg agctgtccca ggtaaagcat   15240
cctgcaggtc tgggagacac tcttattctc cagcccatca cactgtgttt ggcatcagaa   15300
ttaagcaggc actatgccta tcagaaaacc tgacttttgg gggaatgaaa gaagctaaca   15360
ttacaagaat gtctgtgttt aaaaataagt caataaggga gttcccatcg tggctcagtg   15420
gtaacgaacc ctactagtat ccattgagga cacaggttca atatctggcc tcactcagtc   15480
ggctaaggat ccagtgatgc cgtgagctgc agtgtaggcc acagacgtgg ctcagatctg   15540
gtgctgctgt ggctatggtg taggccggcc ccctgtaact ccaattcgac ccctaggctg   15600
ggaacctaaa aagaccccaa aaagtcgct ttaatgaata gtaatacat ccagcccaaa     15660 gtccacagac tctttggtct ggttgtggca acatacagc cagttaacaa acaagacaaa    15720
aattatccta ggtggtcagt gggggttcag agctgaatcc tgaacactgg aaggaaaaca   15780
gcaaccaaat ccaaatactg tatggttttg cttatatgta gaatctaaat tcaaagcaaa   15840
tgagcaaacc aattgaaaca gttatggaag acaagcaggt ggttgtcagg ggggagataa   15900
ggggaggcag gaaagacctg ggcgagggag attaagaggt accaactttc agttgcaaaa   15960
caaatgagtc accagtatga aatgtgcaat gtgggaaata caggccataa ctttataatc   16020 tcttttttt ttttgtcttt tttgccttt ctaaggctgc tcccgtggca tatggaggtt     16080
cccaggctag gagtccaaac agagctgtag ctgccagcct acaccagagc cacagcaaca   16140
cgggaacctt aacccgctga gcaaggccag ggatcgaacc cgagtcctca cagatgccag   16200
tagggttcat taaccactga gccacgacag gaattccagg gtctgttgtg ttcttaaaac   16260
acttccagga gagtgagtgg tatgtcataa gtaaacaata aatgttaacc acaacaagct   16320
tatgaaataa acaggaaagc catatgacct acaatcagtc attgggagaa tccacaaaag   16380
gttgagcaga ggatcaattc cagctcacac tccagtttta gattctcccc tgccttaaag   16440
catcacagac tacataatct gagctgaaga ataaaaatta aaactcaccc cagtgcaaaa   16500
cagaaatgaa aaagtattaa aacgaggttc atactgttgt tcattagcaa tatctttat    16560 tcacaggggt gcccaacaac atgaaaaaat caagaattta ttgctgctac gtcaaagctt   16620
ataccagaga ttatgcctta tagacattag caatggataa ttatatgttg cacttgtgaa   16680
atgtgcacat atcctgttta tgaatcacca catagccaga ttatcaatat tttacttatt   16740
tcgtaaaaaa tccacaattt tccataacag aatcaacgtg tgcaatagga acaagattgc   16800
tatggaaaac gagggtaaca ggaggagata ttaatccaag catagaagaa atagacaaat   16860
gaggggccat aaggggaata tagggaagag aaaaaaatta agatggaatt ttaaaaggag   16920
aatgtaaaaa atagatattt gttccttaat aggttgattc ctcaaataga gcccatgaat   16980
ataatcaaat aggaagggtt catgactgtt ttcaattttt caaaaagctt tgttgaaatc   17040
atagacttgc aaaacaaggc tgtagaggcc accctaaaat ggaaaatttc actgggactg   17100
aaattatttt gattcaatga caaaatttgt tatttactgc ggattataaa ctctaacaaa   17160
tagcgatctc tttgcttcat aaaaacataa acactagcta gtaataaaat gagttctgca   17220
``` g                                                                            17221

<210> SEQ ID NO 51
<211> LENGTH: 26
<212> TYPE: DNA
<213> ORGANISM: artificial sequence
<220> FEATURE:
<223> OTHER INFORMATION: Primer

<400> SEQUENCE: 51
catggacctc aagctggggg acaaga                                                 26

<210> SEQ ID NO 52
<211> LENGTH: 28
<212> TYPE: DNA
<213> ORGANISM: artificial sequence
<220> FEATURE:
<223> OTHER INFORMATION: primer

<400> SEQUENCE: 52
gtgttcgacc cttggttaat cggtcctg                                               28

<210> SEQ ID NO 53
<211> LENGTH: 28
<212> TYPE: DNA
<213> ORGANISM: artificial sequence
<220> FEATURE:
<223> OTHER INFORMATION: Primer

<400> SEQUENCE: 53
caggaccgat taaccaaggg tcgaacac                                               28

<210> SEQ ID NO 54
<211> LENGTH: 26
<212> TYPE: DNA
<213> ORGANISM: artificial sequence
<220> FEATURE:
<223> OTHER INFORMATION: primer

<400> SEQUENCE: 54
tcttgtcccc cagcttgagg tccatg                                                 26

<210> SEQ ID NO 55
<211> LENGTH: 27
<212> TYPE: DNA
<213> ORGANISM: artificial sequence
<220> FEATURE:
<223> OTHER INFORMATION: primer

<400> SEQUENCE: 55
ctcctggaag cttctgtcaa gacgaac                                                27

<210> SEQ ID NO 56
<211> LENGTH: 27
<212> TYPE: DNA
<213> ORGANISM: artificial sequence
<220> FEATURE:
<223> OTHER INFORMATION: primer

<400> SEQUENCE: 56
gcctgataca cagtgctgtg caatggt                                                27

<210> SEQ ID NO 57
<211> LENGTH: 29
<212> TYPE: DNA

<213> ORGANISM: artificial sequence
<220> FEATURE:
<223> OTHER INFORMATION: primer

<400> SEQUENCE: 57
accacccaag tctggaatct tcttacact                                          29

<210> SEQ ID NO 58
<211> LENGTH: 30
<212> TYPE: DNA
<213> ORGANISM: artificial sequence
<220> FEATURE:
<223> OTHER INFORMATION: primer

<400> SEQUENCE: 58
gactctcata caaaagctaa gctgggtaag                                         30

<210> SEQ ID NO 59
<211> LENGTH: 30
<212> TYPE: DNA
<213> ORGANISM: artificial sequence
<220> FEATURE:
<223> OTHER INFORMATION: primer

<400> SEQUENCE: 59
gactctcata caaaacctaa gctgggtaag                                         30

<210> SEQ ID NO 60
<211> LENGTH: 30
<212> TYPE: DNA
<213> ORGANISM: artificial sequence
<220> FEATURE:
<223> OTHER INFORMATION: primer

<400> SEQUENCE: 60
gactctcata caaaacctag gctgggtaag                                         30

<210> SEQ ID NO 61
<211> LENGTH: 30
<212> TYPE: DNA
<213> ORGANISM: artificial sequence
<220> FEATURE:
<223> OTHER INFORMATION: primer

<400> SEQUENCE: 61
gactctcata caaaacctag gctaggtaag                                         30

<210> SEQ ID NO 62
<211> LENGTH: 28
<212> TYPE: DNA
<213> ORGANISM: artificial sequence
<220> FEATURE:
<223> OTHER INFORMATION: primer

<400> SEQUENCE: 62
ccttatactg gccccaattg gatcttac                                           28

<210> SEQ ID NO 63
<211> LENGTH: 28
<212> TYPE: DNA
<213> ORGANISM: artificial sequence
<220> FEATURE:
<223> OTHER INFORMATION: primer

<400> SEQUENCE: 63
ccttatactg gccccaattg gatcttac                                           28

```
<210> SEQ ID NO 64
<211> LENGTH: 30
<212> TYPE: DNA
<213> ORGANISM: artificial sequence
<220> FEATURE:
<223> OTHER INFORMATION: primer

<400> SEQUENCE: 64
cttacctagc ctaggttttg tatgagagtc                                   30

<210> SEQ ID NO 65
<211> LENGTH: 28
<212> TYPE: DNA
<213> ORGANISM: artificial sequence
<220> FEATURE:
<223> OTHER INFORMATION: primer

<400> SEQUENCE: 65
gacaaaccac aattggaatg cactcgag                                     28
```

PORCINE CMP-N-ACETYLNEURAMINIC ACID HYDROXYLASE GENE

CROSS REFERENCE TO RELATED APPLICATIONS

This application claims priority to U.S. Provisional patent application Ser. No. 60/476,396, filed Jun. 6, 2003.

FIELD OF THE INVENTION

The present invention provides porcine CMP-N-Acetyl-neuraminic-Acid Hydroxylase (CMP-Neu5Ac hydroxylase) protein, cDNA, and genomic DNA regulatory sequences. Furthermore, the present invention includes porcine animals, tissues, and organs, as well as cells and cell lines derived from such animals, tissues, and organs, which lack expression of functional CMP-Neu5Ac hydroxylase. Such animals, tissues, organs, and cells can be used in research and in medical therapy, including in xenotransplantation, and in industrial livestock farming operations. In addition, methods are provided to prepare organs, tissues, and cells lacking the porcine CMP-Neu5Ac hydroxylase gene for use in xenotranplantation.

BACKGROUND OF THE INVENTION

The unavailability of acceptable human donor organs, the low rate of long term success due to host versus graft rejection, and the serious risks of infection and cancer are the main challenges now facing the field of tissue and organ transplantation. Because the demand for acceptable organs exceeds the supply, many people die each year while waiting for organs to become available. To help meet this demand, research has been focused on developing alternatives to allogenic transplantation. Dialysis is available to patients suffering from kidney failure, artificial heart models have been tested, and other mechanical systems have been developed to assist or replace failing organs. Such approaches, however, are quite expensive. The need for frequent and periodic access to dialysis machines greatly limits the freedom and quality of life of patients undergoing such therapy.

Xenograft transplantation represents a potentially attractive alternative to artificial organs for human transplantation. The potential pool of nonhuman organs is virtually limitless. Pigs are considered the most likely source of xenograft organs. The supply of pigs is plentiful, breeding programs are well established, and their organ size and physiology are compatible with humans. Therefore, xenotransplantation with pig organs offers a potential solution to the shortage of organs available for clinical transplantation.

Host rejection of such cross-species tissue remains a major concern in this area. The immunological barriers to xenotransplantation have been, and remain, formidable. The first immunological hurdle is "hyperacute rejection" (HAR). HAR is defined by the ubiquitous presence of high titers of pre-formed natural antibodies binding to the foreign tissue. The binding of these natural antibodies to target epitopes on the donor organ endothelium is believed to be the initiating event in HAR. This binding, within minutes of perfusion of the donor organ with the recipient blood, is followed by complement activation, platelet and fibrin deposition, and ultimately by interstitial edema and hemorrhage in the donor organ, all of which cause failure of the organ in the recipient (Strahan, et al. (1996) *Frontiers in Bioscience* 1, pp. 34-41).

Some noted xenotransplants of organs from apes or old-world monkeys (e.g., baboons) into humans have been tolerated for months without rejection. However, such attempts have ultimately failed due to a number of immunological factors. Even with heavy immunosupression to suppress HAR, a low-grade innate immune response, attributable in part to failure of complement regulatory proteins (CRPs) within the graft tissue to control activation of heterologous complement on graft endothelium, ultimately leads to destruction of the transplanted organs (Starzl, Immunol. Rev., 141, 213-44 (1994)). In an effort to develop a pool of acceptable organs for xenotransplantation into humans, researchers have engineered animals that produce human CRPs, an approach which has been demonstrated to delay, but not eliminate, xenograft destruction in primates (McCurry, et al., *Nat. Med.,* 1, 423-27 (1995); Bach et al., *Immunol. Today,* 17, 379-84 (1996)).

In addition to complement-mediated attack, human rejection of discordant xenografts appears to be mediated by a common antigen: the galactose-α(1,3)-galactose (gal-α-gal) terminal residue of many glycoproteins and glycolipids (Galili et al., *Proc. Nat. Acad. Sci., (USA),* 84, 1369-73 (1987); Cooper, et al., *Immunol. Rev.,* 141, 31-58 (1994); Galili, et al., *Springer Sem. Immunopathol,* 15, 155-171 (1993); Sandrin, et al., *Transplant Rev.,* 8, 134 (1994)). This antigen is chemically related to the human A, B, and O blood antigens, and it is present on many parasites and infectious agents, such as bacteria and viruses. Most mammalian tissue also contains this antigen, with the notable exception of old world monkeys, apes and humans. (see, Joziasse, et al., *J. Biol. Chem.,* 264, 14290-97 (1989). Individuals without such carbohydrate epitopes produce abundant naturally occurring antibodies (IgM as well as IgG) specific to the epitopes. Many humans show significant levels of circulating IgG with specificity for gal-α-gal carbohydrate determinants (Galili, et al., *J. Exp. Med.,* 162, 573-82 (1985); Galili, et al., *Proc. Nat. Acad. Sci. (USA),* 84, 1369-73 (1987)). The α-galactosyltransferase (α-GT) enzyme catalyzes the formation of gal-α-gal moieties. Research has focused on the modulation or elimination of this enzyme to reduce or eliminate the expression of gal-α-gal moieties on the cell surface of xenotissue.

The elimination of the α-galactosyltransferase gene from porcine has long been considered one of the most significant hurdles to accomplishing xenotransplantation from pigs to humans. Two alleles in the pig genome encode the α-GT gene. Single allelic knockouts of the α-GT gene in pigs were reported in 2002 (Dai, et al. *Nature Biotechnol.,* 20:251 (2002); Lai, et al., *Science,* 295:1089 (2002)).

Recently, double allelic knockouts of the α-GT gene have been accomplished (Phelps, et al., *Science,* 299: pp. 411-414 (2003)). WO 2004/028243 to Revivicor Inc. describes porcine animal, tissue, organ, cells and cell lines, which lack all expression of functional α1,3 galactosyltransferase (α1,3-GT). Accordingly, the animals, tissues, organs and cells lacking functional expression of α1,3-GT can be used in xenotransplantation and for other medical purposes.

PCT patent application WO 2004/016742 to Immerge Biotherapeutics, Inc. describes α(1,3)-galactosyltransferase null cells, methods of selecting GGTA-1 null cells, α(1,3)-galactosyltransferase null swine produced therefrom (referred to as a viable GGTA-1 null swine), methods for making such swine, and methods of using cells, tissues and organs of such a null swine for xenotransplantation.

One of the earliest known xenoantigens other than gal-α-gal is an epitope that Hanganutiu Deicher antibodies recognize, and which have long been associated with serum disease. The epitope has been identified as N-glycolyl-neuraminic acid (Neu5Gc), a member of the sialic acid family of carbohydrates. Among carbohydrates, sialic acids are abundant and ubiquitous. Sialic acid is a generic designation used for N-acylneuraminic acids (Neu5Acyl) and their derivatives. N-Acetylneuraminic acid (Neu5Ac) and N-glycolylneuraminic acid (Neu5Gc) are two of the most abundant derivatives of sialic acids.

The Neu5Gc epitope is located in the terminal position in the glycan chains of glycoconjugates. Due to this exposed position, it plays an important role in cellular recognition, e.g. in the case of inflammatory reactions, maturation of immune cells, differentiation processes, hormone-, pathogen- and toxin binding (Varki, A., *Glycobiology*, 2, pp. 25-40 (1992)).

Glycoconjugates containing Neu5Gc are immunogenic in humans. In healthy humans, Neu5Gc is not detectable, although Neu5Gc is abundant in most mammals. The lack of Neu5Gc in man is due to an exon deletion in the human gene that prevents the formation of functional enzyme (Chou, H. H., et al. *Proc. Natl. Acad. Sci. (USA)*, 95, pp. 11751-11756 (1998); Irie, A., et al. *J. Biol. Chem.*, 273, pp. 15866-15871 (1998)). Thus, Neu5Gc-containing glycoconjugates act as antigens and can induce the formation of antibodies. Historically, the antibodies have been referred to as Hanganutziu-Deicher (HD) antigens and antibodies (Hanganutziu, M., *CR Soc. Biol. (Paris)*, 91, p. 1457 (1924); Deicher, H., Z. *Hyg.*, 106, p. 561 (1926)). Hanganutziu-Deicher antigens are detectable in many human tumors (colon carcinoma, retinoblastoma, melanoma and carcinoma of the breast) as well as in chicken tumor tissues (Higashi, H., et al. *Cancer Res.*, 45, pp. 3796-3802 (1985)). Although the amount of antigen in tumors is very small (usually less than 1% of the total amount of sialic acid, often in the range of from 0.01 to 0.1%), it is capable of inducing the formation of Hanganutziu-Deicher antibodies (Higashihara, T., et al., *Int Arch Allergy Appl Immunol.*, 95, pp. 231-235 (1991)). This immunological reaction is a potential barrier to xenotransplantation of Neu5Gc-containing pig organs to humans.

The Neu5Gc epitope is formed by the addition of a hydroxyl group to the N-acetyl moiety of Neu5Ac. The enzyme that catalyzes the hydroxylation is CMP-Neu5Ac hydroxylase. Thus, the expression of the CMP-Neu5Ac hydroxylase gene determines the presence of the Neu5Gc epitope on cell surfaces. Purification studies of CMP-Neu5Ac hydroxylase in mammals have shown that it is a soluble, cytosolic oxygenase that is dependent on cytochrome b5 and cytochrome b5 reductase (Kawano, T., et al., *J. Biol. Chem.*, 269, pp. 9024-9029 (1994); Schneckenburger, P., et al., *Glycoconj. J.*, 11, pp. 194-203 (1994); Schlenzka, W., et al., *Glycobiology*, 4, pp. 675-683 (1994); Kozutsumi, Y., et al., *J. Biochem. (Tokyo)*, 108, pp. 704-706 (1990); and, Shaw, L., et al. *Eur. J. Biochem.*, 219, pp. 1001-1011 (1994)).

Another important feature of Neu5Gc is that it acts as an adhesion molecule for pathogens, allowing for entry into the cell (Kelm, S. and Schauer, R., *Int. Rev. Cytol*, 179, pp. 137-240 (1997)). This causes disease and economic losses in certain livestock species. Specifically, enterotoxigenic *Escherichia coli* with K99 fimbriae infect newborn piglets by binding to Neu5Gc in gangliosides such as Nue5Gca2→3Galβ1→4Glcβ1→1' ceramide [GM3 (Neu5Gc)], N-glycolylsialoparagloboside and GM2 (Neu5Gc) attached to intestinal absorptive and mucus secreting cells, causing a potentially lethal diarrhea (Malykh, Y., et. al., *Biochem. J.*, 370, pp. 601-607 (2003); Kyogashima, M., et al., (1993); Teneberg, S., et al., *FEBS Letters*, 263, pp. 10-14 (1990); Isobe, T., et al., *Anal. Biochem.*, 236, pp. 35-40 (1996); Lindahl, M. and Carlstedt, I., *J. Gen. Microbiol.*, 136, pp. 1609-1614 (1990); King, T. P., et al., *Proceedings of the 6th International Symposium on Digestive Physiology in Pigs*, pp. 290-293, (1994)). Pig *rotavirus* infects pig newborns causing diarrhea by binding to GM3(Neu5Gc). Pig transmissible gastroenteritis coronavirus infects pigs via entry into glycoconjugates containing α2,3-bound Neu5Gc (Schultz, B., et al., *J. Virol.*, 70, pp. 5634-5637 (1996)).

CMP-Neu5Ac hydroxylase has been isolated from mouse liver and pig submandibular glands to homogeneity and characterized (Kawano, T., et al., *J. Biol. Chem.*, 269, pp. 9024-9029 (1994); Schneckenburger, P., et al., *Glycoconj. J.*, 11, pp. 194-203 (1994); and, Schlenzka, W., et al., *Glycobiology*, 4, pp. 675-683 (1994)).

Schlenzka, et al. (*Glycobiology*, Vol. 4, pp. 675-683 (1994)) purified the enzyme from pig submandibular glands using ion exchange chromatography, chromatography with immobilized triazin dyes, hydrophobic interaction chromatography and gel filtration. Schneckenburger et al. (*Glycoconj. J.*, Vol. 11, pp. 194-203 (1994)) isolated the CMP-Neu5Ac hydroxylase from mouse liver. Both the CMP-Neu5Ac hydroxylase from pig submandibular glands and the one from mouse liver are soluble monomers having a molecular weight of 65 kDa. Their catalytic interactions with CMP-Neu5Ac and cytochrome b5 are very similar to one another. The activity of these enzymes seems to be dependent on an iron-containing prosthetic group.

JP-A 06 113838 describes the protein and DNA sequences of murine CMP-Neu5Ac hydroxylase, as well as a monoclonal antibody that specifically binds to the hydroxylase.

PCT Publication No. WO 97/03200A1 to Boehringer Manheim GMBH discloses a partial cDNA for the porcine CMP-Neu5Ac hydroxylase. This application discloses a cDNA sequence beginning in the middle of Exon 8 of the CMP-Neu5Ac hydroxylase gene (further disclosed as GenBank accession number Y15010).

Martensen, L., et al. (*Eur. J. Biochem.*, Vol. 268, pp. 5157-5166 (2001)) discloses a full length amino acid sequence of porcine CMP-Neu5Ac hydroxylase.

PCT Publication No. WO 02/088351 to RBC Biotechnology discloses a partial cDNA and genomic sequence (exons 7-11 as well as partial genomic sequence surrounding each exon) of porcine CMP-NeuAc hydroxylase. In addition, methods are provided to generate porcine cells and animals lacking the CMP-NeuAc hydoxylase epitope, optionally, in combination with other genetic modifications, such as inactivation of the alpha-1,3-galactosyltransferase gene and/or insertion of complement proteins.

It is an object of the present invention to provide genomic and regulatory sequences of the porcine CMP-Neu5Ac hydroxylase gene.

It is an object of the present invention to provide the full length cDNA, as well as novel variants of the CMP-Neu5Ac hydroxylase gene.

It is another object of the invention to provide novel nucleic acid and amino acid sequences that encode the CMP-Neu5Ac hydroxylase gene.

It is yet a further object of the present invention to provide cells, tissues and/or organs deficient in the CMP-Neu5Ac hydroxylase gene.

It is another object of the present invention to generate animals, particularly pigs, lacking a functional CMP-Neu5Ac hydroxylase gene.

It is yet a further object of the present invention to provide cells, tissues and/or organs deficient in the CMP-Neu5Ac hydroxylase gene for use in xenotransplantation of non-human organs to human recipients in need thereof.

SUMMARY OF THE INVENTION

The full length cDNA sequence, peptide sequence, and genomic organization of the porcine CMP-Neu5Ac hydroxylase gene has been determined. To date, only partial cDNA and genomic sequences have been identified. The present invention provides novel porcine CMP-Neu5Ac hydroxylase protein, cDNA, cDNA variants, and genomic DNA sequence. Furthermore, the present invention includes porcine animals, tissues, and organs, as well as cells and cell lines derived from such animals, tissue, and organs, which lack expression of functional CMP-Neu5Ac hydroxylase. Such animals, tissues, organs, and cells can be used in research and in medical therapy, including xenotransplantation. In addition, methods are provided to prepare organs, tissues, and cells lacking the porcine CMP-Neu5Ac hydroxylase gene for use in xenotransplantation.

One aspect of the present invention provides the full length cDNA of porcine CMP-Neu5Ac hydroxylase. The full length cDNA is shown in Table 1 (SEQ ID No 1) and the full length peptide sequence is provided in Table 2 (SEQ ID No 2). The start codon for the full-length cDNA is located in the 3' portion of Exon 4, and the stop codon is found in the 3' portion of Exon 17. Nucleotide and amino acid sequences at least 80, 85, 90, 95, 98 or 99% homologous to SEQ ID Nos 1 or 2 are provided. In addition, nucleotide and peptide sequences that contain at least 10, 15, 17, 20, 25 or 30 nucleotide or amino acid sequences of SEQ ID Nos 1 or 2 are also provided. Further provided is any nucleotide sequence that hybridizes, optionally under stringent conditions, to SEQ ID No 1, as well as, nucleotides homologous thereto.

In one embodiment, nucleic acid and peptide sequences encoding three novel variants of CMP-Neu5Ac hydroxylase are provided (Tables 3-8, FIG. 2). SEQ ID No 3 represents the cDNA of a variant of the gene, variant-1, that includes Exons 1, 4, 5, 6, 7, 8, 9, 10, 11, 12, 13, 15a, 16, 17, and 18. SEQ ID No 5 represents the cDNA of a variant of the gene, variant-2, that includes Exons 1, 4, 5, 6, 7, 8, 9, 10, 11, 12 and 12a. SEQ ID No 7 represents the cDNA of a variant of the gene, variant-3, that includes Exons 1, 4, 5, 6, 7, 8, 9, 10, 11 and 11a. SEQ ID Nos 4, 6 and 8 represent the amino acid sequences of variant-1, variant-2 and variant-3, respectively. Nucleotide and amino acid sequences at least 80, 85, 90, 95, 98 or 99% homologous to SEQ ID Nos 3-8 are provided. In addition, nucleotide and peptide sequences that contain at least 10, 15, 17, 20, 25, or 30 nucleotide or amino acid sequence of SEQ ID Nos 3-8 are also provided. Further provided is any nucleotide sequence that hybridizes, optionally under stringent conditions, to SEQ ID Nos 3, 5 and 7, as well as, nucleotides homologous thereto.

A further embodiment provides nucleic acid sequences representing genomic DNA sequences of the CMP-Neu5Ac hydroxylase gene (Table 9, FIG. 1). SEQ ID Nos 10-28 represent Exons 1, 4-11, 11a, 12, 12a, 13-15, 15a, 16-18, respectively, and SEQ ID Nos 29-45 represent Introns 1a, 1b, 4-15, 15a, 16, and 17, respectively. SEQ ID No. 9 represents the 5' untranslated region of the CMP-Neu5Ac hydroxylase gene. SEQ ID No. 46 (Table 10) represents the genomic DNA and regulatory sequence of CMP-Neu5Ac hydroxylase.

In another embodiment, the genomic sequence of the porcine CMP-Neu5Ac hydroxylase gene is represented by SEQ ID No. 47. SEQ ID No. 47 represents the 5' contiguous genomic sequence containing 5' UTR, Exon 1 and a portion of intronic sequence located 3' of Exon 1 (Table 11).

In another embodiment, the genomic sequence of the porcine CMP-Neu5Ac hydroxylase gene is represented by SEQ ID No. 48. SEQ ID NO. 48 represents a contiguous genomic sequence containing intronic sequence located 5' to Exon 4, Exon 4, Intron 4, Exon 5, Intron 5, Exon 6, Intron 6, Exon 7, Intron 7, Exon 8, Intron 8, Exon 9, Intron 9, Exon 10, Intron 10, Exon 11, Intron 11, Exon 12, Intron 12, Exon 13, Intron 13, Exon 14, Intron 14, Exon 15, Intron 15, Exon 16, Intron 16, Exon 17, Intron 17, and Exon 18 (Table 12). In addition, nucleotide sequences that contain at least 2775, 2800, 2900, 3000, 3100, 3200, 3300, 3400, 3500, 3600, 3700, 3800, 3900, 4000, 4500, 5000, 5500, 6000, 6500, 7000, 7500, 8000, 8500, 9000, 9500 or 10,000 contiguous nucleotides of SEQ ID NO. 48 are provided, as well as nucleotide sequences at least 80, 85, 90, 95, 98, or 99% homologous to SEQ ID NO. 48.

In another embodiment, the genomic sequence of the porcine CMP-Neu5Ac hydroxylase gene is represented by SEQ ID No. 49. SEQ ID NO. 49 represents contiguous genomic sequences containing Intronic sequence 5' to Exon 4, Exon 4, Intron 4, Exon 5, Intron 5, Exon 6, Intron 6, Exon 7, Intron 7 and Exon 8. Further, nucleotide sequences that contain at least 1750, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5500, 6000, 6500, 7000, 7500, 8000, 8500, 9000, 9500, 10000, 11000, 12000, 13000, 14000, 15000, 16000, 17000, 18000, 19000, or 20000 contiguous nucleotides of SEQ ID NO. 49 are provided, as well as nucleotide sequences at least 80, 85, 90, 95, 98, or 99% homologous to SEQ ID NO. 49.

In another embodiment, the genomic sequence of the porcine CMP-Neu5Ac hydroxylase gene is represented by SEQ ID No. 50. SEQ ID NO. 50 represents contiguous genomic sequences containing Exon 12, Intron 12, Exon 13, Intron 13, Exon 14, Intron 14, Exon 15, Intron 15, Exon 16, Intron 16, Exon 17, Intron 17, and Exon 18 are provided. Nucleotide sequences that contain at least 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000 or 20,000 contiguous nucleotides of SEQ ID NO. 50 are provided, as well as nucleotide sequences at least 80, 85, 90, 95, 98, or 99% homologous to SEQ ID NO. 50.

In further embodiments, nucleotide and amino acid sequences at least 80, 85, 90, 95, 98 or 99% homologous to SEQ ID Nos 9-45, 46, 47, 48, 49 and 50 are provided. In addition, nucleotide and peptide sequences that contain at least 10, 15, 17, 20, 25, 30, 50, 100, 150, 200, 300, 400, 500 or 1000 contiguous nucleotide or amino acid sequences of SEQ ID Nos 9-45, 46, 47, and 48 are also provided. Further provided is any nucleotide sequence that hybridizes, optionally under stringent conditions, to SEQ ID Nos 9-45, 46, 47, 48, 49 and 50, as well as, nucleotides homologous thereto.

Another aspect of the present invention provides nucleic acid constructs that contain cDNA or variants thereof encoding CMP-Neu5Ac hydroxylase. These cDNA sequences can be derived from Seq ID Nos. 1-8, or any fragment thereof. Constructs can contain one, or more than one, internal ribosome entry site (IRES). The construct can also contain a promoter operably linked to the nucleic acid sequence encoding CMP-Neu5Ac hydroxylase, or, alternatively, the construct can be promoterless. In another embodiment, nucleic acid constructs are provided that contain nucleic acid sequences that permit random or targeted insertion into a host genome. In addition to the nucleic acid sequences the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells.

In another embodiment, nucleic acid targeting vectors constructs are also provided wherein homologous recombination in somatic cells can be achieved. These targeting vectors can be transformed into mammalian cells to target the CMP-Neu5Ac hydroxylase gene via homologous recombination. In one embodiment, the targeting vectors can contain a 3' recombination arm and a 5' recombination arm that is homologous to the genomic sequence of a CMP-Neu5Ac hydroxylase. The homologous DNA sequence can include at least 15 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp of sequence homologous to the CMP-Neu5Ac hydroxylase sequence. In another embodiment, the homologous DNA sequence can include one or more intron and/or exon sequences. In a specific embodiment, the DNA sequence can be homologous to Intron 5 and Intron 6 of the CMP-Neu5Ac hydroxylase gene (see, for example, FIGS. 6-8). In another specific embodiment, the DNA sequence can be homologous to Intron 5, a 55 bp portion of Exon 6, and Intron 6 of the CMP-Neu5Ac hydroxylase gene, and contain enhanced Green Fluorescent Protein sequence in an in-frame orientation 3' to the 55 bp portion of Exon 6 (see, for example, FIGS. 10 and 11).

Another embodiment of the present invention provides oligonucleotide primers capable of hybridizing to porcine CMP-Neu5Ac hydroxylase cDNA or genomic sequence, such as Seq ID Nos. 1, 3, 5, 7, 9-45, 46, 47 or 48. In a preferred embodiment, the primers hybridize under stringent conditions to SEQ ID Nos. 1, 3, 5, 7, 9-45, 46, 47 or 48. Another embodiment provides oligonucleotide probes capable of hybridizing to porcine CMP-Neu5Ac hydroxylase nucleic acid sequences, such as SEQ ID Nos. 1, 3, 5, 7, 9-45, 46, 47, or 48. The polynucleotide primers or probes can have at least 14 bases, 20 bases, preferably 30 bases, or 50 bases which hybridize to a polynucleotide of the present invention. The probe or primer can be at least 14 nucleotides in length, and in a preferred embodiment, are at least 15, 20, 25, 28, or 30 nucleotides in length.

In another aspect of the present invention, mammalian cells lacking at least one allele of the CMP-Neu5Ac hydroxylase gene produced according to the process, sequences and/or constructs described herein are provided. These cells can be obtained as a result of homologous recombination. Particularly, by inactivating at least one allele of the CMP-NeuAc hydroxylase gene, cells can be produced which have reduced capability for expression of functional Hanganutziu-Deicher antigens.

In embodiments of the present invention, alleles of the CMP-Neu5Ac hydroxylase gene are rendered inactive according to the process, sequences and/or constructs described herein, such that the resultant CMP-Neu5Ac hydroxylase enzyme can no longer generate Hanganutziu-Deicher antigens. In one embodiment, the CMP-Neu5Ac hydroxylase gene can be transcribed into RNA, but not translated into protein. In another embodiment, the CMP-Neu5Ac hydroxylase gene can be transcribed in an inactive truncated form. Such a truncated RNA may either not be translated or can be translated into a nonfunctional protein. In an alternative embodiment, the CMP-Neu5Ac hydroxylase gene can be inactivated in such a way that no transcription of the gene occurs. In a further embodiment, the CMP-Neu5Ac hydroxylase gene can be transcribed and then translated into a nonfunctional protein.

In a further aspect of the present invention, porcine animals are provided in which at least one allele of the CMP-Neu5Ac hydroxylase gene is inactivated via a genetic targeting event produced according to the process, sequences and/or constructs described herein. In another aspect of the present invention, porcine animals are provided in which both alleles of the CMP-Neu5Ac hydroxylase gene are inactivated via a genetic targeting event. The gene can be targeted via homologous recombination. In other embodiments, the gene can be disrupted, i.e. a portion of the genetic code can be altered, thereby affecting transcription and/or translation of that segment of the gene. For example, disruption of a gene can occur through substitution, deletion ("knock-out") or insertion ("knock-in") techniques. Additional genes for a desired protein or regulatory sequence that modulate transcription of an existing sequence can be inserted.

In another aspect of the present invention, porcine cells lacking one allele, optionally both alleles of the porcine CMP-Neu5Ac hydroxylase gene can be used as donor cells for nuclear transfer into enucleated oocytes to produce cloned, transgenic animals. Alternatively, porcine CMP-Neu5Ac hydroxylase knockouts can be created in embryonic stem cells, which are then used to produce offspring. Offspring lacking a single allele of the functional CMP-Neu5Ac hydroxylase gene produced according to the process, sequences and/or constructs described herein can be breed to further produce offspring lacking functionality in both alleles through mendelian type inheritance. Cells, tissues and/or organs can be harvested from these animals for use in xenotransplantation strategies. The elimination of the Hanganutziu-Deicher antigens can reduce the immune rejection of the transplanted cell, tissue or organ due to the Neu5Gc epitope.

Alternatively, animals lacking at least one allele of the CMP-Neu5Ac hydroxylase gene produced according to the process, sequences and/or constructs described herein can be less susceptible or resistant to enterotoxigenic infection and disease such as, for example, *E. Coli* infection, *rotavirus* infection, and gastroenteritis coronavirus. Such animals can be used, for example, in commercial farming.

In one aspect of the present invention, a pig can be prepared by a method in accordance with any aspect of the present invention. Genetically modified pigs can be used as a source of tissue and/or organs for transplantation therapy. A pig embryo prepared in this manner or a cell line developed therefrom can also be used in cell-transplantation therapy. Accordingly, there is provided in a further aspect of the invention a method of therapy comprising the administration of genetically modified cells lacking porcine CMP-Neu5Ac hydroxylase to a patient, wherein the cells have been prepared from an embryo or animal lacking CMP-Neu5Ac hydroxylase. This aspect of the invention extends to the use of such cells in medicine, e.g. cell-transplantation therapy, and also to the use of cells derived from such embryos in the preparation of a cell or tissue graft for transplantation. The cells can be organized into tissues or organs, for example, heart, lung, liver, kidney, pancreas, corneas, nervous (e.g. brain, central nervous system, spinal cord), skin, or the cells can be islet cells, blood cells (e.g. haemocytes, i.e. red blood cells, leucocytes) or haematopoietic stem cells or other stem cells (e.g. bone marrow).

In another aspect of the present invention, CMP-Neu5Ac hydroxylase-deficient pigs also lack genes encoding other xenoantigens, such as, for example, porcine iGb3 synthase (see, for example, U.S. Patent Application No. 60/517,524), and/or porcine Forssman synthase (see, for example, U.S. Patent Application No. 60/568,922). In another embodiment, porcine cells are provided that lack the α1,3 galactosyltransferase gene and the CMP-Neu5Ac hydroxylase gene produced according to the process, sequences and/or constructs described herein. In another embodiment, porcine α1,3 galactosyltransferase gene knockout cells are further modified to knockout the CMP-Neu5Ac hydroxylase gene produced according to the process, sequences and/or constructs described herein. In addition, CMP-Neu5Ac hydroxylase deficient pigs produced according to the process, sequences and/or constructs described herein, optionally lacking one or more additional genes associated with an adverse immune response, can be modified to express complement inhibiting proteins, such as, for example, CD59, DAF, and/or MCP can be further modified to eliminate the expression of al least one allele of the CMP-Neu5Ac hydroxylase gene. These animals can be used as a source of tissue and/or organs for transplantation therapy. These animals can be used as a source of tissue and/or organs for transplantation therapy. A pig embryo prepared in this manner or a cell line developed therefrom can also be used in cell-transplantation therapy.

DESCRIPTION OF THE INVENTION

Elimination of the CMP-Neu5Ac hydroxylase gene produced according to the process, sequences and/or constructs described herein can reduce a human beings immunological response to the Neu5Gc epitope and remove an immunological barrier to xenotransplantation. The present invention is directed to novel nucleic acid sequences encoding the full-length cDNA and peptide. Information about the genomic organization, intronic sequences and regulatory regions of the gene are also provided. In one aspect, the invention provides isolated and substantially purified cDNA molecules having one of SEQ ID Nos: 1, 3, 5 or 7, or a fragment thereof. In another aspect of the invention, DNA sequences comprising the full-length genome of the CMP-NeuAc hydrolase gene are provided in SEQ ID Nos 9-45, 46, 47, 48, 49 or 50 or fragments thereof. In another aspect, primers for amplifying porcine CMP-Neu5Ac hydroxylase cDNA or genomic sequence derived from SEQ ID Nos. 1, 3, 5, 7, 9-45, 46, 47, 48, 49 or 50 are provided. Additionally probes for identifying CMP-Neu5Ac hydroxylase nucleic acid sequences derived from SEQ ID Nos. 1, 3, 5, 7, 9-45, 46, 47, 48, 49 or 50, or fragments thereof are provided. DNA represented by SEQ ID Nos 9-45, 46, 47, 48, 49 or 50, or fragments thereof, can be used to construct pigs lacking functional CMP-Neu5Ac hydroxylase genes. Thus, the invention also provides a porcine chromosome lacking a functional CMP-NeuAc hydrolase gene and a transgenic pig lacking a functional CMP-NeuAc hydroxylase protein produced according to the process, sequences and/or constructs described herein. Such pigs can be used as tissue sources for xenotransplantation into humans. In an alternate embodiment, CMP-NeuAc hydroxylase-deficient pigs produced according to the process, sequences and/or constructs described herein also lack other genes associated with adverse immune responses in xenotransplantation, such as, for example, the α1,3 galactosyltransferase gene, iGb3 synthetase gene, or FSM synthase gene. In another embodiment, pigs lacking CMP-Neu5Ac hydroxylase produced according to the process, sequences and/or constructs described herein and/or other genes associated with adverse immune responses in xenotransplantation express complement inhibiting factors such as, for example, CD59, DAF, and/or MCP.

BRIEF DESCRIPTION OF THE FIGURES

FIG. 4 illustrates transcription factor binding sites located within exon 1 (228 bp) and its 5'-flanking region spanning 601 bp. (SEQ ID NO: 70).

FIG. 5 depicts oligonucleotide sequences that can be used for DNA construction of porcine CMP-Neu5Ac hydroxylase gene targeting vector. (pDH1: SEQ ID NO: 57; pDH2: SEQ ID NO: 58; pDH2a: SEQ ID NO: 59; pDH2b: SEQ ID NO: 60; pDH2c: SEQ ID NO: 61; pDH3: SEQ ID NO: 55 and pDH4: SEQ ID NO: 56)

FIG. 9 represents oligonucleotide sequences used in generating an enhanced green fluorescent protein expression vector for use in a Knock-in strategy. (pDH5: SEQ ID NO: 62; pDH6: SEQ ID NO: 67; pDH7: SEQ ID NO: 68; pDH8: SEQ ID NO: 69)

DEFINITIONS

Figure 1:
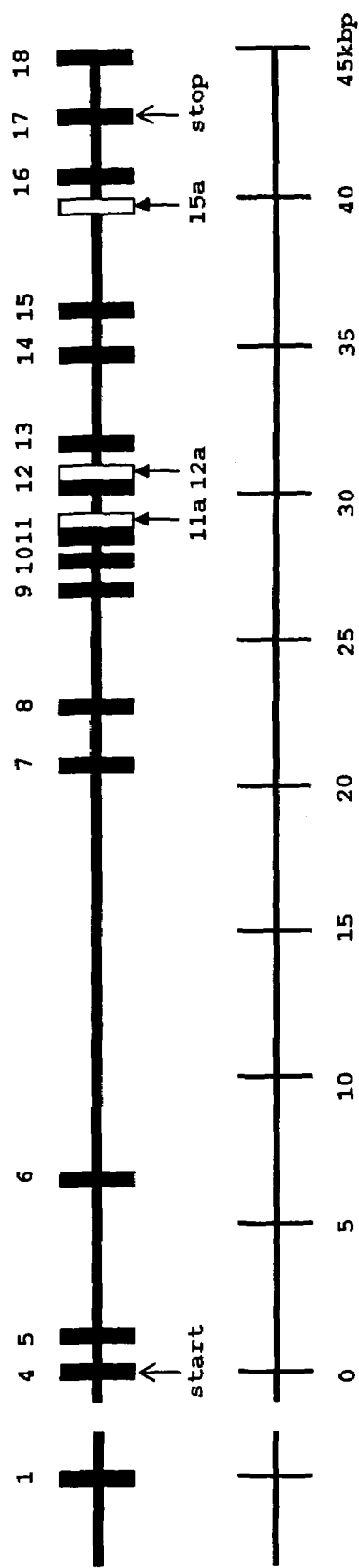
FIG. 1 represents the genomic organization of the porcine CMP-Neu5Ac hydroxylase gene. Closed bars depict each numbered exon. The length of the introns between the exons illustrates relative distances. (Open boxes also represent exons that appear in some variants (see FIG. 2); "start" and "stop" denote start and stop codons, respectively) The approximate scale is depicted in the bottom of the figure.

A "target DNA sequence" is a DNA sequence to be modified by homologous recombination. The target DNA can be in any organelle of the animal cell including the nucleus and mitochondria and can be an intact gene, an exon or intron, a regulatory sequence or any region between genes.

A "targeting DNA sequence" is a DNA sequence containing the desired sequence modifications. The targeting DNA sequence can be substantially isogenic with the target DNA.

A "homologous DNA sequence or homologous DNA" is a DNA sequence that is at least about 80%, 85%, 90%, 95%, 98% or 99% identical with a reference DNA sequence. A homologous sequence hybridizes under stringent conditions to the target sequence, stringent hybridization conditions include those that will allow hybridization occur if there is at least 85% and preferably at least 95% or 98% identity between the sequences.

An "isogenic or substantially isogenic DNA sequence" is a DNA sequence that is identical to or nearly identical to a reference DNA sequence. The term "substantially isogenic" refers to DNA that is at least about 97-99% identical with the reference DNA sequence, and preferably at least about 99.5-99.9% identical with the reference DNA sequence, and in certain uses 100% identical with the reference DNA sequence.

"Homologous recombination" refers to the process of DNA recombination based on sequence homology.

"Gene targeting" refers to homologous recombination between two DNA sequences, one of which is located on a chromosome and the other of which is not.

"Non-homologous or random integration" refers to any process by which DNA is integrated into the genome that does not involve homologous recombination.

A "selectable marker gene" is a gene, the expression of which allows cells containing the gene to be identified. A selectable marker can be one that allows a cell to proliferate on a medium that prevents or slows the growth of cells without the gene. Examples include antibiotic resistance genes and genes which allow an organism to grow on a selected metabolite. Alternatively, the gene can facilitate visual screening of transformants by conferring on cells a phenotype that is easily identified. Such an identifiable phenotype can be, for example, the production of luminescence or the production of a colored compound, or the production of a detectable change in the medium surrounding the cell.

The term "contiguous" is used herein in its standard meaning, i.e., without interruption, or uninterrupted.

The term "porcine" refers to any pig species, including pig species such as Large White, Landrace, Meishan, Minipig.

The term "oocyte" describes the mature animal ovum which is the final product of oogenesis and also the precursor forms being the oogonium, the primary oocyte and the secondary oocyte respectively.

The term "fragment" means a portion or partial sequence of a nucleotide or peptide sequence.

The terms "derivative" and "analog" means a nucleotide or peptide sequence which retains essentially the same biological function or activity as such nucleotide or peptide. For example, an analog includes a proprotein which can be activated by cleavage of the proprotein portion to produce an active mature polypeptide.

DNA (deoxyribonucleic acid) sequences provided herein are represented by the bases adenine (A), thymine (T), cytosine (C), and guanine(G).

Amino acid sequences provided herein are represented by the following abbreviations:

| | |
|---|---|
| A | alanine |
| P | proline |
| B | aspartate or asparagine |
| Q | glutamine |
| C | cysteine |
| R | arginine |
| D | aspartate |
| S | serine |
| E | glutamate |
| T | threonine |
| F | phenylalanine |
| G | glycine |
| V | valine |
| H | histidine |
| W | tryptophan |
| I | isoleucine |
| Y | tyrosine |
| Z | glutamate or glutamine |
| K | lysine |
| L | leucine |
| M | methionine |
| N | asparagine |

"Transfection" refers to the introduction of DNA into a host cell. Cells do not naturally take up DNA. Thus, a variety of technical "tricks" are utilized to facilitate gene transfer. Numerous methods of transfection are known to the ordinarily skilled artisan, for example, $CaPO_4$ and electroporation. (J. Sambrook, E. Fritsch, T. Maniatis, Molecular Cloning: A Laboratory Manual, Cold Spring Laboratory Press, 1989). Transformation of the host cell is the indicia of successful transfection.

Figure 2:
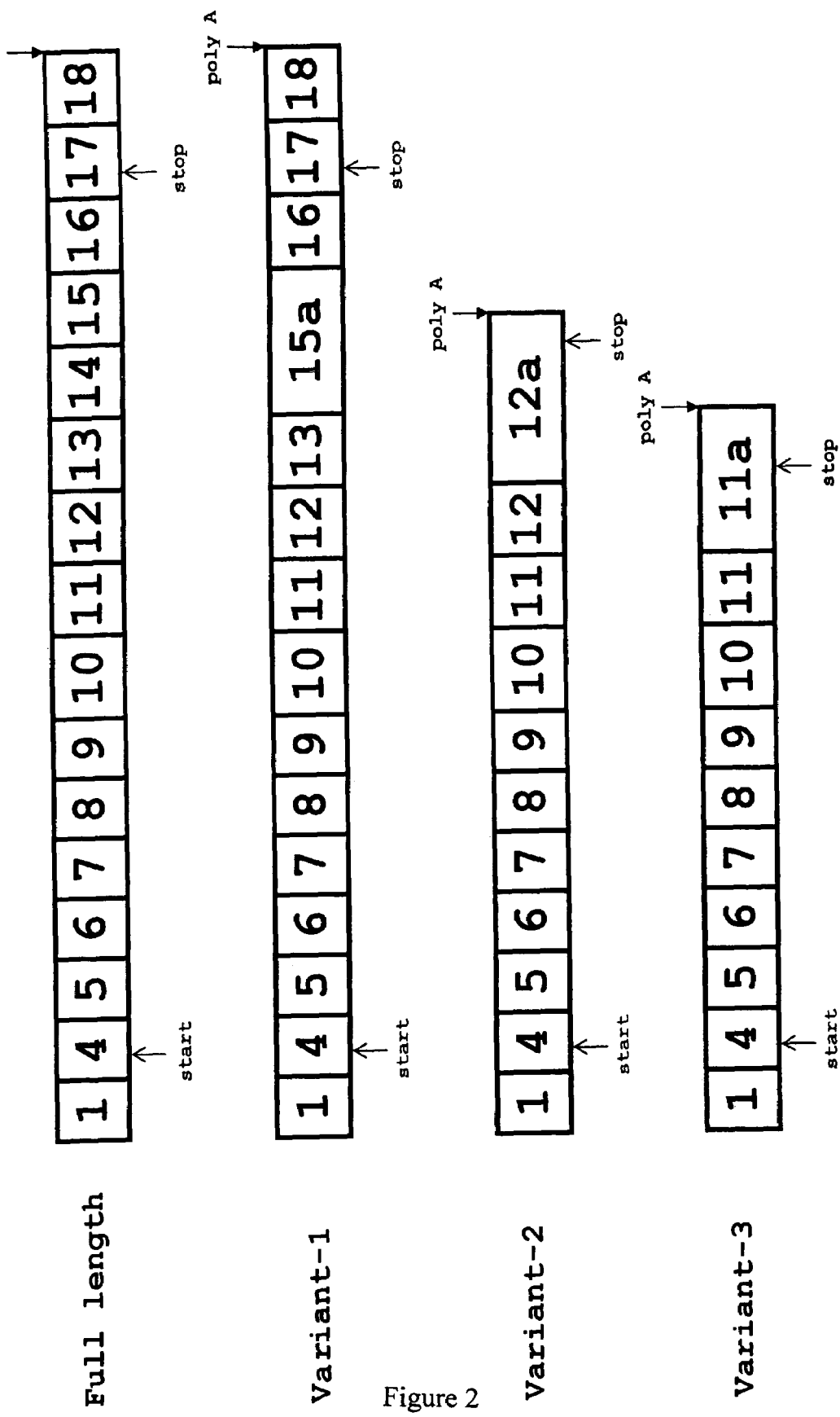
FIG. 2 depicts cDNA sequences of the CMP-Neu5Ac hydroxylase gene. Variant-1 contains exon 15a in place of exons 14 and 15. Variant-2 contains exon 12a, and variant-3 contains exon 11a. "Start" and "stop" denote the start and stop codons, respectively.

I. Complete cDNA Sequence and Variants of the Porcine CMP-Neu5Ac Hydroxylase Gene One aspect of the present invention provides novel, full length nucleic acid cDNA sequences of the porcine CMP-Neu5Ac hydroxylase gene (FIG. 2, Table 1, Seq ID No 1). Another aspect of the present invention provides predicted amino acid peptide sequences of the porcine CMP-Neu5Ac hydroxylase gene (Table 2, Seq ID No 2). The ATG start codon for the full-length cDNA is located in the 3' portion of Exon 4, and the stop codon TAG is found in the 3' portion of Exon 17. Nucleic and amino acid sequences at least 90, 95, 98 or 99% homologous to Seq ID Nos 1 or 2 are provided. In addition, nucleotide and peptide sequences that contain at least 10, 15, 17, 20 or 25 contiguous nucleic or amino acids of Seq ID Nos 1 or 2 are also provided. Further provided are fragments, derivatives and analogs of Seq ID Nos 1-2. Fragments of Seq ID Nos. 1-2 can include any contiguous nucleic acid or peptide sequence that includes at least about 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 700, 750, 800, 850, 900, 1000, 5000 or 10,000 nucleotides.

TABLE 1

| Full length cDNA | |
|---|---|
| CCCGACGTCCTGGCAGCGCCCAGGCACTG | Exons 1 & Seq ID No 1 |
| TTATTGGTGCCTCCTGTGTCCACGCGCTT | 4-18 |
| CCCGGCCAGGCAGCCCTGGCGGATCCTAT | |
| TTTCTGTTCCCCCGATTCTGGTACCTCTC | |
| CCTCCCGCCCTCGGTGCGCAGCCGTCCTC | |
| CTGCAGTGCCTGCTCCTCCAGGGGCGAAA | |
| CCGATCAGGGATCAGGCCACCCGCCTCCT | |
| GAACATCCCTCCTTAGTTCCCACAGTCTA | |
| ATGCCTTGTGGAAGCAAATGAGCCACAGA | |
| AGCTGAAGGAAAAACCACCATTCTTTCTT | |
| AATACCTGGAGAGAGGCAACGACAGACTA | |
| TGAGCAGCATCGAACAAACGACGGAGATC | |
| CTGTTGTGCCTCTCACCTGCCGAAGCTGC | |
| CAATCTCAAGGAAGGAATCAATTTTGTTC | |
| GAAATAAGAGCACTGGCAAGGATTACATC | |
| TTATTTAAGAATAAGAGCCGCCTGAAGGC | |
| ATGTAAGAACATGTGCAAGCACCAAGGAG | |
| GCCTCTTCATTAAAGACATTGAGGATCTA | |
| AATGGAAGGTCTGTTAAATGCACAAAACA | |
| CAACTGGAAGTTAGATGTAAGCAGCATGA | |
| AGTATATCAATCCTCCTGGAAGCTTCTGT | |
| CAAGACGAACTGGTTGTAGAAAAGGATGA | |
| AGAAAATGGAGTTTTGCTTCTAGAACTAA | |
| ATCCTCCTAACCCGTGGGATTCAGAACCC | |
| AGATCTCCTGAAGATTTGGCATTTGGGGA | |
| AGTGCAGATCACGTACCTTACTCACGCCT | |
| GCATGGACCTCAAGCTGGGGGACAAGAGA | |
| ATGGTGTTCGACCCTTGGTTAATCGGTCC | |
| TGCTTTTGCGCGAGGATGGTGGTTACTAC | |
| ACGAGCCTCCATCTGATTGGCTGGAGAGG | |
| CTGAGCCGCGCAGACTTAATTTACATCAG | |
| TCACATGCACTCAGACCACCTGAGTTACC | |
| CAACACTGAAGAAGCTTGCTGAGAGAAGA | |
| CCAGATGTTCCCATTTATGTTGGCAACAC | |
| GGAAAGACCTGTATTTTGGAATCTGAATC | |
| AGAGTGGCGTCCAGTTGACTAATATCAAT | |
| GTAGTGCCATTTGGAATATGGCAGCAGGT | |
| AGACAAAAATCTTCGATTCATGATCTTGA | |
| TGGATGGCGTTCATCCTGAGATGGACACT | |

TABLE 1-continued

| Full length cDNA |
|---|
| TGCATTATTGTGGAATACAAAGGTCATAA |
| AATACTCAATACAGTGGATTGCACCAGAC |
| CCAATGGAGGAAGGCTGCCTATGAAGGTT |
| GCATTAATGATGAGTGATTTTGCTGGAGG |
| AGCTTCAGGCTTTCCAATGACTTTCAGTG |
| GTGGAAAATTTACTGAGGAATGGAAAGCC |
| CAATTCATTAAAACAGAAAGGAAGAAACT |
| CCTGAACTACAAGGCTCGGCTGGTGAAGG |
| ACCTACAACCCAGAATTTACTGCCCCTTT |
| CCTGGGTATTTCGTGGAATCCCACCCAGC |
| AGACAAGTATATTAAGGAAACAAACATCA |
| AAAATGACCCAAATGAACTCAACAATCTT |
| ATCAAGAAGAATTCTGAGGTGGTAACCTG |
| GACCCCAAGACCTGGAGCCACTCTTGATC |
| TGGGTAGGATGCTAAAGGACCCAACAGAC |
| AGCAAGGGCATCGTAGAGCCTCCAGAAGG |
| GACTAAGATTTACAAGGATTCCTGGGATT |
| TTGGCCCATATTTGAATATCTTGAATGCT |
| GCTATAGGAGATGAAATATTTCGTCACTC |
| ATCCTGGATAAAAGAATACTTCACTTGGG |
| CTGGATTTAAGGATTATAACCTGGTGGTC |
| AGGATGATTGAGACAGATGAGGACTTCAG |
| CCCTTTGCCTGGAGGATATGACTATTTGG |
| TTGACTTTCTGGATTTATCCTTTCCAAAA |
| GAAAGACCAAGCCGGGAACATCCATATGA |
| GGAAATTCGGAGCCGGGTTGATGTCATCA |
| GACACGTGGTAAAGAATGGTCTGCTCTGG |
| GATGACTTGTACATAGGATTCCAAACCCG |
| GCTTCAGCGGGATCCTGATATATACCATC |
| ATCTGTTTTGGAATCATTTTCAAATAAAA |
| CTCCCCCTCACACCACCTGACTGGAAGTC |
| CTTCCTGATGTGCTCTGGGTAGAGAGGAC |
| CTGAGCTGTCCCAGGGGTGCCCAACAACA |
| TGAAAAAATCAAGAATTTATTGCTGCTAC |
| GTCAAAGCTTATACCAGAGATTATGCCTT |
| ATAGACATTAGCAATGGATAATTATATGT |
| TGCACTTGTGAAATGTGCACATATCCTGT |
| TTATGAATCACCACATAGCCAGATTATCA |

TABLE 1-continued

Full length cDNA

ATATTTTACTTATTTCGTAAAAAATCCAC

AATTTTCCATAACAGAATCAACGTGTGCA

ATAGGAACAAGATTGCTATGGAAAACGAG

GGTAACAGGAGGAGATATTAATCCAAGCA

TAGAAGAAATAGACAAATGAGGGGCCATA

AGGGGAATATAGGGAAGAGAAAAAAATTA

AGATGGAATTTTAAAAGGAGAATGTAAAA

AATAGATATTTGTTCCTTAATAGGTTGAT

TCCTCAAATAGAGCCCATGAATATAATCA

AATAGGAAGGGTTCATGACTGTTTTCAAT

TTTTCAAAAAGCTTTGTTGAAATCATAGA

CTTGCAAAACAAGGCTGTAGAGGCCACCC

TAAAATGGAAAATTTCACTGGGACTGAAA

TTATTTTGATTCAATGACAAAATTTGTTA

TTTACTGCGGATTATAAACTCTAACAAAT

AGCGATCTCTTTGCTTCATAAAAACATAA

ACACTAGCTAGTAATAAAATGAGTTCTGC

AG

TABLE 2

Full length Amino Acid Sequence

M S S I E Q T T E I L L C L S P A E A A Seq ID No 2

N L K E G I N F V R N K S T G K D Y I L

F K N K S R L K A C K N M C K H Q G G L

F I K D I E D L N G R S V K C T K H N W

K L D V S S M K Y I N P P G S F C Q D E

L V V E K D E E N G V L L L E L N P P N

P W D S E P R S P E D L A F G E V Q I T

Y L T H A C M D L K L G D K R M V F D P

W L I G P A F A R G W W L L H E P P S D

W L E R L S R A D L I Y I S H M H S D H

L S Y P T L K K L A E R R P D V P I Y V

G N T E R P V F W N L N Q S G V Q L T N

I N V V P F G I W Q Q V D K N L R F M I

L M D G V H P E M D T C I I V E Y K G H

K I L N T V D C T R P N G G R L P M K V

A L M M S D F A G G A S G F P M T F S G

G K F T E E W K A Q F I K T E R K K L L

TABLE 2-continued

Full length Amino Acid Sequence

N Y K A R L V K D L Q P R I Y C P F P G

Y F V E S H P A D K Y I K E T N I K N D

P N E L N N L I K K N S E V V T W T P R

P G A T L D L G R M L K D P T D S K G I

V E P P E G T K I Y K D S W D F G P Y L

N I L N A A I G D E I F R H S S W I K E

Y F T W A G F K D Y N L V V R M I E T D

E D F S P L P G G Y D Y L V D F L D L S

F P K E R P S R E H P Y E E I R S R V D

V I R H V V K N G L L W D D L Y I G F Q

T R L Q R D P D I Y H H L F W N H F Q I

K L P L T P P D W K S F L M C S G

Variants

Another aspect of the present invention provides novel nucleic acid cDNA sequences of three novel variants of CMP-Neu5Ac hydroxylase gene transcript (FIG. 2, Tables 3, 5, and 7, Seq ID Nos. 3, 5, and 7). Seq ID No 3 represents the cDNA of a variant of the gene, variant-1, that includes Exons 1, 4, 5, 6, 7, 8, 9, 10, 11, 12, 13, 15a, 16, 17, and 18. Exon 15a is a cryptic Exon that normally appears in Intron 15, approxiametly 460 bp upstream of Exon 16. The start codon for variant-1 is located in Exon 4, while the stop codon is located in Exon 17. Seq ID No 5 represents the cDNA of a variant of the gene, variant-2, that includes Exons 1, 4, 5, 6, 7, 8, 9, 10, 11, 12 and 12a. Exon 12a is a cryptic Exon which is retained from a partial sequence of Intron 12 (see SEQ ID. No. 21). The start codon for variant-2 is located in Exon 4, while the stop condon is located in the terminal end of Exon 12a. Seq ID No 7 represents the cDNA of a variant of the gene, variant-3, that includes Exons 1, 4, 5, 6, 7, 8, 9, 10, 11 and 11a. Exon 11a is a cryptic Exon which is retained from a partial sequence of Intron 11 (see Seq ID No. 19). The start codon for variant-3 is located in Exon 4, while the stop codon is located in Exon 11a. Another aspect of the present invention provides predicted amino acid peptide sequences of three novel variants of the porcine CMP-Neu5Ac Hydroxylase gene transcript. Seq ID Nos 4, 6 and 8 represent the amino acid sequences of variant-1, variant-2 and variant-3, respectively. Nucleotide and amino acid sequences at least 80, 85, 90, 95, 98 or 99% homologous to Seq ID Nos 3-8 are provided. In addition, nucleotide and peptide sequences that contain at least 10, 15, 17, 20, 25, 30, 50, 100, 150, 200, 300, 400, 500 or 1000 contiguous nucleotide or amino acid sequences of Seq ID Nos 3-8 are also provided. Further provided are fragments, derivatives and analogs of Seq ID Nos 3-8. Fragments of Seq ID Nos. 3-8 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

TABLE 3

| Variant-1 cDNA | | |
|---|---|---|
| CCCGACGTCCTGGCAGCGCCCAGGCA | Exons 1, 4- | Seq ID No 3 |
| CTGTTATTGGTGCCTCCTGTGTCCAC | 13, 15a, 16, | |
| GCGCTTCCCGGCCAGGCAGCCCTGGC | 17, 18 | |
| GGATCCTATTTTCTGTTCCCCCGATT | | |
| CTGGTACCTCTCCCTCCCGCCCTCGG | | |
| TGCGCAGCCGTCCTCCTGCAGTGCCT | | |
| GCTCCTCCAGGGGCGAAACCGATCAG | | |
| GGATCAGGCCACCCGCCTCCTGAACA | | |
| TCCCTCCTTAGTTCCCACAGTCTAAT | | |
| GCCTTGTGGAAGCAAATGAGCCACAG | | |
| AAGCTGAAGGAAAAACCACCATTCTT | | |
| TCTTAATACCTGGAGAGAGGCAACGA | | |
| CAGACTATGAGCAGCATCGAACAAAC | | |
| GACGGAGATCCTGTTGTGCCTCTCAC | | |
| CTGCCGAAGCTGCCAATCTCAAGGAA | | |
| GGAATCAATTTTGTTCGAAATAAGAG | | |
| CACTGGCAAGGATTACATCTTATTTA | | |
| AGAATAAGAGCCGCCTGAAGGCATGT | | |
| AAGAACATGTGCAAGCACCAAGGAGG | | |
| CCTCTTCATTAAAGACATTGAGGATC | | |
| TAAATGAAGGTCTGTTAAATGCACA | | |
| AAACACAACTGGAAGTTAGATGTAAG | | |
| CAGCATGAAGTATATCAATCCTCCTG | | |
| GAAGCTTCTGTCAAGACGAACTGGTT | | |
| GTAGAAAAGGATGAAGAAAATGGAGT | | |
| TTTGCTTCTAGAACTAAATCCTCCTA | | |
| ACCCGTGGGATTCAGAACCCAGATCT | | |
| CCTGAAGATTTGGCATTTGGGGAAGT | | |
| GCAGATCACGTACCTTACTCACGCCT | | |
| GCATGGACCTCAAGCTGGGGACAAG | | |
| AGAATGGTGTTCGACCCTTGGTTAAT | | |
| CGGTCCTGCTTTTGCGCGAGGATGGT | | |
| GGTTACTACACGAGCCTCCATCTGAT | | |
| TGGCTGGAGAGGCTGAGCCGCGCAGA | | |
| CTTAATTTACATCAGTCACATGCACT | | |
| CAGACCACCTGAGTTACCCAACACTG | | |
| AAGAAGCTTGCTGAGAGAAGACCAGA | | |
| TGTTCCCATTTATGTTGGCAACACGG | | |
| AAAGACCTGTATTTTGGAATCTGAAT | | |

TABLE 3-continued

| Variant-1 cDNA |
|---|
| CAGAGTGGCGTCCAGTTGACTAATAT |
| CAATGTAGTGCCATTTGGAATATGGC |
| AGCAGGTAGACAAAAATCTTCGATTC |
| ATGATCTTGATGGATGGCGTTCATCC |
| TGAGATGGACACTTGCATTATTGTGG |
| AATACAAAGGTCATAAAATACTCAAT |
| ACAGTGGATTGCACCAGACCCAATGG |
| AGGAAGGCTGCCTATGAAGGTTGCAT |
| TAATGATGAGTGATTTTGCTGGAGGA |
| GCTTCAGGCTTTCCAATGACTTTCAG |
| TGGTGGAAAATTTACTGAGGAATGGA |
| AAGCCCAATTCATTAAAACAGAAAGG |
| AAGAAACTCCTGAACTACAAGGCTCG |
| GCTGGTGAAGGACCTACAACCCAGAA |
| TTTACTGCCCCTTTCCTGGGTATTTC |
| GTGGAATCCCACCCAGCAGACAAGTA |
| TATTAAGGAAACAAACATCAAAAATG |
| ACCCAAATGAACTCAACAATCTTATC |
| AAGAAGAATTCTGAGGTGGTAACCTG |
| GACCCCAAGACCTGGAGCCACTCTTG |
| ATCTGGGTAGGATGCTAAAGGACCCA |
| ACAGACAGATCCTGTGTCAGGAGTTG |
| GGATTCTTTGAAGATTCGGAGCCGGG |
| TTGATGTCATCAGACACGTGGTAAAG |
| AATGGTCTGCTCTGGGATGACTTGTA |
| CATAGGATTCCAAACCCGGCTTCAGC |
| GGGATCCTGATATATACCATCATCTG |
| TTTTGGAATCATTTTCAAATAAAACT |
| CCCCCTCACACCACCTGACTGGAAGT |
| CCTTCCTGATGTGCTCTGGGTAGAGA |
| GGACCTGAGCTGTCCCAGGGGTGCCC |
| AACAACATGAAAAAATCAAGAATTTA |
| TTGCTGCTACGTCAAAGCTTATACCA |
| GAGATTATGCCTTATAGACATTAGCA |
| ATGGATAATTATATGTTGCACTTGTG |
| AAATGTGCACATATCCTGTTTATGAA |
| TCACCACATAGCCAGATTATCAATAT |
| TTTACTTATTTCGTAAAAAATCCACA |

TABLE 3-continued

Variant-1 cDNA

ATTTTCCATAACAGAATCAACGTGTG

CAATAGGAACAAGATTGCTATGGAAA

ACGAGGGTAACAGGAGGAGATATTAA

TCCAAGCATAGAAGAAATAGACAAAT

GAGGGGCCATAAGGGGAATATAGGGA

AGAGAAAAAAATTAAGATGGAATTTT

AAAAGGAGAATGTAAAAAATAGATAT

TTGTTCCTTAATAGGTTGATTCCTCA

AATAGAGCCCATGAATATAATCAAAT

AGGAAGGGTTCATGACTGTTTTCAAT

TTTTCAAAAAGCTTTGTTGAAATCAT

AGACTTGCAAAACAAGGCTGTAGAGG

CCACCCTAAAATGGAAAATTTCACTG

GGACTGAAATTATTTTGATTCAATGA

CAAAATTTGTTATTTACTGCGGATTA

TAAACTCTAACAAATAGCGATCTCTT

TGCTTCATAAAAACATAAACACTAGC

TAGTAATAAAATGAGTTCTGCAG

TABLE 4

Variant-1 Amino Acid Sequence

M S S I E Q T T E I L L C L S P A E A A   Seq ID No 4

N L K E G I N F V R N K S T G K D Y I L

F K N K S R L K A C K N M C K H Q G G L

F I K D I E D L N G R S V K C T K H N W

K L D V S S M K Y I N P P G S F C Q D E

L V V E K D E E N G V L L L E L N P P N

P W D S E P R S P E D L A F G E V Q I T

Y L T H A C M D L K L G D K R M V F D P

W L I G P A F A R G W W L L H E P P S D

W L E R L S R A D L I Y I S H M H S D H

L S Y P T L K K L A E R R P D V P I Y V

G N T E R P V F W N L Q S G V Q L T N

I N V V P F G I W Q Q V D K N L R F M I

L M D G V H P E M D T C I I V E Y K G H

K I L N T V D C T R P N G G R L P M K V

A L M M S D F A G G A S G F P M T F S G

G K F T E E W K A Q F I K T E R K K L L

TABLE 4-continued

Variant-1 Amino Acid Sequence

N Y K A R L V K D L Q P R I Y C P F P G

Y F V E S H P A D K Y I K E T N I K N D

P N E L N N L I K K N S E V V T W T P R

P G A T L D L G R M L K D P T D R S C V

R S W D S L K I R S R V D V I R H V V K

N G L L W D D L Y I G F Q T R L Q R D P

D I Y H H L F W N H F Q I K L P L T P P

D W K S F L M C S G

TABLE 5

Variant-2 cDNA

CCCGACGTCCTGGCAGCGCCCAGGCAC   Exons 1, 4-   Seq ID No 5

TGTTATTGGTGCCTCCTGTGTCCACGC   12, 12a

GCTTCCCGGCCAGGCAGCCCTGGCGGA

TCCTATTTTCTGTTCCCCCGATTCTGG

TACCTCTCCCTCCCGCCCTCGGTGCGC

AGCCGTCCTCCTGCAGTGCCTGCTCCT

CCAGGGGCGAAACCGATCAGGGATCAG

GCCACCCGCCTCCTGAACATCCCTCCT

TAGTTCCCACAGTCTAATGCCTTGTGG

AAGCAAATGAGCCACAGAAGCTGAAGG

AAAAACCACCATTCTTTCTTAATACCT

GGAGAGAGGCAACGACAGACTATGAGC

AGCATCGAACAAACGACGGAGATCCTG

TTGTGCCTCTCACCTGCCGAAGCTGCC

AATCTCAAGGAAGGAATCAATTTTGTT

CGAAATAAGAGCACTGGCAAGGATTAC

ATCTTATTTAAGAATAAGAGCCGCCTG

AAGGCATGTAAGAACATGTGCAAGCAC

CAAGGAGGCCTCTTCATTAAAGACATT

GAGGATCTAAATGGAAGGTCTGTTAAA

TGCACAAAACACAACTGGAAGTTAGAT

GTAAGCAGCATGAAGTATATCAATCCT

CCTGGAAGCTTCTGTCAAGACGAACTG

GTTGTAGAAAAGGATGAAGAAAATGGA

GTTTTGCTTCTAGAACTAAATCCTCCT

AACCCGTGGGATTCAGAACCCAGATCT

CCTGAAGATTTGGCATTTGGGGAAGTG

TABLE 5-continued

Variant-2 cDNA

CAGATCACGTACCTTACTCACGCCTGC
ATGGACCTCAAGCTGGGGACAAGAGA
ATGGTGTTCGACCCTTGGTTAATCGGT
CCTGCTTTTGCGCGAGGATGGTGGTTA
CTACACGAGCCTCCATCTGATTGGCTG
GAGAGGCTGAGCCGCGCAGACTTAATT
TACATCAGTCACATGCACTCAGACCAC
CTGAGTTACCCAACACTGAAGAAGCTT
GCTGAGAGAAGACCAGATGTTCCCATT
TATGTTGGCAACACGGAAAGACCTGTA
TTTTGGAATCTGAATCAGAGTGGCGTC
CAGTTGACTAATATCAATGTAGTGCCA
TTTGGAATATGGCAGCAGGTAGACAAA
AATCTTCGATTCATGATCTTGATGGAT
GGCGTTCATCCTGAGATGGACACTTGC
ATTATTGTGGAATACAAAGGTCATAAA
ATACTCAATACAGTGGATTGCACCAGA
CCCAATGGAGGAAGGCTGCCTATGAAG
GTTGCATTAATGATGAGTGATTTTGCT
GGAGGAGCTTCAGGCTTTCCAATGACT
TTCAGTGGTGGAAAATTTACTGAGGAA
TGGAAAGCCCAATTCATTAAAACAGAA
AGGAAGAAACTCCTGAACTACAAGGCT
CGGCTGGTGAAGGACCTACAACCCAGA
ATTTACTGCCCCTTTCCTGGGTATTTC
GTGGAATCCCACCCAGCAGACAAGTAT
GGCTGGATATTTTATATAACGTGTTTA
CGCATAAGTTAATATATGCTGAATGAG
TGATTTAGCTGTGAAACAACATGAAAT
GAGAAAGAATGATTAGTAGGGGTCTGG
AGCTTATTTTAACAAGCAGCCTGAAAA
CAGAAAGTATGAATAAAAAAAATTAAA
TGCAAAAAAAAAAAAAAAAAAAAAA
AAAA

TABLE 6

Variant-2 Amino Acid Sequence

M S S I E Q T T E I L L C L S P A E A A  Seq ID No 6
N L K E G I N F V R N K S T G K D Y I L

TABLE 6-continued

Variant-2 Amino Acid Sequence

F K N K S R L K A C K N M C K H Q G G L
F I K D I E D L N G R S V K C T K H N W
K L D V S S M K Y I N P P G S F C Q D E
L V V E K D E E N G V L L L E L N P P N
P W D S E P R S P E D L A F G E V Q I T
Y L T H A C M D L K L G D K R M V F D P
W L I G P A F A R G W W L L H E P P S D
W L E R L S R A D L I Y I S H M H S D H
L S Y P T L K K L A E R R P D V P I Y V
G N T E R P V F W N L N Q S G V Q L T N
I N V V P F G I W Q Q V D K N L R F M I
L M D G V H P E M D T C I I V E Y K G H
K I L N T V D C T R P N G G R L P M K V
A L M M S D F A G G A S G F P M T F S G
G K F T E E W K A Q F I K T E R K K L L
N Y K A R L V K D L Q P R I Y C P F P G
Y F V E S H P A D K Y G W I F Y I T C L
R I S

TABLE 7

Variant-3 cDNA

CCCGACGTCCTGGCAGCGCCCAGGCAC  Exons 1, 4- Seq ID No 7
TGTTATTGGTGCCTCCTGTGTCCACGC  11, 11a
GCTTCCCGGCCAGGCAGCCCTGGCGGA
TCCTATTTTCTGTTCCCCCGATTCTGG
TACCTCTCCCTCCCGCCCTCGGTGCGC
AGCCGTCCTCCTGCAGTGCCTGCTCCT
CCAGGGGCGAAACCGATCAGGGATCAG
GCCACCCGCCTCCTGAACATCCCTCCT
TAGTTCCCACAGTCTAATGCCTTGTGG
AAGCAAATGAGCCACAGAAGCTGAAGG
AAAAACCACCATTCTTTCTTAATACCT
GGAGAGAGGCAACGACAGACTATGAGC
AGCATCGAACAAACGACGGAGATCCTG
TTGTGCCTCTCACCTGCCGAAGCTGCC
AATCTCAAGGAAGGAATCAATTTTGTT
CGAAATAAGAGCACTGGCAAGGATTAC
ATCTTATTTAAGAATAAGAGCCGCCTG

TABLE 7-continued

Variant-3 cDNA

AAGGCATGTAAGAACATGTGCAAGCAC
CAAGGAGGCCTCTTCATTAAAGACATT
GAGGATCTAAATGGAAGGTCTGTTAAA
TGCACAAAACACAACTGGAAGTTAGAT
GTAAGCAGCATGAAGTATATCAATCCT
CCTGGAAGCTTCTGTCAAGACGAACTG
GTTGTAGAAAAGGATGAAGAAAATGGA
GTTTTGCTTCTAGAACTAAATCCTCCT
AACCCGTGGGATTCAGAACCCAGATCT
CCTGAAGATTTGGCATTTGGGGAAGTG
CAGATCACGTACCTTACTCACGCCTGC
ATGGACCTCAAGCTGGGGGACAAGAGA
ATGGTGTTCGACCCTTGGTTAATCGGT
CCTGCTTTTGCGCGAGGATGGTGGTTA
CTACACGAGCCTCCATCTGATTGGCTG
GAGAGGCTGAGCCGCGCAGACTTAATT
TACATCAGTCACATGCACTCAGACCAC
CTGAGTTACCCAACACTGAAGAAGCTT
GCTGAGAGAAGACCAGATGTTCCCATT
TATGTTGGCAACACGGAAGACCTGTA
TTTTGGAATCTGAATCAGAGTGGCGTC
CAGTTGACTAATATCAATGTAGTGCCA
TTTGGAATATGGCAGCAGGTAGACAAA
AATCTTCGATTCATGATCTTGATGGAT
GGCGTTCATCCTGAGATGGACACTTGC
ATTATTGTGGAATACAAAGGTCATAAA
ATACTCAATACAGTGGATTGCACCAGA
CCCAATGGAGGAAGGCTGCCTATGAAG
GTTGCATTAATGATGAGTGATTTTGCT
GGAGGAGCTTCAGGCTTTCCAATGACT
TTCAGTGGTGGAAAATTTACTGGTAAT
TCTTTATATCAAATGATGCCAAGGAG
TTGGCATGGCACTTTGCTAAATGCTGT
GTGAATCAATACAAAGATAATTAGGAC
ATGGTTCTTCCTCACAAGAGGTGTGCA
ATCTTATTGGGAAATCATACTTGCAAG
TCACAAATATAGACTAAAGTTTCCAGC
TGAGAATATGCTGATGGAGCATGAAAC
ACTAAGGAGACAGGGAGAATCTCAGGA
AAAATCAAGAATAATTTGGATCAAATG
GATTCCTGACATAGAACATAGAGCTGA
TCAGAAAGAGTCTGACATTGGTAATCC
AGGCTTAAGTGCTCTTTGTATGTGGTT
CAGAACAGAGTGTGGGCAGCCTGAGGG
GGATACATACCCTTGACCTCGTGGAAA
GCTCATACGGGGAGGGATGAGGCTAA
GGAAGCCCCTCTAAAGTGTGGGATTAC
GAGAGGTTGGGGGGTGGTAGGGAAAA
TAGTGGTCAAAGAGTATAAACTTCCAG
TTACAAGATGAATAAATTCTAGGGGTA
TAATAACAGCATGGCACTATAGATAGC
ATATTGTACTATATACTGGAAGTGCTG
AGAGTAGATCTTACATGTTCTAACCAC
ACACACACACACACACACACACACACC
ACACACACACACCACACACACACACGT
GCACACAAACAGAAATGGTAATTATGT
GAGGTGATGGCGGTGTTAACTAACTTT
ATTGTGGTCATCATTTAGCCATACATG
CATGTCATGAAATCACCATGTTGTACA
CCTTAAAGTTATGTAATACTAGATGTC
AGTTATATCTCAAAGCTAGAAAAAATG
TGGGGACCAAGGCAGAAGCTCTTCTGC
TCTGTGTCTAAGGGTGGTTCTGGGGCT
GGGATGGGGAGGATGGTTAAGTGGTAT
ATTTTTTTCATACCTTTGCTCAGTACT
ATCATTGTAAGTGTTCAATATATGTCT
GCTTAATAAATTAATGTTTTTAGTAAA
AAAAAAAAAAAAAAAAAAAAAAAA

TABLE 8

Variant-3 Amino Acid Sequence

M S S I E Q T T E I L L C L S P A E A A Seq ID No 8
N L K E G I N F V R N K S T G K D Y I L
F K N K S R L K A C K N M C K H Q G G L
F I K D I E D L N G R S V K C T K H N W
K L D V S S M K Y I N P P G S F C Q D E
L V V E K D E E N G V L L L E L N P P N

TABLE 8-continued

Variant-3 Amino Acid Sequence

P W D S E P R S P E D L A F G E V Q I T

Y L T H A C M D L K L G D K R M V F D P

W L I G P A F A R G W W L L H E P P S D

W L E R L S R A D L I Y I S H M H S D H

L S Y P T L K K L A E R R P D V P I Y V

G N T E R P V F W N L N Q S G V Q L T N

I N V V P F G I W Q Q V D K N L R F M I

L M D G V H P E M D T C I I V E Y K G H

K I L N T V D C T R P N G G R L P M K V

A L M M S D F A G G A S G F P M T F S G

G K F T G N S L Y Q N D A K E L A W H F

A K C C V N Q Y K D N

In other aspects of the present invention, nucleic acid constructs are provided that contain cDNA or variants thereof encoding CMP-Neu5Ac hydroxylase. These cDNA sequences can be SEQ ID NO 1, 3, 5 or 7, or derived from SEQ ID Nos. 2, 4, 6, or 8 or any fragment thereof. Constructs can contain one, or more than one, internal ribosome entry site (IRES). The construct can also contain a promoter operably linked to the nucleic acid sequence encoding CMP-Neu5Ac hydroxylase, or, alternatively, the construct can be promoterless. In another embodiment, nucleic acid constructs are provided that contain nucleic acid sequences that permit random or targeted insertion into a host genome. In addition to the nucleic acid sequences the expression vector can contain selectable marker sequences, such as, for example, enhanced Green Fluorescent Protein (eGFP) gene sequences, initiation and/or enhancer sequences, poly A-tail sequences, and/or nucleic acid sequences that provide for the expression of the construct in prokaryotic and/or eukaryotic host cells. Suitable vectors and selectable markers are described below. The expression constructs can further contain sites for transcription initiation, termination, and/or ribosome binding sites. The constructs can be expressed in any prokaryotic or eukaryotic cell, including, but not limited to yeast cells, bacterial cells, such as E. Coli, mammalian cells, such as CHO cells, and/or plant cells.

Promoters for use in such constructs, include, but are not limited to, the phage lambda PL promoter, E. coli lac, E. coli trp, E. coli phoA, E. coli tac promoters, SV40 early, SV40 late, retroviral LTRs, PGKI, GALI, GALIO genes, CYCI, PH05, TRPI, ADHI, ADH2, forglymaldehyde phosphate dehydrogenase, hexokinase, pyruvate decarboxylase, phosphofructokinase, triose phosphate isomerase, phosphoglucose isomerase, glucokinase alpha-mating factor pheromone, PRBI, GUT2, GPDI promoter, metallothionein promoter, and/or mammalian viral promoters, such as those derived from adenovirus and vaccinia virus. Other promoters will be known to one skilled in the art.

II. Genomic Sequences of the CMP-Neu5Ac Hydroxylase Gene

Nucleic acid sequences representing the genomic DNA organization of the CMP-Neu5Ac hydroxylase gene (FIG. 1, Table 9) are also provided. Seq ID Nos 10-28 represent Exons 1, 4-11, 11a, 12, 12a, 13-15, 15a, and 16-18, respectively. Exons 11a, 12a, and 15a are cryptic Exons that are retained in certain variant transcripts of CMP-Neu5Ac hydroxylase. SEQ ID Nos 29-45 represent Intronic sequence between Exon 1 and Exon 4 (hereinafter Intron 1a and Intron 1b, respectively), 4-15, 15a, 16, and 17, respectively. Intron 15a is the 3' downstream portion of Intron 15 that follows the cryptic Exon 15a. Seq ID No. 9 represents the 5' untranslated region of the porcine CMP-Neu5Ac hydroxylase gene. Nucleic acid sequence representing the genomic DNA sequence of the porcine CMP-Neu5Ac hydroxylase gene (Table 10, SEQ ID No. 46) is also provided. In addition, contiguous genomic sequence representing the 5' contiguous genomic sequence containing 5' UTR, Exon 1 and a portion of intronic sequence located between Exon 1 and Exon 4 (Intron 1a) (SEQ ID No. 47, Table 11) is provided. Contiguous genomic sequence containing an intronic sequence located between Exon 1 and Exon 4 (Intron 1b) through Exon 18 (SEQ ID No. 48, Table 12) is also provided. Nucleotide and amino acid sequences at least 80, 85, 90, 95, 98 or 99% homologous to SEQ ID Nos 9-45, 46, 47, 48, 49 and 50 are provided. In addition, nucleotide and peptide sequences that contain at least 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 700, 750, 800, 850, 900, 1000, 5000 or 10,000 contiguous nucleotide or amino acid sequences of SEQ ID Nos 9-45, 46, 47, 48, 49 and 50 are also provided, as well as any nucleotide sequence 80, 85, 90, 95, 98 or 99% homologous thereto. Further provided are fragments, derivatives and analogs of SEQ ID Nos 9-45, 46, 47, 48, 49, and 50. Fragments of Seq ID Nos. 9-45, 46, 47, 48, 49, and 50 can include any contiguous nucleic acid or peptide sequence or at least about 10 bp, 15 bp, 17 bp, 20 bp, 50 bp, 100 bp, 500 bp, 1 kbp, 5 kbp or 10 kpb.

In addition, regulatory regions in the form of putative transcription factor binding sites of the genomic sequence have been identified (see FIG. 4). These binding sites are located in the 5'UTR and Exon 1 of the porcine CMP-Neu5Ac hydroxylase genome, and include binding sites for transcription factors such as, for example, ETSF, MZF1, SF1, CMYB, MEF2, TATA, MEF2, NMP4, CAAT, AP1, BRN2, SATB1, ATF, GAT1, USF, WHN, NMP4, ZF5, NFKB, ZBP89, MOK2, ZF5, NFY, and MYCMAX.

TABLE 9

Genomic Organizational Sequences ctgccagcctaagccacagccacagcaac 5'UTR   Seq ID No 9
gctgggtctgagccatgtctgcagcctat
gccagagctccccgcagcgccggatgctt
aacccactgagcaaggccagggattgaac
cctcgtcctcatggatagcagttgagttg
tttccacggaactcttaggggaactcctg
attatttttattaaatttatatttctc
tgactttttcgtgtgctcatcagccactg
actgtgtatctccattagtcatggtttgt
taactctgtcattcaaaccctcttcatcc
ttgctacgcagataacatcattataataa
aatcgtgcctgaagaccagtgacgccccc TABLE 9-continued Genomic Organizational Sequences aagctaagttactgcttcccctgggggga
aaaagaagcaccgcgcgggcgctgacacg
aagtccgggcagaggaagacggggcagag
gaagacggggagcagtgggagcagcggg
cagggcgcgggaagcactgggatgttcc
gcgttggcaggagggtgttgggcgagctc
ccggtgatgcagggggggaggagccttttc
cgaagtagcgggacaagagccacgggaag
gaactgttctgagttcccagt CCCGACGTCCTGGCAGCGCCCAGGCACTG    Exon 1    Seq ID No 10
TTATTGGTGCCTCCTGTGTCCACGCGCTT
CCCGGCCAGGCAGCCCTGGCGGATCCTAT
TTTCTGTTCCCCCGATTCTGGTACCTCTC
CCTCCCGCCCTCGGTGCGCAGCCGTCCTC
CTGCAGTGCCTGCTCCTCCAGGGGCGAAA
CCGATCAGGGATCAGGCCACCCGCCTCCT
GAACATCCCTCCTTAGTTCCCACAG gtgagaaggcttcgccgctgctgccgctg    Intron    Seq ID No 29
gcgccggcagcgccctccacgcacttcgt    1a
agtgggcgcgcgccctcctgcattgtttc
taaaagatttttttttatccgcttatgct
atcagttactgaggaagtatttacaaatc
tactattattttgaatttgccttttctc
cttatagtttatcagtatctcttgagact
gttattggtgcctgcaaatttaaaatgat
tggggttttatgaggaagtgaaccttta
tctttatgaaacgcctaactgaggcaatg
ttaattgcttaaaatactttctttattat
cagtggccatgccagtgtcctcttggt
tagaatttgcctgat ctgccaaagctgggagatgggggaaagta    Intron    Seq ID No 30
gagtgggttattgaaactgaatatagagt    1b
tcagcatctcaaaagcgaggtagtagagga
ggaagctgtgtcaacggaaatactgagct
gggttcacatcctctttctccacacag TCTAATGCCTTGTGGAAGCAAATGAGCCA    Exon 4    Seq ID No 11
CAGAAGCTGAAGGAAAAACCACCATTCTT
TCTTAATACCTGGAGAGAGGCAACGACAG
ACTATGAGCAG gcaagtgagaggggctttagctgtcagg    Intron 4  Seq ID No 31
gaaggcggagataaaccttgatgggtag
gatggccattgaaaggaggggagaaattt
gccccagcaggtagccaccaagcttgggg
acttggagggagggcttcaaacgtattt
tcataaaaaagacctgtggagctgtcaat
gctcagggattctctcttaaaatctaaca
gtattaatctgctaaaacatttgccttt
catag CATCGAACAAACGACGGAGATCCTGTTG    Exon 5    Seq ID No 12
TGCCTCTCACCTGCCGAAGCTGCCAATC
TCAAGGAAGGAATCAATTTTGTTCGAAA
TAAGAGCACTGGCAAGGATTACATCTTA
TTTAAGAATAAGAGCCGCCTGAAGGCAT
GTAAGAACATGTGCAAGCACCAAGGAGG
CCTCTTCATTAAAGACATTGAGGATCTA
AATGGAAG gtactgagaatcctttgctttctccctg    Intron 5 Seq ID No 32
gcgatccttctctcccaattaggtttggc
aggaaatgtgctcattgagaaatttaa
atgatccaatcaacatgctatttccccc
agcacatgcctaacttttttcttaagctc
ctttacggcagctctctgatttttgattt
atgaccttgacttaatttcccatcctct
ctgaagaactattgtttaaaatgtattc
ctagttgataaacagtgaaacttctaag
gacatgtgtgtgtgtgtgtgtgtgtgt
gtgtgtttaccagcttttatattcaaag
actcaagcctcttttggatttcctttcc
tgctctctcagaagtgtgtgtgtgaggt
gagtgcttgtccaaacactgccctagaa TABLE 9-continued Genomic Organizational Sequences cagagagactttccctgatgaaaacccg
aaaaatggcagagctctagctgcacctg
gcctcaacagcggctcttctgatcattt
cttggaagaacgagtgctggtacccctt
ttccccagcccctttgattaaacctgcat
atcgcttgcctccccatctcaggagcaa
ttctaggagggagggtgggctttctttt
caggattgacaaagctacccagcttgca
aaccaggggatctgggggggggtttg
cacctgatgctccccactgataatgaa
tgagggattgaccccatcttttcaagct
ttgcttcagcctaacttgactctcgtag
tgtttcagccgtttccatattaggcttg
tcttccaccgtgtcgtgtcgtcaatctt
atttctcaggtcatctgtgggcagttta
gtgcgaatggactcagaggtaactggta
gctgtccaagagctccctgctctaactg
tatagaagatcaccacccaagtctggaa
tcttcttacactggcccacagacttgca
tcactgcatacttagcttcagggcccag
ctcccaggttaagtgctgtcatacctgt
agcttgcttggctctgcagatagggttg
ctagattaggcaaatagagggtgcccag
tcaaatttgcatttcagataaacaacga
atatatttttagttagatatgtttcagg
cactgcatgggacatacttttggtaggc
agcctactctggaagaaccctcttggttg
tttgctgacagactgcttttgagtccct
tgcatcttctgggtggtttcaagttagg
gagacctcagccataggttgttctgtca
ccaagaagcttctgcaagcacgtgcagg
ccttgaggtcttccgacttgtggcccgg
ggactctgcttttctctgtcctttttt
ctccttagtgggccatgtcctgtggtgt
tgtcttagccagttgtttaagggagtgt
tgcagctttatgattaagagcatgtct
ttccttgcaaactgcttggtttagaagc
ctggctccaccacttagcggctctgtga
cctcggacacatttcttagccttttctgg
gcctcgctcttcttcctcataaagtgaa
aatgaaagtagacaaagccttctctgtc
tggctactgagaggatggagtgatttca
tacacataaagcacttaaaataatgtct
ggcatatgatacatgctcaataaatgct
acttacatttgctattattattactctg
ccatgatcttgtgtagcttaagaacaga
ggtctttacaggaattcaggctgttctt
gaatctggctgctcagcttaatatggt
aattgctttgccacagactggtcttcct
ctccttcacccaaagccttagggggtga
acgatcccagtttcaacctattctgttg
gcaggctaacatggagatggcaccatct
tagctctgctgcaggtggggagccagat
tcacccagctttgctcccagatacagct
ccccaagcatttatatgctgaaactcca
tcccaagacgagtctacatggtacactc
ccccatccatctctcccaaatttggctgc
ttctacttaggctctctgtgcagcaatt
cacctgaaatatctcttccacgatacag
tcaagggcagtgacctacctgttccacc
ttccctttcctcagccattttttcttctt
gtacataatcaagatcaggaactctcat
aagctgtggtcctcattttgtcaatcta
atttcacagcctcttggcacatgaagtc
gtcctctctctcctttctgcctactgcc
catgagcagttgtgacactgccacatt
ctccttaacgacccagcctgctgaata
gctgcatttggaatgttttcaatttttg
ttaatttattttcatcttttttttt
ttttttttttttttttttttttagggcc
gcacccatgggatatggaggttcccagg
ctagggatccaatgggagctgtagctgc
tggcctacaccacgccacagcaatgca
caattcgagccaatctttgacctacacc
agagctcacggcaacactggattcttaa
cccactgattgaggccagggatcaaact
ctcgtcctcatagatacgagtcagattc TABLE 9-continued Genomic Organizational Sequences gttaacctctgagccatgatagttgtta
gttactccattgatgagaaaggaagtgtc
acaaaatatcctccataagtcgaagttt
gaatatgttttctgcctgttactagaa
aagagcattaaaaattcttgattggaat
gaagcttggaaaaaaatcagcatagttta
ctgatatataagtgaaaatagaccttgt
tagtttaaaccatctgatatttctggtg
gaagacatatttgtctgtaaaaaaaaaa
aatcttgaacctgtttaaaaaaaaaact
tgactggaaacactaccaaaatatggga
gttcctactgggacacagcagaaatgaa
tctaactagtatccatgaggacacaggt
ttgatgcctggcctcgctaagtgggtta
aggatatggtgttgctgcagctccaatt
caaccccctatcctgggaaccccccatatg
ccaccctaaaaagcaaaaagaaaggtgc
tgccctaaaaagcaaaaagaaagaaaga
aagacagccagacagactaccaaaatg
gagaggaaatggaacttttaggccctat
ctccaactatcacatccctatcaccgtc
tggtaagaaatggaaaaaatattactaa
gcctcctttgttgctacaattaatctga
ttctcattctgaagcagtgttgccagag
ttaacaaataaaaatgcaaagctgggta
gttaaatttgaattacagataaacaaat
tttcagtatatgttcaatatcgtgtaag
acgttttaaaataatttttttatttatct
gaaatttatattttttcctgtattttatc
tggcaaccatgatcagaaatctttaaac
aatcaggaagtcttttttcttagacaaa
tgaaaatttgagttgatcttaggtttag
tacactatactaggggccaagggttata
gtgtgactattaaatcacagataatctt
tattactacattatttccttatactggc
cccacttggatcttacccagcttagctt
ttgtatgagagtcatccttaaagatgac
tttattcttttaaaaaaaaaaaacaaattt
taagggctgcacccatagcatatagaag
ttcctaggctagcggtcaaattagagct
gcagctgccagcctatgccacagccaca
gcaatgccagatctgagctgcatctgtg
acctacactgcagcttgcagcaatgctg
gatccttaaccattgaacaatgccagg
gattgaacacacatcctcatggatactg
ctcaggttcctaacctgctgagccacag
ttggaactccaaagcagactttattctg
atggctctgctgatctctaacacgttat
tttgtgccatggtgtttatcttcacttt
actcaagtcagggaaacacgaagagtct
catacaggataaacccaaggagaaatgt
gcaaagtcacatacaaatcaaactgaca
aaaatcaaatacaaggaaaaaatatctt
cacttttcaaaatcacctactgatgatga
gttatatttccttggatatttgaatat
tagctatttttttcctttcatgagtttt
gtgttcaaccaactacagtcgtttactt
tgatcacagaataatgcatttaagcctt
aaatagattaatatttattttccaccatt
tcataaacctaagtacaatttccatcca
g GTCTGTTAAATGCACAAAACACAACTGG    Exon 6  Seq ID No 13
AAGTTAGATGTAAGCAGCATGAAGTATA
TCAATCCTCCTGGAAGCTTCTGTCAAGA
CGAACTGG gtaaataccatcaatactgatcaatgtt   Intron 6 Seq ID No 33
ttctgctgttactgtcattggggtccct
cttgtcaacttgtttccaatctcattag
aagccttggatgcattctgattttaaac
tgaggtattttaaaagtaaccatcactg
aaaattctaggcaagttttctctaaaaa
aatcccttcattcattcatttgttcagt
aagtatttgatgagacctaccatgtgta
aacattgcactaggtattaagaaataca
aagatggataagatagagtcggcgtaaa TABLE 9-continued Genomic Organizational Sequences tgagatgatataatgagacgttataatg
aaactcacaattccagttgggaaataaa
gtccttcaaattccatgactctttctgg
cacacgttagaggctacagcttctgtgt
gattctcatgctggctccacttccactt
tttccttcttcctactcaagaaagccta
tagaaatatgagtaagaagggcttaatc
ataggaataaatttgtctctgttctaag
tgattaaaaatgtctttatcagtataaa
aagttacttgggaagattcttaaaactg
cttttacacactgttctagaatgactgt
tatataaataaaaaagtagatttgatct
aacacaattaaatgacctttggaaatat
tgactaattctcaccttgcccctcaaag
ggatgcctgaaccatttccttcttttgc
cagaaagccccccaccctttgtctgttga
cctagcctaggaaatcttcagatcacgt
tgttagcacgaactggttacatgtgctg
tacaaatactatttaattcatctgatta
aaaaaaaagagataagaagcaaaagttt
gactatcttaaactgtttgcgtaggtga
gaggacaattgaccatctactttatgag
tatgtaacccagaaaacttaaagctcctt
aagggagctaagtcttttggataagacc
tatagtgagacctttttagcaaaatggtt
aagactgaatggagctcactagcgtggg
ttcatatcctgatgctcaaacacgcaat
taaatgactttaggtgggttagtctctg
ttccttagtttcctcaatgggagataat
attggtagtagcgattttactgggttgt
tgaaagaacatctgttaaatgttcagaa
cgtgttacgacagagtacagagtaatga
tttgcttgtatatgtatgactcaaatag
tctgccatatgccttgtgactgggtcct
gtgggacaggaaggagggattccccacc
cagcagaaagttgggtaaactggaaaat
agactgaggccaggaaatgatgcaaagc
gttgatgttcactgccacggcaggtgaa
gggcagggccagagttgtcagtagggtc
aggggaggactggaaataaccaagaccc
actgcacttttcagcctttgctccagta
aggtaatgttgtgagagtagaaaatttt
gttaacagaacccacttttcagtacagt
gctaccaatactgtagtgatttcatacc
acatcccaagaaagaaaaagatggctca
atcccatgtgagctgagattatttggtt
ttattgttaaataaatagcattgtgtgg
tcatcattaaaaagtagatgttagga
aagtagaaggaagaagactctcacctac
attttcatcactgttttggtatctgcca
gttgtcaccttggtcccccttccccgcct
ctccctgcctcctcttcctccttctcc
ttttttttggaatacaattcaggtaccat
aaaaatttacccttttagagtgtttgact
caatggttttttagtatttttcacatgttg
tgctattactatcactatataattccag
gtcattcacatcaccccccaaagaaacc
ttctaactattagcagtccattccccttc
ttccctcagcccctggcaaccactaatc
tacttactgctctccatggatgttcctat
attgaatcaagctagcataaaccccact
tgctcatggtcataattcttttttatag
tgctaaattacatttgctaatattcaat
taaggattttctatgtccatattcataag
gaatattggtgttgtgtagttttctcttttgt
gtgatatctttgtctggttggggggatca
gagtaataattactgctctcatagaatg
aattgagaagtgttccctcctttttctat
ttattggaagagtttgtgaagtatattg
gtattgattcttcttttaaacattttggtc
agattcaccagtgaagccatctgggcca
tggctaatctttgtgaaaagtttttttga
ttactaattaaatctctttaatttgtta
tgggtctgctcctcagacgttctagttc
ttcttgagtcagttttgttcatttgttt
cttcctaggactttctcccttttcatttg
gattatttagattgatagtaatatcccc TABLE 9-continued Genomic Organizational Sequences cttttaattcctggctgtagtaatttgg
gtcttttctcttttttctggtcagttt
agctaaaggtttgtaattgtattaatct
tttcaaataactaactttttgttttgt
ttgttttttgttttttgttttttgtttt
ttgtttttttttgcttttttaaggctgca
cctgaggcatatggaagttctcaggcta
gaggtctaatcggagctacagctgctgg
cctataccacaaccatagcaatgccaga
ttcaagctgcatctgcgacctacaccac
aactcggccagggatcacacccgcaacc
tcatggttcctagtcggatttgttaacc
actgtgccacgacgggaactcccgccca
ttttttttaacacctcatacttttaacat
aaagatgggcttcacatggactgatagc
tcaaatgaggaaggtaagactatgaaag
taatggaagaaatgtagactattttttgt
gacctagagattactgatacttcttgac
ttttcaaacaatacttcaaaagtacagc
ccaaagggaaaaagaaagaaaaaagaa
acacacatatacacaaacctagtgaata
agatatcatcgatacactacagatttct
atgaactggaagaccccatggacaaagt
taaagaacatatgatagtttgagtgatt
attttgcaatatttacaaccaatgaggg
aatattatccagcttataggaggaagta
atgcaaatcgacaagaaaaagataggaa
acccaatataaaaaattaagaaaatacaa
aaaattaagaaaggatatgaactagcatt
ttacaaaagaaaaatctccaaaagtcaa
tcagcacatgaaaatatgctcaaaccaa
ttattagaaaactacagactgaagcaat
gaggtgcttacttacatctttttgac
tgataaaaagttagaaacaaaggtgata
tcaaatgtcagggataaaaggatataga
aatcgtcatgcctgtggtgggagtatgg
ccggtgcagtcatgtgggaaggtaatct
gacagtggttaggcagagcaggtttatg
aatacactgtggcccatcaatcccacgc
ctgtttatgtaccaaagaaatcctgttg
tggcagaatctatgggtccacccctggg
agcatgaattaataaaatgtggcaccag
ggtgtgtgaaactccagctagagatgag
atgtccacatggcaacatgaatgcatct
tagaaacatagatttgagtgaaaaagag
taagaaacagccgggaaacccaatacca
tttataaaaattaaagatgcacacatac
aatgtagtaaatattttgcagtgaacttt
caaatggttgcctacagggggggagagt
aaagaagagtagaaaacaaagataaagg
gagtaagtaagtagctctgcctggactg
aatataatgtgtcatgaactgagaaata
tggttaacataatcctcttaacttgagg
tcctaaatgaatgaatgagtccactatt
catttacccattctttaatgtgtattgc
attataatccatttttttagaaccaacg
aattttgttcccataactactaatcagc
ctgccttttctccctcattcccttatca
gctcaggggcattcctagttttttcaaac
gttcctcatttgaaccaaaaaatagcatc
attgtttaaattatacttgtttttcaaat
acgatgcttatatattccaagtgtgttt
gcccatttttcttaggtggtagaaatttt
tcattctacttttctatctactcagatt
ttcccgttggaattatttccattgctat
taaacttagaagtcccccctgtgatatg
ccattttttttcatactttttaagcactt
ggttgcttttctttgtgtctttaagcac
ctagaatacttataaccattgcacagca
ctgtgtatcaggcagccttcctcttcc
actaatttatggtccttctcttagacta
tattaaactgttatttaattaggatcct
ctcttcgtccttatgatttaattattat
agttttctaatatgttttattataatt
ctccttcattattcctcccttattaaaaa
ttttaatgaattccatttgtttgttctt
ctagttaaatattaagtcataatccaaa taacttagatgtcattagtttatgtggt
caaagtaaggataccacatctttataga
tgcaggcagttggcagatgtcatgattt
tctttcagtgcataaatgcaattttatctt
tgagcaaggggcataaaaacttttatgg
tattggctttgaaataatagttaagaac
tgcagactcagttttcctgcttttctt
gaaaaagaacacttctaaagaaggaaaa
tccttaagcatggatatcgatgtaattt
tctgaaagtctcctgtaattccttggga
tttttgttgttgtttggtcggtttttt
gggttttttgtttgtttgttttgttttgt
tttgttttgcttttagggctgcacctgt
ggcatatggaagttcccaggctagggt
ccaactggagctacagctgccagcctac
tccacagccacagcaacatgggatccta
gctgcatctgtgacctaaccacagctct
tggtaatgccagattgttaacccactga
gcaatgccagagatcgaatctgcctcct
catggacactagtcagattagtttctgc
tgagccacaatgggaattcccaattcct
tgtattttgaactggttatgtgctagc
atataattttgtttcttgaatctttgtg
ggttttttttttttttttttttgtctc
ttgtcttttaaggctgcacccacagca
tatggaggttcccaggctagaggtcaaa
ttggagctacagctgccagcctacacaa
caactgcagcaaagtggggcccaactta
tatgacagttcgtggcaatgccggattc
ctaacccactgagcagggccagggatcg
aacctgagtttccagtcagtttcgttaa
ccactgagccatgatagtaactcctgtt
tgttcagtcttgaacctcctttttaatt
ctttattccttgagggtgaaataattgc
cataataactatcatttattacatgc
cttctctgtgctaggcatagtgacactt
taggatttattatatcacttaatccta
caacaactctgcaaagtatgtatcataa
tcctatttgacagatcaggaaattgcag
cccaggatgcagataatatgcatccatc
acaagtgactagatatagtccctctgct
attcagcagggtctcattgccttttccat
tccaaatgcaatagtttgcatctattgt
atatgtgttttgggtttttttgtcttt
tttttttttttgtctttttctggggcct
caccccttggcataggtaggttcccaggc
taggggtcaaattgaagctgcagctgcc
agcctacaccacagccacagcaactcgg
gatctgagcctcatctgcaacctacacc
aaagctcacggcaacaccggatccttaa
cccactgagtgaggccagagatcaaacc
ggcaacctcatggttcctagtcggattc
attaaccactgagccacgatgggaactc
cctaaatgcaatagtttgctctattaac
cccaaactcccagtccatcccactccct
cctcctccctcttggcaaccacaagtct
gttctccatgtccatgattttcttttct
ggggaaagtttcatttgtgccattttc
attttacgggtaattttacttcagttt
cttccactagcagttgtcttaaagtgag
tataattaatattcatttggaaaatgta
agcaaaacattttttaaagggccatgcc
cacagcatatgaaagtttctgggccagg
ggttgaatccaggctccaagttgcagct
gtgccctacactgcagctgggcaatgct
ggatccttttaacccactgtgcccggcta
gggatcaaacctgcatttccacagctac
ccgagccattcagttggattcttaacc
cactgcactcacagctgggaactcccacaa
aacattttttaatgtcctttgaataaag
taggaaagtgctcgtctttgagggcagg
gcggcaatgccatttccacaaggtttgc
tttggcttgggacctcatctgctgtcat
ttagtaatgaataaaattgctgacagta
ataggattaactgtgtgtgggagatagcc
agggttagagataaaaacactggagaag
tcaaataagttgctcgaggtcctctagc TABLE 9-continued Genomic Organizational Sequences taataagctattaagtgggagagtgagg
gctagaaacaggccatctgtctcccaag
cacatgtccattagtggtttgctgatag
ccttccagaacaacagagaggactctca
aacatggtcttgcctccctccaattgat
cccctccatgtgcctcacagcgggtctt
tctaaaattaagttctgattttaattct
cccttgctatagcacttaggtatggctt
tcagccgtgcaataaaaagcaggcaaga
gtggctcaatcatataggaggttgtttt
tcttagatcccaagcaggtaatcctggg
cattatggttgttctgcgtttatcaagg
agccaaattctctatccacctcctgttct
atcctcctcagtatctgcctctattctt
cagcatctcaagatggcttgtgctcctc
caagcatggcagtcaaattccacacaag
agggggaaatatgaagggcagacagtgc
tggtctcctgagctgtccctccttgtcg
gggaaataaattgtattccttcaagtcc
cgtgagacttctgaagtagacgtctgct
tacgtctcacccaccagaactatgtaaa
ctgcacatagtgctaggtctacatagcc
actcataactgccaggggggtgggaaatc
tttaaataggtgtaccaccacacaatta
ggatgctaatagtaagggagaaggagag
aataggttttgcgcaagccaccagcatg
cctgccacaattgcttaaaattcttcat
tgaccctcattgccacaggatgaaatc
caaacgccttcttagttgggaatctgac
ctacctgtctctcccacctggttcagac
accattctccttggtcataaaattccag
tcatttgtgaacatccagctccccatg
cctccatgccttgcacatgctgttctt
ttatcttttatgttgtccttttatcttt
tatccaaaagagatatcccatcatcaca
tctcttttgtcagccccaaatactttg
tcttcaagttcagctggaggattacct
cctatttgaaatcagctttgtctcttac
aaccaaacaaggttttccttccgagaca
ctcccacagcaccttgaactcatctcta
tcaatcattcatttgattgtaatgaagt
tgttggtggtatgcctgtgtctctgaca
catctgcgatctcatgagttccttaagt
ggaatgtgaatagcgggatgaacagtat
tggtcttcagccctcatctctgcagatg
ttgcttgacccaaatgagcgttgccttt
tattttgattttgctttgatttgtctac
tccatgtacttgagccatgcattctgt
cttagcgatgcttttttaaaagtcatttt
ttggttgattatccagatttgtccacct
ttgcttctag TTGTAGAAAAGGATGAAGAAAATGGAGT   Exon 7   Seq ID No 14
TTTGCTTCTAGAACTAAATCCTCCTAAC
CCGTGGGATTCAGAACCCAGATCTCCTG
AAGATTTGGCATTTGGGGAAGTGCAG gtaaggaaatgttaaattgcaatattct   Intron 7 Seq ID No 34
taaaaacacaaataaagctaacatatca
atttatatatatatatatatatatattt
tttttttttttttacatcttatattacct
tgagtattcttggaagtggctagttagg
acatataataaagttattctgaagtctt
ttttttttcttttttccatggtgagcagtg
gcttgatgtggatctcagctcccagacg
aggcactgaacctgagccgcagtggtga
aagcaccaagttctagccactagaccac
cagggaactcccattctcaaattcttga
gcacattatttaggaacctcaggaactt
ggcaggattacaggaaatatatctagat
ttaaaaaaaatcttttaacagagagtcc
caaaggagagtcatgcacagctatggga
ggaagttcagaaactgccctctgctacca
gatcactgtcagataaaatggccagcta
catgtttctgcacattgccctaagatct
ttacaaacttttctgtgcatttttccac
ttttaaaagaaaatttcgggggttcctgt tgttgctcagtggttaacgaacccaact
agtatccatggggacagggggttcgagcc
ctggcctcactcagtgggttaagaatct
ggcattgctgtggctgtggcgtaggctg
gcggctacagctcagattggacccctag
cctgagaacctccatatgccgcaggtat
ggccctaaaaaaaaaaaaaaagagagag
agagaatttcctccagaaaaaacactttt
ggtagtttgggagaagtaaacaaccaaa
aattaattttttctggagtattcgggaag
cttgtaaaaatgggctcttacttttttg
aggagacaaatgggaacctacccagaag
aggcacaatcacctgcatttgatttctt
gacctctccctaccttctttgctggctt
tccacatttggatttctgtgaccttatc
tctgctcctggtgttttcatttttcct
gtggacgtgccagactatgggaagggag
taaggcgttgatttagaatcctgtagtc
tctgcctgtctctagtcattgttttcac
cctctcaaaggaccttgacatcctgag
tgagtccgcaagtaatttaggggagaag
ccttagaagccagtgcagccaggctaca
tgactgtgtcacccactggaaccagtc
atttttatacctattcacagcccccta
ccatttaaatccccagaggtctgccata
acatctgtaactccctttcctggtaaat
tgtgttctaaaagactggtaacaaaaga
tattctgtggtacagagcataattaaat
acctgggagctgatttgagtggggtaaa
tcaactggtttgacccctaaaacccacc
atgagcatttctgttctaataaagtaat
gcccgtgctgggaattgtgttctacgga
aatgctcctgctgtgtcttcttgagtc
ctgtgtcattgaacatgcttaggagcaa
aggtcccccatgtggcttgtctgctaac
cagcccagttccttgttctggctggtaa
tgatccgatcatctgaatctcactgtct
tccaacag ATCACGTACCTTACTCACGCCTGCATGG   Exon 8   Seq ID No 15
ACCTCAAGCTGGGGGACAAGAGAATGGT
GTTCGACCCTTGGTTAATCGGTCCTGCT
TTTGCGCGAGGATGGTGGTTACTACACG
AGCCTCCATCTGATTGGCTGGAGAGGCT
GAGCCGCGCAGACTTAATTTACATCAGT
CACATGCACTCAGACCACCTGAG gtaaggaagggtgagccctcaactccga   Intron 8 Seq ID No 35
agaaaatgctgcaataaaaagcactgttg
gttttcagcttttttttgtaatcactgct
cattctgaggtagattcgcttgggctga
taaaaagaaactaattcagataaatgct
tgcatttgcatagcctcttttttttaaaa
acttttttttttttttttttttttttggc
ttttcagggctgaacctgtggcatatgg
aggttccaggctagggggtcgaatcaga
gctgtagcccgggcctatgccactgcc
atagcaacatgcatagcctccttttttaa
agtgccttcctgttttataccattggga
tgtgagaagtgctattgtgggaaangagc
atggggtnataaccctggacctctcacg
tcctaccctcaggntagtgggaaaactc
tgagtttaaggacatcaaagtgactcct
ttttagttacattatggnggaatcagcn
catattttttacaagggcggagngtaan
ctgttggagtttacaagacatatggtgg
cattgcaactacttaaccctactattat
agcacaaaagcagccatagtcggtcctg
aaggagcctgatgccttcagctttatag
gcaatgacgtgtgaatatcacaaacagt
ttcctgtgtcaccaaacatgattgcctt
tgatttcccttttcaacccttttaaaaaa
aggtaaaagccttcttagcattcagca
gcaggtcgctgtgttttgccaactcctg
atctgtagcatttcgacaacactgagct
ctcaacttttgaaccctgagtccaccac
atccttcagtgaaaccagagccatgtga TABLE 9-continued Genomic Organizational Sequences tactaaggatagaaacggaaacttcctg
aatccaggcgatcaaataggagggagaa
agaggaactttcattgacaaaaccacaa
atattgtgaatggactgttacaaatatt
gtgaatgctcctattcccaaccccctgg
cttcattacagggtcctatgtgttcatc
cttattgagaaatttgtattgctactgc
caggttgccaatacccagcggtgcccat
ggtgttctaaaatgaagcaatttcaact
ttattttttttttcctgtgactttacatg
acaagttcacatgaaggatatactttga
tagtaatgtccatggttagggaatatac
attgtttgctggttgactggcccctgga
tttttctattgaaagtccatgagatctc
gaaggcacaggtgtgttctctcgctttt
taaggaaagggtttaaaaacttaagtaa
ttaacagctttagtaacaaattacctat
aacacacttaaaaaccgaataccaccca
ctggagtattgtgctacgattaaaaatc
tacttgtctactacatgatatctttgtc
ccacagaaggttctggaaccaaacttgt
aatttcaggattatgagagccctgagtt
cacgcattgtgtaataactatgttgtgt
ggtagtcaatttgtacagcttgcttaga
gagaacaatgtcaagttaaggaggcgat
tgctttatagtgcctgtcacaagatgcc
attgccattgtcctagcaagagatattc
tatgggagtatactacattttagtgagg
ataagaacttttatggcatttagtccg
gtcatttcccaaccactgtcctgaaaac
caattcattttgatttcaggggcttgt
gtgggcaaagttgccaggcattaaaaag
ccactttctcaactgtagtatcacaatgc
tttagttgggtagtgtattgcagatagc
ttatggctgaaaagttaccaagccttgc
agttttcactcctttgagtttatttcct
tgacagaattgaccctgagttttttgac
tcttacctgctcaactaataaacaccag
agtcattatctccattgctcttgtctg
acctttatttaccgaataatgccttatg
ggttcacaaaaacaaggggggaggggc
cagcatgccttagaaactgtctttagtc
aagaaatgngatttattatgtaaatat
atgagtattataatagatagtgttatta
atagacaccagcaagaattgtcaataat
ttaaaaatcacaaattaaaatacatcca
tgttagnatcatttatcctaactcccaa
agcccctttaaagtggaagatttagatgt
taacccagagattaaagacatgttcaaa
gaatcctgattttttttgaatccctt
gttttagagaagaaaacctaatgattt
tccccctctggattctacatattaaata
tagttttggaacttgaatattagtatgg
ttaataagtgctgatatgctgattttgt
ttatattttcttatgagtaaatatcct
atatcaccagacattatgtctatgtac
aaatatgattcttaaacctgatagcaca
ttcattagagttggaattgcctttttt
tttttttttttttacagttgcacctgcaac
atatgaaagttcccaggctaggggttga
atccaagctgcagctgccaccctacatt
acagccgtagtaacagcagatccgagct
gcatctgcaacctatgctgcagctcagg
gcaatgccagatccactgagtgaagcca
gggatggaacttgcatcctcatagagac
aacgtcgtgtccttaacccactgagcca
gaacaggaactccagaatttcctttcaa
tagaagaagcaccaagtttaggatcaga
aagcctgaatttgaataccaatttacta
tttgttagtcatatatttctgagtgtgt
ttcctcatttattaaaagcagactaaaa
gatgagagggtcttttgttgagaatcaa
atacaataataacatgtgaaagtgtaaca
ctatgattgaaatatacctacacagcca
tttatttgtttattgttcatgttttgcc
acccacacagtagtatataatcctttta
tgtaataaatgctaataatgaaagttgg caacttatgtaagtactcaaaatgctgg
aggtcatgggatactgactgggatacta
cagaggtaatgtcatttcctctgcgcta
aacttattgtcttgtagttagggactga
ctctctttaggacaaggagttcattctg
tataccatggctatcaccccttcgaagtt
gaaaaactgccccagggtgggcacccat
ccgttctcttagatatatggccgagacc
tttctctcactgggagggaaccacactg
aggaatgagaaaaaaaaaggaaaatca
agatgaaaccagaaacctctttggcata
acttctccactctgtactttttgttaga
actacccttgcacaaagcagcatcagtg
tggaagacagaatttgcacacctggttt
gatatacatgcgtggtatatgggatgt
tctaacaataaagaggactctcccagga
aatctcctcactgttatagtcagccttg
aggaaagagctcttcttttggactctgg
ggagagtctagtttttcagttccttgct
tctcggtcaacgtgttggtgtaaggatc
acactctctcttatactagataattcta
ttttttcacctttcaacctgtctatcct
tctgaccctag

| TTACCCAACACTGAAGAAGCTTGCTGAG<br>AGAAGACCAGATGTTCCCATTTATGTTG<br>GCAACCGGAAAGACCTGTATTTTGGAAT<br>CTGAATCAGAGTGGCGTCCAGTTGACTA<br>ATATCAATGTAGTGCCATTTGGAATATG<br>GCAGCAG | Exon 9 Seq ID No 16 |

| gtctgtgttctttccacatgtttgggtt<br>atcctttctgggataaatttgaggcgag<br>atagaaactttaagactaaagaaacaat<br>ggcctactttttttgtacatggtcctgt<br>gtaaatctctatttgagctgaaataaga<br>tggtcttcctctccaattatccatggta<br>tgactctgatggataacaaatccagttc<br>tgaaaaaggggatttctttccagaaga<br>gaggacagtttcttcaaatattgaatta<br>aaagcaaaatagatgtaaaccgttgttg<br>gttttattgttgaattccag | Intron 9 Seq ID No 36 |

| GTAGACAAAAATCTTCGATTCATGATCT<br>TGATGGATGGCGTTCATCCTGAGATGGA<br>CACTTGCATTATTGTGGAATACAAAG | Exon 10 Seq ID No 17 |

| gtattttcttgccctcatcagcatgaaa<br>ttgctcttggtagaaaggataataatag<br>ttatccaaaacatcatcctatgttcatc<br>tgtttcttccctcttcattttccataga<br>gtacagtatctctatctctgtcttagg<br>aaaatggactgtcattcatataatcctta<br>cagagaatcaattagtaatgtactctat<br>gccgtgacaggtgcgaaggttttttttg<br>aaggcaacagataaaaaatatcctatatt<br>tcacctattgtaatttccttaaaactga<br>cattattgaataaatgttttactttcat<br>cttgaatattattatgttatggaatcat<br>acactttaccccaataatcatcgaaaag<br>aatttccaaaaggttgagagagttgtgt<br>tgatctgattacttcctctgcatcctt<br>tgagcttaacctttgaatatagtttgct<br>aaggaaagtagtctgtttatgatcctgg<br>agtggaatcaggctaagtgtcctcattc<br>agaacccactgaatcagacagaatgaat<br>ttatttccttgaaagttcaaaatgtgtc<br>actcaagagtataaattttcaaatctta<br>ctctctcttttccttggatgtgagcaat<br>tcttcgataattgaatgaggcagattat<br>atagacttacatgaagactgttggcct<br>gagaattcaaactatggtgttcaagact<br>tcacngngagtccgatgccatttgtttc<br>ccacag | Intron 10 Seq ID No 37 |

| GTCATAAAATACTCAATACAGTGGATTG<br>CACCAGACCCAATGGAGGAAGGCTGCCT | Exon 11 Seq ID No 18 |

TABLE 9-continued

Genomic Organizational Sequences

| | |
|---|---|
| ATGAAGGTTGCATTAATGATGAGTGATT<br>TTGCTGGAGGAGCTTCAGGCTTTCCAAT<br>GACTTTCAGTGGTGGAAAATTTACTG | |
| GTAATTCTTTATATCAAAATGATGCCAA<br>GGAGTTGGCATGGCACTTTGCTAAATGC<br>TGTGTGAATCAATACAAAGATAATTAGG<br>ACATGGTTCTTCCTCACAAGAGGTGTGC<br>AATCTTATTGGGAAATCATACTTGCAAG<br>TCACAAATATAGACTAAAGTTTCCAGCT<br>GAGAATATGCTGATGGAGCATGAAACAC<br>TAAGGAGACAGGGAGAATCTCAGGAAAA<br>ATCAAGAATAATTTGGATCAAATGGATT<br>CCTGACATAGAACATAGAGCTGATCAGA<br>AAGAGTCTGACATTGGTAATCCAGGCTT<br>AAGTGCTCTTTGTATGTGGTTCAGAACA<br>GAGTGTGGGCAGCCTGAGGGGATACAT<br>ACCCTTGACCTCGTGGAAAGCTCATACG<br>GGGGAGGGATGAGGCTAAGGAAGCCCCT<br>CTAAAGTGTGGGATTACGAGAGGTTGGG<br>GGGGTGGTAGGGAAAATAGTGGTCAAAG<br>AGTATAAACTTCCAGTTACAAGATGAAT<br>AAATTCTAGGGGTATAATAACAGCATGG<br>CACTATAGATAGCATATTGTACTATATA<br>CTGGAAGTGCTGAGAGTAGATCTTACAT<br>GTTCTAACCACACACACACACACACACA<br>CACACACCACACACACACACACCACACA<br>CACACACGTGCACACAAACAGAAATGGT<br>AATTATGTGAGGTGATGGCGGTGTTAAC<br>TAACTTTATTGTGGTCATCATTTAGCCA<br>TACATGCATGTCATGAAATCACCATGTT<br>GTACACCTTAAAGTTATGTAATACTAGA<br>TGTCAGTTATATCTCAAAGCTAGAAAAA<br>ATGTGGGGACCAAGGCAGAAGCTCTTCT<br>GCTCTGTGTCTAAGGGTGGTTCTGGGGC<br>TGGGATGGGGAGGATGGTTAAGTGGTAT<br>ATTTTTTTCATACCTTTGCTCAGTACTA<br>TCATTGTAAGTGTTCAATATATGTCTGC<br>TTAATAAATTAATGTTTTTAGTAAAAAA<br>AAAAAAAAAAAAAAAAAAAAAAAAAAAA<br>AAAAAA | Exon 11a Seq ID No 19 |
| gtaattctttatatcaaaatgatgccaa<br>ggagttggcatggcactttgctaaatgc<br>tgtgtgaatcaatacaaagataattagg<br>acatggttcttcctcacaagaggtgtgc<br>aatcttattgggaaatcatacttgcaag<br>tcacaaatatagactaaagtttccagct<br>gagaatatgctgatggagcatgaaacac<br>taaggagacagggagaatctcaggaaaa<br>atcaagaataatttggatcaaatggatt<br>cctgacatagaacatagagctgatcaga<br>aagagtctgacattggtaatccaggctt<br>aagtgctctttgtatgtggttcagaaca<br>gagtgtgggcagcctgaggggatacat<br>acccttgacctcgtggaaagctcatacg<br>ggggagggatgaggctaaggaagcccct<br>ctaaagtgtgggattacgagaggttggg<br>ggggtggtagggaaaatagtggtcaaag<br>agtataaacttccagttacaagatgaat<br>aaattctaggggtataataacagcatgg<br>cactatagatagcatattgtactatata<br>ctggaagtgctgagagtagatcttacat<br>gttctaaccacacacacacacacacaca<br>cacacaccacacacacacacaccacaca<br>cacacacgtgcacacaaacagaaatggt<br>aattatgtgaggtgatggcggtgttaac<br>taactttattgtggtcatcatttagcca<br>tacatgcatgtcatgaaatcaccatgtt<br>gtacaccttaaagttatgtaatactaga<br>tgtcagttatatctcaaagctagaaaaa<br>atgtggggaccaaggcagaagctcttct<br>gctctgtgtctaagggtggttctggggc<br>tgggatggggaggatggttaagtggtat<br>attttttcataccttgctcagtacta<br>tcattgtaagtgttcaatatatgtctgc<br>ttaataaattaatgttttagtaagtaa | Intron Seq ID No 38<br>11 |
| tctctgtttagtaatgtgtcagaaatgc<br>cctacttgcaataggaagaaaacctgtc<br>cagtcccttcctttttctgtaagtctg<br>atttcattgcctcccagaatgcatcacc<br>atgtgagagatagagggaaggtgctgtc<br>cttatgggggttaacagtgtgactaggga<br>ggcaaaatatacctactaaagggtggta<br>gcataattcagttcttatgtgagtatgt<br>gtatgtgtgtgagtatgtgcacatgcac<br>atacattttaaaaggtctgtaatatact<br>aacatgttcatagtggttacacctagct<br>tataggtaacatttttccctgtatcc<br>ttgtttgtgtttatcaaattttcataac<br>agtaatggtagaaggagtacctgacatg<br>gtaccatacatgctnggncctgcctaat<br>ttctcnatttccttattgcccataccc<br>ccattgcttgacaagcataagtccatac<br>tggcttgttttcgttcctcagactcagt<br>acaccatgtagctccatgccctgggtct<br>tgtatgtgctatttctactgcttagagt<br>gctattgccctgaccaccacgtggtca<br>gcaacttctcttctgcgtctgtgtctat<br>ggtctatgattccagatgtcatcttcac<br>taactacccttctaatatgcccttccat<br>cccaccgtcctcatccttacccagcc<br>actctctatttggtggctctgattttct<br>tcctagctcatcactctttgaaatgaac<br>ttatttacttattcaatatttgcttctt<br>tcactagaatgaatgctccatgagagca<br>gggacctgctttatcttgctcgccactg<br>tattcacagtgcctagaactacgtctgg<br>cacatagtaggtgctcaataaatatcga<br>tcaaatgaaagaatgagcaaacgaacaa<br>atgaacaacacgtgaggtaggcatcatg<br>attccatcaacagaggagaaaaccagac<br>ttaaagnaatgaagtggnggagctgcat<br>ttgatcttgactgactccaacatccatg<br>ctcttgaccactgtgcatctccagagtg<br>taatgaacatactttacttttatattcc<br>accaaaataacaaagccatgcccatgtt<br>agtagagagttaatcgacagtgcccctta<br>aaatatgcatgcacccagggtacaacta<br>tgcatgctgccctgtgttttcagttgga<br>tccaaatgaattgccgtaaacaaagagg<br>ggattcaatgtctttgactagtttggga<br>tatttcctagtaaccaacttgcaaaa<br>taaagccactaatgacaaggagctttgt<br>tctacttctgctcactcaactgtcaat<br>ttttatctcttgcaagacttctaatcta<br>ctagaacttttgttttctgtgatttct<br>gaacagagaagactaatccaaaccctgt<br>cattccag | |
| AGGAATGGAAAGCCCAATTCATTAAAAC<br>AGAAAGGAAGAAACTCCTGAACTACAAG<br>GCTCGGCTGGTGAAGGACCTACAACCCA<br>GAATTTACTGCCCCTTTCCTGGGTATTT<br>CGTGGAATCCCACCCAGCAGACAA | Exon 12 Seq ID No 20 |
| GTATGGCTGGATATTTTATATAACGTGT<br>TTACGCATAAGTTAATATATGCTGAATG<br>AGTGATTTAGCTGTGAAACAACATGAAA<br>TGAGAAAGAATGATTAGTAGGGGTCTGG<br>AGCTTATTTTAACAAGCAGCCTGAAAAC<br>AGAGAGTATGAATAAAAAAAATTAAATA<br>C | Exon 12a Seq ID No.21 |
| gtatggctggatattttataaacgtgt<br>ttacgcataagttaatatatgctgaatg<br>agtgatttagctgtgaaacaacatgaaa<br>tgagaaagaatgattagtaggggtctgg<br>agcttattttaacaagcagcctgaaaac<br>agagagtatgaataaaaaaattaaata<br>caagagtgtgctattaccaattatgtat<br>aatagtcttgtacatctaacttcaattc<br>caatcactatatgcttatactaaaaaac<br>gaagtatagagtcaaccttctttgacta | Intron Seq ID No 39<br>12 |

TABLE 9-continued

Genomic Organizational Sequences acagctcttccctagtcagggacattag
ctcaagtatagtctttatttttcctggg
gtaagaaaagaaggattgggaagtagga
atgcaaagaaataaaaaataattctgtc
attgttcaaataagaatgtcatctgaaa
ataaactgccttacatgggaatgctctt
atttgtcag

| | | |
|---|---|---|
| GTATATTAAGGAAACAAACATCAAAAAT GACCCAAATGAACTCAACAATCTTATCA AGAAGAATTCTGAGGTGGTAACCTGGAC CCCAAGACCTGGAGCCACTCTTGATCTG GGTAGGATGCTAAAGGACCCAACAGACA G | Exon 13 | Seq ID No 22 |

| | | |
|---|---|---|
| gtttgacttgaatatttacagggaacaa aaatgatttctgaatttttttcatgttta tgagaaaataaagggcatacctatggcc tcttggcaggtccctgtttgtaggaata ttaagttttttcttgactagcatcctgag cttgtcatgcattaagatctacacacca cccctttaaagtggggagtcttactgtata aaataaactattaaataagtatctttca actctggggtggggggggagactgagtt ttttcacagtcctatataataattttct tatcctataaaataattaggagttcccg tagtggctcagcaatagcaaacccgact agtatcgatgaggatgcgggttcgattc ctggcccccctcagtgggttaaggatct ggcattgccgtgagctgtggtgtaggtg gcagacacggctcagatcccacgttact gtggctgtggcataggccagcagctcca gctctgattagacccttagcctgggaac ttccatatgctgtgggtgtggccttgaa aaaaaataaataaataagataattactc aaatgttttccttgtctcagaaccttac ttcaggataaagagtgagaaagttttt ttatgaagggccattattacagctcaaa aataagttgtcttcagcaagtagaaagc aataagcctgagagttagtgttcctatc agtgtaaatattacctcctcgccaatcc ccagacagtccatttgaacaattaacgg tgccctgggagtacagttcagaaacatt aatgtggatgttccagacctgtattttt ataagtaccttgagccggatgaaccat cattcctcaccattatttagaagtggac tgtgactctgttggagatcagggcacac ggttaccaaaagcacacccttctcctgg ccttacctttgcaaagctggggtctggg acacagtcagctgattataccctttac taacttcccacagctcaaatctggtcaa ttctccttcacaaatctcttaaaaatcc atcactcacctccagcctcttctgctgt ggccttgattcagcctctcacaattttt ttttaaccagaattctggcagtggcccc tgacttgcctctgtgctcccagcccgc tgtcctctgatccatcctccatgccagc cttttttcaatctgctggtcacgattcat tgatgggttaggaaatcaatggcatcac aactagcatttagaaaaggaaataggc gttcccgccgtggcacagcagaaataaa tccgactaggaaccataaggttgcggt tcaacccctggccttgttcagtgggtta aggatccggcattgccgtgggctgtttt gtaagtcacagacatggctctgatccgg cattgctgtggctctggcgtaggcctgc agcatcagctccaattagacccctatcc tgggagcctccatatgctgcaagtgcag ccctaaaaaaaataaaaaaaataaaaaa aaataaataaaagaagtagacaaattgt atagaacaaccctgagtatgttgcctga gcacatataacaagggtaagtattactt caggaaatctggtttcacagatactct tggcatatggaccctagagtcctgatg taaaatatattcttcctgggatcttagg caagaagtttgaaagctccaactctgca ctgctgccaaagaaatgattttttaagtg | Intron 13 | Seq ID No 40 | caaaactcttcccgttcccttccctgta
taaaattccataggatctctccagtgcc
tctaggataaaggcagttttcattctct
agttcaaggtgagagaagattttaatta
tttcacgttttagtggggaattcaagag
tctggcacctgacatttgctgaactctc
tccattatccctctctagttccccagac
gcatcctatggtagaaattcgcaaacta
gagtgagcgtcagagtaacccaaggaaa
ctgggtaaatgcagctccctgggctcta
cccctgagattctgattcagtagatct
gaagcagagccctggaatatgcatatgc
atcattgtgtcacaccaagcattctggg
taatgagagttgatgttaggttctcagt
agtaagacaagtatagagattccgggggg
actgagtgctcagctctgcctggggag
gagggagggctaaagagaacaggaga
tggggacagggaatgctcaacctccaat
cttaggcatttgagctatgtcttaggg
tcaggaggaggttaccaatatagtgatt
aagagattgaggttccagtcagagggat
atgctgagaagggggggtgaaaataatg
tcataggtttggtgagtgcagatacttt
gagttttttaatattttttattgaaatat
agttgatttacaatgctcttagtgagta
caattactttgaataagtgcatagatgt
atgccattcttccagaaatgattttattg
agctcctttgggcatcatgctaagtaca
ggggaaacagctgtgaagaggtcttcc
cttatgaagtcattcatccccttcagta
aatgaaggtaaaggaaaaggatgagaca
gggacgccgtgttggaccagggtcagaa
aggcctataagaccttgcctggagggc
aaggaacttgcctgtgagtaaggagagc
ttgagaaagcgataaagcaaagaaggaa
cattactgcattgtgttttagaaaaacc
atgtcctggggaagaactcctagagtca
gggggggccagttgggagactgtgcttt
ttccaggaggagataagtgaggctgctg
gctgagatggagcaaggattagagaag
cagatatgagattcattagaagttaga
catttaggatctgacacataatttatc
accaaaaccagtgcatctctggcttgg
gccaccagttttggagaagtggaatgta
gggacctaccattacctgccaatcttta
ctacacagatgcctatttccctcctcat
attcctttctccagatcacgtcctattc
tattgccaggactcaagattccacccttg
catgcagtgatccatcttcacactggat
ggacagctctagggatgtcagagcacac
tctttgtccatactgctgactgggtctcc
tgtcagcccatctgtctatcagctgtgg
tattattagtataataagagggctgtat
atgagagacacaaaattctaggtgtagc
tcaaagataggctagagttattcctatg
tacaacaaatatttatgggaccccttct
gtgtactgtcatggttgctgctttcatc
atacttgtagtctaatggaggtggggc
agggcaggaataagcggatgtccacaaa
atcagtaagcacacttatattcaacatt
ttcataatttagttatttgagcccaaag
ggtccacatccgtggtattccaactttt
tttttccccggacatggatctttatcttt
ttttttttttcttttttgcggccagacc
tgcggcatatggaagttcccaggccagg
ggttgaatgggagttcagctgcctggt
ctacaccacagccacagcaaggtgggat
ctgagctgcatctgtgacatacaccgca
gctgaggtaacaccagattctgaaccca
ctgaatgaggccagggatggaacccgtc
tccttatgaacactatgtcatgttcttc
accctctgagccacaacgggaactccag
acttcgtctttaaatgtattctgacttg
gagagctatcacactaagcaattaacag
gagctgacctggtttaggctggggtggg
gccctactcctcaatgttccctgaggca
catctgtgggacccctgggcatcatcta

TABLE 9-continued
Genomic Organizational Sequences

```
tctgagcagccttagagctgctcatcca
gttgactgttgatgtagaagtgcaaact
tctgccttccttatttgttgctttcttt
tttcattgttctctcccctttgtgtctt
taag
```

| | | |
|---|---|---|
| CAAGGGCATCGTAGAGCCTCCAGAAGGG<br>ACTAAGATTTACAAGGATTCCTGGGATT<br>TTGGCCCATATTTGAATATCTTGAATGC<br>TGCTATAGGAGATGAAATATTTCGTCAC<br>TCATCCTGGATAAAAGAATACTTCACTT<br>GGGCTGGATTTAAGGATTATAACCTGGT<br>GGTCAGG | Exon 14 | Seq ID No 23 |

```
gtatgctatgaagttattatttgttttt       Intron    Seq ID No 41
gttttcttgtattacagagctatatgaa       14
aacctcttagtattccagttggtttctc
aataagcattcattgagccttactgact
gtcagacggagggcgtattggactatgt
gctgaaacaatcctttgttgaaaatgta
gggaatgttgaaaatgtagggaatgaaa
tgtagatccagctctgtttctcttttgg
aggattcttttcctccatcaccgtgtc
ttggttcttgtttgttttgggttttgt
gggtgttgtattgtgttgtgttggttat
ggcagtgacagctatttaaactgtgaaa
cgggggagttcccgtcgtgcgcagtgg
ttaacgaatccgactgggaaccatgagg
ttgcgggttcggtccctgcccttgctca
gtgggttaacgatccggcgttgccgtga
gctgtggtgtaggttgcagacacggctt
ggatcccgcgttgctgtggctctagcgt
aggccagcggctacagctccgattggac
ccctagcctgggaacctccatatgccgc
aggagcggcccaaagaaatagcaaaaag
acaaaataaataaataaataaataagta
agtaaaataaaactgtgaaacggggagtt
cccttcatggctcagcagttaacaaacc
cagctaggatccatgaggatgtaggttc
gatccctggccttgctcagtgggttaag
aatccagcgttgctgtgagctgtgatgt
aggtcgcagatgcagcccagatcctgca
ttgctgtggctgtggcgtaggctggcag
ctgaagctccgattcaacccctagcctg
ggaacatccatatgctgcaggtgtggcc
ttaagaggcaaaaaataaaaaaataaa
aaataaataaattgtgggacagacaggt
ggctccactgcagagctggtcctgta
gcagcctggaagcaggtaaggtaaggac
tgcagctgggtaaggactgaattgcacc
aactgggaagtaagcctagatctagaac
ttaagttagccctgacatagacacacag
agctcaccagctaagtggttcagcttat
aagctggtcactgaaactgaggatgtcc
acaaaagcaaaataagtagcaacaggca
gcgggatgcaagagaaagaggaggccta
aaatggtctgggaatccctgccatacct
atattttatcctacttatatttagtgcc
tgaatgtgtgcctggagagcaaagttta
gggaaagcatcgggaaatgcacagtatt
catacccttaggaacaaagatcagttac
ctccagggtaaagactatttccaagttt
aaatttcaacccctgaacattagtactg
ggtaccaggcaacacttgccatcctcaa
aatcaatgaatcctaaaattcaacctgg
gggtcagtgacagtctgtgacaaagttt
ttgctggtcagtaacgaaataagtatga
gcaccatctgagtatggtcaccaagatg
tcaactctcttttccttttggacgaacatt
attccaagattaggtcctttctattttt
gaggtgtgaaaacatctttcctttcata
aaataaaaggatagtaggtggaagaatt
tttttttgtttttggtgttttttgctatt
tctttgggccgcttctgcagcatatgga
ggttcccaggccagggggtcgaatcggag
ctttagccaccggcccacgccagagcca
cagcaacacgggatccaagccgcatctg
```

```
cagcctacaccacagctcacggcaatgc
cggatcgttaacccactgagcaagggca
gggaccgaacccgcaacctcatggttcc
tagtcggattcgttaaccactgcgccac
gacgggaactcctaatgatactctttta
tatttagctactatgtgatgatgagaaa
cagtccacattttattatttttttagcca
atttgatatctcattactaagataatga
taattttctctataaatttttatttaagt
tagtgttatgaagtggttttgctagtgt
agaaggctaggatttgaattcagttcaa
gaaagaagagagggagggagggagaggg
atgggtagagggatggggcagtgggaga
gagcaaagaggagagacagtttttgtat
taattctgcttcattgctatcatttaag
ggcacttgggtcttgcacattctagaat
tttctaaggaccttgaccgccagattga
tatgcttcttcccttaccatgttgtca
tttgaacag
```

| | | |
|---|---|---|
| ATGATTGAGACAGATGAGGACTTCAGCC<br>CTTTGCCTGGAGGATATGACTATTTGGT<br>TGACTTTCTGGATTTATCCTTTCCAAAA<br>GAAAGACCAAGCCGGGAACATCCATATG<br>AGGAA | Exon 15 | Seq ID No 24 |

```
gtaagcaggaataccagtggaagtgcc       Intron    Seq ID No 42
cctttcttccttccttcctaaataaac       15
ttttttattttggaacaacttagagt
tacagaaaagttgcaaagatattatag
acagtagtgtttatatatatatataaa
ttttttttttgcttttatgaccacacc
tgtggcatatggaggttcccagtctag
gggttgaattggagctacagctgccag
tctgtgccataaccacagcaatgcagg
atctgggcacgtctgtgacctacacc
aaagctcacagctggattcttaaccca
ctgagcaaggccagggattgaacctgc
atcctcgtggttcctagttggattcgt
ttccgctttgccgcaatgggaactcca
aattattgttaatatcttacttttactg
gggtacatttgttacaaccaatactct
gatactgaaacattactgttaactccg
tacttgcttcttttttgagtcatttgca
aagactggcttcttgacctgcttcctt
ccaaacagctggcctgcctatgctgtt
ctcagacctgcaagcactgatctctgc
ccccttgccttctctccagtggtgtc
tccttcccaaacaaacccagtgtggc
tctggaaagggagttaagtcaacataa
accaacacatatttttgttgagctccaa
ttttgagcaaatccctccacctacggca
gacaggcatgatgttaagaactagggc
tttggacacaaggtcaagaccaagaag
ggttcctcacccctactgattcagata
accaataatgaggctttgaatccctgt
ccaaaggttgttttttttcccttctat
tgagcttcttgccaccttatcagtttt
tttatgacagtcaaatgacatgatat
atgtgagcatacatggtaatttttaat
tctatataaatgaatcactaaataaat
taggaggatatatagtccaccttaag
cgtattacacgtgtcacatgaatgtgt
ggcgacttaattgtagaggtttaaatg
tagcttcctataatagatgtgttccta
aactacattttaatcattggacttgta
ttttatgttagcacttgctgttgaag
aaaagcctatgccaaaagttcagtgaa
accaataatccactgccagctttctga
gttaaaaaaatccctgggttttcaca
cacaggaacaccctgtgtgaaacactc
atttagagcaaaatgcatctgataagg
agttcctgttgtgcctcaactggttaa
ggacctgacattctccatgagaatgtg
agtttgatccccgccccactcgatgg
gttaaggatctggtgttgccacaaact
gcagctccgattcatctcctagcctag
```

TABLE 9-continued

Genomic Organizational Sequences aaacttccacagcccagaatatgccac
agaattcggctgtttaaaaaaaaaaag
aaaaaaaaaagaatcataaatgtgttg
gtttgttcaccaaatacatgataactt
gctcttgccaagctcagcttcataaat
attaagtcatttaatacagcagccacc
ttatgaacagatattactatacttccc
atttacagataaggaaaatgccatatt
taaccaagagattaaataacttttccg
aggtcttatagcaagtaaatcatggtg
caggggtttgaccacacgcagtctatc
tccagagtctgtgtatttagccactgt
tttactttcaaatttaaatttataaaa
cttctaaattatctgttaaccataatc
tttgaattttttaaaaccacgagttcc
tataaaatgtttcattgaaagtaagtc
acttttccatagcttttgataatacat
ctgtaggataaagtaagccacagctct
cttgcagacttggtacaccctggggca
aagcatcatgcctgtcacgtacatggt
ggtccttactttgactctcagtgcttt
tattgcccaggaattttgtgagatttc
tagttgttgaggtttgttaaagaggt
tatgccggtacttggaagagctctttt
cttgctacctggagccttctcatattt
ccttttttgaggagggacatgaattgcc
tttcaaactcataaatatattttctag
tacacaagtctccatcttccttagacg
catggctcctggagttctccatcctcc
tgctccactttgggtgggctcctctct
gggtctgccaccaatctgccacccaga
gacatccttgacccacttccagacccc
accatgggcttcactttcttcgctttcc
tcctttgtggaaccttctgcttaagaa
tctgaggaagaaaattttgcacgtgagc
taaactggaggtacttttcctgcctggt
cttgcacgatagcttggctgagcccat
gatgctgggtggctgttactttccatg
gacacccgaaggcgttgctccttttggc
ttctagttgcatgcagtgttgcttatc
ccaggctgatctttcttccactgtagg
tgacttttaagaattaagggattaatc
tatatctacaacaacaacaacaaagac
cttttcaagctgaggtagggctttctg
tatatgtttggagtggttatccagcag
acttacttgaaggcaggggtcatatc
ctcaagtgctcataaacggaccacaga
aagatctcataactgggtggagctggg
tggggaccgtgtcatgtggccaggaaa
tgccagatgggaagggagtggcccctta
ctgagctccagctgaactctgaatttt
ctagaaaactcagaaatctggatttt
catgtgtaatacccagatttatagatg
tggaaagctaattcttttttttttttaa
gggactataggcaatgaactaagatct
aggttgtatttggacaagggtgcatca
gtttaagctgtgtagttgagcgctcag
ctattgggctgagggaccccctaaatac
tgagacggggaggtccttgctctgggg
catccacaagtacactccctggtctcat
tcaaacacttttcctacaaaattgatc
ccatttcttcagtgcactgtctgaatg
catttggcccagagccgtgctgaggca
tagggaaggggtccacggtttcatgc
atcgttttgtgctgtgtgtccctgctg
tcgtccaggatacctacctctcctcct
cctgcatctgaatgtcccccccacagac
tctctgggattctcagcctctggcct
gttcctcagacacctcttacctgccag
cttttccagattcacattagttagtcca
aatctactgccgtcagtgactcacttc
atttcttcttctccgaggcagttcagc
ccggtacagttgttttgtcaacacttc
agttgagtctggaagatgtgcatggg
tatgcacgagagcggtccatcatttt
agctagaagtcctttctcagcccagag
acaagtcctcatctcctttacttcctg actcttcttcctctgcatccttccaag
atatctcttttctccagccaccacctaa
atctcttcttttcccggggttccgtgc
tcaacccactcttcttcttaaatctgt
ggctgggtgaacgcatctgctggcacc
acttctctgctaaagactccaaaaatc
cataggtcctgcccggcctttgcccac
ctctctccaacactgtccagctttaga
tgtagagctaatccccccagagatatc
attccctggatgtctaagtcctttggt
atctcactttcagcgtgttcaaaatcc
tcttacaactgttctttctccttttcc
atcttgattattggcaacatgccagcc
tttcccctacccccagcagtgagccaa
gctagaaacaagggcttaatcttcaat
cttttccttctccatccctaaacctaat
gagtctccaagcccttcccagtttaca
ccctaaatgttgctcaaaaacatcccct
agttcttccacgtgctctcctctatat
tgaaaggtcaagaaaggccatcttccc
tccactgtgaggaaatagatcttgata
ctgcccctgagctgggcagtcctcgac
ctgacaaactgtgcagtgtttctaaat
ctctactggcaaaatgagagtgcctttt
gacctgtgttgcgatctcagatcacag
tggatgtaattgttttataggaatggt
gaacgaaaaagaagtaaatccctaatg
ccaaactcctgatcattctatgtcatt
taatagcctgtcatttatgataaagtt
tcctctactggcattagcacaatactt
ctcaggaaaaaaaaatatgatgccaga
tactgaaaagctcctgggtaaacatga
acatgggtaccgataaaatggtgaagc
cagtccaatcttagagtgacttccctt
catgctacttcatgctctttttttttt
tttttttttaagaaaaaccccttttttt
tttctcacaccagtcacagaggagacc
gaggcttagcaaggttaaggtcacatg
attagtaagtgctgggctgaaactcaa
aaccatctctgcttgtctcctaaccct
gtgcacctctgactattcaacag ATCCTGTGTCAGGAGTTGGGATTCTTT Exon 15a Seq ID No 25
GAAG gtaaggccttgaccaccgaattaagg Intron Seq ID No 43
taatcttgctctgtggcaggccttgtt 15a
ttcagtattttaagtacactggctcag
gtaatcctcacaacagcccaggagga
atgttctattacctccactgtatagat
gaggaacttgaggcacagaatggttgc
caaggtcacacagctatattgggggtt
catacccagccatccaactctgtctgt
actctctgccactctgcacccccagct
cctgatccacttcctgtttccatccct
cgatttctgctgcactcaggggcccct
ctcccccctcggcctgtgagatctgctt
cagtaggcttttctccctgactcctcc
atccctgtccttacaggcagctgcttc
tctccgggacagcgagggggtccatacgg
acactctctactggctgggttgcgcct
aactcgtgattcctcctctgtttcag ATTCGGAGCCGGGTTGATGTCATCAGA Exon 16 Seq ID No 26
CACGTGGTAAAGAATGGTCTGCTCTGG
GATGACTTGTACATAGGATTCCAAACC
CGGCTTCAGCGGGATCCTGATATATAC
CATCATCT gtaagtccgaaaatgcctgtcgtgtgt Intron Seq ID No 44
gccttaggctgctgcggaggaggccag 16
ggctatataagcagagtcagtgactga
ctgtgccctgcagtgttgatggccatg
gagattccaccgttagagcttttttct
ttgttaaccttgaaggcaaatctggtt
aggaagataactttcaaagagtcacca
tctggacattcatgccatgtgcttca

TABLE 9-continued

Genomic Organizational Sequences

```
atcctgtatacaagcagtttagagtac
agggaagggaaggacattatgaaaggg
agaggggtgtgtttggatccagcagctc
catcctcagaatttatctgaagacact
gcaaaattactaagaatcactatgaca
agaatggggatggggtgatatgacaaa
gttgtgatcctggaagaccttcatctc
ccatgttgcccaactctgaacatgaat
ttggtgaactagttggttaaggggatg
atcctccaagtttctccctggttgagc
tccaaaaaccatgtaagtttctcatag
caaaaccgtataggtccttagggcttt
agttggaatatttgtgctgaaatgctg
gaaagcccattttgccattttttgtatt
tgcaaaataatcatcaagaggggagaa
tgcattctttcatgaccactgaccctc
tgaaaaggtcaggaatttagtctgaag
taggcaagcctcctacccccgctctgc
catgagcttgcacgcacaggcctgtc
tgacatttcttctttatagatttcttt
ttgaatatcttgaaattgctttaaaaa
tatttaaagaatgtagaattatataaa
ataaaaggaaataaccccacacctcc
cacaaaaccctgtttcctgcctttctc
cacccactctccagggtaacacttggt
aacagcatagttgtatcaccccaggcc
tattttttgagcatatcagcattttcaag
aaatgtattttttctcaataaaacatc
ccttatagttgaggaggggaggttatc
attcctgggttttgtttttttttttttt
tttaatgtaatcctggtacatcggtaa
tttgcatttttttattcattaatatctt
tggtatttctagtgttgggacacacag
gtcaacctcagttttttgggtttttttt
tttgtcttttatgtcttttctagggccac
aacctgcagcatatggacgttcccaagc
taggagtctaatcagagctgtagccac
cagcctacgtcatagccatagcaacgt
cagatccaagccgtgtctgtgacctac
aagcacagctcatggcaacaccggatc
cttaaccactgaacgaggcaggggat
cgaacacacatcctcatggatcctagt
catgttcattaaccactgagtcatgat
gggaactccaacttcaactatttaat
gtctgtaaaacattccatttggaaacc
atttcatttgtaaagcaaaatgaaaac
atttttgttcattttcaacagagttcgt
agctgacttctgttctggaaaaagga
aatggagcaaatttgagtgagaaagat
tcaaagataacttttcttttaaaaaaa
attatatcttggaaacttctgggctat
tgattctgaagactattttttctatata
ctgttttgatagcaaagttcataaatg
tgaaaggatcctgcgatgaatcttggg
aagcagtcatagcccaatatatctttg
ttgctttaaaatgagatttagtttac
taaatattttctgatcataaaaataa
cacagatctaccgcagaaaatttggaa
aaaaaaaaacttttaaattcaaaaaac
agttcaaccacaaatgatcccaccatc
cagagagcaatttgtactttggtgtct
agttcatctttcttttctgtttacaa
gcacatataccacaagcatttttttcaa
aaaatgaaaatgggataatactataca
tacgtctgtacacctgcatagttactg
aacagtctttgatctaccctgtaagtt
tctaactttttcattatttgaaatgatg
ttttggcaaagaaatatgtaggtgtgt
ctcgcacactttcataatgatttctta
ggataaatttcttaggataaattcata
atgatttcttataatcctactct
gccaactgatcttcagggaagccaact
cgccttctcagaaataacatataaccc
atttacttgccctctcaccaatactag
gtcctaatgttttgtgtacagattct
atattttacatacaagaattccttaa
agcaaggcatgtcacagaaaaaatgaa
```

```
ggaagacacaattgtcatgtttaagga
ctgcattctgtaccaaaaatgctaagt
taaatgaacatctgaaacagtacagaa
acgctatctttcagggaaagctgagta
ccaggtactgaacagattttggcaaat
acagcaggcatggatgtttccaaaaca
tgttttttctactttatctcttacag
```

| | |
|---|---|
| GTTTTGGAATCATTTTCAAATAAAACT<br>CCCCCTCACACCACCTGACTGGAAGTC<br>CTTCCTGATGTGCTCTGGGTAGAGAGG<br>ACCTGAGCTGTCCCAG | Exon 17 Seq ID No 27 |
| gtaaagcatcctgcaggtctgggagac<br>actcttattctccagcccatcacactg<br>tgtttggcatcagaattaagcaggcac<br>tatgcctatcagaaaacctgacttttg<br>ggggaatgaaagaagctaacattacaa<br>gaatgtctgtgtttaaaaataagtcaa<br>taagggagttcccatcgtggctcagtg<br>gtaacgaacctactagtatccattga<br>ggacacaggttcaatatctggcctcac<br>tcagtcggctaaggatccagtgatgcc<br>gtgagctgcagtgtaggccacagacgt<br>ggctcagatctggtgctgctgtggcta<br>tggtgtaggccggcccctgtaactcc<br>aattcgaccctaggctgggaacctaa<br>aaagaccccaaaaaagtcgcttaatga<br>atagtgaatacatccagcccaaagtcc<br>acagactctttggtctggttgtggcaa<br>acatacagccagttaacaaacaagaca<br>aaaattatcctaggtggtcagtgggg<br>ttcagagctgaatcctgaacactggaa<br>ggaaaacagcaaccaaatccaaatact<br>gtatggttttgcttatatgtagaatct<br>aaattcaaagcaaatgagcaaaccaat<br>tgaaacagttatggaagacaagcaggt<br>ggttgtcagggggggagataaggggagg<br>caggaaagacctgggcgagggagatta<br>agaggtaccaactttcagttgcaaaac<br>aaatgagtcaccagtatgaaatgtgca<br>atgtgggaaatacaggccataacttta<br>taatctcttttttttttttgtctttt<br>tgccttttctaaggctgctcccgtggc<br>atatggaggttcccaggctaggagtcc<br>aaacagagctgtagctgccagcctaca<br>ccagagccacagcaacacgggaacctt<br>aacccgctgagcaaggccagggatcga<br>acccgagtcctcacagatgccagtagg<br>gttcattaaccactgagccacgacagg<br>aattccagggtctgttgtgttcttaaa<br>acacttccaggagagtgagtggtatgt<br>cataagtaaacaataaatgttaaccac<br>aacaagcttatgaaataaacaggaaag<br>ccatatgacctacaatcagtcattggg<br>agaatccacaaaaggttgagcagagga<br>tcaattccagctcacactccagtttta<br>gattctcccctgccttaaagcatcaca<br>gactacataatctgagctgaagaataa<br>aaattaaaactcaccccagtgcaaaac<br>agaaatgaaaagtattaaaacgaggt<br>tcatactgttgttcattagcaatatct<br>tttattcacag | Intron 17 Seq ID No 45 |
| GGGTGCCCAACAACATGAAAAAATCAA<br>GAATTTATTGCTGCTACGTCAAAGCTT<br>ATACCAGAGATTATGCCTTATAGACAT<br>TAGCAATGGATAATTATATGTTGCACT<br>TGTGAAATGTGCACATATCCTGTTTAT<br>GAATCACCACATAGCCAGATTATCAAT<br>ATTTTACTTATTTCGTAAAAAATCCAC<br>AATTTCCATAACAGAATCAACGTGTG<br>CAATAGGAACAAGATTGCTATGGAAAA<br>CGAGGGTAACAGGAGGAGATATTAATC<br>CAAGCATAGAAGAAATAGACAAATGAG<br>GGGCCATAAGGGGAATATAGGGAAGAG<br>AAAAAAATTAAGATGGAATTTTAAAAG | Exon 18 Seq ID No 28 |

TABLE 9-continued
Genomic Organizational Sequences

```
GAGAATGTAAAAAATAGATATTTGTTC
CTTAATAGGTTGATTCCTCAAATAGAG
CCCATGAATATAATCAAATAGGAAGGG
TTCATGACTGTTTTCAATTTTTCAAAA
AGCTTTGTTGAAATCATAGACTTGCAA
AACAAGGCTGTAGAGGCCACCCTAAAA
TGGAAAATTTCACTGGGACTGAAATTA
TTTTGATTCAATGACAAAATTTGTTAT
TTACTGCGGATTATAAACTCTAACAAA
TAGCGATCTCTTTGCTTCATAAAAACA
TAAACACTAGCTAGTAATAAAATGAGT
TCTGCAG
```

TABLE 10
Genomic Sequence of CMP-Neu5Ac Hydroxylase gene

Seq ID No. 46
```
ctgccagcctaagccacagccacagcaacgctgggtctgagccatgtct
gcagcctatgccagagctcccgcagcgccggatgcttaacccactgag
caaggccagggattgaaccctcgtcctcatggatagcagttgagttgtt
tccacggaactcttaggggaactcctgattatttttttatttaaatttat
atttctctgacttttcgtgtgctcatcagccactgactgtgtatctcc
attagtcatggtttgttaactctgtcattcaaaccctcttcatccttgc
tacgcagataacatcattataataaaatcgtgcctgaagaccagtgacg
cccccaagctaagttactgcttcccctgggggaaaagaagcaccgcg
cgggcgctgacacgaagtccgggcagaggaagacggggcagaggaagac
ggggagcagtgggagcagcgggcagggcgcgggaagcactgggatgt
tccgcgttggcaggagggtgttgggcgagctcccggtgatgcaggggg
aggagccttttccgaagtagcgggacaagagccacgggaaggaactgtt
ctgagttcccagtCCCGACGTCCTGGCAGCGCCCAGGCACTGTTATTGG
TGCCTCCTGTGTCCACGCGCTTCCCGGCCAGGCAGCCCTGGCGGATCCT
ATTTTCTGTTCCCCCGATTCTGGTACCTCTCCCTCCCGCCCTCGGTGCG
CAGCCGTCCTCCTGCAGTGCCTGCTCCTCCAGGGGCGAAACCGATCAGG
GATCAGGCCACCCGCCTCCTGAACATCCCTCCTTAGTTCCCACAGgtga
gaaggcttcgccgctgctgccgctggcgccggcagcgccctccacgcac
ttcgtagtgggcgcgcgccctcctgcattgttctaaaagatttttttt
tatccgcttatgctatcagttactgaggaagtatttacaaatctactat
tattttgaatttgccttttctccttatagtttatcagtatctcttgag
actgttattggtgcctgcaaatttaaaatgattggggttttatgaggaa
gtgaaccttttatctttatgaaacgcctaactgaggcaatgttaattgc
ttaaaatactttctttattatcagtgtggccatgccagtgtcctcttgg
ttagaatttgcctgat................
........ctgccaaagctgggagatgggggaaagtagagtgggttatt
gaaactgaatatagagttcagcatctaaaagcgaggtagtagaggagga
agctgtgtcaacggaaatactgagctgggttcacatcctcttttctccac
acagTCTAATGCCTTGTGGAAGCAAATGAGCCACAGAAGCTGAAGGAAA
AACCACCATTCTTTCTTAATACCTGGAGAGAGGCAACGACAGACTATGA
GCAGgcaagtgagagggggctttagctgtcagggaaggcggagataaac
ccttgatgggtaggatggccattgaaaggaggggagaaatttgccccag
caggtagccaccaagcttggggacttggagggagggctttcaaacgtat
tttcataaaaaagacctgtggagctgtcaatgctcagggattctctctt
aaaatctaacagtattaatctgctaaaacatttgccttttcatagCATC
GAACAAACGACGGAGATCCTGTTGTGCCTCTCACCTGCCGAAGCTGCCA
ATCTCAAGGAAGGAATCAATTTTGTTCGAAATAAGAGCACTGGCAAGGA
TTACATCTTATTTAAGAATAAGAGCCGCCTGAAGGCATGTAAGAACATG
TGCAAGCACCAAGGAGGCCTCTTCATTAAAGACATTGAGGATCTAAATG
GAAGgtactgagaatcctttgctttctccctggcgatcctttctcccaa
ttaggtttggcaggaaatgtgctcattgagaaattttaaatgatccaat
caacatgctatttcccccagcacatgcctaacttttttcttaagctcctt
tacggcagctctctgattttgatttatgaccttgacttaattcccatc
ctctctgaagaactattgtttaaaatgtattcctagttgataaacagtg
aaacttctaaggcacatgtgtgtgtgtgtgtgtgtgtgtgtttac
cagcttttatattcaaagactcaagcctcttttggatttccttcctgc
tctctcagaagtgtgtgtgtgaggtgagtgcttgtccaaacactgccct
agaacagagagactttccctgatgaaaacccgaaaaatggcagagctct
agctgcacctggcctcaacagcggctcttctgatcatttcttggaagaa
cgagtgctggtaccccttttcccagccccttgattaaacctgcatatc
gcttgcctcccatctcaggagcaattctaggagggagggtgggctttc
ttttcaggattgacaaagctacccagcttgcaaaccaggggatctggg
gggggggtttgcacctgatgctccccactgataatgaatgagggattg
accccatcttttcaagctttgcttcagcctaacttgactctcgtagtgt
ttcagccgtttccatattaggcttgtcttccaccgtgtcgtgtcgtcaa
tcttatttctcaggtcatctgtgggcagtttagtgcgaatggactcaga
ggtaactggtagctgtccaagagctccctgctctaactgtatagaagat
caccacccaagtctggaatcttcttacactggcccacagacttgcatca
ctgcatacttagcttcagggcccagctcccaggttaagtgctgtcatac
ctgtagcttgcttggctctgcagataggttgctagattaggcaaatag
agggtgcccagtcaaatttgcatttcagataaacaacgaatatattttt
agttagatatgtttcaggcactgcatgggacatacttttggtaggcagc
ctactctggaagaacctcttggttgtttgctgacagactgcttttgagt
cccttgcatcttctgggtggtttcaagttagggagacctcagccataag
ttgttctgtcaccaagaagcttctgcaagcacgtgcaggccttgaggtc
ttccgacttgtggcccggggactctgcttttctctgtcctttttctc
cttagtgggccatgtcctgtggtgttgtcttagccagttgtttaaggga
```

TABLE 10-continued

Genomic Sequence of CMP-Neu5Ac Hydroxylase gene gtgttgcagctttatgattaagagcatggtctttccttgcaaactgctt ggtttagaagcctggctccaccacttagcggctctgtgacctcggacac atttcttagcctttctgggcctcgctcttcttcctcataaagtgaaaat gaaagtagacaaagcctttctctgtctggctactgagaggatggagtgat ttcatacacataaagcacttaaaataatgtctggcatatgatacatgct caataaatgtcacttacatttgctattattattactctgccatgatctt gtgtagcttaagaacagaggtctttacaggaattcaggctgttcttgaa tctggcttgctcagcttaatatggtaattgctttgccacagactggtct tcctctccttcacccaaagccttagggggtgaacgatcccagtttcaac ctattctgttggcaggctaacatggagatggcaccatcttagctctgct gcaggtggggagccagattcacccagctttgctcccagatacagctccc caagcatttatatgctgaaactccatcccaagagcagtctacatggtac actcccccatccatctctccaaatttggctgcttctacttaggctctct gtgcagcaattcacctgaaatatctcttccacgatacagtcaagggcag tgacctacctgttccaccttcccttcctcagccattttcttcttttgta cataatcaagatcaggaactctcataagctgtggtcctcattttgtcaa tctaatttcacagcctcttggcacatgaagctgtcctctctctcctttc tgcctactgcccatgagcagttgtgacactgccacatttctcctttaac gacccagcctgctgaatagctgcatttggaatgttttcaattttgtta atttatttatttcatctttttttttttttttttttttttttttttttag ggccgcacccatgggatatggaggttcccaggctagggatccaatggga gctgtagctgctggcctacaccacagccacagcaatgcacaattcgagc caatctttgacctacaccagagctcacggcaacactggattcttaaccc actgattgaggccagggatcaaactctcgtcctcatagatacgagtcag attcgttaacctctgagccatgatagttgttagttactcattgatgaga aaggaagtgtcacaaaatatcctccataagtcgaagtttgaatatgttt tctgccttgttactagaaaagagcattaaaaattcttgattggaatgaa gcttggaaaaatcagcatagtttactgatatataagtgaaaatagacc ttgttagtttaaaccatctgatatttctggtggaagacatatttgtctg taaaaaaaaaatcttgaacctgtttaaaaaaaaaacttgactggaaa cactaccaaaatatgggagttcctactgggacacagcagaaatgaatct aactagtatccatgaggacacaggtttgatgcctggcctcgctaagtgg gttaaggatatggtgttgctgcagctccaattcaaccccatcctggga accccatatgccaccctaaaaagcaaaagaaaggtgctgccctaaaa agcaaaagaaagaaagaaagacagccagacagactaccaaatatggag aggaaatggaacttttaggccctatctccaactatcacatccctatcac cgtctggtaagaaatggaaaaaatattactaagcctcctttgttgctac aattaatctgattctcattctgaagcagtgttgccagagttaacaaata aaaatgcaaagctgggtagttaaatttgaattacagataaacaaatttt cagtatatgttcaatatcgtgtaagacgttttaaaataattttttattt atctgaaatttatattttcctgtattttatctggcaaccatgatcaga aatcttaaacaatcaggaagtcttttttcttagacaaatgaaaatttg agttgatcttaggtttagtacactatactaggggccaagggttatagtg tgactattaaatcacagataatctttattactacattatttccttatac tggccccacttggatcttacccagcttagcttttgtatgagagtcatcc ttaaagatgactttattctttaaaaaaaaaaacaaattttaagggctgc acccatagcatatagaagttcctaggctagcggtcaaattagagctgca gctgccagcctatgccacagccacagcaatgccagatctgagctgcatc tgtgacctacactgcagcttgcagcaatgctggatccttaacccattga acaatgccagggattgaacacacatcctcatggatactgctcaggttcc taacctgctgagccacagttggaactccaaagcagactttattctgatg gctctgctgatctctaacacgttattttgtgccatggtgtttatcttca ctttactcaagtcagggaaacacgaagagtctcataggataaaccca aggagaaatgtgcaaagtcacatacaaatcaaactgacaaaaatcaaat acaaggaaaaaatatcttcactttcaaaatcacctactgatgatgagtt tatatttccttggatatttgaatattagctattttttcctttcatgag ttttgtgttcaaccaactacagtcgtttactttgatcacagaataatgc atttaagccttaaatagattaatatttattttcaccatttcataaacct aagtacaatttccatccagGTCTGTTAAATGCACAAAACACAACTGGAA

GTTAGATGTAAGCAGCATGAAGTATATCAATCCTCCTGGAAGCTTCTGT

CAAGACGAACTGGgtaaataccatcaatactgatcaatgttttctgctg ttactgtcattggggtccctcttgtcaacttgtttccaatctcattaga agccttggatgcattctgattttaaactgaggtattttaaaagtaacca tcactgaaaattctaggcaagttttctctaaaaaatcccttcattcatt catttgttcagtaagtatttgatgagaccttaccatgtgtaaacattgc actaggtattaagaaatacaaagatggataagatagagtcggcgtaaat gagatgatataatgagacgttataatgaaactcacaattccagttggga aataaagtccttcaaattccatgactcttctggcacacgttagaggct acagcttctgtgtgattctcatgctggctccacttccactttttccttc ttcctactcaagaaagcctatagaaatatgagtaagaagggcttaatca taggaataaatttgtctctgttctaagtgattaaaaatgtctttatcag tataaaaagttacttgggaagattcttaaaactgcttttacacactgtt ctagaatgactgttatataaataaaaaagtagatttgatctaacacaat taaatgacctttggaaatattgactaattctcaccttgcccctcaaagg gatgcctgaaccatttccttcttttgccagaaagcccccacccttgtc tgttgacctagcctaggaaatcttcagatcacgttgttagcacgaactg gttacatgtgctgtacaaatactatttaattcatctgattaaaaaaaaa TABLE 10-continued Genomic Sequence of CMP-Neu5Ac Hydroxylase gene gagataagaagcaaaagtttgactatcttaaactgtttgcgtaggtgag
aggacaattgaccatctactttatgagtatgtaacccagaaacttaaag
ctccttaagggagctaagtcttttggataagacctatagtgagaccttt
tagcaaaatggttaagactgaatggagctcactagcgtgggttcatatc
ctgatgctcaaacacgcaattaaatgactttaggtgggttagtctctgt
tccttagtttcctcaatgggagataatattggtagtagcgattttactg
ggttgttgaaagaacatctgttaaatgttcagaacgtgttacgacagag
tacagagtaatgatttgcttgtatatgtatgactcaaatagtctgccat
atgccttgtgactgggtcctgtggagcaggaaggagggatttcccaccc
agcagaaagttgggtaaactggaaaatagactgaggccaggaaatgatg
caaagcgttgatgttcactgccacggcaggtgaagggcagggccagagt
tgtcagtagggtcaggggaggactggaaataaccaagacccactgcact
tttcagccttttgctccagtaaggtaatgttgtgagagtagaaaattttg
ttaacagaacccacttttcagtacagtgctaccaatactgtagtgatttt
cataccacatcccaagaaagaaaaagatggctcaatcccatgtgagctg
agattatttggttttattgttaaataaatagcattgtgtggtcatcatt
aaaaaaggtagatgttaggaaagtagaaggaagaagactctcacctaca
ttttcatcactgttttggtatctgccagttgtcaccttggtccccttcc
ccgcctctcccctgcctcctcttcctccttctcctttttttggaataca
attcaggtaccataaaatttacccttttagagtgtttgactcaatggtt
tttagtattttcacatgttgtgctattactatcactatataattccagg
tcattcacatcaccccccaaagaaaccttctaactattagcagtccatt
cccttcttccctcagccctggcaaccactaatctacttactgtctcca
tggatgttcctatattgaatcaagctagcataaaccccacttgctcatg
gtcataattctttttatagtgctaaattacatttgctaatattcaatt
aaggatttctatgtccatattcataaggaatattggtgtgtagttttct
ctttgtgtgatatctttgtctggttgggggatcagagtaataattactg
ctctcatagaatgaattgagaagtgttccctccttttctatttattgga
agagtttgtgaagtatattggtattgattcttctttaaacatttggtca
gattcaccagtgaagccatctgggccatggctaatctttgtgaaaagtt
ttttgattactaattaaatctcttaatttgttatgggtctgctcctca
gacgttctagttcttcttgagtcagttttgttcatttgtttcttcctag
gactttctcccctttcatttggattatttagattgatagtaatatcccc
ttttaattcctggctgtagtaatttgggtcttttctcttttttcttggt
cagtttagctaaaggtttgtaattgtattaatcttttcaaataactaac
tttttgttttgtttgttttttgttttttgttttttgttttttgtttttt
ttttgctttttaaggctgcacctgaggcatatggaagttctcaggctag
aggtctaatcggagctacagctgctggcctataccacaaccatagcaat TABLE 10-continued Genomic Sequence of CMP-Neu5Ac Hydroxylase gene gccagattcaagctgcatctgcgacctacaccacaactcggccagggat
cacacccgcaacctcatggttcctagtcggatttgttaaccactgtgcc
acgacgggaactcccgcccatttttttttaacacctcatactttaacata
aagatgggcttcacatggactgatagctcaaatgaggaaggtaagacta
tgaaagtaatggaagaaatgtagactattttttgtgacctagagattact
gatacttcttgactttttcaaacaatacttcaaaagtacagcccaaaggg
aaaaaagaaagaaaaaagaaacacacatatacacaaacctagtgaataa
gatatcatcgatacactacagatttctatgaactggaagaccccatgga
caaagttaaagaacatatgatagtttgagtgattattttgcaatatttta
caaccaatgagggaatattatccagcttataggaggaagtaatgcaaat
cgacaagaaaagataggaaacccaatataaaaattaagaaaatacaaa
aattaagaaaggatatgaactagcattttacaaaagaaaaatctccaaa
agtcaatcagcacatgaaaatatgctcaaacctattaattattagaaaa
ctacagactgaagcaatgaggtgctttactttacatctttttgactgat
aaaaagttagaaacaaaggtgatatcaaatgtcagggataaaaggatat
agaaatcgtcatgcctgtggtgggagtatggccggtgcagtcatgtggg
aaggtaatctgacagtggttaggcagagcaggtttatgaatacactgtg
gcccatcaatcccacgcctgtttatgtaccaaagaaatcctgttgtggc
agaatctatgggtccacccctgggagcatgaattaataaaatgtggcac
cagggtgtgtgaaactccagctagagatgagatgtccacatggcaacat
gaatgcatcttagaaacatagatttgagtgaaaaagagtaagaaacagc
cgggaaacccaataccatttataaaaattaaagatgcacacatacaatg
tagtaaatattttgcatgaacttttcaaatggttgcctacagggggggag
agtaaagaagagtagaaaacaaagataaagggagtaagtaagtagctct
gcctggactgaatataatgtgtcatgaactgagaaatatggttaacata
atcctcttaacttgaggtcctaaatgaatgaatgagtccactattcatt
tacccattctttaatgtgtattgcattataatccattttttagaacca
acgaattttgttcccataactactaatcagcctgccttttctccctcat
tcccttatcagctcaggggcattcctagttttttcaaacgttcctcattt
gaaccaaaaatagcatcattgtttaaattatacttgtttttcaaatacga
tgcttatatattccaagtgtgtttgcccatttttcttaggtggtagaaat
ttttcattctacttttctatctactcagattttcccgttggaattattt
ccattgctattaaacttagaagtccccccctgtgatatgccattttttc
atacttttaagcacttggttgcttttctttgtgtctttaagcacctag
aatacttataaccattgcacagcactgtgtatcaggcagcccttcctct
tccactaatttatggtccttctcttagactatattaaactgttatttaa
ttaggatcctctcttcgtccttatgatttaattattatagttttctaat
atgttttattataattcctcttcattattcctccctattaaaaatttt
aatgaattccatttgtttgttcttctagttaaatattaagtcataatcc TABLE 10-continued Genomic Sequence of CMP-Neu5Ac Hydroxylase gene aaataacttagatgtcattagtttatgtggtcaaagtaaggataccaca
tctttatagatgcaggcagttggcagatgtcatgattttcttcagtgca
taaatgcaatttatctttgagcaaggggcataaaaacttttatggtatt
ggctttgaaataatagttaagaactgcagactcagttttttcctgctttt
cttgaaaagaacacttctaaagaaggaaaatccttaagcatggatatc
gatgtaattttctgaaagtctcctgtaattccttgggattttttgttgtt
gtttgttggtcggttttttttgggttttttgtttgtttgttttgttttgtt
ttgttttgcttttagggctgcacctgtggcatatggaagttcccaggct
aggggtccaactggagctacagctgccagcctactccacagccacagca
acatgggatcctagctgcatctgtgacctaaccacagctcttggtaatg
ccagattgttaacccactgagcaatgccagagatcgaatctgcctcctc
atggacactagtcagattagtttctgctgagccacaatgggaattccca
attccttgtatttttgaactggttatgtgctagcatataattttgtttc
ttgaatcttgtgggttttttttttttttttttttgtctcttgtctttt
ttaaggctgcacccacagcatatggaggttcccaggctagaggtcaaat
tggagctacagctgccagcctacacaacaactgcagcaaagtggggccc
aacttatatgacagttcgtggcaatgccggattcctaacccactgagca
gggccagggatcgaacctgagtttccagtcagtttcgttaaccactgag
ccatgatagtaactcctgtttgttcagtcttgaacctccttttttaattc
tttattccttgagggtgaaataattgccataataatactatcatttatt
acatgccttctctgtgctaggcatagtgacactttaggatttattatat
cacttaatccctacaacaactctgcaaagtatgtatcataatcctattt
gacagatcaggaaattgcagcccaggatgcagataatatgcatccatca
caagtgactagatatagtccctctgctattcagcagggtctcattgcct
ttccattccaaatgcaatagtttgcatctattgtatatgtgttttgggg
tttttttgtcttttttttttttttttgtcttttctggggcctcacccttg
gcataggtaggttcccaggctagggtgcaaattgaagctgcagctgcca
gcctacaccacagccacagcaactcgggatctgagcctcatctgcaacc
tacaccaaagctcacggcaacaccggatccttaacccactgagtgaggc
cagagatcaaaccggcaacctcatggttcctagtcggattcattaacca
ctgagccacgatgggaactccctaaatgcaatagtttgctctattaacc
ccaaactcccagtccatcccactccctcctcctccctcttggcaaccac
aagtctgttctccatgtccatgattttcttttctggggaaagtttcatt
ttgccattttcattttacgggtaattttttacttcagtttcttccacta
gcagttgtcttaaagtgagtataattaatattcatttggaaaatgtaag
caaaacattttttaaagggccatgcccacagcatatgaaagtttctggg
ccaggggttgaatccaggctccaagttgcagctgtgccctacactgcag
ctgggcaatgctggatcctttaacccactgtgcccggctagggatcaaa TABLE 10-continued Genomic Sequence of CMP-Neu5Ac Hydroxylase gene cctgcatttccacagctacccgagccattgcagttggattcttaaccca
ctgcactacagtgggaactcccacaaaaacattttttaatgtccttttgaa
taaagtaggaaagtgctcgtctttgagggcagggcggcaatgccatttc
cacaaggtttgctttggcttgggacctcatctgctgtcatttagtaatg
aataaaattgctgacagtaataggattaactgtgtgtggagatagccag
ggttagagataaaaacactggagaagtcaaataagttgctcgaggtcct
ctagctaataagctattaagtgggagagtgagggctagaaacaggccat
ctgtctcccaagcacatgtccattagtggtttgctgatagccttccaga
acaacagagaggactctcaaacatggtcttgcctccctccaattgatcc
cctccatgtgcctcacagcgggtctttctaaaattaagttctgattttta
attctcccttgctatagcacttaggtatggctttcagccgtgcaataaa
aagcaggcaagagtggctcaatcatataggaggttgttttttcttagatc
ccaagcaggtaatcctgggcattatggttgttctgcgtttatcaaggag
ccaaattctctatcacctcctgttctatcctcctcagtatctggctcta
ttcttcagcatctcaagatggcttgtgctcctccaagcatggcagtcaa
attccacacaagagggggaaatatgaagggcagacagtgctggtctcct
gagctgtccctctttgtcgggaaataaatgtattccttcatcccgtga
gacttctgaagtagacgtctgcttacgtctcacccaccagaactatgta
aactgcacatagtgctaggtctacatagccactcataactgccaggggg
tgggaaatctttaaataggtgtaccaccacacaattaggatgctaatag
taagggagaaggagagaataggttttgcgcaagccaccagcatgcctgc
acaattgcttaaaattcttcattgaccctcattgccacaggatgaaa
tccaaacgccttcttagttgggaatctgacctacctgtctctcccacct
ggttcagacaccattctccttggtcataaaattccagtcatttgtgaac
atccagctccccatgcctccatgcctttgcacatgctgttcttttatc
ttttatgttgtcctttatcttttatccaaaagagatatcccatcatca
catctcttttgtcagcccccaaatactttgtctttcaagttcagctgga
ggattacctcctatttgaaatcagctttgtctcttacaaccaaacaagg
ttttccttccgagacactcccacagcaccttgaactcatctctatcaat
cattcatttgattgtaatgaagttgttggtggtatgcctgtgtctctga
cacatctgcgatctcatgagttccttaagtggaatgtgaatagcgggat
gaacagtattggtcttcagccctcatctctgcagatgttgcttgaccca
aatgagcgttgccttttattttgattttgctttgatttgtctactccat
gtacttgagccatgcatttctgtcttagcgatgcttttaaagtcatt
ttttggttgattatccagatttgtccacctttgcttctagTTGTAGAAA
AGGATGAAGAAATGGAGTTTGCTTCTAGAACTAAATCCTCCTAACCC
GTGGGATTCAGAACCCAGATCTCCTGAAGATTTGGCATTTGGGGAAGTG
CAGgtaaggaaatgttaaattgcaatattcttaaaaacacaaataaagc
taacatatcaatttatatatatatatatatatatattttttttttttttt TABLE 10-continued Genomic Sequence of CMP-Neu5Ac Hydroxylase gene tacatcttatattaccttgagtattcttggaagtggctagttaggacat
ataataaagttattctgaagtcttttttttttcttttccatggtgagca
gtggcttgatgtggatctcagctcccagacgaggcactgaacctgagcc
gcagtggtgaaagcaccaagttctagccactagaccaccagggaactcc
ctattctaaattcttgagcacattatttaggaacctcaggaacttggca
ggattacaggaaatatatctagatttaaaaaaaaatcttttaacagagg
tcccaaaggagagtcatgcacagctatggaggaagttcagaaactgcc
cttgctaccagatcactgtcagataaaatggccagctacatgtttctgc
acattgccctaagatctttacaaacttttctgtgcattttttccactttt
aaaagaaatttcggggttcctgttgttgctcagtggttaacgaaccca
actagtatccatggggacagggttcgagccctggcctcactcagtggg
ttaagaatctggcattgctgtggctgtggcgtaggctggcggctacagc
tcagattggaccctagcctgagaacctccatatgccgcaggtatggcc
ctaaaaaaaaaaaaagagagagagagaatttcctccagaaaaaacac
tttggtagtttgggagaagtaaacaaccaaaaattaattttttctggagt
attcgggaagcttgtaaaaatgggctcttactttttgaggagacaaat
gggaacctacccagaagaggcacaatcacctgcatttgatttcttgacc
tctccctaccttctttgctggctttccacatttggatttctgtgaccttt
atctctgctccttggtgttttcattttttcctgtggacgtgccagactat
gggaagggagtaaggcgttgatttagaatcctgtagtctctgcctgtct
ctagtcattgttttcacccttctcaaaggaccttgacatcctgagtgag
tccgcaagtaatttaggggagaagccttagaagccagtgcagccaggct
acatgactgtgtccacccactggaaccagtcattttttatacctattcac
agccccctaccatttaaatccccagaggtctgccataacatctgtaac
tcccttcctggtaaattgtgttctaaaagactggtaacaaaagatatt
ctgtggtacagagcataattaaatacctgggagctgatttgagtggggt
aaatcaactggtttgacccctaaaacccaccatgagcatttctgttcta
ataaagtaatgcccgtgctgggaattgtgttctacggaaatgctcctgc
tgtgtctttcttgagtcctgtgtcattgaacatgcttaggagcaaaggt
cccccatgtggctgtctgctaaccagcccagttccttgttctggctggt
aatgatccgatcatctgaatctcactgtcttccaacagATCACGTACCT
TACTCACGCCTGCATGGACCTCAAGCTGGGGACAAGAGAATGGTGTTC
GACCCTTGGTTAATCGGTCCTGCTTTTGCGCGAGGATGGTGGTTACTAC
ACGAGCCTCCATCTGATTGGCTGGAGAGGCTGAGCCGCGCAGACTTAAT
TTACATCAGTCACATGCACTCAGACCACCTGAGgtaaggaagggtgagc
cctcaactccgaagaaaatgctgcaataaaagcactgttggttttcagc
ttttttttgtaatcactgctcattctgaggtagattcgcttgggctgata
aaaagagaactaattcagataaatgcttgcatttgcatagcctctttt TABLE 10-continued Genomic Sequence of CMP-Neu5Ac Hydroxylase gene ttaaaaactttttttttttttttttttttttggcttttcagggctgaac
ctgtggcatatggaggttcccaggctaggggtcgaatcagagctgtagc
cccgggcctatgccactgccatagcaacatgcatagcctcctttttaaa
gtgccttcctgttttataccattgggatgtgagaagagctattgtggaa
angagcatggggtnataaccctggacctctcacgtcctaccctcaggnt
agtgggaaaactctgagtttaaggacatcaaagtgactccttttttagtt
acattatggnggaatcagcncatattttttacaaggggcggagngtaanc
tgttggagtttacaagacatggtggcattgcaactacttaaccctac
tattatagcacaaaagcagccatagtcggtcctgaaggagcctgatgcc
ttcagctttataggcaatgacgtgtgaatatcacaaacagtttcctgtg
tcaccaaacatgattgccttttgatttcccttttcaaccctttaaaaaaa
ggtaaaagcccttcttagcattcagcagcaggtcgctgtgttttgccaa
ctcctgatctgtagcatttcgacaacactgagctctcaacttttgaacc
ctgagtccaccacatccttcagtgaaaccagagccatgtgatactaagg
atagaaacggaaacttcctgaatccaggcgatcaaataggagggagaaa
gaggaactttcattgacaaaaccacaaatattgtgaatggactgttaca
aatattgtgaatgctcctattcccaaccccctggcttcattacagggtc
ctatgtgttcatccttattgagaaatttgtattgctactgccaggttgc
caataccccagcggtgcccatggtgttctaaaatgaagcaatttcaactt
tatttttttttcctgtgactttacatgacaagttcacatgaaggatata
ctttgatagtaatgtccatggttagggaatacacattgtttgctggttg
actggcccctggattttctattgaaagtccatgagatctcgaaggcac
aggtgtgttctctcgcttttttaaggaaagggtttaaaaacttaagtaat
taacagctttagtaacaaattacctataacacacttaaaaaccgaatac
cacccactggagtattgtgctacgattaaaaatctacttgtctactaca
tgatatcttgtcccacagaaggttctggaaccaaacttgtaatttcag
gattatgagagccctgagttcacgcattgtgtaataactatgttgtgtg
gtagtcaatttgtacagcttgcttagagagaacaatgtcaagttaagga
ggcgattgctttatagtgcctgtcacaagatgccattgccattgtccta
gcaagagatattctatgggagtatactacattttagtgaggataagaac
tttttatggcatttagtccggtcatttcccaaccactgtcctgaaaacc
aatttcattttgatttcaggggcttgtgtgggcaaagttgccaggcatt
aaaaagccacttctcaactgtagtatcacaatgctttagttgggtagtg
tattgcagatagcttatggctgaaaagttaccaagccttgcagttttca
ctcctttgagtttatttccttgacagaattgaccctgagttttttgact
cttacctgctcaactaataaacaccagagtcatttatctccattgctct
tgtctgaccttatttaccgaataatgccttatgggttcacaaaaacaa
ggggggagggggccagcatgccttagaaactgtcttagtcaagaaatg
ngatttattatgtaaatatatgagtattataatagatagtgttattaa

TABLE 10-continued

Genomic Sequence of CMP-Neu5Ac Hydroxylase gene tagacaccagcaagaattgtcaataatttaaaaatcacaaattaaaata
catccatgttagnatcatttatcctaactcccaaagcccttaaagtgg
aagatttagatgttaacccagagattaaagacatgttcaaagaatcctt
gatttttttttgaatcccttgtttttagagaagaaaacctaatgatttt
cccctctggattctacatattaaatatagttttggaacttgaatatta
gtatggttaataagtgctgatatgctgattttgtttatatttttcttat
gagtaaatatcctatatcaccagacattatagtctatgtacaaatatga
ttcttaaacctgatagcacattcattagagttggaattgccttttttt
tttttttttacagttgcacctgcaacatatgaaagttcccaggctagg
ggttgaatccaagctgcagctgccaccctacattacagccgtagtaaca
gcagatccgagctgcatctgcaacctatgctgcagctcagggcaatgcc
agatccactgagtgaagccagggatggaacttgcatcctcatagagaca
acgtcgtgtccttaacccactgagccagaacaggaactccagaattttcc
tttcaatagaagaagcaccaagtttaggatcagaaagcctgaatttgaa
taccaatttactatttgttagtcatatatttctgagtgtgtttcctcat
ttattaaaagcagactaaaagatgagagggtcttttgttgagaatcaaa
tacaataacatgtgaaagtgtgtaacactatgattgaaatatacctaca
cagccatttatttgtttattgttcatgttttgccacccacacagtagta
tataatccttttatgtaataaatgctaataatgaaagttggcaacttat
gtaagtactcaaaatgctggaggtcatgggatactgactgggatactac
agaggtaatgtcatttcctctgcgctaaacttattgtctgtagttaggg
actgactctctttaggacaaggagttcattctgtataccatgtgtggct
atcaccccttcgaagttgaaaaactgccccagggtgggcacccatccgtt
ctcttagatatatggccgagacctttctctcactgggagggaaccacac
tgaggaatgagaaaaaaaaaggaaaatcaagatgaaaccagaaacctc
tttggcataacttctccactctgtactttttgttagaactacccttgca
caaagcagcatcagtgtggaagacagaatttgcacacctggtttgatat
acatgccgtggtatatgggatgttctaacaataaagaggactctcccag
gaaatctcctcactgttatagtcagccttgaggaaagagctcttcttt
ggactctggggagagtctagttttttcagttccttgcttctcggtcaacg
tgttggtgtaaggatcacactctctcttatactagataattctattttt
tcacctttcaacctgtctatccttctgaccctagTTACCCAACACTGAA
GAAGCTTGCTGAGAGAAGACCAGATGTTCCCATTTATGTTGGCAACACG
GAAAGACCTGTATTTTGGAATCTGAATCAGAGTGGCGTCCAGTTGACTA
ATATCAATGTAGTGCCATTTGGAATATGGCAGCAGgtctgtgttcttc
cacatgtttgggttatcctttctgggataaatttgaggcgagatagaaa
ctttaagactaaagaaacaatggcctactttttttgtacatggtcctgt
gtaaatctctatttgagctgaaataagatggtcttcctctccaattatc

TABLE 10-continued

Genomic Sequence of CMP-Neu5Ac Hydroxylase gene catggtatgactctgatggataacaaatccagttctgaaaaaagggggat
ttctttccagaagagaggacagtttcttcaaatattgaattaaaagcaa
aatagatgtaaaccgttgttggttttattgttgaattccagGTAGACAA
AAATCTTCGATTCATGATCTTGATGGATGGCGTTCATCCTGAGATGGAC
ACTTGCATTATTGTGGAATACAAAGgtattttcttgccctcatcagcat
gaaattgctcttggtagaaaggataataatagttatccaaaacatcatc
ctatgttcatctgtttcttccctcttcattttccatagagtacagtata
ttctatctctgtcttaggaaaatggactgtcattcatataatcttacag
agaatcaattagtaatgtactctatgccgtgacaggtgcgaaggttttt
tttgaaggcaacagataaaaatatcctatatttcacctattgtaatttc
cttaaaactgacattattgaataaatgttttacttctcatcttgaatatt
attatgttatggaatcatacactttaccccaataatcatcgaaaagaat
tccaaaaggttgagagagttgtgttgatctgattacttcctctgcat
cctttgagcttaaccttgaatatagtttgctaaggaaagtagtctgtt
tatgatcctggagtggaatcaggctaagtgtcctcattcagaacccact
gaatcagacagaatgaatttatttccttgaaagttcaaaatgtgtcact
caagagtataaattttcaaatcttactctctcttttccttggatgtgag
caattcttcgataattgaatgaggcagattatatagacttacatggaag
actgttggcctgagaattcaaactatggtgttcaagacttcacngngag
tccgatgccatttgtttcccacagGTCATAAAATACTCAATACAGTGGA
TTGCACCAGACCCAATGGAGGAAGGCTGCCTATGAAGGTTGCATTAATG
ATGAGTGATTTTGCTGGAGGAGCTTCAGGCTTTCCAATGACTTTCAGTG
GTGGAAAATTTACTGgtaattctttatatcaaaatgatgccaaggagtt
ggcatggcactttgctaaatgctgtgtgaatcaatacaaagataattag
gacatggttcttcctcacaagaggtgtgcaatcttattgggaaatcata
cttgcaagtcacaaatatagactaaagtttccagctgagaatatgctga
tggagcatgaaacactaaggagacagggagaatctcaggaaaaatcaag
aataatttggatcaaatggattcctgacatagaacatagagctgatcag
aaagagtctgacattggtaatccaggcttaagtgctcttttgtatgtggt
tcagaacagagtgtgggcagcctgaggggatacataccttgacctcg
tggaaagctcatacggggagggatgaggctaaggaagcccctctaaag
tgtgggattacgagaggttggggggtggtagggaaaatagtggtcaaa
gagtataaacttccagttacaagatgaataaattctagggg tataataa
cagcatggcactatagatagcatattgtactatatactggaagtgctga
gagtagatcttacatgttctaaccacacacacacacacacacacacaca
caccacacacacaccacacacacacgtgcacacaaacagaaatgg
taattatgtgaggtgatggcggtgttaactaactttattgtggtcatca
tttagccatacatgcatgtcatgaaatcaccatgttgtacaccttaaag
ttatgtaatactagatgtcagttatatctcaaagctagaaaaaatgtgg TABLE 10-continued Genomic Sequence of CMP-Neu5Ac Hydroxylase gene ggaccaaggcagaagctcttctgctctgtgtctaagggtggttctgggg
ctgggatggggaggatggttaagtggtatatttttttcatacctttgct
cagtactatcattgtaagtgttcaatatatgtctgcttaataaattaat
gttttagtaagtaatctctgtttagtaatgtgtcagaaatgccctact
tgcaataggaagaaaacctgtccagtcccttccttttttctgtaagtct
gatttcattgcctcccagaatgcatcaccatgtgagagatagagggaag
gtgctgtccttatggggttaacagtgtgactagggaggcaaaatatacc
tactaaaggtggtagcataattcagttcttatgtgagtatgtgtatgt
gtgtgagtatgtgcacatgcacatacattttaaaaggtctgtaatatac
taacatgttcatagtggttacacctagcttataggtaacattttttccc
ctgtatccttgtttgtgtttatcaaattttcataacagtaatggtagaa
ggagtacctgacatggtaccatacatgctnggncctgcctaatttctcn
atttcctttattgcccataccccattgcttgacaagcataagtccata
ctggcttgttttcgttcctcagactcagtacaccatgtagctccatgcc
ctgggtctttgtatgtgctatttctactgcttagagtgctattgcccct
gaccaccacgtggtcagcaacttctcttctgcgtctgtgtctatggtct
atgattccagatgtcatcttcactaactacccttctaatatgcccttcc
atcccaccccgtcctcatccttaccccagccactctctatttggtggctc
tgttttattttcttcctagctcatcactctttgaaatgaacttatttac
ttattcaatatttgcttctttcactagaatgaatgctccatgagagcag
ggacctgctttatcttgctcgccactgtattcacagtgcctagaactac
gtctggcacatagtaggtgctcaataaatatcgatcaaatgaaagaatg
agcaaacgaacaaatgaacaacacgtgaggtaggcatcatgattccatc
aacagaggagaaaaccagacttaaagnaatgaagtggnggagctgcatt
tgatcttgactgactccaacatccatgctcttgaccactgtgcatctcc
agagtgtaatgaacatactttacttttatattccaccaaaataacaaag
ccatgcccatgttagtagagagttaatcgacagtgcccttaaaatatgc
atgcacccagggtacaactatgcatgctgccctgtgttttcagttggat
ccaaatgaattgccgtaaacaagaggggattcaatgtctttgactagt
ttgggatattttcctagtaaccaactttgcaaaataaagccactaatga
caaggagctttgttctacttctgcatcactcaactgtcaatttttatct
cttgcaagacttctaatctactagaacttttgttttctgtgatttctg
aacagagaagactaatccaaaccctgtcattccagAGGAATGGAAAGCC
CAATTCATTAAAACAGAAAGGAAGAAACTCCTGAACTACAAGGCTCGGC
TGGTGAAGGACCTACAACCCAGAATTTACTGCCCCTTTCCTGGGTATTT
CGTGGAATCCCACCCAGCAGACAAgtatggctggatatttttatataacg
tgtttacgcataagttaatatatgctgaatgagtgatttagctgtgaaa
caacatgaaatgagaaagaatgattagtaggggtctggagcttattta TABLE 10-continued Genomic Sequence of CMP-Neu5Ac Hydroxylase gene acaagcagcctgaaaacagagagtatgaataaaaaaaattaaatacaag
agtgtgctattaccaattatgtataatagtcttgtacatctaacttcaa
ttccaatcactatatgcttatactaaaaaacgaagtatagagtcaacct
tctttgactaacagctcttccctagtcagggacattagctcaagtatag
tcttttatttttcctggggtaagaaaagaaggattgggaagtaggaatgc
aaagaaataaaaaataattctgtcattgttcaaataagaatgtcatctg
aaaataaactgccttacatgggaatgctcttatttgtcagGTATATTAA
GGAAACAAACATCAAAAATGACCCAAATGAACTCAACAATCTTATCAAG
AAGAATTCTGAGGTGGTAACCTGGACCCCAAGACCTGGAGCCACTCTTG
ATCTGGGTAGGATGCTAAAGGACCCAACAGACAGgtttgacttgaatat
ttacagggaacaaaaatgatttctgaatttttcatgtttatgagaaaa
taaagggcatacctatggcctcttggcaggtccctgtttgtaggaatat
taagttttcttgactagcatcctgagcttgtcatgcattaagatctac
acaccacccttttaaagtgggagtcttactgtataaaataaactattaaa
taagtatctttcaactctggggtgggggggggagactgagttttttcaca
gtcctatataataattttcttatcctataaaataattaggagttcccgt
agtggctcagcaatagcaaacccgactagtatcgatgaggatgcgggtt
cgattcctggcccccctcagtgggttaaggatctggcattgccgtgagc
tgtggtgtaggtggcagacacggctcagatcccacgttactgtggctgt
ggcataggccagcagctccagctctgattagacccttagcctgggaact
tccatatgctgtgggtgtggccttgaaaaaaaataaataaataagataa
ttactcaaatgttttccttgtctcagaaccttacttcaggataaagagt
gagaaagttttttttatgaagggccattattacagctcaaaaataagtt
gtcttcagcaagtagaaagcaataagcctgagagttagtgttcctatca
gtgtaaatattacctcctcgccaatcccagacagtccatttgaacaat
taacggtgccctgggagtacagttcagaaacattaatgtggatgttcca
gacctgtatttttataagtacttgtcttgagccggatggaaccatcatt
cctcaccattatttagaagtggactgtgactctgttggagatcagggca
cacggttaccaaaagcacacccttctcctggccttacctttgcaaagct
ggggtctgggacacagtcagctgattatacccttttactaacttcccac
agctcaaatctggtcaattctccttcacaaatctcttaaaaatccatca
ctcacctccagcctcttctgctgtggccttgattcagcctctcacaatt
ttttttaaccagaattctggcagtggcccctgacttgcctctgtgctc
ccagccccgctgtcctctgatccatcctccatgccagccttttcaatc
tgctggtcacgattcattgatgggttaggaaatcaatggcatcacaact
agcatttagaaaaaggaaataggcgftcccgccgtggcacagcagaaat
aaatccgactaggaaccataaggttgcgggttcaaccccctggccttgtt
cagtgggttaaggatccggcattgccgtgggctgttttgtaagtcacag
acatggctctgatccggcattgctgtggctctggcgtaggcctgcagca TABLE 10-continued Genomic Sequence of CMP-Neu5Ac Hydroxylase gene tcagctccaattagacccctatcctgggagcctccatatgctgcaagtg
cagccctaaaaaaaataaaaaaataaaaaaaaataaataaagaagtaga
caaattgtatagaacaaccctgagtatgttgcctgagcacatataacaa
gggtaagtattatttcaggaaactctggtttcacagatactcttggcat
atggacccctagagtcctgatgtaaaatatattcttcctgggatcttag
gcaagaagtttgaaagctccaactctgcactgctgccaaagaaatgatt
tttaagtgcaaaactcttcccgttcccttccctgtataaaattccatag
gatctctccagtgcctctaggataaaggcagttttcattctctagttca
aggtgagagaagattttaattatttcacgttttagtggggaattcaaga
gtctggcacctgacatttgctgaactctctccattatccctctctagtt
ccagacgcatcctatggtagaaattcgcaaactagagtgagcgtcagag
taacccaaggaaactgggtaaatgcagctccctgggctctaccccctga
gattctgattcagtagatctgaagcagagccctggaatatgcatatgca
tcattgtgtcacaccaagcattctgggtaatgagagttgatgttaggtt
ctcagtagtaagacaagtatagagattccggggactgagtgctcagct
ctgccttggggaggagggagagggctaaagagaacaggagatggggaca
gggaatgctcaacctccaatcttaggcatttgagctatgtcttagggt
caggaggaggttaccaatatagtgattaagagattgaggttccagtcag
agggatatgctggagaaggggggtgaaaataatgtcataggtttggtga
gtgcagatactttgagttttttaatattttattgaaatatagttgatt
tacaatgctcttagtgagtacaattactttgaataagtgcatagatgta
tgccattcttccagaaatgatttattgagctcctttgggcatcatgcta
agtacagggggaaacagctgtgaagaggtccttcccttatgaagtcattc
atcccccttcagtaaatgaaggtaaaggaaaggatgagacagggacgcc
gtgttggaccagggtcagaaaggccttataagaccttgcctggagggca
aggaacttgcctgtgagtaaggagagcttgagaaagcgataaagcaaag
aaggaacattactgcattgtgttttagaaaaaccatgtcctggggaaga
actcctagagtcagggggggccagttgggagactgtgcttttttccagga
ggagataagtgaggctgctggctgagatggagcaaggatttagagaagc
agatatgagattcatttagaagttagacatttaggatctgacacataa
tttatcaccaaaaccagtgcatctctggctttgggccaccagttttgga
gaagtggaatgtagggacctaccattacctgccaatctttactacacag
atgcctatttccctcctcatatttcctttctccagatcacgtcctattc
tattgccaggactcaagattccaccttgcatgcagtgatccatcttcac
actggatggacagctctagggatgtcagagcacactcttgtccatactg
ctgactgggtctcctgtcagcccatctgtctatcagctgtggtattatt
agtataataagagggctgtatatgagagacacaaaattctaggtgtagc
tcaaagataggctagagttattcctatgtacaacaaatatttatgggac TABLE 10-continued Genomic Sequence of CMP-Neu5Ac Hydroxylase gene cccttctgtgtactgtcatggttgctgctttcatcatacttgtagtctca
atggaggtgggggcagggcaggaataagcggatgtccacaaaatcagta
agaccacttatattcaacattttcataatttagttattttgagcccaaag
ggtccacatccgtggtattccaactttttttccccggacatggatctt
tatcttttttttttttctttttgcggccagacctgcggcatatggaa
gttcccaggccaggggttgaatgggagttgcagctgcctggtctacacc
acagccacagcaaggtgggatctgagctgcatctgtgacatacaccgca
gctgaggtaacaccagattctgaacccactgaatgaggccagggatgga
acccgtctccttatgaacactatgtcatgttcttcaccctctgagccac
aacgggaactccagacttcgtctttaaatgtattctgacttggagagct
atcacactaagcaattaacaggagctgacctggtttaggctggggtggg
gccctactcctcaatgttccctgaggcacatctgtgggaccctgggca
tcatctatctgagcagccttagagctgctcatccagttgactgttgatg
tagaagtgcaaacttctgccttccttattgttgcttcttttttcattg
ttctctccccttttgtgtctttaagCAAGGGCATCGTAGAGCCTCCAGAA
GGGACTAAGATTTACAAGGATTCCTGGGATTTTGGCCCATATTTGAATA
TCTTGAATGCTGCTATAGGAGATGAAATATTTCGTCACTCATCCTGGAT
AAAAGAATACTTCACTTGGGCTGGATTTAAGGATTATAACCTGGTGGTC
AGGgtatgctatgaagttattatttgttttgttttcttgtattacaga
gctatatgaaaacctcttagtattccagttggtttctcaataagcattc
attgagcccttactgactgtcagacgcgagggcgtattggactatgtgctg
aaacaatcctttgttgaaaatgtagggaatgttgaaaatgtagggaatg
aaatgtagatccagctctgtttctcttttggaggattctttttcctcca
tcaccgtgtcttggttcttgtttgttttgggtttttgtgggtgttgtat
tgtgttgtgttggttatggcagtgacagctatttaaactgtgaaacggg
ggagttcccgtcgtggcgcagtggttaacgaatccgactgggaaccatg
aggttgcgggttcggtccctgcccttgctcagtgggttaacgatccggc
gttgccgtgagctgtggtgtaggttgcagacacggctcggatcccgcgt
tgctgtggctctagcgtaggccagcggctacagctccgattggacccct
agcctgggaacctccatatgccgcaggagcggcccaaagaaatagcaaa
aagacaaatataaatataaaataagtaagtaaaataaactgtgaa
acggggagttcccttcatggctcagcagttaacaaacccagctaggatc
catgaggatgtaggttcgatccctggccttgctcagtgggttaagaatc
cagcgttgctgtgagctgtgatgtaggtcgcagatgcagcccagatcct
gcattgctgtggctgtggcgtaggctggcagctgaagctccgattcaac
ccctagcctgggaacatccatatgctgcaggtgtggccttaagaggcaa
aaaaataaaaaataaaaaataaaaattgtgggacagacaggtggct
ccactgcagagctggtgtcctgtagcagcctggaagcaggtaaggtaag
gactgcagctgggtaaggactgaattgcaccaactgggaagtaagccta TABLE 10-continued Genomic Sequence of CMP-Neu5Ac Hydroxylase gene gatctagaacttaagttagccctgacatagacacacagagctcaccagc
taagtggttcagcttataagctggtcactgaaactgaggatgtccacaa
aagcaaaataagtagcaacaggcagcgggatgcaagagaaagaggaggc
ctaaaatggtctggggaatccctgccatacctatattttatcctacttat
atttagtgcctgaatgtgtgcctggagagcaaagtttagggaaagcatc
gggaaatgcacagtattcatacccttaggaacaaagatcagttacctcc
agggtaaagactatttccaagtttaaatttcaacccctgaacattagta
ctgggtaccaggcaacacttgccatcctcaaaatcaatgaatcctaaaa
ttcaacctgggggtcagtgacagtctgtgacaaagttttgctggtcag
taacgaaataagtatgagcaccatctgagtatggtcaccaagatgtcaa
ctctctttcctttggacgaattgtcattattccaagattaggtcctttc
tattttgaggtgtgaaaacatctttcctttcataaaataaaaggatag
taggtggaagaatttttttgttttttggtctttttgctatttctttgg
gccgcttctgcagcatatggaggttcccaggccaggggtcgaatcggag
ctttagccaccggcccacgccagagccacagcaacacgggatccaagcc
gcatctgcagcctacaccacagctcacggcaatgccggatcgttaaccc
actgagcaagggcagggaccgaacccgcaacctcatggttcctagtcgg
attcgttaaccactgcgccacgacgggaactcctaatgatactctttta
tatttagctactatgtgatgatgagaaacagtccacattttattatttt
ttagccaattttgatatctcattactaagataatgataattttctctata
aattttatttaagttagtgttatgaagtggttttgctagtgtagaaggc
taggatttgaattcagttcaagaaagaagagaggaggagggagaggg
atgggtagagggatgggcagtgggagagagcaaagaggagagacagtt
tttgtattaattctgcttcattgctatcatttaagggcacttgggtctt
gcacattctagaattttctaaggaccttgaccgccagattgatatgctt
cttcccttaccatgttgtcatttgaacagATGATTGAGACAGATGAGG
ACTTCAGCCCTTTGCCTGGAGGATATGACTATTTGGTTGACTTTCTGGA
TTTATCCTTTCCAAAAGAAAGACCAAGCCGGGAACATCCATATGAGGAA
gtaagcaggaataccagtggaagtgcccctttcttccttccttcctaaa
taaacttttttatttttggaacaactttagagttacagaaaagttgcaaa
gatattatagacagtagtgtttatatatatatataaattttttttgct
ttttatgaccacacctgtggcatatggaggttcccagtctaggggttga
attggagctacagctgccagtctgtgccataaccacagcaatgcaggat
ctgggccacgtctgtgacctacaccaaagctcacagctggattcttaac
ccactgagcaaggccagggattgaacctgcatcctcgtggttcctagtt
ggattcgtttccgctttgccgcaatgggaactccaaattattgttaata
tcttactttactggggtacatttgttacaaccaatactctgatactgaa
acattactgttaactccgtacttgcttcttttgagtcatttgcaaaga TABLE 10-continued Genomic Sequence of CMP-Neu5Ac Hydroxylase gene ctggcttcttgacctgcttccttccaaacagctggcctgcctatgctgt
tctcagacctgcaagcactgatctctgccccccttgccttctctccagt
ggtgtctccttccccaaacaaaccccagtgtggctctggaaagggagtta
agtcaacataaaccaacacatattttgttgagctccaattttgagcaaa
tccctcacctacggcagacaggcatgatgttaagaactagggctttgga
cacaaggtcaagaccaagaagggttcctcacccctactgattcagataa
ccaataatgaggctttgaatccctgtccaaaggttgttttttttcccttt
ctattgagcttcttgccaccttatcagtttttttttatgacagtcaaatg
acatgatatatgtgagcatacatggtaatttttaattctatataaatga
atcactaaataaattaggaggatatatagtccacctttaagcgtattac
acgtgtcacatgaatgtggcgacttaattgtagaggtttaaatgtagct
tcctataatagatgtgttcctaaaactacattttaatcattggacttgta
ttttatgttagcacttgctgttgaagaaaagcctatgccaaaagttca
gtgaaaccaataatccactgccagctttctgagttaaaaaaaatccctg
ggttttcacacacaggaacaccctgtgtgaaacactcatttagagcaaa
atgcatctgataaggagttcctgttgtgcctcaactggttaaggacctg
acattctccatgagaatgtgagtttgatccccggccccactcgatgggt
taaggatctggtgttgccacaaactgcagctccgattcatctcctagcc
tagaaacttccacagcccagaatgccacagaattcggctgttaaaa
aaaaaaagaaaaaaaaagaatcataaatgtgttggtttgttcaccaaa
tacatgataacttgctcttgccaagctcagcttcataaatattaagtca
tttaatacagcagccaccttatgaacagatattactatacttcccatttt
acagataaggaaaatgccatatttaaccaagagattaaataactttccc
gaggtcttatagcaagtaaatcatggtgcaggggtttgaccacacgcag
tctatctccagagtctgtgtatttagccactgttttactttcaaattta
aatttataaaacttctaaattatctgttaaccataatctttggaattttt
taaaaccacgagttcctataaaatgtttcattgaaagtaagtcactttt
ccatagcttttgataatacatctgtaggataaagtaagccacagctctc
ttgcagacttggtacaccctggggcaaagcatcatgcctgtcacgtaca
tggtggtccttactttgactctcagtgcttttattgcccaggaattttg
tgagatttctagttgttgaggtttgttaaagaggttatgccggtactt
ggaagagctcttttcttgctacctggagccttctcatatttcctttttg
aggagggacatgaattgcctttcaaactcataaatatattttctagtac
acaagtctccatcttcttagacgcatggctcctggagttctccatcct
cctgctccactttgggtgggctcctctctgggtctgccaccaatctgcc
acccagagacatccttgacccacttccagaccccaccatggcttcactt
tcttcgctttcctccttttgtggaaccttctgcttaagaatctgaggaag
aaaatttgcacgtgagctaaactggaggtactttcctgcctggtcttgc
acgatagcttggctgagcccatgatgctgggtggctgttacttttccatg

TABLE 10-continued

Genomic Sequence of CMP-Neu5Ac Hydroxylase gene

```
gacacccgaaggcgttgctcctttggcttctagttgcatgcaggttgct
tatcccaggctgatctttcttccactgtaggtgacttttaagaattaag
ggattaatctatatctacaacaacaacaaagaccttttcaagctga
ggtagggctttctgtatatgtttggagtggttatccagcagactttact
tgaaggcaggggtcatatcctcaagtgctcataaacggaccacagaaag
atctcataattgggtggagctgggtggggaccgtgtcatgtggccagga
aatgccagatgggaagggagtggcccttactgagctccagctgaactct
gaattttctagaaaactcagaaatctggattttcatgtgtaatacccca
gatttatagatgtggaaagctaattcttttttttttaagggactatag
gcaatgaactaagatctaggttgtatttggacaagggggtcatcagttta
agctgtgtagttgagcgctcagctattgggctgagggacccctaaatac
tgagacggggaggtccttgctctggggcatcacaagtacactccctggt
ctcattcaaacactttttcctacaaaattgatcccatttcttcagtgcac
tgtctgaatgcatttggcccagagccgtgctgaggcatagggaagggt
ccacggtttcatggcatcgttttgtgctgtgtgtccctgctgtcgtcca
ggatacctacctctcctcctcctgcatctgaatgtccccccacagactc
tctgggattctacagcctctggcctgttcctcagacacctcttacctgc
cagctttccagattcacattagttagtccaaatctactgccgtcagtga
ctcacttcatttcttcttctccgaggcagttcagcccggtacagttgtt
ttgtcaacacttcagttgagtctggaagatgtgcatgggttatgcacga
gagcggtccatcattttgagctagaagtccttctcagcccagagacaa
gtcctcatctcctttacttcctgactcttcttcctctgcatccttccaa
gatatctcttctccagccaccacctaaatctcttcttttcccgggtt
ccgtgctcaacccactcttcttcttaaatctgtggctgggtgaacgcat
ctgctggcaccacttctctgctaaagactccaaaaatccataggtcctg
cccggcctttgcccacctctctccaacactgtccagctttagatgtaga
gctaatcccccagagatatcattccctggatgtctaagtcctttggta
tctcactttcagcgtgttcaaaatcctcttacaactgttctttctcctt
ttccatcttgattattggcaacatgccagcctttcccctaccccagca
gtgagccaagctagaaacaagggcttaatcttcaatctttccttctcca
tccctaaacctaatgagtctccaagcccttcccagtttacaccctaaat
gttgctcaaaacatcccctagttcttccacgtgctctcctctatattga
aaggtcaagaaaggccatcttccctccactgtgaggaaatagatcttga
tactgcccctgagctgggcagtcctcgacctgacaaactgtgcagtgtt
tctaaatctctactggcaaaatgagagtgcctttgacctgtgttgcgat
ctcagatcacagtggatgtaattgttttataggaatggtgaacgaaaaa
gaagtaaatccctaatgccaaactcctgatcattctatgtcatttaata
gcctgtcattttatgataaagtttcctctactggcattagcacaatactt
```

```
ctcaggaaaaaaaaatatgatgccagatactgaaaagctcctgggtaaa
catgaacatgggtaccgataaaatggtgaagccagtccaatcttagagt
gacttcccttcatgctacttcatgctctttttttttttttttttaaga
aaaacccctttttttttctcacaccagtcacagaggagaccgaggctt
agcaaggttaaggtcacatgattagtaagtgctgggctgaaactcaaaa
ccatctctgcttgtctcctaaccctgtgcacctctgactattcaacagA
TCCTGTGTCAGGAGTTGGGATTCTTTGAAGgtaagggccttgaccaccg
aattaaggtaatcttgctctgtggcaggccttgttttcagtattttaag
tacactggctcaggtaatcctcacaacgccccaggaggaatgttctat
tacctccactgtatagatgaggaacttgaggcacagaatggttgccaag
gtcacacagctatattgggggttcatacccagccatccaactctgtctg
tactctctgccactctgcaccccagctcctgatccacttcctgtttcc
atccctcgatttctgctgcactcaggggcccctctcccctcggcctgt
gagatctgcttcagtaggcttttctccctgactcctccatccctgtcct
tacaggcagctgcttctctccgggacacgaggggtccatacggacactc
tctactggctgggttgcgcctaactcgtgattcctcctctgtttcagAT
TCGGAGCCGGGTTGATGTCATCAGACACGTGGTAAAGAATGGTCTGCTC
TGGGATGACTTGTACATAGGATTCCAAACCCGGCTTCAGCGGGATCCTG
ATATATACCATCATCTGtaagtccgaaaatgcctgtcgtgtgtgcctta
ggctgctgcggaggaggccagggctatataagcagagtcagtgactgac
tgtgccctgcagtgttgatggccatggagattccaccgttagagctttt
ttctttgttaaccttgaaggcaaatctggttaggaagataactttcaaa
gagtcaccatctggacattcatgcccatgtgcttcaatcctgtatacaa
gcagtttagagtacagggaagggaaggacattatgaaagggagagggtg
tgtttggatccagcagctccatcctcagaatttatctgaagacactgca
aaattactaagaatcactatgacaagaatgaggatggggtgatatggca
aagttgtgatcctggaagaccttcatctcccatgttgcccaactctgaa
catgaatttggtgaactagttggttaaggggatgatcctccaagtttct
ccctggttgagctccaaaaaccatgtaagtttctcatagcaaaaccgta
taggtccttagggcttagttggaatatttgtgctgaaatgctggaaag
ccccatttgccattttgtatttgcaaaataatcatcaagaggggagaa
tgcattctttcatgaccactgaccctctgaaaaggtcaggaatttagtc
tgaagtaggcaagcctcctacccgcttctgccatgagcttgcacgcac
aggcctgtcttgacatttcttctttatagatttcttttgaatatcttg
aaattgctttaaaaatatttaaagaatgtagaattataaaataaaaaa
ggaaataaccccacacctcccacaaaaccctgtttcctgcctttctcca
cccactctccagggtaacacttggtaacagcatagttgtatcaccccag
gcctattttgagcatatcagcatttcaagaaatgtatttttctcaat
aaaacatcccttatagttgaggaggggaggttatcattcctgggttttg
```

TABLE 10-continued

Genomic Sequence of CMP-Neu5Ac Hydroxylase gene tttttttttttttttaatgtaatcctggtacatcggtaatttgcattt
tttattcattaatatctttggtatttctagtgttgggacacacaggtca
acctcagttttggggtttttttttttgtcttttttgtctttctagggcca
cacctgcagcatatggacgttcccaagctaggagtctaatcagagctgt
agccaccagcctacgtcatagccatagcaacgtcagatccaagccgtgt
ctgtgacctacaagcacagctcatggcaacaccggatccttaaccactg
aacgaggccaggggatcgaacacacatcctcatggatcctagtcatgtt
cattaaccactgagtcatgatgggaactccaacttcaactattttaatg
tctgtaaaacattccatttggaaaccatttcatttgtaaagcaaaatga
aaacattttgttcattttcaacagagttcgtagctgacttctgttctgg
aaaaaaggaaatggagcaaatttgagtgagaaagattcaaagataactt
ttcttttaaaaaaaattatatcttggaaacttctgggctattgattctg
aagactattttttctatatactgttttgatagcaaagttcataaatgtga
aaggatcctgcgatgaatcttgggaagcagtcatagcccaatatatctt
tgttgcttttaaaatgagatttagtttactaaatatttttctgatcata
aaaataacacagatctaccgcagaaaatttggaaaaaaaaaaacttttta
aattcaaaaaacagttaaaccacaaatgatccccaccatccagagagcaa
tttgtactttggtgtctagttcatcttttcttttctgtttacaagcaca
tataccacaagcattttttcaaaaaatgaaatgggataatactataca
tacgtctgtacacctgcatagttactgaacagtctttgatctaccctgt
aagtttctaacttttcattatttgaaatgatgttttggcaaagaaatat
gtaggtgtgtctcgcacactttcataatgatttcttaggataaatttct
taggataaattcataatgatttcttataataatccatactctgccaact
gatcttcagggaagccaactcgccttctcagaaataacatataacccat
ttacttgccctctcaccaatactaggtcctaatgttttgtgtacagat
tctatattttttacataacaagaattccttaaagcaaggcatgtcacagaa
aaatagaaggaagcacacaattgtcatgtttaaggactgcattctgtacc
aaaaatgctaagttaaatgaacatctgaaacagtacagaaacgctatct
ttcagggaaagctgagtaccaggtactgaacagattttggcaaatacag
caggcatggatgttttccaaaacatgtttttctactttatctcttacagG
TTTTGGAATCATTTTCAAATAAAACTCCCCCTCACACCACCTGACTGGA
AGTCCTTCCTGATGTGCTCTGGGTAGAGAGGACCTGAGCTGTCCCAGgt
aaagcatcctgcaggtctgggagacactcttattctccagcccatcaca
ctgtgtttggcatcagaattaagcaggcactatgcctatcagaaaacct
gacttttggggaatgaaagaagctaacattacaagaatgtctgtgtttt
aaaaataagtcaataagggagttcccatcgtggctcagtggtaacgaac
cctactagtatccattgaggacacaggttcaatatctggcctcactcag
tcggctaaggatccagtgatgccgtgagctgcagtgtaggccacagacg TABLE 10-continued Genomic Sequence of CMP-Neu5Ac Hydroxylase gene tggctcagatctggtgctgctgtggctatggtgtaggccggcccctgt
aactccaattcgacccctaggctgggaacctaaaaagaccccaaaaaag
tcgctttaatgaatagtgaatacatccagcccaaagtccacagactctt
tggtctggttgtggcaaacatacagccagttaacaaacaagacaaaaat
tatcctaggtggtcagtgggggttcagagctgaatcctgaacactggaa
ggaaaacagcaaccaaatccaaatactgtatggttttgcttatatgtag
aatctaaattcaaagcaaatgagcaaaccaattgaaacagttatggaag
acaagcaggtggttgtcaggggggagataaggggaggcaggaaagacct
gggcgagggagattaagaggtaccaactttcagttgcaaaacaaatgag
tcaccagtatgaaatgtgcaatgtgggaaatacaggccataactttata
atctcttttttttttttgtcttttttgccttttctaaggctgctcccgt
ggcatatggaggttcccaggctaggagtccaaacagagctgtagctgcc
agcctacaccagagccacagcaacacgggaaccttaaccgctgagcaa
ggccagggatcgaacccgagtcctcacagatgccagtagggttcattaa
ccactgagccacgacaggaattccagggtctgttgtgttcttaaaacac
ttccaggagtgagtggtatgtcataagtaaacaataaatgttaacca
caacaagcttatgaaataaacaggaaagccatatgacctacaatcagtc
attgggagaatccacaaaaggttgagcagaggatcaattccagctcaca
ctccagttttagattctcccctgccttaaagcatcacagactacataat
ctgagctgaagaataaaaattaaaactcaccccagtgcaaaacagaaat
gaaaaagtattaaaacgaggttcatactgttgttcattagcaatatctt
ttattcacagGGGTGCCCAACAACATGAAAAAATCAAGAATTTATTGCT
GCTACGTCAAAGCTTATACCAGAGATTATGCCTTATAGACATTAGCAAT
GGATAATTATATGTTGCACTTGTGAAATGTGCACATATCCTGTTTATGA
ATCACCACATAGCCAGATTATCAATATTTTACTTATTTCGTAAAAAATC
CACAATTTTCCATAACAGAATCAACGTGTGCAATAGGAACAAGATTGCT
ATGGAAAACGAGGGTAACAGGAGGAGATATTAATCCAAGCATAGAAGAA
ATAGACAAATGAGGGGCCATAAGGGGAATATAGGG

TABLE 11

Contiguous 5' Genomic Sequence of
CMP-Neu5Ac Hydroxylase gene ctgccagcctaagccacagccacagcaacgctgggtc    Seq ID No. 47
tgagccatgtctgcagcctatgccagagctccccgca
gcgccggatgcttaacccactgagcaaggccagggat
tgaaccctcgtcctcatggatagcagttgagttgttt
ccacggaactcttaggggaactcctgattattttta
tttaaatttatatttctctgacttttcgtgtgctca
tcagccactgactgtgtatctccattagtcatggttt

TABLE 11-continued

Contiguous 5' Genomic Sequence of CMP-Neu5Ac Hydroxylase gene gttaactctgtcattcaaaccctcttcatccttgcta cgcagataacatcattataataaaatcgtgcctgaag accagtgacgccccaagctaagttactgcttcccct gggggaaaagaagcaccgcgcgggcgctgacacga agtccgggcagaggaagacggggcagaggaagacggg ggagcagtgggagcagcgggcagggcgcgggaagcac tggggatgttccgcgttggcaggagggtgttgggcga gctcccggtgatgcaggggggaggagccttttccgaa gtagcgggacaagagccacgggaaggaactgttctga gttcccagtCCCGACGTCCTGGCAGCGCCCAGGCACT

GTTATTGGTGCCTCCTGTGTCCACGCGCTTCCCGGCC

AGGCAGCCCTGGCGGATCCTATTTTCTGTTCCCCCGA

TTCTGGTACCTCTCCCTCCCGCCCTCGGTGCGCAGCC

GTCCTCCTGCAGTGCCTGCTCCTCCAGGGGCGAAACC

GATCAGGGATCAGGCCACCCGCCTCCTGAACATCCCT

CCTTAGTTCCCACAGgtgagaaggcttcgccgctgct gccgctggcgccggcagcgccctccacgcacttcgta gtgggcgcgcgcccctcctgcattgtttctaaaagatt tttttttatccgcttatgctatcagttactgaggaag tatttacaaatctactattattttgaatttgcctttt tctccttatagtttatcagtatctcttgagactgtta ttggtgcctgcaaatttaaaatgattgggttttatg aggaagtgaacctttttatctttatgaaacgcctaact gaggcaatgttaattgcttaaaatactttcttttatta tcagtgtggccatgccagtgtcctcttggttagaatt tgcctgat

TABLE 12

Contiguous 3'Genomic Sequence of the Porcine CMP-Neu5Ac Hydroxylase Gene ctgccaaagctgggagatgggggaaagtagagtgggt Seq ID No. 48 tattgaaactgaatatagagttcagcatctaaaagcg aggtagtagaggaggaagctgtgtcaacggaaatact gagctgggttcacatcctctttctccacacagTCTAA

TGCCTTGTGGAAGCAAATGAGCCACAGAAGCTGAAGG

AAAAACCACCATTCTTTCTTAATACCTGGAGAGAGGC

AACGACAGACTATGAGCAGgcaagtgagaggggggctt tagctgtcaGggaaggcggagataaacccttgatggg

TABLE 12-continued

Contiguous 3'Genomic Sequence of the Porcine CMP-Neu5Ac Hydroxylase Gene taggatggccattgaaaggaggggagaaatttgcccc agcaggtagccaccaagcttgggggacttggagggagg gctttcaaacgtattttcataaaaaagacctgtggag ctgtcaatgctcagggattctctcttaaaatctaaca gtattaatctgctaaaacatttgccttttcatagCAT

CGAACAAACGACGGAGATCCTGTTGTGCCTCTCACCT

GCCGAAGCTGCCAATCTCAAGGAAGGAATCAATTTTG

TTCGAAATAAGAGCACTGGCAAGGATTACATCTTATT

TAAGAATAAGAGCCGCCTGAAGGCATGTAAGAACATG

TGCAAGCACCAAGGAGGCCTCTTCATTAAAGACATTG

AGGATCTAAAATGGAAGgtactgagaatcctttgctt tctccctggcgatcctttctcccaattaggtttggca ggaaatgtgctcattgagaaattttaaatgatccaat caacatgctatttcccccagcacatgcctaacttttt cttaagctccttttacggcagctctctgattttgattt atgaccttgacttaatttcccatcctctctgaagaac tattgtttaaaatgtattcctagttgataaacagtga aacttctaaggcacatgtgtgtgtgtgtgtgtgtgtg tgtgtgtttaccagcttttatattcaaagactcaagc ctcttttggatttccttttcctgctctctcagaagtgt gtgtgtgaggtgagtgcttgtccaaacactgccctag aacagagagactttccctgatgaaaacccgaaaaatg gcagagctctagctgcacctggcctcaacagcggctc ttctgatcattcttggaagaacgagtgctggtaccc cttttccccagcccttgattaaacctgcatatcgct tgcctccccatctcaggagcaattctaggagggaggg tgggctttcttttcaggattgacaaagctacccagct tgcaaaccagggggatctggggggggggtttgcacct gatgctcccccactgataatgaatgagggattgaccc catcttttcaagctttgcttcagcctaacttgactct cgtagtgtttcagccgtttccatattaggcttgtctt ccaccgtgtcgtgtcgtcaatcttatttctcaggtca tctgtgggacagtttagtgcgaatggactcagaggta actggtagctgtccaagagctccctgctctaactgta tagaagatcaccacccaagtctggaatcttcttacac tggcccacagacttgcatcactgcatacttagcttca gggcccagctcccaggttaagtgctgtcatacctgta gcttgcttggctctgcagatagggttgctagattagg TABLE 12-continued Contiguous 3'Genomic Sequence of the Porcine
CMP-Neu5Ac Hydroxylase Gene caaatagagggtgcccagtcaaatttgcatttcagat aaacaacgaatatattttagttagatatgtttcagg cactgcatgggacatacttttggtaggcagcctactc tggaagaacctcttggttgtttgctgacagactgctt ttgagtcccttgcatcttctgggtggtttcaagttag ggagacctcagccataggttgttctgtcaccaagaag cttctgcaagcacgtgcaggccttgaggtcttccgac ttgtggcccggggactctgcttttttctctgtcctttt ttctccttagtgggccatgtcctgtggtgttgtctta gccagttgtttaagggagtgttgcagctttatgatta agagcatggtctttccttgcaaactgcttggtttaga agcctggctccaccacttagcggctctgtgacctcgg acacatttcttagcctttctgggcctcgctcttcttc ctcataaagtgaaaatgaaagtagacaagccttctct gtctggctactgagaggatggagtgatttcatacaca taaagcacttaaaataatgtctggcatatgatacatg ctcaataaatgtcacttacatttgctattattattac tctgccatgatcttgtgtagcttaagaacagaggtct ttacaggaattcaggctgttcttgaatctggcttgct cagcttaatatggtaattgctttgccacagactggtc ttcctctccttcacccaaagccttagggggtgaacga tcccagtttcaacctattctgttggcaggctaacatg gagatggcaccatcttagctctgctgcaggtggggag ccagattcacccagcttgtctcccagatacagctccc caagcatttatatgctgaaactccatcccaagagcag tctacatggtacactccccatccatctctccaaattt ggctgcttctacttaggctctctgtgcagcaattcac ctgaaatatctcttccacgatacagtcaagggcagtg accatacctgttccaccttccttcctcagccatttt tcttctttgtacataatcaagatcaggaactctcata agctgtggtcctcattttgtcaatctaatttcacagc ctcttggcacatgaagctgtcctctctctcctttctg cctactgcccatgagcagttgtgacactgccacattt ctcctttaacgacccagcctgctgaatagctgcattt ggaatgttttcaattttgttaatttatttatttcat cttttttttttttttttttttttttttttagggc cgcacccatgggatatggaggttcccaggctagggat ccaatgggagctgtagctgctggcctacaccacagcc TABLE 12-continued Contiguous 3'Genomic Sequence of the Porcine
CMP-Neu5Ac Hydroxylase Gene acagcaatgcacaattcgagccaatctttgacctaca ccagagctcacggcaacactggattcttaacccactg attgaggccagggatcaaactctcgtcctcatagata cgagtcagattcgttaacctctgagccatgatagttg ttagttactcattgatgagaaggaagtgtcacaaaa tatcctccataagtcgaagtttgaatatgttttctgc cttgttactagaaaagagcattaaaaattcttgattg gaatgaagcttggaaaaaatcagcatagtttactgat atataagtgaaaatagaccttgttagtttaaaccatc tgatatttctggtggaagacatatttgtctgtaaaaa aaaaaaatcttgaacctgtttaaaaaaaaaacttgac tggaaacactaccaaaatatgggagttcctactggga cacagcagaaatgaatctaactagtatccatgaggac acaggtttgatgcctggcctcgctaagtgggttaagg atatggtgttgctgcagctccaattcaaccccctatcc tgggaaccccatatgccaccctaaaaagcaaaaaga aaggtgctgccctaaaaagcaaaaagaaagaaagaca gccagacagactaccaaatatggagaggaaatggaac tttttaggccctatctccaactatcacatccctatcac cgtctggtaagaaatggaaaaaatattactaagcctc ctttgttgctacaattaatctgattctcattctgaag cagtgttgccagagttaacaaataaaaatgcaaagct gggtagttaaatttgaattacagataaacaaattttc agtatatgttcaatatcgtgtaagacgttttaaaata attttttatttatctgaaatttatattttcctgtat tttatctggcaaccatgatcagaaatctttaaacaat caggaagtcttttttcttagacaaatgaaaatttgag ttgatcttaggtttagtacactatactaggggccaag ggttatagtgtgactattaaatcacagataatctttta ttactacattatttccttatactggccccacttggat cttacccagcttagcttttgtatgagagtcatccttca aagatgactttattctttaaaaaaaaaaacaaatttt aagggctgcacccatagcatatagaagttcctaggct agcggtcaaattagagctgcagctgccagcctatgcc acagccacagcaatgccagatctgagctgcatctgtg acctacactgcagcttgcagcaatgctggatccttaa cccattgaacaatgccagggattgaacacacatcctc atggatactgctcaggttcctaacctgctgagccaca TABLE 12-continued Contiguous 3'Genomic Sequence of the Porcine
CMP-Neu5Ac Hydroxylase Gene gttggaactccaaagcagactttattctgatggctct
gctgatctctaacacgttattttgtgccatggtgttt
atcttcactttactcaagtcagggaaacacgaagagt
ctcatacaggataaacccaaggagaaatgtgcaaagt
cacatacaaatcaaactgacaaaaatcaaatacaagg
aaaaaatatcttcactttcaaaatcacctactgatga
tgagtttatatttccttggatatttgaatattagcta
ttttttttcctttcatgagttttgtgttcaaccaacta
cagtcgtttactttgatcacagaataatgcatttaag
ccttaaatagattaatatttattttcaccatttcata
aacctaagtacaatttccatccagGTCTGTTAAATGC
ACAAAACACAACTGGAAGTTAGATGTAAGCAGCATGA
AGTATATCAATCCTCCTGGAAGCTTCTGTCAAGACGA
ACTGGgtaaataccatcaatactgatcaatgttttct
gctgttactgtcattggggtccctcttgtcaacttgt
ttccaatctcattagaagccttggatgcattctgatt
ttaaactgaggtattttaaaagtaaccatcactgaaa
attctaggcaagttttctctaaaaaatcccttcattc
attcatttgttcagtaagtatttgatgagaccttacc
atgtgtaaacattgcactaggtattaagaaatacaaa
gatggataagatagagtcggcgtaaatgagatgatat
aatgagacgttataatgaaactcacaattccagttgg
gaaataaagtccttcaaattccatgactctttctggc
acacgttagaggctacagcttctgtgtgattctcatg
ctggctccacttccactttttccttcttcctactcaa
gaaagcctatagaaatatgagtaagaagggcttaatc
ataggaataaatttgtctctgttctaagtgattaaaa
atgtctttatcagtataaaaagttacttgggaagatt
cttaaaactgcttttacacactgttctagaatgactg
ttatataaataaaaagtagatttgatctaacacaat
taaatgacctttggaaatattgactattctcaccttg
cccctcaaagggatgcctgaaccatttccttcttttg
ccagaaagcccccacccttttgtctgttgacctagcct
aggaaatcttcagatcacgttgttagcacgaactggt
tacatgtgctgtacaaatactatttattcatctgatt
aaaaaaaaagagataagaagcaaaagtttgactatct
taaactgtttgcgtaggtgagaggacaattgaccatc
tactttatgagtatgtaacccagaaacttaaagctcc TABLE 12-continued Contiguous 3'Genomic Sequence of the Porcine
CMP-Neu5Ac Hydroxylase Gene ttaagggagctaagtcttttggataagacctatagtg
agacctttagcaaaatggttaagactgaatggactg
aatggagctcactagcgtgggttcatatcctgatgct
caaacacgcaattaaatgactttaggtgggttagtct
ctgttccttagtttcctcaatgggagataatattggt
agtagcgattttactgggttgttgaaagaacatctgt
taaatgttcagaacgtgttacgacagagtacagagta
atgatttgcttgtatatgtatgactcaaatagtctgc
catatgccttgtgactgggtcctgtggagcaggaagg
agggatttcccacccagcagaaagtttgggtaaactgg
aaaatagactgaggccaggaaatgatgcaaagcgttg
atgttcactgccacggcaggtgaagggcagggccaga
gttgtcagtagggtcaggggaggactggaaataacca
agacccactgcacttttcagcctttgctccagtaagg
taatgttgtgagagtagaaaattttgttaacagaacc
cacttttcagtacagtgctaccaatactgtagtgatt
tcataccacatcccaagaaagaaaaagatggctcaat
cccatgtgagctgagattatttggttttattgttaaa
taaatagcattgtgtggtcatcattaaaaaaggtaga
tgttaggaaagtagaaggaagaagactctcacctaca
ttttcatcactgttttggtatctgccagttgtcacct
tggtccccttccccgcctctccctgcctcctcttcc
tccttctccttttttttggaatacaattcaggtaccat
aaaatttacccttttagagtgtttgactcaatggttt
ttagtattttcacatgttgtgctattactatcactat
ataattccaggtcattcacatcaccccccaaagaaac
cttctaactattagcagtccattcccttcttccctca
gcccctggcaaccactaatctacttactgtctccatg
gatgttcctatattgaatcaagctagcataaacccca
cttgctcatggtcataattctttttatagtgctaaa
ttacatttgctaatattcaattaaggatttctatgtc
catattcataaggaatattggtgtgtagttttctctt
tgtgtgatatctttgtctggttggggatcagagtaa
taattactgctctcatagaatgaattgagaagtgttc
cctcctttctatttattggaagagtttgtgaagtat
attggtattgattcttcttttaaacatttggtcagatt
caccagtgaagccatctgggccatggctaatctttgt
gaaaagttttttgattactaattaaatctctttaatt

TABLE 12-continued

Contiguous 3'Genomic Sequence of the Porcine CMP-Neu5Ac Hydroxylase Gene

```
tgttatgggtctgtcctcagacgttctagttcttctt
gagtcagttttgttcatttgtttcttcctaggacttt
ctccctttcatttggattatttagattgatagtaata
tccccttttaattcctggctgtagtaatttgggtct
tttctcttttttcttggtcagtttagctaaaggtttg
taattgtattaatcttttcaaataactaacttttttg
ttttgtttgttttttgttttttgttttttgtttttg
tttttttttgcttttttaaggctgcacctgaggcata
tggaagttctcaggctagaggtctaatcggagctaca
gctgctggcctataccacaaccatagcaatgccagat
tcaagctgcatctgcgacctacaccacaactcggcca
gggatcacaccgcaacctcatggttcctagtcggat
ttgttaaccactgtggccacgacgggaactcccgccc
atttttttaacacctcatactttaacataaagatgg
gcttcacatggactgatagctcaaatgaggaaggtaa
gactatgaaagtaatggaagaaatgtagactattttt
gtgacctagagattactgatacttcttgacttttcaa
acaatacttcaaaagtacagcccaaagggaaaaaaga
aagaaaaagaaacacacatatacacaaacctagtga
ataagatatcatcgatacactacagatttctatgaac
tggaagaccccatggacaaagttaaagaacatatgat
agtttgagtgattattttgcaatatttacaaccaatg
agggaatatatccagcttataggaggaagtaatgca
aatcgacaagaaaagataggaaacccaatataaaaa
ttaagaaaatacaaaaattaagaaaggatatgaacta
gcattttacaaaagaaaaatctccaaaagtcaatcag
cacatgaaaatatgctcaaacctattaattattagaa
aactacagactgaagcaatgaggtgctttactttaca
tcttttgactgataaaaagttagaaacaaggtgata
tcaaatgtcagggataaaaggatatagaaatcgtcat
gcctgtggtgggagtatggccggtgcagtcatgtggg
aaggtaatctgacagtggttaggcagagcaggtttat
gaatacactgtggcccatcaatcccacgcctgttat
gtaccaaagaaatcctgttgtggcagaatctatgggt
ccaccctgggagcatgaattaataaaatgtggcacc
agggtgtgtgaaactccagctagagatgagatgtcca
catggcaacatgaatgcatcttagaaacatagatttg
agtgaaaaagagtaagaaacagccgggaaacccaata
ccatttataaaaattaaagatgcacacatacaatgta
gtaaatattttgcatgaactttcaaatggttgcctac
agggggggagagtaaagaagagtagaaaacaaagata
aagggagtaagtaagtagctctgcctggactgaatat
aatgtgtcatgaactgagaaatatggttaacataatc
ctcttaacttgaggtcctaaatgaatgaatgagtcca
ctattcatttacccattctttaatgtgtattgcatta
taatccattttttagaaccaacgaattttgttccca
taactactaatcagcctgccttttctccctcattccc
ttatcagctcaggggcattcctagttttcaaacgtt
cctcatttgaaccaaaaatagcatcattgtttaaatt
atacttgttttcaaatacgatgcttatatattccaag
tgtgtttgcccattttcttaggtggtagaaattttttc
attctacttttctatctactcagattttcccgttgga
attatttccattgctattaaacttagaagtccccccc
gtgatatgccatttttttcatactttttaagcacttg
gttgcttttctttgtgtctttaagcacctagaatact
tataaccattgcacagcactgtgtatcaggcagccct
tcctcttccactaatttatggtccttctcttagacta
tattaaactgttatttaattaggatcctctcttcgtc
cttatgatttaattattatagttttctaatatgttttt
attataattcctcttcattattcctccctattaaaaa
ttttaatgaattccatttgtttgttcttctagttaaa
tattaagtcataatccaaataacttagatgtcattag
tttatgtggtcaaagtaaggataccacatctttatag
atgcaggcagttggcagatgtcatgattttcttcagt
gcataaatgcaatttatctttgagcaaggggcataaa
aacttttatggtattggctttgaaataatagttaaga
actgcagactcagttttcctgcttttcttgaaaaag
aacacttctaaagaaggaaaatccttaagcatggata
tcgatgtaattttctgaaagtctcctgtaattccttg
ggatttttgttgttgtttgttggtcggttttttggg
ttttttgtttgtttgttttgttttgttttgctt
ttagggctgcacctgtggcatatggaagttcccaggc
taggggtccaactggagctacagctgccagcctactc
cacagccacagcaacatgggatcctagctgcatctgt
gacctaaccacagctcttggtaatgccagattgttaa
cccactgagcaatgccagagatcgaatctgcctcctc
```

TABLE 12-continued

Contiguous 3'Genomic Sequence of the Porcine
CMP-Neu5Ac Hydroxylase Gene atggacactagtcagattagtttctgctgagccacaa
tgggaattcccaattccttgtattttgaactggtta
tgtgctagcatataattttgtttcttgaatctttgtg
ggtttttttttttttttttttttgtctcttgtctttt
taaggctgcacccacagcatatggaggttcccaggct
agaggtcaaattggagctacagctgccagcctacaca
acaactgcagcaaagtggggcccaacttatatgacag
ttcgtggcaatgccggattcctaacccactgagcagg
gccagggatcgaacctgagtttccagtcagtttcgtt
aaccactgagccatgatagtaactcctgtttgttcag
tcttgaacctccttttaattctttattccttgaggg
tgaaataattgccataataatactatcatttattaca
tgccttctctgtgctaggcatagtgacactttaggat
ttattatacacttaatccctacaacaactctgcaaag
tatgtatcataatcctatttgacagatcaggaaattg
cagcccaggatgcagataatatgcatccatcacaagt
gactagatatagtccctctgctattcagcagggtctc
attgcctttccattccaaatgcaatagtttgcatcta
ttgtatatgtgttttggggtttttttgtctttttttt
tttttttgtcttttctggggcctcacccttggcatag
gtaggttcccaggctaggggtcaaattgaagctgcag
ctgccagcctacaccacagccacagcaactcgggatc
tgagcctcatctgcaacctacaccaaagctcacggca
acaccggatccttaacccactgagtgaggccagagat
caaaccggcaacctcatggttcctagtcggattcatt
aaccactgagccacgatgggaactccctaaatgcaat
agtttgctctattaaccccaaactcccagtccatccc
actccctcctcctccctcttggcaaccacaagtctgt
tctccatgtccatgatttctttctgggggaaagtt
tcatttgtgccatttttcattttacgggtaattttta
cttcagtttcttccactagcagttgtcttaaagtgag
tataattaatattcatttggaaaatgtaagcaaaaca
ttttttaaagggccatgcccacagcatatgaaagttt
ctgggccaggggttgaatccaggctccaagttgcagc
tgtgccctacactgcagctgggcaatgctggatcctt
taacccactgtgcccggctagggatcaaacctgcatt
tccacagctacccgagccattgcagttggattcttaa
cccactgcactacagtgggaactcccacaaaacattt TABLE 12-continued Contiguous 3'Genomic Sequence of the Porcine
CMP-Neu5Ac Hydroxylase Gene tttaatgtcctttgaataaagtaggaaagtgctcgtc
tttgagggcagggcggcaatgccatttccacaaggtt
tgctttggcttgggacctcatctgctgtcatttagta
atgaataaaattgctgacagtaataggattaactgtg
tgtggagatagccagggttagagataaaaacactgga
gaagtcaaataagttgctcgaggtcctctagctaata
agctattaagtgggagagtgagggctagaaacaggcc
atctgtctcccaagcacatgtccattagtggtttgct
gatagccttccagaacaacagagaggactctcaaaca
tggtcttgcctccctccaattgatccctccatgtgc
ctcacagcgggtctttctaaaattaagttctgatttt
aattctcccttgctatagcacttaggtatggctttca
gccgtgcaataaaaagcaggcaagagtggctcaatca
tataggaggttgttttcttagatcccaagcaggtaa
tcctgggcattatggttgttctgcgtttatcaaggag
ccaaattctctatcacctcctgttctatcctcctcag
tatctggctctattcttcagcatctcaagatggcttg
tgctcctccaagcatggcagtcaaattccacacaaga
gggggaaaatatgaagggcagacagtgctggtctcct
gagctgtccctctttgtcggggaaataaatgattcct
tcaagtcccgtgagacttctgaagtagacgtctgctt
acgtctcacccaccagaactatgtaaactgcacatag
tgctaggtctacatagccatcataactgccaggggt
gggaaatctttaaataggtgtaccaccacacaattag
gatgctaatagtaagggagaaggagagaataggtttt
gcgcaagccaccagcatgcctgccacaattgcttaaa
attcttcattgaccctcattgccacaggatgaaatc
caaacgccttcttagttgggaatctgacctacctgtc
tctcccacctggttcagacaccattctccttggtcat
aaaattccagtcatttgtgaacatccagctcccccat
gcctccatgcctttgcacatgctgttcttttatctttt
tatgttgtccttttatctttatccaaaagagatatc
ccatcatcacatctcttttgtcagcccccaaatactt
tgtctttcaagttcagctggaggattacctcctatttt
gaaatcagctttgtctcttacaaccaaaacaaggttt
tccttccgagacactcccacagcaccttgaactcatc
tctatcaatcattcatttgattgtaatgaagttgttg
gtggtatgcctgtgtctcgacacatctgcgatctcat TABLE 12-continued Contiguous 3'Genomic Sequence of the Porcine CMP-Neu5Ac Hydroxylase Gene gagttccttaagtggaatgtgaatagcgggatgaaca
gtattggtcttcagccctcatctctgcagatgttgct
tgacccaaatgagcgttgccttttattttgattttgc
tttgatttgtctactccatgtacttgagccatgcatt
tctgtcttagcgatgcttttttaaaagtcattttttgg
ttgattatccagatttgtccacctttgcttctagTTG
TAGAAAAGGATGAAGAAAATGGAGTTTTGCTTCTAGA
ACTAAATCCTCCTAACCCGTGGGATTCAGAACCCAGA
TCTCCTGAAGATTTGGCATTTGGGGAAGTGCAGgtaa
ggaaatgttaaattgcaatattcttaaaaacacaaat
aaagctaacatatcaatttatatatatatatatatat
atatttttttttttttttacatcttatattaccttg
agtattcttggaagtggctagttaggacatataataa
agttattctgaagtcttttttttttctttttccatggt
gagcagtggcttgatgtggatctcagctcccagacga
ggcactgaacctgagccgcagtggtgaaagcaccaag
ttctagccactagaccaccagggaactccctattcta
aattcttgagcacattatttaggaaccctcaggaactt
ggcaggattacaggaaatatatctagatttaaaaaaa
aatcttttaacagaggtcccaaaggagagtcatgcac
agctatgggaggaagttcagaaactgcccttgctacc
agatcactgtcagataaaatggccagctacatgtttc
tgcacattgccctaagatcttacaaacttttctgtg
cattttccacttttaaaagaaaatttcggggttcct
gttgttgctcagtggttaacgaacccaactagtatcc
atggggacaggggttcgagccctggctcactcagtgg
gttaagaatctggcattgctgtggctgtggcgtaggc
tggcggctacagctcagattggacccctagcctgaga
acctccatgccgcaggtatggcctaaaaaaaaaaa
aaaagagagagagaatttcctccagaaaaaacact
ttggtagtttgggagaagtaaacaaccaaaaattaat
ttttctggagtattcgggaagcttgtaaaaatgggct
cttactttttgaggagacaaatgggaacctacccag
aagaggcacaatcacctgcatttgatttcttgacctc
tccctaccttctttgctggctttccacatttggattt
ctgtgaccttatctctgctccttggtgttttcatttt
tcctgtggacgtgccagactatgggaagggagtaagg
cgttgatttagaatcctgtagtctctgcctgtctcta
gtcattgttttcacccttctcaaaggaccttgacatc
ctgagtgagtccgcaagtaatttagggagagaagcctt
agaagccagtgcagccaggctacatgactgtgtccac
ccactggaaccagtcatttttatacctattcagcccc
cctaccatttaaatccccagaggtctgccataacatc
tgtaactcccctttcctggtaaattgtgttctaaaaga
ctggtaacaaaagatattctgtggtacagagcataat
taaatacctgggagctgatttgagtggggtaaatcaa
ctggtttgaccctaaaacccaccatgagcatttctg
ttctaataaagtaatgcccgtgctgggaattgtgttc
tacggaaatgctcctgctgtgtctttcttgagtcctg
tgtcattgaacatgcttaggagcaaaggtcccccatg
tggcttgtctgctaaccagcccagttccttgttctgg
ctggtaatgatccgatcatctgaatctcactgtcttc
caacagATCACGTACCTTACTCACGCCTGCATGGACC
TCAAGCTGGGGGACAAGAGAATGGTGTTCGACCCTTG
GTTAATCGGTCCTGCTTTTGCGCGAGGATGGTGGTTA
CTACACGAGCCTCCATCTGATTGGCTGGAGAGGCTGA
GCCGCGCAGACTTAATTTACATCAGTCACATGCACTC
AGACCACCTGAGgtaaggaagggtgagccctcaatcc
gaagaaaatgctgcaataaaagcactgttggttttca
gcttttttttgtaatcactgctcattctgaggtagatt
cgcttgggctgataaaaagagaactattcagataaat
gcttgcatttgcatagcctctttttttaaaaacttttt
ttttttttttttttttttggcttttcagggctgaac
ctgtggcatatggaggttcccaggctaggggtcgaat
cagagctgtagccccgggcctatgccactgccatagc
aacatgcatagcctccttttaaagtgccttcctgtt
ttataccattgggatgtgagaagagctattgtggaaa
ngaagcatggtnataaccctggacctctcacgtccta
ccctcaggntagtgggaaaactctgagtttaaggaca
tcaaagtgactccttttagttacattatggnggaat
cagcncatattttacaaggggcggagngtaanctgt
tggagtttacaagacatatggtggcattgcaactact
taacctactattatagcacaaaagcagccatagtcg
gtcctgaaggagcctgatgccttcagctttataggca
atgacgtgtgaatatcacaaacagttgcctgtgtcac
caaacatgattgccttttgatttcccttttcaacccctt

TABLE 12-continued

Contiguous 3'Genomic Sequence of the Porcine CMP-Neu5Ac Hydroxylase Gene

```
taaaaaaaggtaaaagcccttcttagcattcagcagc
aggtcgctgtgttttgccaactcctgatctgtagcat
ttcgacaacactgagctctcaacttttgaaccctgag
tccaccacatccttcagtgaaaccagagccatgtgat
actaaggatagaacggaaacttcctgaatccaggcga
tcaaataggagggagaaagaggaactttcattgacaa
aaccacaaatattgtgaatggactgttacaaatattg
tgaatgctcctattcccaaccccctggcttcattaca
gggtcctatgtgttcatccttattgagaaatttgtat
tgctactgccaggttgccaatacccagcggtgcccat
ggtgttctaaaatgaagcaatttcaactttattttt
tttcctgtgactttacatgacaagttcacatgaagga
tatactttgatagtaatgtccatggttagggaatata
cattgtttgctggttgactggcccctggattttcta
ttgaaagtccatgagatctcgaaggcacaggtgtgtt
ctctcgcttttaaggaaagggtttaaaaacttaagt
aattaacagctttagtaacaaattacctataacacac
ttaaaaaccgaataccacccactggagtattgtgcta
cgattaaaaatctacttgtctactacatgatatcttt
gtcccacagaaggttctggaaccaaacttgtaatttc
aggattatgagagccctgagttcacgcattgtgtaat
aactatgttgtgtggtagtcaatttgtacagcttgct
tagagagaacaatgtcaagttaaggaggcgattgctt
tatagtgcctgtcacaagatgccattgccattgtcct
agcaagagatattctatgggagtatactacattttag
tgaggataagaacttttatggcatttagtccggtca
tttcccaaccactgtcctgaaaaccaatttcattttg
atttcaggggcttgtgtgggcaaagttgccaggcatt
aaaaagccacttctcaactgtagtatcacaatgcttt
agttgggtagtgtattgcagatagcttatggctgaaa
agttaccaagccttgcagttttcactcctttgagttt
atttccttgacagaattgaccctgagttttttgactc
ttacctgctcaactaataaacacagagtcatttatct
ccattgctcttgtctgacctttatttaccgaataatg
ccttatgggttcacaaaacaagggggagggggccagc
atgccttagaactgtctttagtcaagaaatgngattt
tattatgtaaatatgagtattataatagatagtgt
tattaatagacaccagcaagaattgtcaataatttaa
aaatcacaaattaaaatacatccatgttagnatcatt
tatcctaactcccaaagcccttaaagtggaaagatt
tagatgttaacccagagattaaagacatgttcaaaga
atccttgatttttttttgaatcccttgttttagaga
agaaaacctaatgattttcccctctggattctacat
attaaatatagttttggaacttgaatattagtatggt
taataagtgctgatatgctgattttgtttatatttt
cttatgagtaaatatcctatatcaccagacattatag
tctatgtacaaatatgattcttaaacctgatagcaca
ttcattagagttggaattgccttttttttttttttt
ttacagttgcacctgcaacatatgaaagttcccaggc
taggggttgaatccaagctgcagctgccaccctacat
tacagccgtagtaacagcagatccgagctgcatctgc
aacctatgctgcagctcagggcaatgccagatccact
gagtgaagccagggatggaacttgcatcctcatagag
acaacgtcgtgtccttaacccactgagccagaacagg
aactccagaatttctttcaatagaagaagcaccaagt
ttaggatcagaaagcctgaatttgaataccaatttac
tatttgttagtcatatatttctgagtgtgtttcctca
tttattaaaagcagactaaaagatgagagggtcttt
gttgagaatcaaatacaataacatgtgaaagtgtgta
acactatgattgaaatatacctacacagccatttatt
tgtttattgttcatgttttgccacccacacagtagta
tataatcctttatgtaataaatgctaataatgaaag
ttggcaacttatgtaagtactcaaaatgctggaggtc
atgggatactgactgggatactacagaggtaatgtca
tttcctctgcgctaaacttattgtcttgtagttaggg
actgactctctttaggacaaggagttcattctgtata
ccatgtgtggctatcacccttcgaagttgaaaaactg
ccccagggtgggcacccatccgttctcttagatatat
ggccgagacctttctctcactgggagggaaccacact
gaggaatgagaaaaaaaaggaaaatcaagatgaaa
ccagaaacctctttggcataacttctccactctgtac
tttttgttagaactacccttgcacaaagcagcatcag
tgtggaagacagaatttgcacacctggtttgatatac
atgccgtggtatatgggatgttctaacaataaagagg
gactctcccaggaaatctcctcactgttatagtcagc
cttgaggaaagagctcttcttttggactctggggaga
```

TABLE 12-continued

Contiguous 3'Genomic Sequence of the Porcine
CMP-Neu5Ac Hydroxylase Gene gtctagtttttcagttccttgcttctcggtcaacgtg
ttggtgtaaggatcacactctctcttatactagtaaa
ttctattttttcacctttcaacctgtctatccttctg
accctagTTACCCAACACTGAAGAAGCTTGCTGAAGA
GAAGACCAGATGTTCCCATTTATGTTGGCAACACGGA
AAGACCTGTATTTTGGAATCTGAATCAGAGTGGCGTC
CAGTTGACTAATATCAATGTAGTGCCATTTGGAATAT
GGCAGCAGgtctgtgttctttccacatgtttgggtta
tcctttctgggataaatttgaggcgagatagaaactt
taagactaaagaaacaatggcctactttttttgtaca
tggtcctgtgtaaatctctatttgagctgaaataaga
tggtcttcctctccaattatccatggtatgactctga
tggataacaaatccagttctgaaaaaagggggatttct
ttccagaagagaggacagtttcttcaaatattgaatt
aaaagcaaaatagatgtaaaccgttggttttattgtt
gaattccagGTAGACAAAAATCTTCGATTCATGATCT
TGATGGATGGCGTTCATCCTGAGATGGACACTTGCAT
TATTGTGGAATACAAAGgtatttcttgccctcatcag
catgaaattgctcttggtagaaaggataataatagtt
atccaaaacatcatcctatgttcatctgtttcttccc
tcttcattttccatagagtacagtatattctatctct
gtcttaggaaaatggactgtcattcatataatcttac
agagaatcaattagtaatgtactctatgccgtgacag
gtgcgaaggttttttttgaaggcaacagataaaaata
tcctatatttcacctattgtaatttccttaaaactga
cattattgaataaatgttttacttttcatcttgaatat
tattatgttatggaatcatacacttttaccccaataat
catcgaaaagaatttccaaaaggttgagagagttgtg
ttgatctgattacttttcctctgcatcctttgagctta
acctttgaatatagtttgctaaggaaagtagtctgtt
tatgatcctggagtggaatcaggctaagtgtcctcat
tcagaacccactgaatcagacagaatgaatttatttc
cttgaaagttcaaaatgtgtcactcaagagtataaat
tttcaaatcttactctctcttttccttggatgtgagc
aattcttcgataattgaatgaggcagattatatagac
ttacatggaagactgttggcctgagaattcaaactat
ggtgttcaagacttcacngngagtccgatgccatttg
tttcccacagGTCATAAAATACTCAATACAGTGGATT TABLE 12-continued Contiguous 3'Genomic Sequence of the Porcine
CMP-Neu5Ac Hydroxylase Gene GCACCAGACCCAATGGAGGAAGGCTGCCTATGAAGGT
TGCATTAATGATGAGTGATTTTGCTGGAGGAGCTTCA
GGCTTTCCAATGACTTTCAGTGGTGGAAAATTTACTG
gtaattctttatatcaaaatgatgccaaggagttggc
atggcactttgctaaatgctgtgtgaatcaatacaaa
gataattaggacatggttcttcctcacaagaggtgtg
caatcttattgggaaatcatacttgcaagtcacaaat
atagactaaagtttccagctgagaatatgctgatgga
gcatgaaacactaaggagacagggagaatctcaggaa
aaatcaagaataatttggatcaaatggattcctgaca
tagaacatagagctgatcagaaagagtctgacattgg
taatccaggcttaagtgctctttgtatgtggttcaga
acagagtgtgggcagcctgaggggggatacataccctt
gacctcgtggaaagctcatacggggagggatgaggc
taaggaagcccctctaaagtgtgggattacgagaggt
tgggggggtggtagggaaaatagtggtcaaagagtat
aaacttccagttacaagatgaataaattctagggta
taataacagcatggcactatagatagcatattgtact
atatactggaagtgctgagagtagatcttacatgttc
taaccacacacacacacacacacacacaccaca
cacacacaccacacacacacacgtgcacacaaacaga
aatggtaattatgtgaggtgatggcggtgttaactaa
ctttattgtggtcatcatttagccatacatgcatgtc
atgaaatcaccatgttgtacaccttaaagttatgtaa
tactagatgtcagttatatctcaaagctagaaaaat
gtggggaccaaggcagaagctcttctgctctgtgtct
aagggtggttctggggctgggatggggaggatggtta
agtggtatattttttcatacctttgctcagtactat
cattgtaagtgttcaatatatgtctgcttaataaatt
aatgttttagtaagtaatctctgtttagtaatgtgt
cagaaatgccctacttgcaataggaagaaaacctgtc
cagtcccttccttttttctgtaagtctgatttcattg
cctcccagaatgcatcaccatgtgagagatagaggga
aggtgctgtccttatggggttaacagtgtgactaggg
aggcaaaatatacctactaaagggtggtagcataatt
cagttcttatgtgagtatgtgtatgtgtgtgagtatg
tgcacatgcacatacatttttaaaaggtctgtaatata
ctaacatgttcatagtggttacacctagcttataggt TABLE 12-continued Contiguous 3'Genomic Sequence of the Porcine
CMP-Neu5Ac Hydroxylase Gene aacattttttcccctgtatccttgtttgtgtttatca
aattttcataacagtaatggtagaaggagtacctgac
atggtaccatacatgctnggncctgcctaatttctcn
atttcctttattgcccataccccattgcttgacaag
cataagtccatactggcttgttttcgttcctcagact
cagtacaccatgtagctccatgccctgggtctttgta
tgtgctatttctactgcttagagtgctattgcccctg
accaccacgtggtcagcaacttctcttctgcgtctgt
gtctatggtctatgattccagatgtcatcttcactaa
ctaccottctaatatgcccttccatcccaccсgtcct
catccttaccccagccactctctatttggtggctctg
ttttattttcttcctagctcatcactctttgaaatga
acttatttacttattcaatttgcttctttcactagaa
tgaatgctccatgagagcagggacctgctttatcttg
ctcgccactgtattcacagtgcctagaactacgtctg
gcacatagtaggtgctcaataaatatcgatcaaatga
aagaatgagcaaacgaacaaatgaacaacacgtgagg
taggcatcatgattccatcaacagaggagaaaaccag
acttaaagnaatgaagtggnggagctgcatttgatct
tgactgactccaacatccatgctcttgaccactgtgc
atctccagagtgtaatgaacatactttacttttatat
tccaccaaaataacaaagccatgcccatgttagtaga
gagttaatcgacagtgcccttaaaatatgcatgcacc
cagggtacaactatgcatgctgccctgtgttttcagt
tggatccaaatgaattgccgtaaacaaagagggggatt
caatgtctttgactagtttgggatattttcctagtaa
ccaactttgcaaaataaagccactaatgacaaggagc
tttgttctacttctgcatcactcaactgtcaattttt
atctcttgcaagacttctaatctactagaactttttgt
ttttctgtgatttctgaacagagaagactaatccaaa
ccctgtcattccagAGGAATGGAAAGCCCAATTCATT
AAAACAGAAAGGAAGAAACTCCTGAACTACAAGGCTC
GGCTGGTGAAGGACCTACAACCCAGAATTTACTGCCC
CTTTCCTGGGTATTTCGTGGAATCCCACCCAGCAGAC
AAgtatggctggatattttatataacgtgtttacgca
taagttaatatatgctgaatgagtgatttagctgtga
aacaacatgaaatgagaaagaatgattagtaggggtc
tggagcttattttaacaagcagcctgaaaacagagag TABLE 12-continued Contiguous 3'Genomic Sequence of the Porcine
CMP-Neu5Ac Hydroxylase Gene tatgaataaaaaaaattaaatacaagagtgtgctatt
accaattatgtataatagtcttgtacatctaacttca
attccaatcactatatgcttatactaaaaaacgaagt
atagagtcaaccttctttgactaacagctcttcccta
gtcagggacattagctcaagtatagtctttatttttc
ctggggtaagaaaagaaggattgggaagtaggaatgc
aaagaaataaaaaataattctgtcattgttcaaataa
gaatgtcatctgaaaataaactgccttacatgggaat
gctcttatttgtcagGTATATTAAGGAAACAAACATC
AAAAATGACCCAAATGAACTCAACAATCTTATCAAGA
AGAATTCTGAGGTGGTAACCTGGACCCCAAGACCTGG
AGCCACTCTTGATCTGGGTAGGATGCTAAAGGACCCA
ACAGACAGgtttgacttgaatatttacagggaacaaa
aatgatttctgaatttttcatgtttatgagaaaata
aagggcatacctatggcctcttggcaggtccctgttt
gtaggaatattaagttttttcttgactagcatcctgag
cttgtcatgcattaagatctacacaccacccttaaa
gtgggagtcttactgtataaaataaactattaaataa
gtatctttcaactctggggtgggggggagactgagt
tttttcacagtcctatataataattttcttatcctat
aaaataggagttcccgtagtggctcagcaatagcaaa
cccgactagtatcgatgaggatgcgggttcgattcct
ggccccctcagtgggttaaggatctggcattgccgt
gagctgtggtgtaggtggcagacacggctcagatccc
acgttactgtggctgtggcataggccagcagctccag
ctctgattagacccttagcctgggaacttccatatgc
tgtgggtgtggccttgaaaaaaataaataaataaga
taattactcaaatgttttccttgtctcagaaccttac
ttcaggataaagagtgagaaagttttttttatgaagg
gccattattacagctcaaaaataagttgtcttcagca
agtagaaagcaataagcctgagagttagtgttcctat
cagtgtaaatattacctcctcgccaatccccagacag
tccatttgaacaattaacggtgccctgggagtacagt
tcagaaacattaatgtggatgttccagacctgtattt
ttataagtacttgtcttgagccggatggaaccatcat
tcctcaccattatttagaagtggactgtgactctgtt
ggagatcagggcacacggttaccaaaagcacacccctt
ctcctggccttacctttgcaaagctggggtctgggac TABLE 12-continued Contiguous 3'Genomic Sequence of the Porcine
CMP-Neu5Ac Hydroxylase Gene acagtcagctgattataccttttactaacttcccac
agctcaaatctggtcaattctccttcacaaatctctt
aaaaatccatcactcacctccagcctcttctgctgtg
gccttgattcagcctctcacaattttttttttaaccag
aattctggcagtggcccctgacttgcctctgtgctcc
cagccccgctgtcctctgatccatcctccatgccagc
cttttttcaatctgctggtcacgattcattgatgggtt
aggaaatcaatggcatcacaactagcatttagaaaaa
ggaaataggcgttcccgccgtggcacagcagaaataa
atccgactaggaaccataaggttgcgggttcaacccc
tggccttgttcagtgggttaaggatccggcattgccg
tgggctgttttgtaagtcacagacatggctctgatcc
ggcattgctgtggctctggcgtaggcctgcagcatca
gctccaattagaccccctatcctgggagcctccatatg
ctgcaagtgcagccctaaaaaaaataaaaaaataaaa
aaaaataaataaaagaagtagacaaattgtatagaac
aaccctgagtatgttgcctgagcacatataacaaggg
taagtattatttcaggaaactctggtttcacagatac
tcttggcatatggaccccctagagtcctgatgtaaaat
atattcttcctgggatcttaggcaagaagtttgaaag
ctccaactctgcactgctgccaaagaaatgattttta
agtgcaaaactcttcccgttcccttccctgtataaaa
ttccataggatctctccagtgcctctaggataaaggc
agttttcattctctagttcaaggtgagagaagatttt
aattatttcacgttttagtggggaattcaagagtctg
gcacctgacatttgctgaactctctccattatccctc
tctagttccccagacgcatcctatggtagaaattcgc
aaactagagtgagcgtcagagtaacccaaggaaactg
ggtaaatgcagctccctgggctctacccctgagatt
ctgattcagtagatctgaagcagagccctggaatatg
catatgcatcattgtgtcacaccaagcattctgggta
atgagagttgatgttaggttctcagtagtaagacaag
tatagagattccggggactgagtgctcagctctgcc
ttggggaggagggagagggctaaagagaacaggagat
ggggacaggggaatgctcaacctccaatcttaggcatt
tgagctatgtcttaggggtcaggaggaggttaccaat
atagtgattaagagattgaggttccagtcagagggat
atgctggagaagggggggtgaaaataatgtcataggtt TABLE 12-continued Contiguous 3'Genomic Sequence of the Porcine
CMP-Neu5Ac Hydroxylase Gene tggtgagtgcagatactttgagtttttttaatatttt
attgaaatatagttgatttacaatgctcttagtgagt
acaattacttgaataagtgcatagatgtatgccatt
cttccagaaatgatttattgagctcctttgggcatca
tgctaagtacaggggaaacagctgtgaagaggtcctt
cccttatgaagtcattcatccccttcagtaaatgaag
gtaaaggaaaggatgagacagggacgccgtgttgga
ccagggtcagaaaggccttataagaccttgcctggag
ggcaaggaacttgcctgtgagtaaggagagcttgaga
aagcgataaagcaaagaaggaacattactgcattgtg
ttttagaaaaaccatgtcctggggaagaactcctaga
gtcagggggccagttgggagactgtgctttttttcca
ggaggagataagtgaggctgctggctgagatggagca
aggatttagagaagcagatatgagattcatttagaag
ttagacattttaggatctgacacataatttatcacca
aaaccagtgcatctctggctttgggccaccagttttg
gagaagtggaatgtagggacctaccattacctgccaa
tcttactacacagatgcctatttccctcctcatatt
tcctttctccagatcacgtcctattctattgccagga
ctcaagattccaccttgcatgcagtgatccatcttca
cactggatggacagctctagggatgtcagagcacact
cttgtccatactgctgactgggtctcctgtcagccca
tctgtctatcagctgtggtattattagtataataaga
gggctgtatatgagagacacaaaattctaggtgtagc
tcaaagataggctagagttattcctatgtacaacaaa
tatttatgggaccccttctgtgtactgtcatggttgc
tgctttcatcatacttgtagtctaatggaggtggggg
cagggcaggaataagcggatgtccacaaaatcagtaa
gaccacttatattcaacattttcataatttagttatt
tgagcccaaagggtccacatccgtggtattccaactt
ttttttccccggacatggatctttatcttttttttt
tttcttttttgcggccagacctgcggcatatggaagt
tcccaggccaggggttgaatgggagttgcagctgcct
ggtctacaccacagccacagcaaggtgggatctgagc
tgcatctgtgacataccacgcagctgaggtaacacca
gattctgaacccactgaatgaggccagggatggaacc
cgtctccttatgaacactatgtcatgttcttcaccct
ctgagccacaacgggaactccagacttcgtctttaaa TABLE 12-continued Contiguous 3'Genomic Sequence of the Porcine CMP-Neu5Ac Hydroxylase Gene tgtattctgacttggagagctatcacactaagcaatt
aacaggagctgacctggtttaggctggggtggggccc
tactcctcaatgttccctgaggcacatctgtgggacc
cctgggcatcatctatctgagcagccttagagctgct
catccagttgactgttgatgtagaagtgcaaacttct
gccttccttatttgttgctttcttttttcattgttct
ctcccctttgtgtctttaagCAAGGGCATCGTAGAGC
CTCCAGAAGGGACTAAGATTTACAAGGATTCCTGGGA
TTTTGGCCCATATTTGAATATCTTGAATGCTGCTATA
GGAGATGAAATATTCGTCACTCATCCTGGATAAAAG
AATACTTCACTTGGGCTGGATTTAAGGATTATAACCT
GGTGGTCAGGgtatgctatgaagttattatttgtttt
tgttttcttgtattacagagctatatgaaaacctctt
agtattccagttggtttctcaataagcattcattgag
ccttactgactgtcagacggagggcgtattggactat
gtgctgaaacaatcctttgttgaaaatgtagggaatg
ttgaaaatgtagggaatgaaatgtagatccagctctg
tttctcttttggaggattctttttcctccatcaccgt
gtcttggttcttgtttgttttgggtttttgtgggtgt
tgtattgtgttgtgttggtatggcagtgacagctat
ttaaactgtgaaacggggagttcccgtcgtggcgca
gtggttaacgaatccgactgggaaccatgaggttgcg
ggttcggtccctgcccttgctcagtgggttaacgatc
cggcgttgccgtgagctgtggtgtaggttgcagacac
ggctcggatcccgcgttgctgtggctctagcgtaggc
cagcggctacagctccgattggaccccctagcctggga
acctccatatgccgcaggagcggcccaaagaaatagc
aaaaagacaaaatataatataataatataataaagtaagt
aaaataaactgtgaaacggggagttcccttcatggct
cagcagttaacaaacccagctaggatccatgaggatg
taggttcgatccctggccttgctcagtgggttaagaa
tccagcgttgctgtgagctgtgatgtaggtcgcagat
gcagcccagatcctgcattgctgtggctgtggcgtag
gctggcagctgaagctccgattcaaccctagcctgg
gaacatccatatgctgcaggtgtggccttaagaggca
aaaaataaaaaataaaaataaataaattgtggga
cagacaggtggctccactgcagagctggtgtcctgta
gcagcctggaagcaggtaaggtaaggactgcagctgg TABLE 12-continued Contiguous 3'Genomic Sequence of the Porcine CMP-Neu5Ac Hydroxylase Gene gtaaggactgaattgcaccaactgggaagtaagccta
gatctagaacttaagttagccctgacatagacacaca
gagctcaccagctaagtggttcagcttataagctggt
cactgaaactgaggatgtccacaaaagcaaaataagt
agcaacaggcagcgggatgcaagagaaagaggaggcc
taaaatggtctgggaatccctgccatacctatatttt
atcctacttatatttagtgcctgaatgtgtgcctgga
gagcaaagtttagggaaagcatcgggaaatgcacagt
attcataccttaggaacaaagatcagttacctccag
ggtaaagactatttccaagtttaaatttcaacccctg
aacattagtactgggtaccaggcaacacttgccatcc
tcaaaatcaatgaatcctaaaattcaacctgggggtc
agtgacagtctgtgacaaagttttgctggtcagtaa
cgaaataagtatgagcaccatctgagtatggtcacca
agatgtcaactctctttcctttggacgaattgtcatt
attccaagattaggtcctttctatttttgaggtgtga
aaacatctttcctttcataaaataaaaggatagtagg
tggaagaattttttttgtttttggtcttttgctat
ttctttgggccgcttctgcagcatatggaggttccca
ggccaggggtcgaatcggagctttagccaccggccca
cgccagagccacagcaacacgggatccaagccgcatc
tgcagcctacaccacagctcacggcaatgccggatcg
ttaacccactgagcaagggcagggaccgaacccgcaa
cctcatggttcctagtcggattcgttaaccactgcgc
cacgacgggaactcctaatgatactcttttatattta
gctactatgtgatgatgagaaacagtccacattttat
tattttttagccaatttgatatctcattactaagata
atgataattttctctataaattttatttaagttagtg
ttatgaagtggttttgctagtgtagaaggctaggatt
tgaattcagttcaagaagaagagagggagggaggga
gagggatgggtagagggatggggcagtgggagagagc
aaagaggagagacagttttttgtattaattctgcttca
ttgctatcatttaagggcacttgggtcttgcacattc
tagaattttctaaggaccttgaccgccagattgatat
gcttcttcccttaccatgttgtcatttgaacagATG
ATTGAGACAGATGAGGACTTCAGCCCTTTGCCTGGAG
GATATGACTATTTGGTTGACTTTCTGGATTTATCCTT
TCCAAAAGAAAGACCAAGCCGGGAACATCCATATGAG

TABLE 12-continued

Contiguous 3'Genomic Sequence of the Porcine CMP-Neu5Ac Hydroxylase Gene

```
GAAgtaagcaggaataccagtggaagtgccccttct
tccttccttcctaaataaactttttttattttggaaca
actttagagttacagaaaagttgcaaagatattatag
acagtagtgtttatatatatatataaattttttttttg
cttttttatgaccacacctgtggcatatggaggttccc
agtctaggggttgaattggagctacagctgccagtct
gtgccataaccacagcaatgcaggatctgggccacgt
ctgtgacctacaccaaagctcacagctggattcttaa
cccactgagcaaggccagggattgaacctgcatcctc
gtggttcctagttggattcgtttccgctttgccgcaa
tgggaactccaaattattgttaatatcttactttact
ggggtacatttgttacaaccaatactctgatactgaa
acattactgttaactccgtacttgcttcttttttgagt
catttgcaaagactggcttcttgacctgcttccttcc
aaacagctggcctgcctatgctgttctcagacctgca
agcactgatctctgccccccttgccttctctccagtg
gtgtctccttccccaaacaaacccagtgtggctctgg
aaagggagttaagtcaacataaaccaacacatatttt
gttgagctccaattttgagcaaatccctcacctacgg
cagacaggcatgatgttaagaactagggctttggaca
caaggtcaagaccaagaagggttcctcacccctactg
attcagataaccaataatgaggctttgaatccctgtc
caaaggttgtttttttttcccttctattgagcttcttg
ccaccttatcagttttttttatgacagtcaaatgaca
tgatatatgtgagcatacatggtaattttttaattcta
tataaatgaatcactaaataaattaggaggatatata
gtccacctttaagcgtattacacgtgtcacatgaatg
tgtggcgacttaattgtagaggtttaaatgtagcttc
ctataatagatgtgttcctaaactacattttaatcat
tggacttgtattttatgttagcacttgctgttgaag
aaaagcctatgccaaaagttcagtgaaaccaataatc
cactgccagctttctgagttaaaaaaaatccctgggt
tttcacacacaggaacaccctggaaacactcatttag
agcaaaatgcatctgataaggagttcctgttgtgcct
caactggttaaggacctgacattctccatgagaatgt
gagtttgatccccggccccactcgatgggttaaggat
ctggtgttgccacaaactgcagctccgattcatctcc
tagcctagaaacttccacagcccagaatatgccacag
aattcggctgtttaaaaaaaaaagaaaaaaaaaga
atcataaatgtgttggtttgttcaccaaatacatgat
aacttgctcttgccaagctcagcttcataaatattaa
gtcatttaatacagcagccaccttatgaacagatatt
actatacttcccatttacagataaggaaaatgccata
tttaaccaagagattaaataactttcccgaggtctta
tagcaagtaaatcatggtgcaggggtttgaccacacg
cagtctatctccagagtctgtgtatttagccactgtt
ttactttcaaatttaaatttataaaacttctaaatta
tctgttaaccataatctttggaattttaaaaccacg
agttcctataaaatgtttcattgaaagtaagtcactt
ttccatagcttttgataatacatctgtaggataaagt
aagccacagctctcttgcagacttggtacaccctggg
gcaaagcatcatgcctgtcacgtacatggtggtcctt
actttgactctcagtgcttttattgcccaggaatttt
gtgagatttctagttgttgaggtttgtttaaagaggt
tatgccggtacttggaagagctcttttcttgctacct
ggagccttctcatatttccttttttgaggagggacatg
aattgcctttcaaactcataaatatattttctagtac
acaagtctccatcttccttagacgcatggctcctgga
gttctccatcctcctgctccactttgggtgggctcct
ctctgggtctgccaccaatctgccacccagagacatc
cttgacccacttccagaccccaccatggcttcacttt
cttcgctttcctccttgtgggaacctctgcttaaga
atctgaggaagaaaatttgcacgtgagctaaactgga
ggtactttcctgcctggtcttgcacgatagcttggct
gagcccatgatgctgggtggctgttacttccatgga
cacccgaaggcgttgctcctttggcttctagttgcat
gcagtgttgcttatcccaggctgatctttcttccact
gtaggtgactttaagaattaagggattaatctatat
ctacaacaacaacaacaaagacctttcaagctgagg
tagggctttctgtatatgtttggagtggttatccagc
agacttacttgaaggcagggtcatatcctcaagtg
ctcataaacggaccacagaaagatctcataattgggt
ggagctgggtggggaccgtgtcatgtggccaggaaat
gccagatgggaagggagtggcccttactgagctccag
ctgaactctgaattttctagaaaactcagaaatctgg
attttttcatgtgtaataccagatttatagatgtgga
```

TABLE 12-continued

Contiguous 3'Genomic Sequence of the Porcine CMP-Neu5Ac Hydroxylase Gene aagctaattcttttttttttaagggactataggcaa
tgaactaagatctaggttgtatttggacaaggggtca
tcagtttaagctgtgtagttgagcgctcagctattgg
gctgagggaccctaaatactgagacggggaggtcct
tgctctggggcatcacaagtacactccctggtctcat
tcaaacacttttcctacaaaattgatcccatttcttc
agtgcactgtctgaatgcatttggcccagagccgtgc
tgaggcatagggaaggggtccacggtttcatggcatc
gttttgtgctgtgtgtccctgctgtcgtccaggatac
ctacctctcctcctcctgcatctgaatgtcccccac
agactctctgggattctacagcctctggcctgttcct
cagacacctcttacctgccagctttccagattcacat
tagttagccaaatctactgccgtcagtgactcacttc
atttcttcttctccgaggcagttcagcccggtacagt
tgttttgtcaacacttcagttgagtctggaagatgtg
catgggttatgcacgagagcggtccatcattttgagc
tagaagtcctttctcagcccagagacaagtcctcatc
tcctttacttcctgactcttcttcctctgcatccttc
caagatatctctttctccagccaccacctaaatctct
tcttttcccggggttccgtgctcaacccactcttctt
cttaaatctgtggctgggtgaacgcatctgctggcac
cacttctctgctaaagactccaaaaatccataggtcc
tgcccggcctttgcccacctctctccaacactgtcca
gctttagatgtgagctaatcccccagagatatcat
tccctggatgtctaagtcctttggtatctcactttca
gcggttcaaaatcctcttacaactgttctttctcctt
ttccatcttgattattggcaacatgccagcctttccc
ctaccccagcagtgagccaagctagaaacaagggct
taatcttcaatctttccttctccatccctaaacctaa
tgagtctccaagcccttcccagtttacaccctaaatg
ttgctcaaaacatccctagttcttccacgtgctctc
ctctatattgaaaggtcaagaaaggccatcttccctc
cactgtgaggaaatagatcttgatactgcccctgagc
tgggcagtcctcgacctgacaaactgtgcagtgtttc
taaatctctactggcaaaatgagagtgcctttgacct
gtgttgcgatctcagatcacagtggatgtaattgttt
tataggaatggtgaacgaaaaagaagtaaatccctaa
tgccaaactcctgatcattctatgtcatttaatagcc tgtcatttatgataaagtttcctctactggcattagc
acaatacttctcaggaaaaaaaaatatgatgccagat
actgaaaagctcctgggtaaacatgaacatgggtacc
gataaaatggtgaagccagtccaatcttagagtgact
tcccttcatgctacttcatgctctttttttttttttt
ttttaagaaaaaccccttttttttttctcacaccagt
cacagaggagaccgaggcttagcaaggttaaggtcac
atgattagtaagtgctgggctgaaactcaaaaccatc
tctgcttgtctcctaaccctgtgcacctctgactatt
caacagATCCTGTGTCAGGAGTTGGGATTCTTTGAAG
gtaagggccttgaccaccgaattaaggtaatcttgct
ctgtggcaggccttgttttcagtattttaagtacact
ggctcaggtaatcctcacaacagccccaggaggaatg
ttctattacctccactgtatagatgaggaacttgagg
cacagaatggttgccaaggtcacacagctatattggg
ggttcatacccagccatccaactctgtctgtactctc
tgccactctgcaccccagctcctgatccacttcctg
tttccatccctcgatttctgctgcactcaggggcccc
tctcccctcggcctgtgagatctgcttcagtaggct
tttctccctgactcctccatccctgtccttacaggca
gctgcttctctccgggacacgaggggtccatacggac
actctctactggctggggttgcgcctaactcgtgattc
ctcctctgtttcagATTCGGAGCCGGGTTGATGTCAT
CAGACACGTGGTAAAGAATGGTCTGCTCTGGGATGAC
TTGTACATAGGATTCCAAACCCGGCTTCAGCGGGATC
CTGATATACCATCATCTgtaagtccgaaaatgcct
gtcgtgtgtgccttaggctgctgcggaggaggccagg
gctatataagcagagtcagtgactgactgtgccctgc
agtgttgatggccatggagattccaccgttagagctt
ttttctttgttaaccttgaaggcaaatctggttagga
agataactttcaaagagtcaccatctggacattcatg
cccatgtgcttcaatcctgtatacaagcagtttagag
tacagggaaggaaggacattatgaaagggagaggt
gtgtttggatccagcagctccatcctcagaatttatc
tgaagacactgcaaaattactaagaatcactatgaca
agaatgaggatggggtgatatggcaaagttgtgatcc
tggaagaccttcatctcccatgttgcccaactctgaa
catgaatttggtgaactagttggttaaggggatgatc TABLE 12-continued Contiguous 3'Genomic Sequence of the Porcine
CMP-Neu5Ac Hydroxylase Gene ctccaagtttctccctggttgagctccaaaaaccatg taagtttctcatagcaaaaccgtataggtccttaggg ctttagttggaatatttgtgctgaaatgctggaaagc cccatttgccattttttgtatttgcaaaataatcatca agagggagaatgcattctttcatgaccactgaccct ctgaaaaggtcaggaatttagtctgaagtaggcaagc ctcctaccccgcttctgccatgagcttgcacgcacag gcctgtcttgacatttcttctttatagatttcttttt gaatatcttgaaattgctttaaaaatatttaaagaat gtagaattatataaaataaaaaggaaataaccccaca cctcccacaaaaccctgtttcctgcctttctccaccc actctccagggtaacacttggtaacagcatagttgta tcaccccaggcctattttttgagcatatcagcatttca agaaatgtattttttctcaataaaacatcccttatag ttgaggagggggaggttatcattcctgggttttgtttt ttttttttttttaatgtaatcctggtacatcggtaat ttgcatttttattcattaatatctttggtatttcta gtgttgggacacacaggtcaacctcagttttttgggtt ttttttttttgtcttttgtcttctagggccacacct gcagcatatggacgttcccaagctaggagtctaatca gagctgtagccaccagcctacgtcatagccatagcaa cgtcagatccaagccgtgtctgtgacctacaagcaca gctcatggcaacaccggatccttaaccactgaacgag gccaggggatcgaacacacatcctcatggatcctagt catgttcattaaccactgagtcatgatgggaactcca acttcaactatttaatgtctgtaaaacattccatttg gaaaccatttcatttgtaaagcaaaatgaaaacattt tgttcattttcaacagagttcgtagctgacttctgtt ctggaaaaaggaaatggagcaaatttgagtgagaaa gattcaaagataacttttctttttaaaaaaaattatat cttggaaacttctgggctattgattctgaagactatt tttctatatactgttttgatagcaaagttcataaatg tgaaaggatcctgcgatgaatcttgggaagcagtcat agcccaatatatctttgttgcttttaaaatgagatttt agtttactaaatattttctgatcataaaaataacac agatctaccgcagaaaatttggaaaaaaaaaactttt taaattcaaaaaacagttaaaccacaaatgatcccac catccagagagcaatttgtactttggtgtctagttca tcttttcttttttctgtttacaagcacatataccacaag cattttttcaaaaaatgaaaatgggataatactatac atacgtctgtacacctgcatagttactgaacagtctt tgatctaccctgtaagtttctaacttttcattatttg aaatgatgttttggcaaagaaatatgtaggtgtgtct cgcacactttcataatgatttcttaggataaatttct taggataaattcataatgatttcttataataatccat actctgccaactgatcttcagggaagccaactcgcct tctcagaaataacatataacccatttacttgccctct caccaatactaggtcctaatgttttgtgtacagatt ctatattttacatacaagaattccttaaagcaaggc atgtcacagaaaaatagaaggaagacacaattgtcat gtttaaggactgcattctgtaccaaaaatgctaagtt aaatgaacatctgaaacagtacagaaacgctatctt cagggaaagctgagtaccaggtactgaacagatttg gcaaatacagcaggcatggatgtttccaaaacatgtt tttctactttatctcttacagGTTTTGGAATCATTTT

CAAATAAAACTCCCCCTCACACCACCTGACTGGAAGT

CCTTCCTGATGTGCTCTGGGTAGAGAGGACCTGAGCT

GTCCCAGgtaaagcatcctgcaggtctgggagacact cttattctccagcccatcacactgtgtttggcatcag aattaagcaggcactatgcctatcagaaaacctgact tttggggaatgaaagaagctaacattacaagaatgt ctgtgtttaaaaataagtcaataagggagttcccatc gtggctcagtggtaacgaaccctactagtatccattg aggacacaggttcaatatctggcctcactcagtcggc taaggatccagtgatgccgtgagctgcagtgtaggcc acagacgtggctcagatctggtgctgctgtggctatg gtgtaggccggccccctgtaactccaattcgacccct aggctgggaacctaaaaagaccccaaaaaagtcgctt taatgaatagtgaatacatccagcccaaagtccacag actctttggtctggttgtggcaaacatacagccagtt aacaaacaagacaaaaattatcctaggtggtcagtgg gggttcagagctgaatcctgaacactggaaggaaaac agcaaccaaatccaaatactgtatggttttgcttata tgtagaatctaaattcaaagcaaatgagcaaaccaat tgaaacagttatggaagacaagcaggtggttgtcagg ggggagataaggggaggcaggaaagacctgggcgagg

TABLE 12-continued

Contiguous 3'Genomic Sequence of the Porcine
CMP-Neu5Ac Hydroxylase Gene gagattaagaggtaccaactttcagttgcaaaacaaa tgagtcaccagtatgaaatgtgcaatgtgggaaatac aggccataactttataatctcttttttttttttgtct tttttgccttttctaaggctgctcccgtggcatatgg aggttcccaggctaggagtccaaacagagctgtagct gccagcctacaccagagccacagcaacacgggaacct taacccgctgagcaaggccagggatcgaacccgagtc ctcacagatgccagtagggttcattaaccactgagcc acgacaggaattccagggtctgttgtgttcttaaaac acttccaggagagtgagtggtatgtcataagtaaaca ataaatgttaaccacaacaagcttatgaaataaacag gaaagccatatgacctacaatcagtcattgggagaat ccacaaaaggttgagcagaggatcaattccagctcac actccagttttagattctcccctgccttaaagcatca cagactacataatctgagctgaagaataaaaattaaa actcacccagtgcaaaacagaaatgaaaaagtatta aaacgaggttcatactgttgttcattagcaatatctt ttattcacagGGGTGCCCAACAACATGAAAAAATCAA

GAATTTATTGCTGCTACGTCAAAGCTTATACCAGAGA

TTATGCCTTATAGACATTAGCAATGGATAATTATATG

TTGCACTTGTGAAATGTGCACATATCCTGTTTATGAA

TCACCACATAGCCAGATTATCAATATTTTACTTATTT

CGTAAAAAATCCACAATTTTCCATAACAGAATCAACG

TGTGCAATAGGAACAAGATTGCTATGGAAAACGAGGG

TAACAGGAGGAGATATTAATCCAAGCATAGAAGAAAT

AGACAAATGAGGGGCCATAAGGGGAATATAGGG

TABLE 13

SEQ ID NO. 49

TCTAATGCCTTGTGGAAGCAAATGAGCCACAGAAGCT   SEQ ID NO 49
GAAGGAAAAACCACCATTCTTTCTTAATACCTGGAGA
GAGGCAACGACAGACTATGAGCAG gcaagtgagaggggctttagctgtcaggaaggcgg
agataaacccttgatgggtaggatggccattgaagg
aggggagaaatttgccccagcaggtagccaccaagct
tgggacttggagggagggcttcaaacgtattttca
taaaaaagacctgtggagctgtcaatgctcagggatt
ctctcttaaaatctaacagtattaatctgctaaaaca
tttgccttttcatag CATCGAACAAACGACGGAGATCCTGTTGTGCCTCTCA
CCTGCCGAAGCTGCCAATCTCAAGGAAGGAATCAATT
TTGTTCGAAATAAGAGCACTGGCAAGGATTACATCTT
ATTTAAGAATAAGAGCCGCCTGAAGGCATGTAAGAAC

TABLE 13-continued

SEQ ID NO. 49

ATGTGCAAGCACCAAGGAGGCCTCTTCATTAAAGACA
TTGAGGATCTAAATGGAAG gtactgagaatcctttgctttctccctggcgatcctt
tctcccaattaggtttggcaggaaatgtgctcattga
gaaattttaaatgatccaatcaacatgctatttcccc
cagcacatgcctaacttttcttaagctccttacgg
cagctctctgattttgatttatgaccttgacttaatt
tcccatcctctctgaagaactattgtttaaaatgtat
tcctagttgataaacagtgaaacttctaaggcacatg
tgtgtgtgtgtgtgtgtgtgtgtgtttaccagctt
ttatattcaaagactcaagcctcttttggatttcctt
tcctgctctctcagaagtgtgtgtgtgaggtgagtgc
ttgtccaaacactgccctagaacagagagacttttccc
tgatgaaaacccgaaaaatggcagagctctagctgca
cctggcctcaacagcggctcttctgatcatttcttgg
aagaacgagtgctggtaccccttttccccagccctt
gattaaacctgcatatcgcttgcctccccatctcagg
agcaattctaggagggagggtgggctttcttttcagg
attgacaaagctacccagcttgcaaaccaggggggatc
tgggggggggggtttgcacctgatgctccccactgat
aatgaatgagggattgaccccatctttcaagctttg
cttcagcctaacttgactctcgtagtgtttcagccgt
ttccatattaggcttgtcttccaccgtgtcgtgtcgt
caatcttatttctcaggtcatctgtgggcagtttagt
gcgaatggactcagaggtaactggtagctgtccaaga
gctccctgctctaactgtatagaagatcaccacccaa
gtctggaatcttcttacactggcccacagacttgcat
cactgcatacttagcttcagggcccagctcccaggtt
aagtgctgtcatacctgtagcttgcttggctctgcag
ataggggttgctagattaggcaaatagagggtgcccag
tcaaatttgcatttcagataaacaacgaatatattt
tagttagatatgtttcaggcactgcatgggacatact
tttggtaggcagcctactctggaagaacctcttggtt
gtttgctgacagactgcttttgagtccccttgcatctt
ctgggtggtttcaagttagggagacctcagccatagg
ttgttctgtcaccaagaagcttctgcaagcacgtgca
ggccttgaggtcttccgacttgtggcccggggactct
gcttttttctctgtccttttttctcccttagtgggccat
gtcctgtggtgttgtcttagccagttgtttagggag
tgttgcagctttatgattaagagcatggtctttcctt
gcaaactgcttggtttagaagcctggctccaccactt
agcggctctgtgacctcggacacatttcttagccttt
ctgggcctcgctcttcttcctcataaagtgaaaatga
aagtagacaaagccttctctgtctggctactgagagg
atggagtgatttcatacacataaagcacttaaaataa
tgtctggcatatgatacatgctcaataaatgtcactt
acatttgctattattattactctgccatgatcttgtg
tagcttaagaacgaggtcttacaggaattcaggct
gttcttgaatctgcttgctcagcttaatatggtaat
tgctttgccacagactggtcttcctctccttcaccca
aagccttaggggtgaacgatcccagtttcaacctat
tctgttggcaggctaacatggagatggcaccatctta
gctctgctgcaggtggggagccagattcacccagctt
tgctcccagatacagctccccaagcatttatatgctg
aaactccatcccaagagcagtctacatggtacactcc
cccatccatctctccaaatttggctgcttctacttag
gctctctgtgcagcaattcacctgaaatatctcttcc
acgatacagtcaagggcagtgacctacctgttccacc
ttccttcctcagccattttctcttctttgtacataat
caagatcaggaactctcataagctgtggtcctcattt
tgtcaatctaatttcacagcctcttggcacatgaagc
tgtcctctctctccttctgcctactgcccatgagca
gttgtgacactgccacatttctcctttaacgaccag
cctgctgaatagctgcatttggaatgttttcaatttt
tgttaattattttatttcatctttttttttttttttt
ttttttttttttttaggggccgcacccatgggatatg
gaggttcccaggctagggatccaatgggagctgtagc
tgctggcctacaccagccacagcaatgcacaattc
gagccaatctttgacctacaccagagctcacgcaac
actggattcttaacccactgattgaggccagggatca
aactctcgtcctcatagatacgagtcagattcgttaa
cctctgagccatgatagttgttagttactcattgatg
agaaaggaagtgtcacaaaatatcctccataagtcga
agtttgaatatgttttctgccttgttactagaaagaa
gcattaaaaattcttgattggaatgaagcttggaaaa
aatcagcatagtttactgatatataagtgaaaatagaa TABLE 13-continued

SEQ ID NO. 49 ccttgttagtttaaaccatctgatatttctggtggaa
gacatatttgtctgtaaaaaaaaaaaatcttgaacct
gtttaaaaaaaaaacttgactggaaacactaccaaaa
tatgggagttcctactgggacacagcagaaatgaatc
taactagtatccatgaggacacaggtttgatgcctgg
cctcgctaagtgggttaaggatatggtgttgctgcag
ctccaattcaacccctatcctgggaaccccatatgc
caccctaaaaagcaaaaagaaaggtgctgccctaaaa
agcaaaaagaaagaaagaaagacagccagacagacta
ccaaatatggagaggaaatggaactttaggccctat
ctccaactatcacatccctatcaccgtctggtaagaa
atggaaaaaatattactaagcctcctttgttgctaca
attaatctgattctcattctgaagcagtgttgccaga
gttaacaaataaaaatgcaaagctgggtagttaaatt
tgaattacagatcaaacaaattttcagtatatgttcaa
tatcgtgtaagacgttttaaaataattttttatttat
ctgaaatttatattttcctgtattttatctggcaac
catgatcagaaatctttaaacaatcaggaagtctttt
ttcttagacaaatgaaaatttgagttgatcttaggtt
tagtacactatactaggggccaagggttatagtgtga
ctattaaatcacagataatctttattactacattatt
tccttatactggccccacttggatcttaccagctta
gcttttgtatgagagtcatccttaaagatgacttttat
tctttaaaaaaaaaaacaaattttaagggctgcaccc
atagcatatagaagttcctaggctagcggtcaaatta
gagctgcagctgccagcctatgccacagccacagcaa
tgccagatctgagctgcatctgtgacctacactgcag
cttgcagcaatgctggatccttaacccattgaacaat
gccaggattgaacacacatcctcatggatactgctc
aggttcctaacctgctgagccacagttggaactccaa
agcagactttaattcttgatggctctgctgatctctaac
acgttatttttgtgccatggtgtttatcttcactttac
tcaagtcagggaaacacgaagagtctcatacaggata
aacccaaggagaaatgtgcaaagtcacatacaaatca
aactgacaaaaatcaaatacaaggaaaaaaatatcttc
actttcaaaatcacctactgatgatgagtttatattt
ccttggatatttgaatattagctattttttttccttc
atgagttttgtgttcaaccaactacagtcgtttactt
tgatcacagaataatgcatttaagcctaaatagatt
aatatttattttcaccattttcataaacctaagtacaa
tttccatccag GTCTGTTAAATGCACAAAACACAACTGGAAGTTAGAT
GTAAGCAGCATGAAGTATATCAATCCTCCTGGAAGCT
TCTGTCAAGACGAACTGG gtaaataccatcaatactgatcaatgttttctgctgt
tactgtcattggggtccctcttgtcaacttgtttcca
atctcattagaagccttggatgcattctgattttaaa
ctgaggtattttaaaagtaaccatcactgaaaattct
aggcaagttttctctaaaaaatcccttcattcattca
tttgttcagtaatatttgatgagaccttaccatgtg
taaacattgcactaggtattaagaaatacaaagatgg
ataagatagagtcggcgtaaatgagatgatataatga
gacgttataatgaaactcacaattccagttgggaaat
aaagtccttcaaattccatgactcttctggcacacg
ttagaggctacagctctgtgtgattctcatgctggc
tccacttccactttttccttcttcctactcaagaaag
cctatagaaatatgagtaagaagggcttaatcatagg
aataaatttgtctctgttctaagtgattaaaaatgtc
tttatcagtataaaaagttacttgggaagattcttaa
aactgcttttacacactgttctagaatgactgttata
taaataaaaagtagatttgatctaacacaattaaat
gacctttggaaatattgactaattctcaccttgcccc
tcaaagggatgcctgaaccattttccttcttttgccag
aaagcccccacccttgtctgttgacctagcctagga
aatcttcagatcacgttgttagcacgaactggttaca
tgtgctgtacaaatactatttaattcatctgattaaa
aaaaaagagataaagaagcaaaagtttgactatcttaa
actgtttgcgtaggtgagaggacaattgaccatctac
tttatgagtatgtaacccagaaacttaaagctcctta
agggagctaagtcttttggataagacctatagtgaga
ccttttagcaaaatggttaagacagtgaatggagctcac
tagcgtgggttcatatcctgatgctcaaacacgcaat
taaatgactttaggtgggtagtctctgttccttagt
ttcctcaatgggagataatattggtagtagcgatttt
actggggttgttgaaagaacatctgttaaatgttcaga TABLE 13-continued

SEQ ID NO. 49 acgtgttacgacagagtacagagtaatgatttgcttg
tatatgtatgactcaaatagtctgccatatgccttgt
gactgggtcctgtggagcaggaaggagggatttccca
cccagcagaaagttgggtaaactggaaaatagactga
ggccaggaaatgatgcaaagcgttgatgttcactgcc
acggcaggtgaagggcagggccagagtttgtcagtagg
gtcaggggaggactggaaataaccaagacccactgca
cttttcagcctttgctccagtaaggtaatgttgtgag
agtagaaattttgttaacagaacccacttttcagta
cagtgctaccaatactgtagtgatttcataccacatc
ccaagaaagaaaaagatggctcaatcccatgtgagct
gagattatttggttttattgttaaataaatagcattg
tgtggtcatcattaaaaaaggtagatgttaggaaagt
agaaggaagaagactctcacctacattttcatcactg
ttttggtatctgccagttgtcaccttggtccccttcc
ccgcctctccctgcctcctcttcctccttctccttt
ttttggaatacaattcaggtaccataaaatttaccct
tttagagtgtttgactcaatgtttttagtattttca
catgttgtgctattactatccactatatataattccaggt
cattcacatcaccccccaaagaaacctctaactatt
agcagtccattcccttcttccctcagcccctggcaac
cactaatctacttactgtctccatggatgttcctata
ttgaatcaagctagcataaaccccacttgctcatggt
cataattctttttttatagtgctaaattacatttgcta
atattcaattaaggattctctatgtccatattcataag
gaatattggtgtgtagttttctctttgtgtgatatct
ttgtctggttgggggatcagagtaataattactgctc
tcatagaatgaattgagaagtgttccctccttttcta
tttattggaagagtttgtgaagtatattggtattgat
tcttctttaaacatttggtcagattcaccagtgaagc
catctgggccatggctaatcttttgtgaaaagttttt
gattactaattaaatctctttaatttgttatgggtct
gctcctcagacgttctagttcttcttgagtcagtttt
gttcatttgtttcttcctaggactttctcccctttcat
ttggattatttagattgatagtaatatcccccttttta
attcctggctgtagtaatttgggtcttttctctttt
tcttggtcagtttagctaaaggtttgtaattgtatta
atcttttcaaataactaacttttttgttttgtttgtt
ttttgttttttgttttttgttttttgttttttttttgc
tttttaaggctgcacctgaggcatatggaagttctca
ggctagaggtctaatcggagctacagctgctggccta
taccacaaccatagcaatgccagattcaagctgcatc
tgcgacctacaccacaacctcggccagggatcacaccc
gcaacctcatggttcctagtcggatttgttaaccact
gtgccacgacgggaactcccgcccattttttttaaca
cctcatactttaacataaagatgggcttcacatggac
tgatagctcaaatgaggaaggtaagactatgaaagta
atggaagaaatgtagactattttttgtgacctagagat
tactgatacttcttgacttttcaaacaatacttcaaa
agtacagcccaaagggaaaaagaaagaaaaaagaaa
cacacatatacacaaacctagtgaataagatatcatc
gatacactacagattctatgaactggaagacccccat
ggacaaagttaaagaacatatgatagtttgagtgatt
attttgcaatatttacaaccaatgagggaatattatc
cagcttataggaggaagtaatgcaaatcgacaagaaa
aagataggaaaccaatataaaaattaagaaaatca
aaaattaagaaaggatatgaactagcattttacaaaa
gaaaaatctccaaaagtcaatcagcacatgaaaatat
gctcaaacctattaattattagaaaactacagactga
agcaatgaggtgctttacttcatctttttttgactga
taaaaagttagaaacaaaggtgatatcaaatgtcagg
gataaaggatatagaaatcgtcatgcctgtggtgggg
agtatggccggtgcagtcatgtgggaaggtaatctga
cagtggttaggcagagcaggtttatgaatacactgtg
gcccatcaatcccacgcctgtttatgtaccaaagaaa
tcctgttgtggcagaatctatgggtccacccctggga
gcatgaattaataaaatgtggcaccagggtgtgtgaa
actccagctagagatgagatgtccacatggcaacatg
aatgcatcttagaaacatagatttgagtgaaaaagag
taagaaacagccgggaaacccaataccatttataaaa
attaaagatgcacacatacaatgtagtaaatattttg
catgaacttcaaatggttgcctacaggggggagag
taagaagagtagaaacaaagataaaggagtaagt
aagtagctctgcctggactgaatataatgtgtcatga
actgagaaatatggttaacataatcctctaacttgag
gtcctaaatgaatgaatgagtccactattcatttacc
cattctttaatgtgtattgcattataatccattttt TABLE 13-continued

SEQ ID NO. 49 tagaaccaacgaattttgttcccataactactaatca
gcctgccttttcctcctcattccctatcagctcagg
ggcattcctagtttttcaaacgttcctccatttgaacc
aaaaatagcatcattgtttaaattatacttgttttca
aatacgatgcttatatattccaagtgtgtttgcccat
tttcttaggtggtagaaattttttcattctactttttct
atctctactcagattttcccgttggaattattttccattg
ctattaaacttagaagtcccccctgtgatatgccatt
tttttcatacttttttaagcacttggttgcttttctttt
gtgtcttttaagcacctagaatacttataaccattgca
cagcactgtgtatcaggcagcccttcctcttccacta
atttatggtcctctcttagactatattaaactgtta
tttaattaggatcctctcttcgtccttatgatttaat
tattatagtttttctaatatgttttttattataattcct
cttcattattcctccctattaaaaattttaatgaatt
ccatttgtttgttcttctagttaaatattaagtcata
atccaaataacttagatgtcattagtttatgtggtca
aagtaaggatacccacatctttatagatgcaggcagtt
ggcagatgtcatgattttcttcagtgcataaatgcaa
tttatctttgagcaaggggcataaaaaacttttatggt
attggctttgaaataatagttaagaactgcagactca
gttttttcctgcttttcttgaaaaagaacacttctaaa
gaaggaaaatccttaagcatggatatcgatgtaattt
tctgaaagtctcctgtaattccttgggattttttgttg
ttgtttgttggtcggttttttttgggttttttgtttgtt
tgttttgttttgttttgttttgcttttagggctgcac
ctgtggcatatggaagttcccagcctagggggtccaac
tggagctacagctgccagcctactccacagccacagc
aacatgggatcctagctgcatctgtgacctaaccaca
gctcttggtaatgccagattgttaacccactgagcaa
tgccagagatcgaatctgcctcctcatggacactagt
cagattagttctgctgagccacaatgggaattccca
attccttgtattttttgaactggttatgtgctagcata
taattttgtttcttgaatctttgtgggttttttttttt
ttttttttttttgtctcttgtcttttaaggctgcacc
cacagcatatggaggttcccaggctagaggtcaaatt
ggagctacagctgccagcctacacaacaactgcagca
aagtggggcccaacttatatgacagttcgtggcaatg
ccggattcctaaccactgagcagggccagggatcga
acctgagtttccagtcagtttcgttaaccactgagcc
atgatagtaactcctgctttgttcagtcttgaacctcc
tttttaattcttttattccttgagggtgaaataattgc
cataataatactatcatttattacatgccttctctgt
gctaggcatagtgacacttaggatttattatatcac
ttaatccctacaacaactctgcaaagtatgtatcata
atcctatttgacagatcaggaaattgcagcccaggat
gcagataatatgcatccatcacaagtgactagatata
gtcccctctgctattcagcagggtcttcattgcctttcc
attccaaatgcaatagtttgcatctattgtatatgtg
ttttgggtttttttttgtctttttttttttttttgtct
tttctggggcctcacccttggcataggtaggttccca
ggctagggtcaaattgaagctgccagcctgccagcca
caccacagccacagcaactcgggatctgagcctcatc
tgcaacctacaccaaagctcacggcaacaccggatcc
ttaacccactgagtgaggccagagatcaaaccggcaa
cctcatcgttcctagtcggattcattaaccactgagc
cacgatgggaactccctaaatgcaatagtttgctcta
ttaaccccaaactcccagtccatcccactccctcctc
ctccctcttggcaaccacaagtctgttctccatgtcc
atgatttttctttctgggggaaattttcatttgtgcca
ttttcatttttacgggtaattttttacttcagtttctt
ccactagcagttgtcttaaagtgagtataattaatat
tcatttggaaatgtaagcaaaacattttttaaaggg
ccatgcccacagcatatgaaagttttctgggccagggg
ttgaatccaggctccaagttgcagctgtgcctacac
tgcagctgggcaatgctggatccttttaacccactgtg
cccggctagggatcaaacctgcatttccacagctacc
cgagccattgcagttggattcttaaccactgcacta
cagtgggaactcccacaaaacattttttaatgtcctt
tgaataaagtaggaaagtgctcgtcttttgagggcagg
gcggcaatgccatttccacaaggtttgctttggcttg
ggacctcatctgctgtcatttagtaatgaataaaatt
gctgacgtaataggattaactgtgtgtggagatagc
cagggttagagataaaaacactggagaagtcaaataa
gttgctcgaggtcctctagctaataagctattaagtg
ggagagtgagggctagaaacaggccatctgtctccca
agcacatgtccattagtggtttgctgatagccttcca TABLE 13-continued

SEQ ID NO. 49 gaacaacagagaggactctcaaacatggtcttgcctc
cctccaattgatcccctccatgtgcctcacagcgggt
ctttctaaaattaagttctgattttaattctcccttg
ctatagcacttaggtatggctttcagccgtgcaataa
aaagcaggcaagagtggctcaatcatataggaggttg
ttttttcttagatcccaagcaggtaatcctgggcatta
tggttgttctgcgtttatcaaggagccaaattctcta
tcacctcctgttctatcctcctcagtatctggctcta
ttcttcagcatctcaagatggcttgtgctcctccaag
catggcagtcaaattccacacaagaggggggaaatatg
aagggcagacagtgctggtctcctgagctgtccctct
ttgtcggggaaaatgtattccttcaagtcccgtgaga
cttctgaagtagacgtctgcttacgtctcacccacca
gaactatgtaaactgcacatagtgctaggtctacata
gccactcataactgccagggggtgggaaatcttttaaa
taggtgtaccaccacacaattaggatgctaatagtaa
gggagaaggagagaataggttttgcgcaagccaccag
catgcctgccacaaattgcttaaaattcttcattgacc
cctcattgccacaggatgaaatccaaacgccttctta
gttgggaatctgacctacctgtctctcccacctggtt
cagacaccattctccttggtcataaaattccagtcat
ttgtgaacatccagctccccatgcctccatgcctt
gcacatgctgttctttttatcttttatgttgtccttt
atcttttatccaaaagagatatcccatcatcacatct
cttttgtcagccccaaatactttgtctttcaagttc
agctggaggattacctcctatttgaaatcagctttgt
ctcttacaaccaaacaaggttttccttccgagacact
cccacagcacctttgaactcatctctatcaatcattca
tttgattgtaatgaagttgttggtggtatgcctgtgt
ctctgacacatctgcgatctcatgagttccttaagtg
gaatgtgaatagcggagtgaacagtattggtcttcag
ccctcatctctgcagatgttgcttgacccaaatgagc
gttgccttttattttgattttgcttgatttgtctac
tccatgtacttgagccatgcatttctgtcttagcgat
gcttttttaaaagtcattttttggttgattatccagat
ttgtccacctttgcttctag TTGTAGAAAAGGATGAAGAAAATGGAGTTTTGCTTCT
AGAACTAAATCCTCCTAACCCGTGGGATTCAGAACCC
AGATCTCCTGAAGATTTGGCATTTGGGGAAGTGCAG gtaaggaaatgttaaattgcaatattcttaaaaacac
aaataaagctaacatatcaattatatatatatatat
atatatatttttttttttttttttacatcttatattacc
ttgagtattcttggaagtggctagttaggacatataa
taaagttattctgaagtctttttttttttctttttccat
ggtgagcagtggcttgatgtggatctcagctcccaga
cgaggcactgaacctgagccgcagtggtgaaagcacc
aagttctagccactagaccaccagggaactccctatt
ctaaattcttgagcacattatttaggaacctcaggaa
cttggcaggattacaggaaatatatctagatttaaaa
aaaaatcttttaaccagaggtcccaaaggagagtcatg
cacagctatggaggaagttcagaaactgcccttgct
accagatcactgtcagataaaatggccagctacatgt
ttctgcacattgccctaagatctttacaaactttttct
gtgcattttttcaatttaaaagaaaatttcggggtt
cctgttgttgctcagtggttaacgaacccaactagta
tccatgggacaggggttcgagccctggcctcactca
gtgggtaagaatctggcattgctgtggctgtggcgt
aggctggcctgcagctcagattggaccctagcct
gagaacctccatatgccgcaggtgatgggcctaaaaaa
aaaaaaaagagagagagaatttcctccagaaaaa
acactttggtagtttgggagaagtaaacaaccaaaaa
ttaattttctggagtattcgggaagcttgtaaaaat
gggctcttactttttgaggagacaaatgggaaccta
cccagaagaggcacaatcacctgcatttgatttcttg
acctctccctaccttctttgctggctttccacatttg
gattctgtgacctctatctctgctccttggtgtttc
attttttcctgtgacgtgccagctcagctatgggaaggag
taaggcgttgatttagaatcctgtagtctctgcctgt
ctctagtcattgttttcaccctctcaaaggaccttg
acatcctgagtgagtccgcaagtaatttaggggagaa
gcctagaagccagtgcagcaggctacatgactgtg
tccacccactggaaccagtcattttttataccattca
cagccccctaccatttaaatcccagaggtctgcca
taacatctgtaactcccttttcctggtaaattgtgttc
taaaagactggtaacaaaagatattctgtggtacaga

TABLE 13-continued

SEQ ID NO. 49

```
gcataattaaatacctgggagctgatttgagtggggt
aaatcaactggtttgacccctaaaacccaccatgagc
atttctgttctaataaagtaatgcccgtgctgggaat
tgtgttctacggaaatgctcctgctgtgtctttcttg
agtcctgtgtcattgaacatgcttaggagcaaaggtc
ccccatgtggcttgtctgctaaccagcccagttcctt
gttctggctggtaatgatccgatcatctgaatctcac
tgtcttccaacag ATCACGTACCTTACTCACGCCTGCATGGACCTCAAGC
TGGGGGACAAGAGAATGGTGTTCGACCCTTGGTTAAT
CGGTCCTGCTTTTGCGCGAGGATGGTGGTTACTACAC
GAGCCTCCATCTGATTGGCTGGAGAGGCTGAGCCGCG
CAGACTTAATTTACATCAGTCACATGCACTCAGACCA
CCTGAG
```

SEQ ID NO. 49 represents contiguous genomic sequences containing Intronic sequence 5' to Exon 4, Exon 4, Intron 4, Exon 5, Intron 5, Exon 6, Intron 6, Exon 7, Intron 7 and Exon 8 (Table 13). Further, nucleotide sequences that contain at least 1750, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5500, 6000, 6500, 7000, 7500, 8000, 8500, 9000, 9500, 10000, 11000, 12000, 13000, 14000, 15000, 16000, 17000, 18000, 19000, or 20000 contiguous nucleotides of SEQ ID NO. 49 are provided, as well as nucleotide sequences at least 80, 85, 90, 95, 98, or 99% homologous to SEQ ID NO. 49.

TABLE 14

SEQ ID NO. 50

```
AGGAATGGAAAGCCCAATTCATTAAAACAGAAAGGAA   SEQ ID NO. 50
GAAACTCCTGAACTACAAGGCTCGGCTGGTGAAGGAC
CTACAACCCAGAATTTACTGCCCCTTTCCTGGGTATT
TCGTGGAATCCCACCCAGCAGACAA
GTATGGCTGGATATTTTATATAACGTGTTTACGCATA
AGTTAATATATGCTGAATGAGTGATTTAGCTGTGAAA
CAACATGAAATGAGAAAGAATGATTAGTAGGGGTCTG
GAGCTTATTTTAACAAGCAGCCTGAAAACAGAGAGTA
TGAATAAAAAAAATTAAATAC gtatggctggatattttatataacgtgtttacgcata
agttaatatatgctgaatgagtgatttagctgtgaaa
caacatgaaatgagaaagaatgattagtaggggtctg
gagcttattttaacaagcagcctgaaaacagagagta
tgaataaaaaaaattaaatacaagagtgtgctattac
caattatgtataatagtcttgtacatctaacttcaat
tccaatcactatatgcttatactaaaaaacgaagtat
agagtcaaccttctttgactaacagctcttccctagt
cagggacattagctcaagtatagtctttattttttcct
ggggtaagaaaagaaggattgggaagtaggaatgcaa
agaaataaaaaataattctgtcattgttcaaataaga
atgtcatctgaaaataaactgccttacatgggaatgc
tcttatttgtcag GTATATTAAGGAAACAAACATCAAAAATGACCCAAA
TGAACTCAACAATCTTATCAAGAAGAATTCTGAGGT
GGTAACCTGGACCCCAAGACCTGGAGCCACTCTTGA
TCTGGGTAGGATGCTAAAGGACCCAACAGACAG gtttgacttgaatatttacagggaacaaaaatgattt
ctgaattttttcatgtttatgagaaaataaagggcat
acctatggcctcttggcaggtccctgtttgtaggaat
attaagttttcttgactagcatcctgagcttgtcat
gcattaagatctacacaccaccctttaaagtgggagt
cttactgtataaaataaactattaaataagtatcttt
caactctggggtggggggggagactgagttttttcac
agtcctatataataattttcttatcctataaaataat
taggagttcccgtagtggctcagcaatagcaaacccg actagtatcgatgaggatgcgggttcgattcctggcc
cccctcagtgggttaaggatctggcattgccgtgagc
tgtggtgtaggtggcagacacggctcagatcccacgt
tactgtggctgtggcataggccagcagctccagctct
gattagaccettagcctgggaacttccatatgctgtg
ggtgtggccttgaaaaaaaataaataaataagataat
tactcaaatgttttccttgtctcagaaccttacttca
ggataaagagtgagaaagttttttttatgaagggcca
ttattacagctcaaaaataagttgtcttcagcaagta
gaaagcaataagcctgagagttagtgttcctatcagt
gtaaatattacctcctcgccaatccccagacagtcca
tttgaacaattaacggtgccctgggagtacagttcag
aaacattaatgtggatgttccagacctgtattttat
aagtacttgtcttgagccggatggaaccatcattcct
caccattatttagaagtggactgtgactctgttggag
atcagggcacacggttaccaaaagcacacccttctcc
tggccttacctttgcaaagctggggtctgggacacag
tcagctgattatacccttttactaacttcccacagct
caaatctggtcaattctccttcacaaatctcttaaaa
atccatcactcacctccagcctcttctgctgtggcct
tgattcagcctctcacaatttttttttaaccagaatt
ctggcagtggccctgacttgcctctgtgctcccage
cccgctgtcctctgatccatcctccatgccagccttt
ttcaatctgctggtcacgattcattgatgggttagga
aatcaatggcatcacaactagcatttagaaaaaggaa
ataggcgttcccgccgtggcacagcagaaataaatcc
gactaggaaccataaggttgcgggttcaaccccctggc
cttgttcagtgggttaaggatccggcattgccgtggg
ctgttttgtaagtcacagacatggctctgatccggca
ttgctgtggctctggcgtaggcctgcagcatcagctc
caattagaccoctatcctgggagcctccatatgctgc
aagtgcagccctaaaaaaaataaaaaaataaaaaaaa
ataaataaaagaagtagacaaattgtatagaacaacc
ctgagtatgttgcctgagcacatataacaagggtaag
tattatttcaggaaactctggtttcacagatactctt
ggcatatggaccoctagagtcctgatgtaaaatatat
tcttcctgggatcttaggcaagaagtttgaaagctcc
aactctgcactgctgccaaagaaatgattttaagtg
caaaactcttcccgttcccttccctgtataaaattcc
ataggatctctccagtgcctctaggataaaggcagtt
ttcattctctagttcaaggtgagagaagattttaatt
atttcacgttttagtggggaattcaagagtctggcac
ctgacatttgctgaactctctccattatccctctcta
gttccccagacgcatcctatggtagaaattcgcaaac
tagagtgagcgtcagagtaacccaaggaaactgggta
aatgcagctccctgggctctaccccctgagattctga
ttcagtagatctgaagcagagccctggaatatgcata
tgcatcattgtgtcacaccaagcattctgggtaatga
gagttgatgttaggttctcagtagtaagacaagtata
gagattccgggggactgagtgctcagctctgccttgg
ggaggagggagagggctaaagagaacaggagatgggg
acagggaagtgctcaacctccaatcttaggcatttgag
ctatgtcttaggggtcaggaggaggttaccaatatag
tgattaagagattgaggttccagtcagagggatatgc
tggagaaggggggtgaaaataatgtcataggtttggt
gagtgcagatactttggatttttttaatattttttattg
aaatatagttgatttacaatgctcttagtgagtacaa
ttacttttgaataagtgcatagatgtatgccattcttc
cagaaatgatttattgagctccttttgggcatcatgct
aagtacaggggaaacagctgtgaagaggtccttccct
tatgaagtcattcatccccttcagtaaatgaaggtaa
aggaaaaggatgagacagggacgccgtgttggaccag
ggtcagaaaggcctttataagaccttgcctggagggca
aggaacttgcctgtgagtaagagagcttgagaaagc
gataaagcaaagaaggaacattactgcattgtgtttt
agaaaaaccatgtcctggggaagaactcctagagtca
gggggggccagttgggagactgtgcttttttccaggag
gagataagtgaggctgctggctgagatggagcaagga
tttagagaagcagatatgagattcatttagaagttag
acattttaggatctgacacataatttatcaccaaaac
cagtgcatctctggctttgggccaccagttttggaga
agtggaatgtagggacctaccattacctgccaatctt
tactacacagatgctatttccctcctcatatttcct
ttctccagatcacgtcctattctattgccaggactca
agattccaccttgcatgcagtgatccatcttcacact
ggatggacagctctagggatgtcagagcacactcttg
tccatactgctgactgggtctcctgtcagcccatctg
```

TABLE 14-continued

SEQ ID NO. 50 tctatcagctgtggtattattagtataataagagggc
tgtatatgagagacacaaaattctaggtgtagctcaa
agataggctagagttattcctatgtacaacaaatatt
tatgggaccccttctgtgtactgtcatggttgctgct
ttcatcatacttgtagtctaatggaggtggggcagg
gcaggaataagcggatgtccacaaaatcagtaagacc
acttatattcaacattttcataatttagttatttgag
cccaaagggtccacatccgtggtattccaactttttt
ttccccggacatggatctttatctttttttttttttc
tttttgcggccagacctgcggcatatggaagttccc
aggccaggggttgaatgggagttgcagctgcctggtc
tacaccacagccacagcaaggtgggatctgagctgca
tctgtgacatacaccgcagctgaggtaacaccagatt
ctgaacccactgaatgaggccagggatggaacccgtc
tccttatgaacactatgtcatgttcttcaccctctga
gccacaacgggaactccagacttcgtctttaaatgta
ttctgacttggagagctatcacactaagcaattaaca
ggagctgacctggtttaggctggggtggggccctact
cctcaatgttccctgaggcacatctgtgtggaccccgtc
ggcatcatctatctgagcagccttagagctgctcatc
cagttgactgttgatgtagaagtgcaaacttctgcct
tccttatttgttgctttcttttttcattgttctctcc
cctttgtgtctttaag CAAGGGCATCGTAGAGCCTCCAGAAGGGACTAAGATT
TACAAGGATTCCTGGGATTTTGGCCCATATTTGAATA
TCTTGAATGCTGCTATAGGAGGCTAAATATTTCGTCA
CTCATCCTGGATAAAAGAATACTTCACTTGGGCTGGA
TTTAAGGATTATAACCTGGTGGTCAGG gtatgctatgaagttattatttgtttttgttttcttg
tattacagagctatatgaaaacctcttagtattccag
ttggttttctcaaaagcattcattgagccttactgact
gtcagacggagggcgtattggactatgtgctgaaaca
atcctttgttgaaaatgtagggaatgttgaaaatgta
gggaatgaaatgtagatccagctctgtttctcttttg
gaggattcttttttcctccatcaccgtgtcttggttct
tgtttgttttggttttttgtgggtgttgtattgtgtt
gtgttggttatggcagtgacagctatttaaactgtga
aacggggagttcccgtcgtggcgcagtggttaacga
atccgactgggaaccatgaggttgcgggttcggtccc
tgcccttgctcagtgggttaacgatccggcgttgccg
tgagctgtggtgtaggttgcagacacggctcggatcc
cgcgttgctgtggctctagcgtaggccagcggctaca
gctccgattggaccccctagcctgggaacctccatatg
ccgcaggagcgggcccaaagaaatagcaaaaagacaaa
ataaataaataaataaagtaagtaaaataaactg
tgaaacgggagttccctttcatggctcagcagttaac
aaaccccagctaggatccatgaggatgtaggttcgatc
cctggccttgctcagtgggttaagaatccagcgttgc
tgtgagctgtgatgtaggtcgcagatgcagcccagat
cctgcattgctgtggcctgtaggctggcagctg
aagctccgattcaaccctagcctgggaacatccata
tgctgcaggtgtggcctaagaggcaaaaaaatiaaa
aaataaaaaataaataaattgtgggacagacaggtgg
ctccactgcagctggtgtcctgtaggacgcctggaa
gcaggtaaggtaaggactgcagctgggtaaggactga
attgcaccaactgggaagtaagcctagatctagaact
taagttagccctgacatagacacacagagctcaccag
ctaagtggttcagttctataagctggtcactgaaactg
aggatgtccacaaaagcaaaataagtagcaacagtca
gcgggatgcaagagaaagaggaggcctaaaatggtct
gggaatccctgccatacctatattttatcctacttat
atttagtgcctgaatgtgtgcctggagacgcaaagttt
agggaaagcatcgggaaatgcacagtattcatacctc
taggaacaaagatcagttacctccagggtaaagacta
tttccaagtttaaatttcaaccctgaacattagtac
tgggtaccaggcaacacttgccatcctcaaatcaat
gaatcctaaaattcaacctgggggtcagtgacagtct
gtgacaaagttttttgctggtcagtaacgaaataagta
tgagcaccatctgagtatggtcaccaagatgtcaact
tctctttcctttggacgaattgtcattattccaagatt
aggtccttctcattttttgaggtgtgaaaacatctttc
ctttcataaaataaaaggatagtggtggaagaatttt
tttttgttttttggtctttttgctatttcttggcc
gcttctgcagcatatggaggttcccaggccaggggtc
gaatcggagcttagccaccggcccacgccagagcca TABLE 14-continued

SEQ ID NO. 50 cagcaacacgggatccaagccgcatctgcagcctaca
ccacagctcacggcaatgccggatcgttaacccactg
agcaagggcagggaccgaacccgcaacctcatggttc
ctagtcggattcgttaaccactgcgccacgacgggaa
ctcctaatgatactcttttatatttagctactatgtg
atgatgagaaacagtccacattttattatttttttagc
caatttgatatctcattactaagataatgataatttt
ctctataaatttttatttaagttagtgttatgaagtgg
ttttgctagtgtagaaaggctaggattttgaattcagtt
caagaaagaagagaggagggaaggggagagggatgggt
agagggatggggcagtgggagagagcaaagaggagag
acagttttttgtattaattctgcttcattgctatcatt
taagggcacttgggtcttgcacattctagaattttct
aaggaccttgaccgccagattgatatgcttcttccct
ttaccatgttgtcatttgaacag ATGATTGAGACAGATGAGGACTTCAGCCCTTTGCCTG
GAGGATATGACTATTTGGTTGACTTTCTGGATTTATC
CTTTCCAAAAGAAAGACCAAGCCGGGAACATCCATAT
GAGGAA gtaagcaggaataccagtggagtgccccttcttcct
tccttcctaaataaacttttttattttggaacaactt
tagagttacagaaaagttgcaaagatattatagacag
tagtgtttatatatatatataaatttttttttgctttt
ttatgaccacacctgtggcatatggaggttcccagtc
taggggttgaattggagctacagctgccagtctgtgc
cataaccacagcaatgcaggatctgggccacgtctgt
gacctacaccaaagctcacagctggattcttaaccca
ctgagcaaggccagggattgaacctgcatcctcgtgg
ttcctagttggattcgtttccgcttgccgcaatgg
aactccaaattattgttaatatcttacttacttactggg
tacatttgttacaaccaatactctgatactgaaacat
tactgttaactccgtacttgcttctttttgagtcatt
tgcaaagactggaggctgacctgcttccttccaaac
agctggcctgcctatgctgttctcagacctgcaagca
ctgatctctgcccccttgccttctctccagtggtgt
ctccttccccaaacaaacccagtgtggctctggaaag
ggagttaagtcaacataaaccaacacatattttgttg
agctccaattttgagcaaatccctcacctacggcaga
caggcatgatgttaagaactagggctttggacacaag
gtcaagaccaagaagggttcctcacccctactgattc
agataaccaataatgagggctttgaatccctgtccaaa
ggttgtttttttccttctattgagcttcttgccac
cttatcagttttttttatgacagtcaaatgacatgat
atatgtgagcatacatggtaattttttaattctatata
aatgaatcactaaataaattaggaggatatatagtcc
acctttaagcgtattacacgtgtcacatgaatgtgtg
gcgacttaattgtagaggtttaaatgtagcttcctat
aatagatgtgttcctaaactacattttaatcattgga
cttgtattttatgttagcacttgctgttgaagaaaa
gcctatgccaaaagttcagtgaaaccaataatccact
gccagctttctgagttaaaaaaatccctgggttttc
acacacaggaaccctgtgtgaaacactcatttaga
gcaaaatgcatctgataaggagttcctgttgtgcctc
aactggttaaggacctgacattctccatgagaatgtg
agtttgatccccggccccactcgatgggtaaggatc
tggtgttgccacaaactgcagctccgattcatctcct
agcctagaaacttccacagcccagaatatgccacaga
attcggctgtttaaaaaaaagaaaaaaaaaaagaa
tcataaatgtgttggtttgttcaccaaatacatgata
acttgctcttgccaagctcagcttcataaatattaag
tcatttaatacagcagccaccttatgaacagatatta
ctatacttcccatttacagataaggaaaatgccatat
ttaaccaagagattaaataactttcccgaggtcttat
agcaagtaaatcatggtcagggggtttgaccacacgc
agtctatctccagagtctgtgtatttagccactgttt
tactttcaaatttaaatttataaaacttctaaattat
ctgttaaccataatcttttgaatttttaaaaaccacga
gttcctataaaatgtttcattgaaagtaagtcactttt
tccatagcttttgataatacatctgtaggataaagta
agccacagctctcttgcagacttggtacaccctgggg
caaagcatcatgcctgtcagctacatggtggtccttta
ctttgactctcagtgcttttattgcccaggaattttg
tgagatttctagttgttgaggtttgtttaaagaggtt
atgccggtacttggaagagctcttttcttgctacctg
gagccttctcatatttccttttttgaggagggacatga

TABLE 14-continued

SEQ ID NO. 50 attgcctttcaaactcataaatatattttctagtaca
caagtctccatcttccttagacgcatggcctggag
ttctccatcctcctgctccactttgggtgggctcctc
tctgggtctgccaccaatctgccaccccagagacatcc
ttgacccacttccagacccaccatggcttcacttc
ttcgcttcctcctttgtggaaccttctgcttaagaa
tctgaggaagaaaatttgcacgtgagctaaactggag
gtactttcctgcctggtcttgcacgatagcttggctg
agccatgatgctgggtggctgttacttccatggac
acccgaaggcgttgctcctttggcttctagttgcatg
cagtgttgcttatcccaggctgatctttcttccactg
taggtgacttttaagaattaagggattaatctatatc
tacaacaacaacaaagaccttttcaagctgaggt
agggctttctgtatatgtttggagtggttatccagca
gactttacttgaaggcagggtcatatcctcaagtgc
tcataaacggaccacagaaagatctcataattgggtg
gagctgggtggggaccgtgtcatgtggccaggaaatg
ccagatgggaagggagtggcccttactgagctccagc
tgaactctgaattttctagaaaactcagaaatctgga
tttttcatgtgtaatacccagatttatagatgtggaa
agctaattcttttttttttaagggactataggcaat
gaactaagatctaggttgtatttggacaagggtcat
cagttaagctgtgtagttgagcgctcagctattggg
ctgagggaccccctaaatactgagacgggggaggtcctt
gctctggggcatcacaagtacactccctggtctcatt
caaacacttttcctacaaaattgatcccatttcttca
gtgcactgtctgaatgcatttggcccagagccgtgct
gaggcatagggaaggggtccacggtttcatggcatcg
ttttgtgctgtgtgtccctgctgtcgtccaggatacc
tacctctcctcctcctgcatctgaatgtcccccaca
gactctctggattctacagcctctgaccctgttcctc
agacacctcttacctgccagctttccagattcacatt
agttagtccaaatctactgccgtcagtgactcacttc
atttcttcttctccgaggcagttcagcccggtacagt
tgttttgtcaacttcagttgagtctggaagatgtg
catgggttatgcacgagagcggtccatcattttgagc
tagaagtcctttctcagcccagagacaagtcctcatc
tccttttacttcctgactcttcttcctctgcatcttc
caagatatctctttctccagccaccacctaaatctct
tcttttcccggggttccgtgctcaaccactcttctt
cttaaatctgtggctgggtgaacgcatctgctggcac
cacttctctgctaaagactccaaaaatccataggtcc
tgcccggcctttgcccacctctctccaacactgtcca
gcttagatgtagagctaatccccccagagatatcat
tccctggatgtctaagtccttggtatctcactttca
gcgtgttcaaaatcctcttacaactgttctttctcct
tttccatcttgattattggcaacatgccagccttcc
cctacccccagcagtgagccaagctagaaacaaggc
ttaatcttcaatctttccttctccatccctaaaccta
atgagtctccaagccctccccagtttacaccctaaat
gttgctcaaaacatcccctagttcttccacgtgctct
cctctatattgaaaggtcaagaaaggccattcttccct
ccactgtgaggaaatagatcttgatactgcccctgag
ctgggcagtcctcgacctgacaaactgtgcagtgttt
ctaaatctctactggcaaaatgagagtgcctttgacc
tgtgttgcgatctcagatcacagtggatgtaattgtt
ttataggaatggtgaacgaaaaagaagtaaatccta
atgccaaactcctgatcattctatgtcatttaatagc
ctgtcatttatgataaagtttcctctactggcattag
cacaatacttctcaggaaaaaaaaatatgatgccaga
tactgaaaagctcctgggtaaacatgaacatggtac
cgataaaatggtgaagccagtccaatcttagagtgac
ttccccttcatgctacttcatgctctttttttttttt
tttttaagaaaaaccccttttttttctcacaccag
tcacagaggagaccgaggcttagcaaggttaaggtca
catgattagtaagtgctgggctgaaactcaaaaccat
ctctgcttgtctcctaaccctgtgcacctctgactat
tcaacag

ATCCTGTGTCAGGAGTTGGGATTCTTTGAAG gtaagggccttgaccaccgaattaaggtaatcttgct
ctgtggcaggccttgttttcagtatttttaagtacact
ggctcaggtaatcctcacaacagcccaggaggaatg
ttctattacctccactgtatagatgaggaacttgagg
cacagaatggttgccaaggtcacacagctatattggg
ggttcataccaagccatccaactctgtctgtactctc tgccactctgcaccccagctcctgatccacttcctg
tttccatccctcgatttctgctgcactcagggggccc
tctccccctcggcctgtgagatctgcttcagtaggct
tttctccctgactcctccatccctgtccttacaggca
gctgcttctctccgggacacgaggggtccatacggac
actctctactggctgggttgcgcctaactcgtgattc
ctcctctgtttcag ATTCGGAGCCGGGTTGATGTCATCAGACACGTGGTAA
AGAATGGTCTGCTCTGGGATGACTTGTACATAGGATT
CCAAACCCGGCTTCAGCGGGATCCTGATATATACCAT
CATCT gtaagtccgaaaatgcctgtcgtgtgtgccttaggct
gctgcggaggaggccagggctatataagcagagtcag
tgactgactgtgccctgcagtgttgatggccatggag
attccaccgttagagctttttctcttgttaaccttga
aggcaaatctggttaggaagataactttcaaagagtc
accatctggacattcatgcccatgtgcttcaatcctg
tatacaagcagtttagagtacagggaagggaaggaca
ttatgaaagggagagggtgtgtttggatccagcagct
ccatcctcagaatttatctgaagacactgcaaaatta
ctaagaatcactatgacaagaatgaggatggggtgat
atggcaaagttgtgatcctggaagaccttcatctccc
atgttgcccaactctgaacatgaatttggtgaactag
ttggttaaggggatgatcctccaagtttctccctggt
tgagctccaaaaaccatgtaagtttctcatagcaaaa
ccgtataggtccttagggctttagttggaatatttgt
gctgaaatgctggaaagccccatttgccattttgta
tttgcaaaataatcatcaagagggagaatgcattct
ttcatgaccactgaccctctgaaaaggtcaggaattt
agtctgaagtaggcaagcctcctacccgcttctgcc
atgagcttgcacgcacaggcctgtcttgacatttctt
ctttatagatttctttttgaatatcttgaaattgctt
taaaaatatttaaagaatgtagaattatataaaataa
aaaggaaataaccccacacctcccacaaaacccctgtt
tcctgccttttctccaccactctccagggtaacactt
ggtaacagcatagttgtatcacccccaggcctatttt
gagcatatcagcatttcaagaaatgtattttttctca
ataaaaacatccctttatagttgaggagggggaggttatc
attcctgggtttttgtttttttttttttttaatgtaa
tcctggtacatcggtaatttgcattttttattcatta
atatctttggtatttctagtgttgggacacacaggtc
aacctcagttttttgggttttttttttttgtctttttgt
ctttctagggccacacctgcagcatatggacgttccc
aagctaggagtctaatcagagctgtagccaccagcct
acgtcatagccatagcaacgtcagatccaagccgtgt
ctgtgacctacaagcaccagctcatggcaacaccggat
ccttaaccactgaacgaggccaggggatcgaacacac
atcctcatggatcctagtcatgttcattaaccactga
gtcatgatgggaactccaacttcaactattttaatgt
ctgtaaaacattccatttggaaaccattcatttgta
aagcaaaatgaaaacattttgttcattttcaacagag
ttcgtagctgacttctgttctggaaaaaaggaaatgg
agcaaatttgagtgagaaagattcaaagataactttt
cttttaaaaaaaattatatcttggaaacttctgggct
attgattctgaagactattttctctatatactgttttg
atagcaaagttcataaatgtgaaaggatcctgcgatg
aatcttgggaagcagtcatagcccaatatatctttgt
tgcttttaaaatgagattttagtttactaaatatttt
ctgatcataaaaataacacagatctaccgcagaaaat
ttggaaaaaaaaaactttttaaattcaaaaaacagtt
aaaccacaaatgatcccaccatcagagagcaatttg
tactttggtgtctagttcatcttttcttttttctgttta
caagcacatataccacaagcatttttccaaaaaatga
aaatgggataatactatacatacgtctgtacacctgc
atagttactgaacagtctttgatctaccctgtaagtt
tctaacttttcattatttgaaatgatgtttttggcaaa
gaaatatgtaggtgtgtctcgcacacttcataatga
tttcttaggataaatttcttaggataaattcataatg
atttcttataatatccatactctgccaactgatctt
cagggaagccaactcgccttctcagaaataacatata
acccatttacttgccctctccaccaatactaggtccta
atgtttttgtgtacagattctatatttttacatacaa
gaattcctaaaagcaaggcatgtcacagaaaaatga
aggaagacacaattgtcatgtttaaggactgcattct
gtaccaaaaatgctaagttaaatgaacatctgaaaca

TABLE 14-continued

SEQ ID NO. 50 gtacagaaacgctatctttcagggaaagctgagtacc
aggtactgaacagattttggcaaatacagcaggcatg
gatgtttccaaaacatgttttctactttatctctta
cag GTTTTGGAATCATTTTCAAATAAAACTCCCCCTCACA
CCACCTGACTGGAAGTCCTTCCTGATGTGCTCTGGGT
AGAGAGGACCTGAGCTGTCCCAG gtaaagcatcctgcaggtctgggagacactcttattc
tccagcccatcacactgtgtttggcatcagaattaag
caggcactatgcctatcagaaaacctgacttttgggg
gaatgaaagaagctaacattacaagaatgtctgtgtt
taaaaataagtcaataagggagttcccatcgtggctc
agtggtaacgaaccctactagtatccattgaggacac
aggttcaatatctggcctcactcagtcggctaaggat
ccagtgatgccgtgagctgcagtgtaggccacagacg
tggctcagatctggtgctgctgtggctatggtgtagg
ccggcccctgtaactccaattcgacccctaggctgg
gaacctaaaaagaccccaaaaaagtcgctttaatgaa
tagtgaatacatccagcccaaagtccacagactcttt
ggtctggttgtggcaaacatacagccagttaacaaac
aagacaaaaattatcctaggtggtcagtgggggttca
gagctgaatcctgaacactggaaggaaaacagcaacc
aaatccaaatactgtatggttttgcttatatgtagaa
tctaaattcaaagcaaatgagcaaaccaattgaaaca
gttatggaagacaagcaggtggttgtcagggggggaga
taagggaggcaggaaagacctgggcgagggagatta
agaggtaccaactttcagttgcaaaacaaatgagtca
ccagtatgaaatgtgcaatgtgggaaatacaggccat
aactttataatctctttttttttttgtcttttttgc
cttttctaaggctgctcccgtggcatatggaggttcc
caggctaggagtccaaacagagctgtagctgccagcc
tacaccagagccacagcaacacgggaaccttaacccg
ctgagcaaggccagggatcgaacccgagtcctcacag
atgccagtagggttcattaaccactgagccacgacag
gaattccagggtctgttgtgttcttaaaacacttcca
ggagagtgagtggtatgtcataagtaaacaataaatg
ttaaccacaacaagcttatgaaataaacaggaaagcc
atatgacctacaatcagtcattgggagaatccacaaa
aggttgagcagaggatcaattccagctcacactccag
ttttagattctcccctgccttaaagcatcacagacta
cataatctgagctgaagaataaaaattaaaactcacc
ccagtgcaaaacagaaatgaaaaagtattaaaacgag
gttcatactgttgttcattagcaatatcttttattca
cag GGGTGCCCAACAACATGAAAAAATCAAGAATTTATTG
CTGCTACGTCAAAGCTTATACCAGAGATTATGCCTTA
TAGACATTAGCAATGGATAATTATATGTTGCACTTGT
GAAATGTGCACATATCCTGTTTATGAATCACCACATA
GCCAGATTATCAATATTTTACTTATTTCGTAAAAAAT
CCACAATTTTCCATAACAGAATCAACGTGTGCAATAG
GAACAAGATTGCTATGAAAACGAGGGTAACAGGAGG
AGATATTAATCCAAGCATAGAAGAAATAGACAAATGA
GGGGCCATAAGGGGAATATAGGGAAGAGAAAAAAATT
AAGATGGAATTTTAAAAGGAGAATGTAAAAAATAGAT
ATTTGTTCCTTAATAGGTTGATTCCTCAAATAGAGCC
CATGAATATAATCAAATAGGAAGGGTTCATGACTGTT
TTCAATTTTTCAAAAAGCTTTGTTGAAATCATAGACT
TGCAAAACAAGGCTGTAGAGGCCACCCTAAAATGGAA
AATTTCACTGGGACTGAAATTATTTTGATTCAATGAC
AAAATTTGTTATTTACTGCGGATTATAAACTCTAACA
AATAGCGATCTCTTTGCTTCATAAAAACATAAACACT
AGCTAGTAATAAAATGAGTTCTGCAG SEQ ID NO. 50 represents contiguous genomic sequences containing Exon 12, Intron 12, Exon 13, Intron 13, Exon 14, Intron 14, Exon 15, Intron 15, Exon 16, Intron 16, Exon 17, Intron 17, and Exon 18. Nucleotide sequences that contain at least 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500, 10000, 11000, 12000, 13000, 14000, 15000, 16000, 17000, 18000, 19000 or 20,000 contiguous nucleotides of SEQ ID NO. 50 are provided, as well as nucleotide sequences at least 80, 85, 90, 95, 98, or 99% homologous to SEQ ID NO. 50.

VIII. Oligonucleotide Probes and Primers

The present invention further provides oligonucleotide probes and primers which hybridize to the hereinabove-described sequences (SEQ ID Nos. 1, 3, 5, 7, 9-45, 46, 47, 48, 49 and 50). Oligonucleotides are provided that can be homologous to SEQ ID Nos. 1, 3, 5, 7, 9-45, 46, 47, 48, 49 and 50, and fragments thereof. Oligonucleotides that hybridize under stringent conditions to SEQ ID Nos. 1, 3, 5, 7, 9-45, 46, 47, 48, 49 and 50 and fragments thereof, are also provided. Stringent conditions describe conditions under which hybridization will occur only if there is at least about 85%, about 90%, about 95%, or at least about 98% homology between the sequences. Alternatively, the oligonucleotide can have at least 20, 21, 22, 23, 24, 25, 26, 27, 28, 29, 30, 31, 32, 33, 34, 35, 36, 37, 38, 39, 40, 41, 42, 43, 45, 46, 47, 48, 49, 50, 75 or 100 bases which hybridize to SEQ ID Nos. 1, 3, 5, 7, 9-45, 46, 47, 48, 49 and 50, and fragments thereof. Such oligonucleotides can be used as primers and probes to detect the sequences provided herein. The probe or primer can be at least 14 nucleotides in length, and in a preferred embodiment, are at least 15, 20, 25, 28, 30, or 35 nucleotides in length.

Given the above sequences, one of ordinary skill in the art using standard algorithms can construct oligonucleotide probes and primes that are complementary to sequences contained in Seq ID Nos. 1, 3, 5, 7, 9-45, 46, 47, 48, 49 and 50, and fragments thereof. The rules for complementary pairing are well known: cytosine ("C") always pairs with guanine ("G") and thymine ("T") or uracil ("U") always pairs with adenine ("A"). It is recognized that it is not necessary for the primer or probe to be 100% complementary to the target nucleic acid sequence, as long as the primer or probe sufficiently hybridizes and can recognize the corresponding complementary sequence. A certain degree of pair mismatch can generally be tolerated.

Oligonucleotide sequences used as the hybridizing region of a primer can also be used as the hybridizing region of a probe. Suitability of a primer sequence for use as a probe depends on the hybridization characteristics of the primer. Similarly, an oligonucleotide used as a probe can be used as a primer.

It will be apparent to those skilled in the art that, provided with these specific embodiments, specific primers and probes can be prepared by, for example, the addition of nucleotides to either the 5' or 3' ends, which nucleotides are complementary to the target sequence or are not complimentary to the target sequence. So long as primer compositions serve as a point of initiation for extension on the target sequences, and so long as the primers and probes comprise at least 14 consecutive nucleotides contained within the above mentioned SEQ ID Nos. such compositions are within the scope of the invention.

The probes and primers herein can be selected by the following criteria, which are factors to be considered, but are not exclusive or determinative. The probes and primers are selected from the region of the CMP-Neu5Ac hydroxylase nucleic acid sequence identified in SEQ ID Nos. 1, 3, 5, 7, 9-45, 46, 47, 48, 49, 50, and fragments thereof. The probes and primers lack homology with sequences of other genes that would be expected to compromise the test. The probes or primers lack secondary structure formation in the amplified nucleic acid which can interfere with extension by the amplification enzyme such as *E. coli* DNA polymerase, preferably that portion of the DNA polymerase referred to as the Klenow fragment. This can be accomplished by employing up to about 15% by weight, preferably 5-10% by weight, dimethyl sulfoxide (DMSO) in the amplification medium and/or increasing the amplification temperatures to 30°-40° C.

Preferably, the probes or primers should contain approximately 50% guanine and cytosine nucleotides, as measured by the formula adenine (A)+thymine (T)+cytosine (C)+ guanine (G)/cytosine (C)+guanine (G). Preferably, the probe or primer does not contain multiple consecutive adenine and thymine residues at the 3' end of the primer which can result in less stable hybrids.

The probes and primers of the invention can be about 10 to 30 nucleotides long, preferably at least 10, 11, 12, 13, 14, 15, 20, 25, or 28 nucleotides in length, including specifically 14, 15, 16, 17, 18, 19, 20, 21, 22, 23, 24, 25, 26, 27, 28, 29 or 30 nucleotides. The nucleotides as used in the present invention can be ribonucleotides, deoxyribonucleotides and modified nucleotides such as inosine or nucleotides containing modified groups which do not essentially alter their hybridization characteristics. Probe and primer sequences are represented throughout the specification as single stranded DNA oligonucleotides from the 5' to the 3' end. Any of the probes can be used as such, or in their complementary form, or in their RNA form (wherein T is replaced by U).

The probes and primers according to the invention can be prepared by cloning of recombinant plasmids containing inserts including the corresponding nucleotide sequences, optionally by cleaving the latter out from the cloned plasmids upon using the adequate nucleases and recovering them, e.g. by fractionation according to molecular weight. The probes and primers according to the present invention can also be synthesized chemically, for instance by the conventional phosphotriester or phosphodiester methods or automated embodiments thereof. In one such automated embodiment diethylphosphoramidites are used as starting materials and can be synthesized as described by Beaucage, et al., *Tetrahedron Letters* 22:1859-1862 (1981). One method of synthesizing oligonucleotides on a modified solid support is described in U.S. Pat. No. 4,458,066. It is also possible to use a probe or primer which has been isolated from a biological source (such as a restriction endonuclease digest).

The oligonucleotides used as primers or probes can also comprise nucleotide analogues such as phosphorothiates (Matsukura S., *Naibunpi Gakkai Zasshi.* 43(6):527-32 (1967)), alkylphosphorothiates (Miller P., et al., *Biochemistry* 18(23):5134-43 (1979), peptide nucleic acids (Nielsen P., et al., *Science* 254(5037):1497-500 (1991); Nielsen P., et al., *Nucleic-Acids-Res.* 21(2):197-200 (1993)), morpholino nucleic acids, locked nucleic acids, pseudocyclic oligonucleobases, 2'-O,4'-C-ethylene bridged nucleic acids or can contain intercalating agents (Asseline J., et al., *Proc. Natl. Acad. Sci. USA* 81(11):3297-301 (1984)).

For designing probes and primers with desired characteristics, the following useful guidelines known to the person skilled in the art can be applied. Because the extent and specificity of hybridization reactions are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the probe and primer to target nucleic acid hybrid should be chosen to be compatible with the assay conditions. This can be accomplished by avoiding long AT-rich sequences, by terminating the hybrids with GC base pairs, and/or by designing the probe with an appropriate Tm. The beginning and end points of the probe should be chosen so that the length and % GC result in a Tm about 2-10° C. higher than the temperature at which the final assay will be performed. The base composition of the probe is significant because G-C base pairs exhibit greater thermal stability compared to A-T base pairs due to additional hydrogen bonding. Thus, hybridization involving complementary nucleic acids of higher G-C content will be stable at higher temperatures. Conditions such as ionic strength and incubation temperature under which probe will be used should also be taken into account when designing a probe. It is known that hybridization will increase as the ionic strength of the reaction mixture increases, and that the thermal stability of the hybrids will increase with increasing ionic strength. Chemical reagents, such as formamide, urea, DIVISO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10-50 bases in length occurs approximately 5° C. below the melting temperature for a given duplex. Incubation at temperatures below the optimum can allow mismatched base sequences to hybridize and can therefore result in reduced specificity. It is desirable to have probes which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the non-target nucleic acid. In the present case, single base pair changes need to be detected, which requires conditions of very high stringency.

The length of the target nucleic acid sequence and, accordingly, the length of the probe sequence can also be important. In some cases, there can be several sequences from a particular region, varying in location and length, which will yield probes and primers with the desired hybridization characteristics. In other cases, one sequence can be significantly better than another which differs merely by a single base.

While it is possible for nucleic acids that are not perfectly complementary to hybridize, the longest stretch of perfectly complementary base sequence will normally primarily determine hybrid stability. While oligonucleotide probes and primers of different lengths and base composition can be used, preferred oligonucleotide probes and primers of this invention are between about 14 and 30 bases in length and have a sufficient stretch in the sequence which is perfectly complementary to the target nucleic acid sequence.

Regions in the target DNA or RNA which are known to form strong internal structures inhibitory to hybridization are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid, it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization can be greatly increased. Computer programs are available to search for this type of interaction. However, in certain instances, it may not be possible to avoid this type of interaction.

Specific primers and sequence specific oligonucleotide probes can be used in a polymerase chain reaction that enables amplification and detection of CMP-Neu5Ac hydroxylase nucleic acid sequences.

IV. Genetic Targeting of the CMP-Neu5Ac Hydroxylase Gene

Gene targeting allows for the selective manipulation of animal cell genomes. Using this technique, a particular DNA sequence can be targeted and modified in a site-specific and precise manner. Different types of DNA sequences can be targeted for modification, including regulatory regions, coding regions and regions of DNA between genes. Examples of regulatory regions include: promoter regions, enhancer regions, terminator regions and introns. By modifying these regulatory regions, the timing and level of expression of a gene can be altered. Coding regions can be modified to alter, enhance or eliminate the protein within a cell. Introns and exons, as well as inter-genic regions, are suitable targets for modification.

Figure 3:
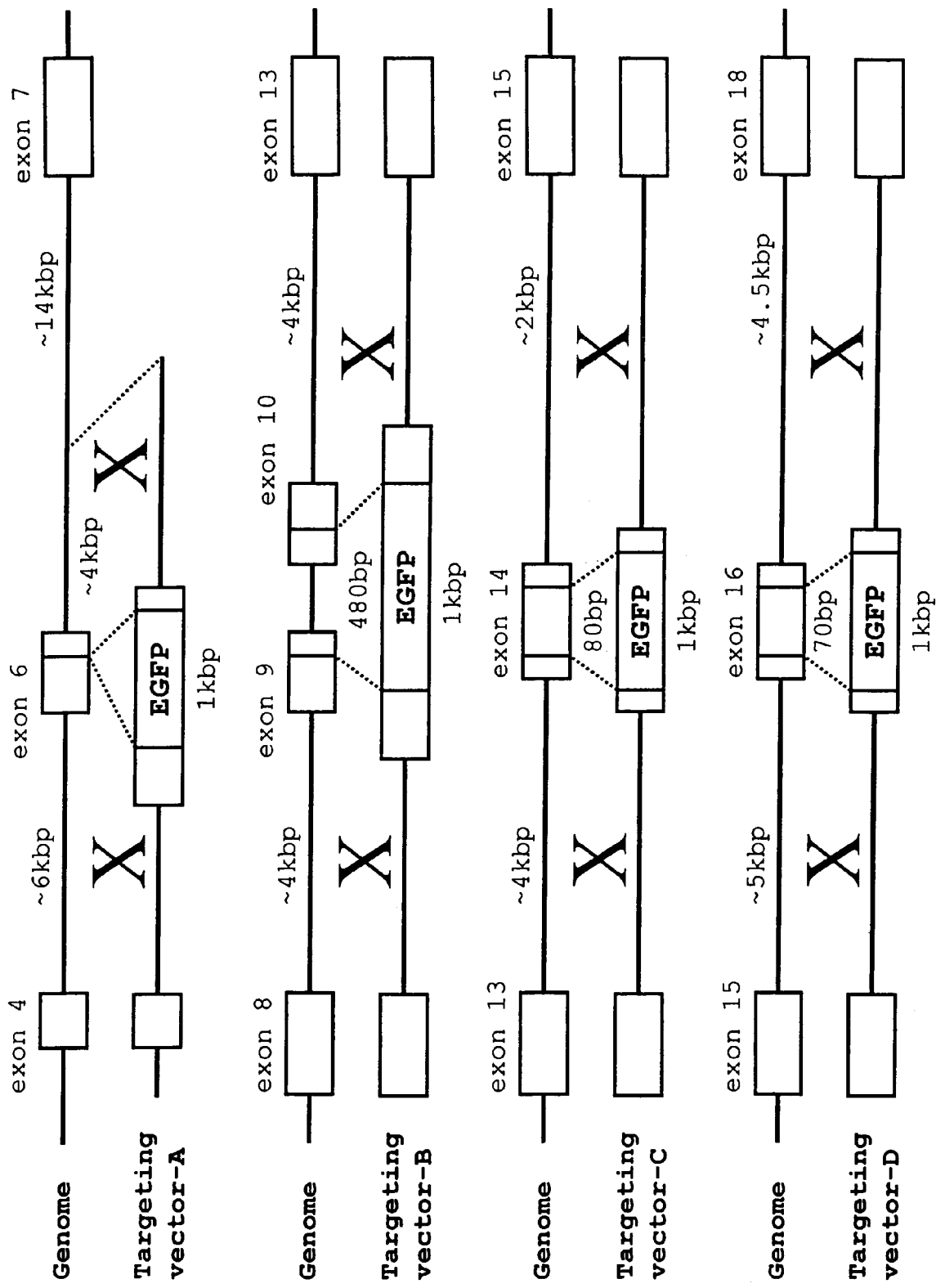
FIG. 3 illustrates four non-limiting examples of targeting vectors, along with their corresponding genomic organization. The selectable marker gene in this particular non-limiting example is eGFP (enhanced green fluorescent protein). eGFP can be inserted in the DNA constructs to inactivate the porcine CMP-NeuAc hydroxylase gene.
Figure 6:
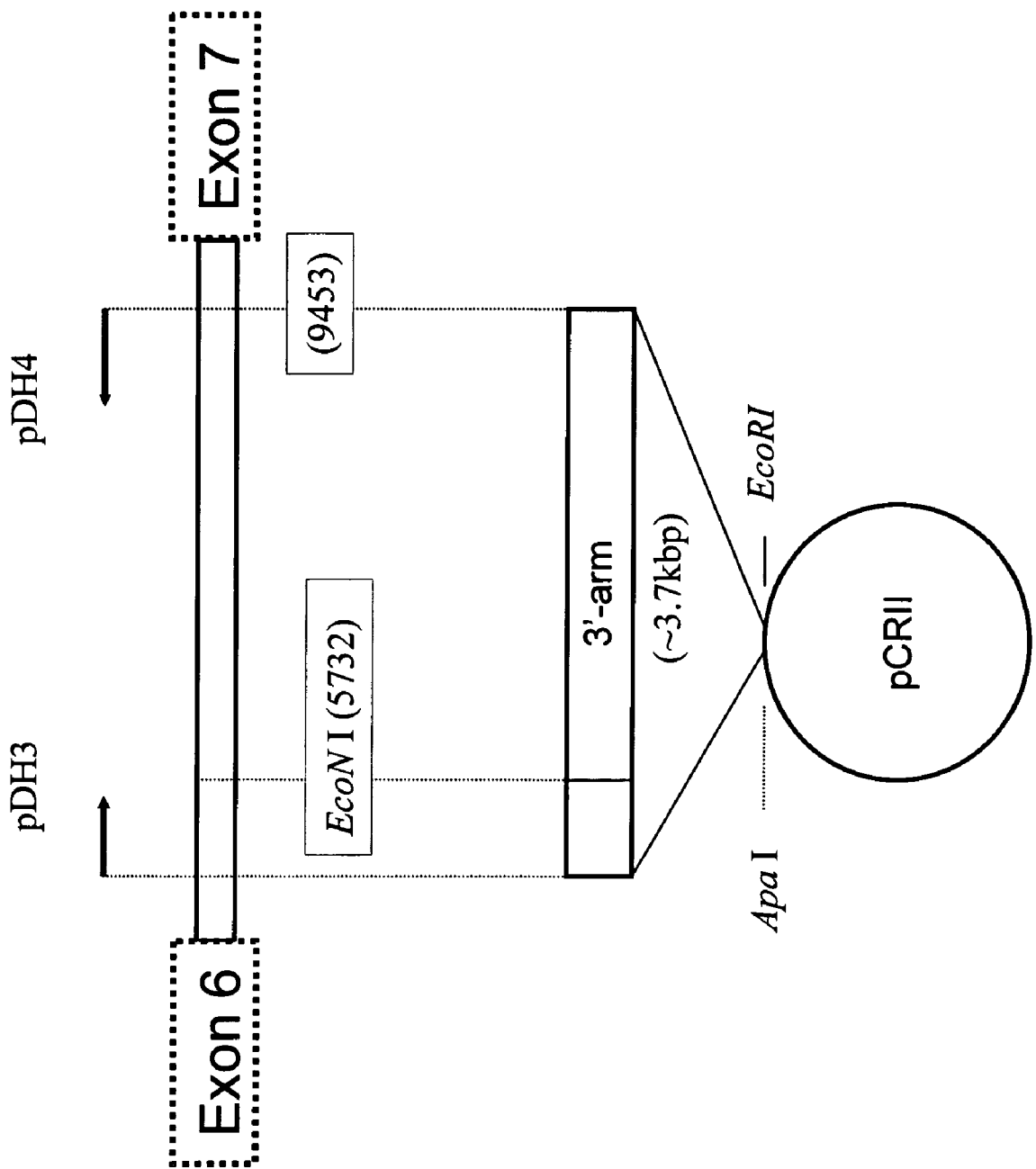
FIG. 6 is a schematic diagram illustrating the production of a 3'-arm segment from the porcine CMP-Neu5Ac hydroxylase gene using primers pDH3 and pDH4, and its insertion into a vector (pCRII).
Figure 7:
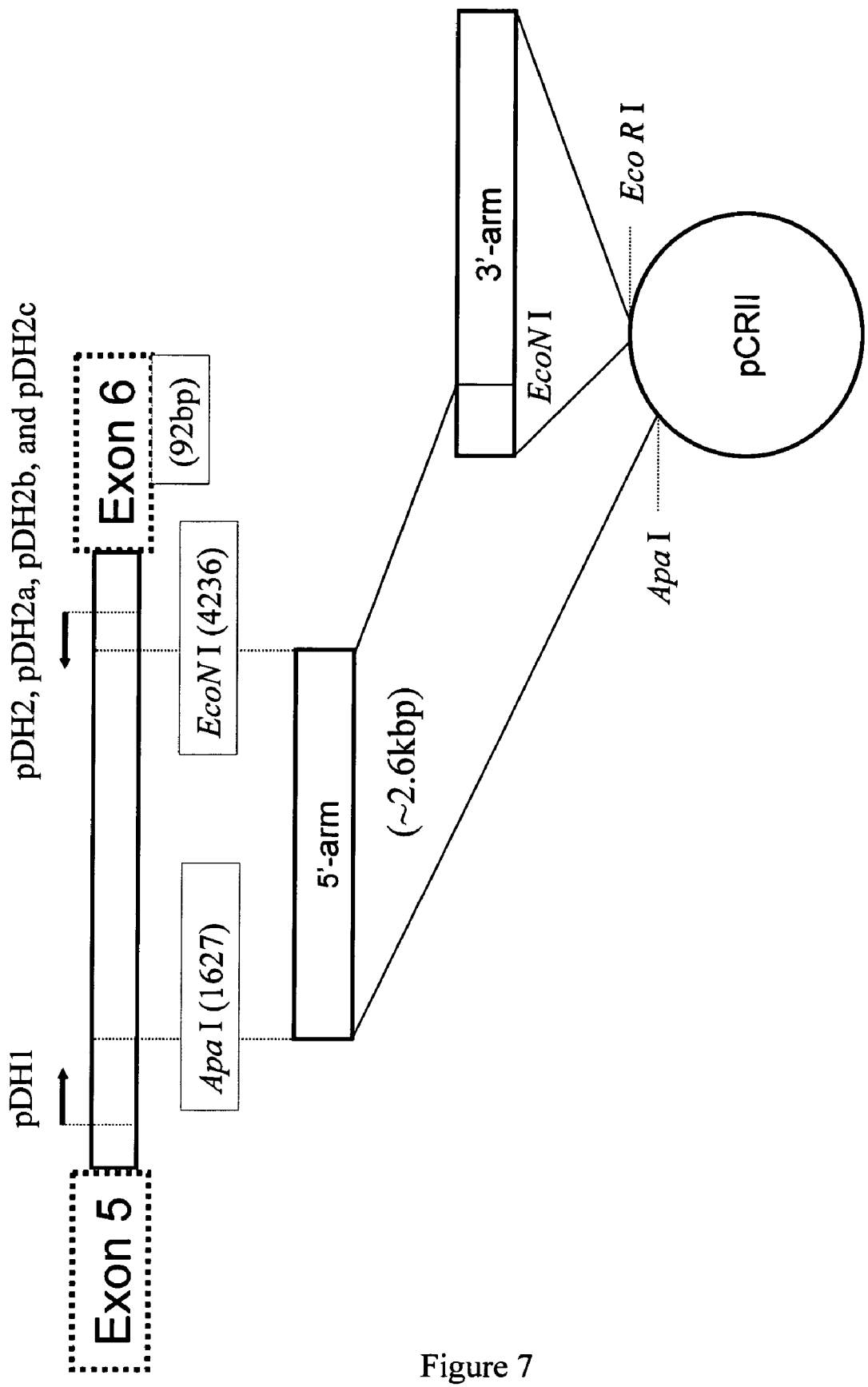
FIG. 7 is a schematic diagram illustrating the production of a 5'-arm segment from the porcine CMP-Neu5Ac hydroxylase gene using primers pDH1 and pDH2, followed by pDH2a, pDH2b, and pDH2c, and its insertion into a vector (pCRII) in which a 3'-arm has previously been inserted.
Figure 8:
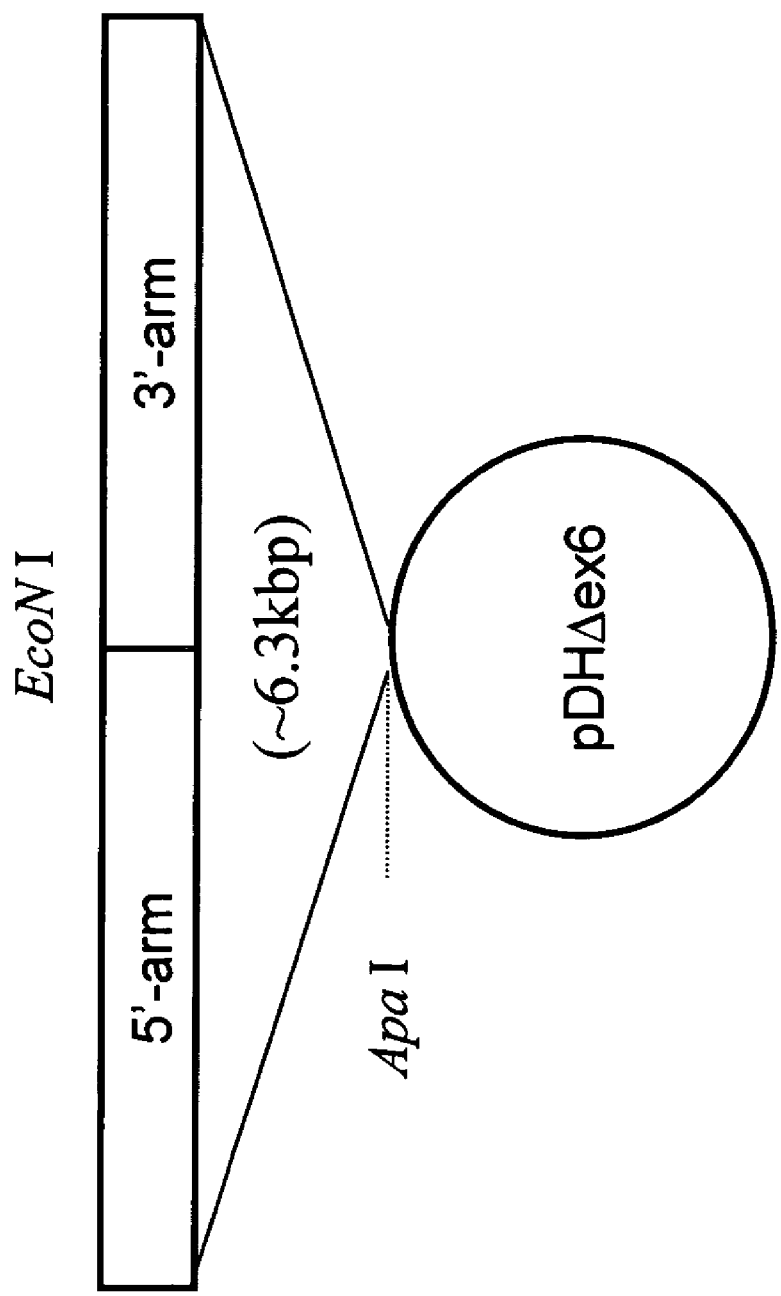
FIG. 8 is a non-limiting example of a schematic illustrating a targeting vector that can be utilized to delete Exon 6 of the porcine CMP-Neu5Ac hydroxylase gene through homologous recombination.
Figure 10:
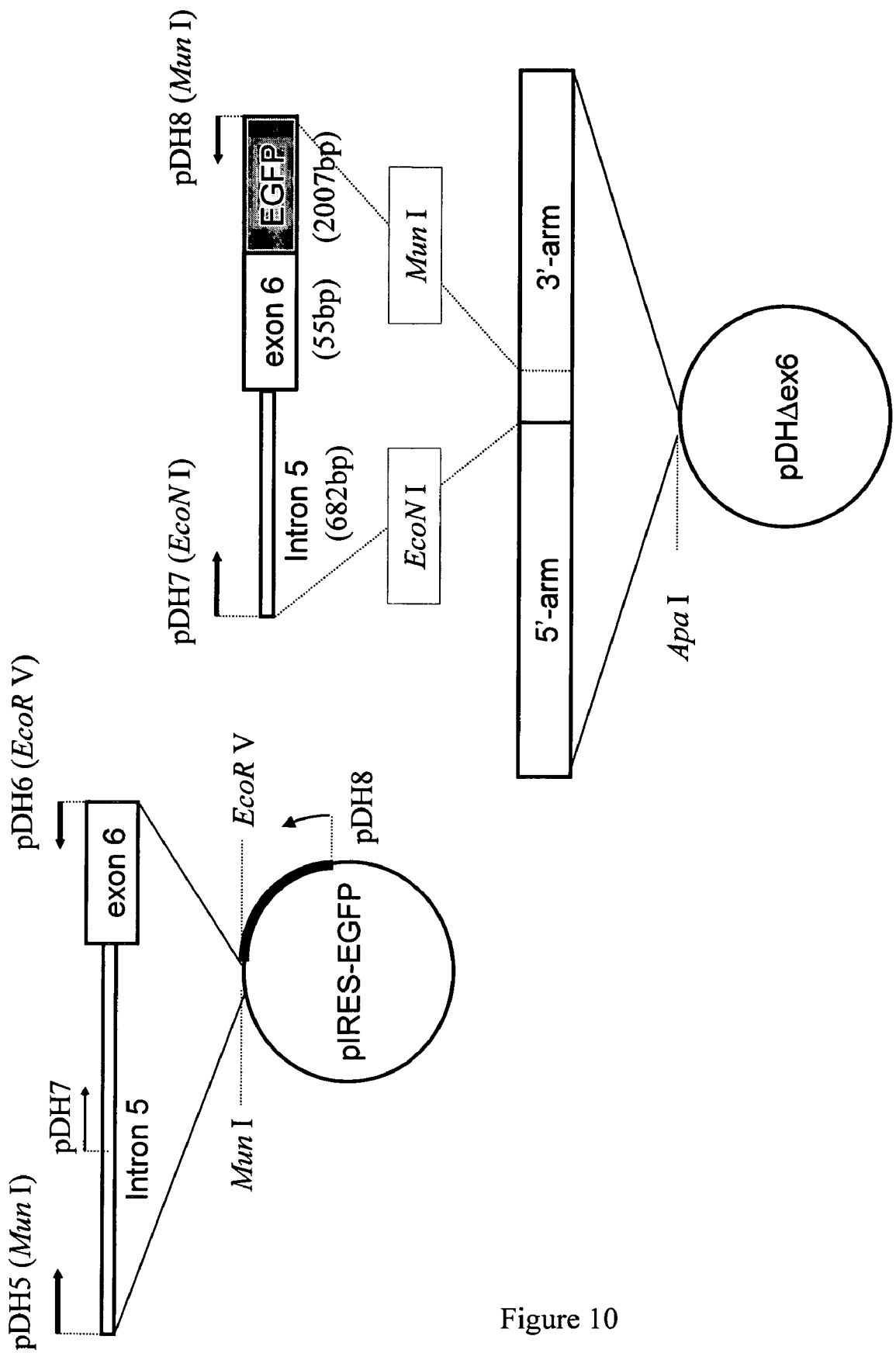
FIG. 10 is a schematic illustrating the insertion of a EGFP fragment with a polyA signal into the targeting vector pDHΔex6.
Figure 12:
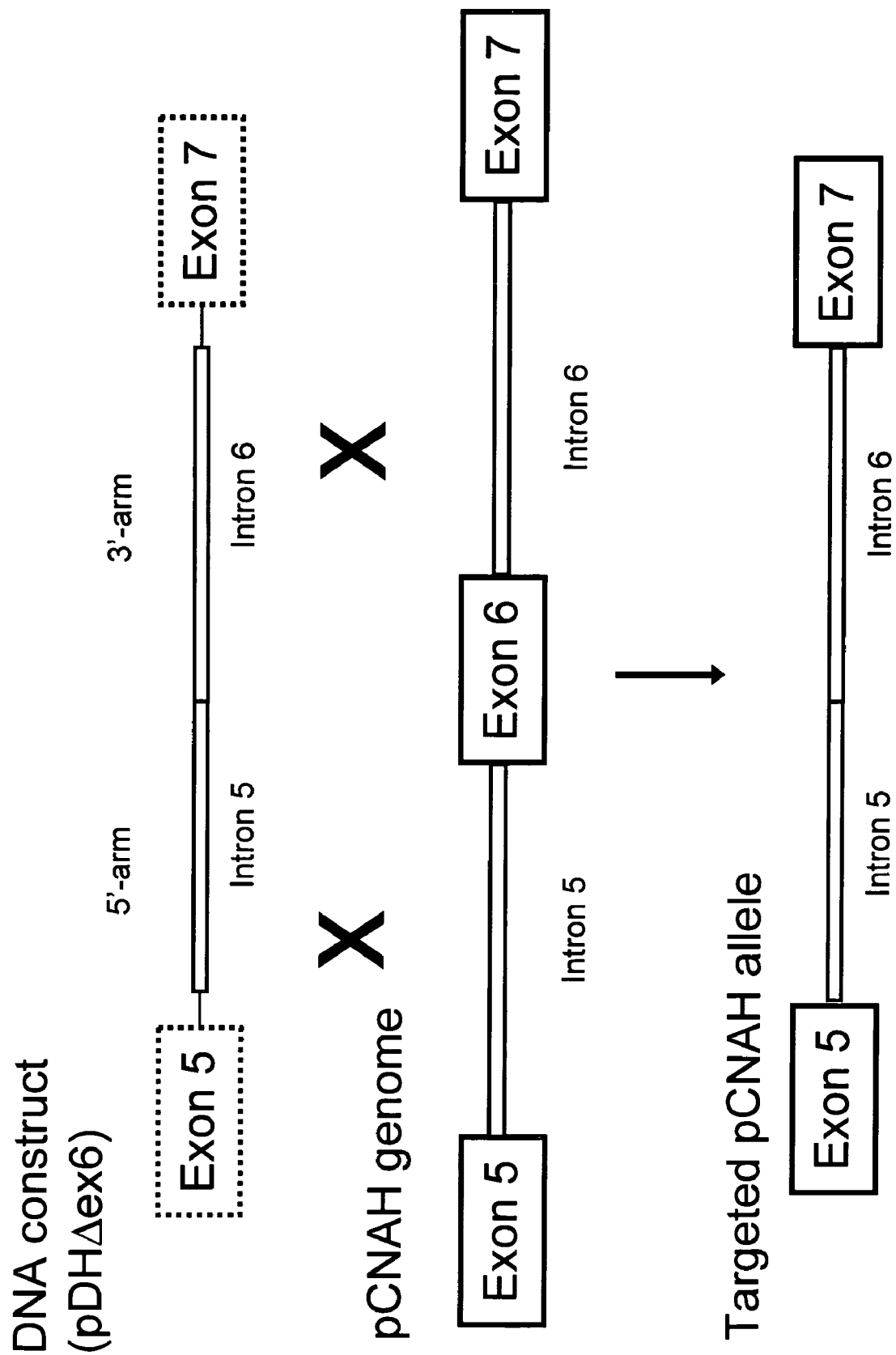
FIG. 12 is a schematic illustrating homologous recombination resulting in a frameshift between the targeting cassette DNA construct (pDHΔex6) and genomic DNA.
Figure 13:
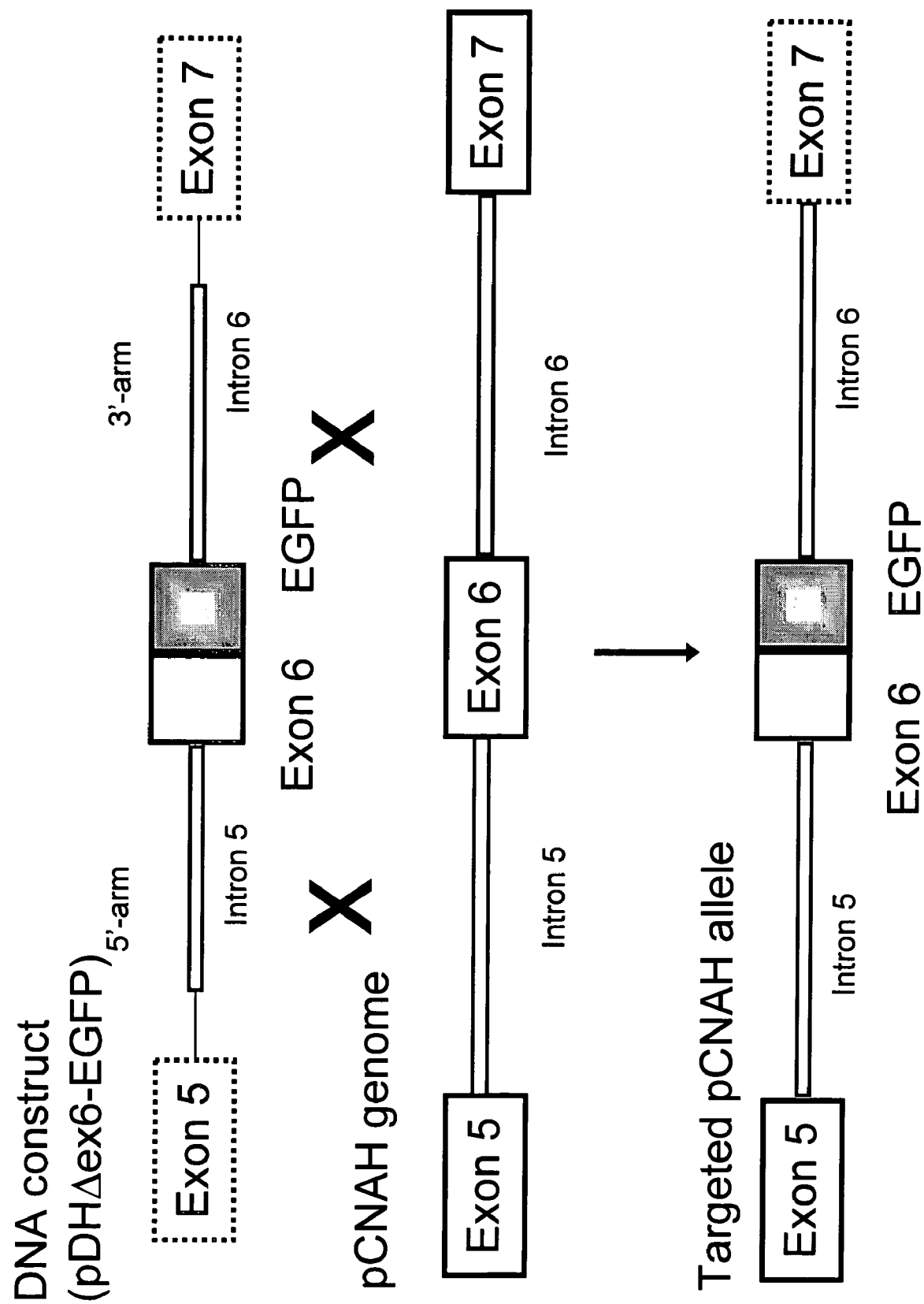
FIG. 13 is a schematic illustrating homologous recombination resulting in a frameshift between the targeting cassette DNA construct (pDHΔex6) and genomic DNA.

Modifications of DNA sequences can be of several types, including insertions, deletions, substitutions, or any combination thereof. A specific example of a modification is the inactivation of a gene by site-specific integration of a nucleotide sequence that disrupts expression of the gene product, i.e. a "knock out". For example, one approach to disrupting the CMP-Neu5Ac hydroxylase gene is to insert a selectable marker into the targeting DNA such that homologous recombination between the targeting DNA and the target DNA can result in insertion of the selectable marker into the coding region of the target gene. For example, see FIGS. 3, 12, and 13. In this way, for example, the CMP-Neu5Ac hydoxylase gene sequence is disrupted, rendering the encoded enzyme nonfunctional.

Homologous Recombination

Homologous recombination permits site-specific modifications in endogenous genes and thus novel alterations can be engineered into the genome. A primary step in homologous recombination is DNA strand exchange, which involves a pairing of a DNA duplex with at least one DNA strand containing a complementary sequence to form an intermediate recombination structure containing heteroduplex DNA (see, for example Radding, C. M. (1982) *Ann. Rev. Genet.* 16: 405; U.S. Pat. No. 4,888,274). The heteroduplex DNA can take several forms, including a three DNA strand containing triplex form wherein a single complementary strand invades the DNA duplex (Hsieh, et al., *Genes and Development* 4: 1951 (1990); Rao, et al., (1991) PNAS 88:2984)) and, when two complementary DNA strands pair with a DNA duplex, a classical Holliday recombination joint or chi structure (Holliday, R., *Genet. Res.* 5: 282 (1964)) can form, or a double-D loop ("Diagnostic Applications of Double-D Loop Formation" U.S. Ser. No. 07/755,462, filed Sep. 4, 1991). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (Genes, $3^{rd}$ Ed. (1987) Lewin, B., John Wiley, New York, N.Y.; Lopez, et al., *Nucleic Acids Res.* 15: 5643(1987)). Whether by the mechanism of breakage and rejoining or by the mechanism(s) of gene conversion, formation of heteroduplex DNA at homologously paired joints can serve to transfer genetic sequence information from one DNA molecule to another.

The ability of homologous recombination (gene conversion and classical strand breakage/rejoining) to transfer genetic sequence information between DNA molecules renders targeted homologous recombination a powerful method in genetic engineering and gene manipulation.

In homologous recombination, the incoming DNA interacts with and integrates into a site in the genome that contains a substantially homologous DNA sequence. In non-homologous ("random" or "illicit") integration, the incoming DNA is not found at a homologous sequence in the genome but integrates elsewhere, at one of a large number of potential locations. In general, studies with higher eukaryotic cells have revealed that the frequency of homologous recombination is far less than the frequency of random integration. The ratio of these frequencies has direct implications for "gene targeting" which depends on integration via homologous recombination (i.e. recombination between the exogenous "targeting DNA" and the corresponding "target DNA" in the genome).

A number of papers describe the use of homologous recombination in mammalian cells. Illustrative of these papers are Kucherlapati, et al., *Proc. Natl. Acad. Sci.* (*USA*) 81:3153-3157, 1984; Kucherlapati, et al., *Mol. Cell. Bio.* 5:714-720, 1985; Smithies, et al, *Nature* 317:230-234, 1985; Wake, et al., *Mol. Cell. Bio.* 8:2080-2089, 1985; Ayares, et al., *Genetics* 111:375-388, 1985; Ayares, et al., *Mol. Cell. Bio.* 7:1656-1662, 1986; Song, et al., *Proc. Natl. Acad. Sci USA* 84:6820-6824, 1987; Thomas, et al. *Cell* 44:419-428, 1986; Thomas and Capecchi, *Cell* 51: 503-512, 1987; Nandi, et al., *Proc. Natl. Acad. Sci. USA* 85:3845-3849, 1988; and Mansour, et al., *Nature* 336:348-352, 1988; Evans and Kaufman, *Nature* 294:146-154, 1981; Doetschman, et al., Nature 330:576-578, 1987; Thoma and Capecchi, *Cell* 51:503-512,4987; Thompson, et al., *Cell* 56:316-321, 1989.

The present invention uses homologous recombination to inactivate the porcine CMP-Neu5Ac hydroxylase gene in cells, such as fibroblasts. The DNA can comprise at least a portion of the gene(s) at the particular locus with introduction of an alteration into at least one, optionally both copies, of the native gene(s), so as to prevent expression of a functional enzyme and production of a Hanganutziu-Deicher antigen molecule. The alteration can be an insertion, deletion, replacement or combination thereof. When the alteration is introduce into only one copy of the gene being inactivated, the cells having a single unmutated copy of the target gene are amplified and can be subjected to a second targeting step, where the alteration can be the same or different from the first alteration, usually different, and where a deletion, or replacement is involved, can be overlapping at least a portion of the alteration originally introduced. In this second targeting step, a targeting vector with the same arms of homology, but containing a different mammalian selectable markers can be used. The resulting transformants are screened for the absence of a functional target antigen and the DNA of the cell can be further screened to ensure the absence of a wild-type target gene. Alternatively, homozygosity as to a phenotype can be achieved by breeding hosts heterozygous for the mutation.

Porcine cells that can be genetically modified can be obtained from a variety of different organs and tissues such as, but not limited to, brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels. In one embodiment of the invention, porcine cells can be selected from the group consisting of, but not limited to, epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, □hosphate cells, cumulus cells, epidermal cells, endothelial cells, Islets of Langerhans cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, squamous epithelial cells, osteocytes, osteoblasts, and osteoclasts.

In one alternative embodiment, embryonic stem cells can be used. An embryonic stem cell line can be employed or embryonic stem cells can be obtained freshly from a host, such as a porcine animal. The cells can be grown on an appropriate fibroblast-feeder layer or grown in the presence of leukemia inhibiting factor (LIF). In a preferred embodiment, the porcine cells can be fibroblasts; in one specific embodiment, the porcine cells can be fetal fibroblasts. Fibroblast cells are a preferred somatic cell type because they can be obtained from developing fetuses and adult animals in large quantities.

These cells can be easily propagated in vitro with a rapid doubling time and can be clonally propagated for use in gene targeting procedures.

Targeting Vectors

Cells homozygous at a targeted locus can be produced by introducing DNA into the cells, where the DNA has homology to the target locus and includes a marker gene, allowing for selection of cells comprising the integrated construct. The homologous DNA in the target vector will recombine with the chromosomal DNA at the target locus (see, for example, FIGS. 3, 12, and 13). The marker gene can be flanked on both sides by homologous DNA sequences, a 3'recombination arm and a 5' recombination arm (See, for example, FIG. 11). Methods for the construction of targeting vectors have been described in the art, see, for example, Dai et al., Nature Biotechnology 20: 251-255, 2002; WO 00/51424.

Various constructs can be prepared for homologous recombination at a target locus. Usually, the construct can include at least 50 bp, 100 bp, 500 bp, 1 kbp, 2 kbp, 4 kbp, 5 kbp, 10 kbp, 15 kbp, 20 kbp, or 50 kbp of sequence homologous with the target locus. The sequence can include any contiguous sequence of the porcine CMP-Neu5Ac hydroxylase gene, including at least 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 700, 750, 800, 850, 900, 1000, 5000 or 10,000 contiguous nucleotides of Seq ID Nos 9-45, 46, 47, 48, 49, and 50, or any combination or fragment thereof. Fragments of Seq ID Nos. 9-45, 46, 47, 48, 49 and 50 can include any contiguous nucleic acid or peptide sequence that includes at least about 10 bp, 15 bp, 17 bp, 20 bp, 50 bp, 100 bp, 500 bp, 1 kbp, 5 kbp or 10 kpb.

Various considerations can be involved in determining the extent of homology of target DNA sequences, such as, for example, the size of the target locus, availability of sequences, relative efficiency of double cross-over events at the target locus and the similarity of the target sequence with other sequences.

The targeting DNA can include a sequence in which DNA substantially isogenic flanks the desired sequence modifications with a corresponding target sequence in the genome to be modified. The substantially isogenic sequence can be at least about 95%, 97-98%, 99.0-99.5%, 99.6-99.9%, or 100% identical to the corresponding target sequence (except for the desired sequence modifications). The targeting DNA and the target DNA preferably can share stretches of DNA at least about 75, 150 or 500 base pairs that are 100% identical. Accordingly, targeting DNA can be derived from cells closely related to the cell line being targeted; or the targeting DNA can be derived from cells of the same cell line or animal as the cells being targeted.

The DNA constructs can be designed to modify the endogenous, target CMP-Neu5Ac hydroxylase. The homologous sequence for targeting the construct can have one or more deletions, insertions, substitutions or combinations thereof designed to disrupt the function of the resultant gene product. In one embodiment, the alteration can be the insertion of a selectable marker gene fused in reading frame with the upstream sequence of the target gene.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See, for example, Song, K-Y., et al. *Proc. Nat'l Acad. Sci. U.S.A.* 84:6820-6824 (1987); Sambrook, J., et al., *Molecular Cloning—A Laboratory Manual*, Cold Spring Harbor Laboratory, Cold Spring Harbor, N.Y. (1989), Chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo) (Southern, P., and P. Berg, J. *Mol. Appl. Genet.* 1:327-341 (1982)); and the hygromycin resistance gene (hyg) (Nucleic Acids Research 11:6895-6911 (1983), and Te Riele, H., et al., *Nature* 348:649-651 (1990)). Other selectable marker genes include: acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. Nos. 6,080,576; 6,136,566; Niwa, et al., *J. Biochem.* 113: 343-349 (1993); and Yoshida, et al., *Transgenic Research,* 4:277-287 (1995)).

Additional selectable marker genes useful in this invention, for example, are described in U.S. Pat. Nos. 6,319,669; 6,316,181; 6,303,373; 6,291,177; 6,284,519; 6,284,496; 6,280,934; 6,274,354; 6,270,958; 6,268,201; 6,265,548; 6,261,760; 6,255,558; 6,255,071; 6,251,677; 6,251,602; 6,251,582; 6,251,384; 6,248,558; 6,248,550; 6,248,543; 6,232,107; 6,228,639; 6,225,082; 6,221,612; 6,218,185; 6,214,567; 6,214,563; 6,210,922; 6,210,910; 6,203,986; 6,197,928; 6,180,343; 6,172,188; 6,153,409; 6,150,176; 6,146,826; 6,140,132; 6,136,539; 6,136,538; 6,133,429; 6,130,313; 6,124,128; 6,110,711; 6,096,865; 6,096,717; 6,093,808; 6,090,919; 6,083,690; 6,077,707; 6,066,476; 6,060,247; 6,054,321; 6,037,133; 6,027,881; 6,025,192; 6,020,192; 6,013,447; 6,001,557; 5,994,077; 5,994,071; 5,993,778; 5,989,808; 5,985,577; 5,968,773; 5,968,738; 5,958,713; 5,952,236; 5,948,889; 5,948,681; 5,942,387; 5,932,435; 5,922,576; 5,919,445; and 5,914,233.

Combinations of selectable markers can also be used. For example, to target CMP-Neu5Ac hydroxylase, a neo gene (with or without its own promoter, as discussed above) can be cloned into a DNA sequence which is homologous to the CMP-Neu5Ac hydroxylase gene. To use a combination of markers, the HSV-tk gene can be cloned such that it is outside of the targeting DNA (another selectable marker could be placed on the opposite flank, if desired). After introducing the DNA construct into the cells to be targeted, the cells can be selected on the appropriate antibiotics. In this particular example, those cells which are resistant to G418 and gancyclovir are most likely to have arisen by homologous recombination in which the neo gene has been recombined into the CMP-Neu5Ac hydroxylase gene but the tk gene has been lost because it was located outside the region of the double crossover.

Deletions can be at least about 50 bp, more usually at least about 100 bp, and generally not more than about 20 kbp, where the deletion can normally include at least a portion of the coding region including a portion of or one or more exons, a portion of or one or more introns, and can or can not include a portion of the flanking non-coding regions, particularly the 5'-non-coding region (transcriptional regulatory region). Thus, the homologous region can extend beyond the coding region into the 5'-non-coding region or alternatively into the 3'-non-coding region. Insertions can generally not exceed 10 kbp, usually not exceed 5 kbp, generally being at least 50 bp, more usually at least 200 bp.

The region(s) of homology can include mutations, where mutations can further inactivate the target gene, in providing for a frame shift, or changing a key amino acid, or the mutation can correct a dysfunctional allele, etc. Usually, the mutation can be a subtle change, not exceeding about 5% of the homologous flanking sequences.

The construct can be prepared in accordance with methods known in the art, various fragments can be brought together, introduced into appropriate vectors, cloned, analyzed and then manipulated further until the desired construct has been achieved (see, for example FIGS. 5-11). Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed.

The construct can be prepared using a bacterial vector, including a prokaryotic replication system, e.g. an origin recognizable by *E. coli*, at each stage the construct can be cloned and analyzed. A marker, the same as or different from the marker to be used for insertion, can be employed, which can be removed prior to introduction into the target cell. Once the vector containing the construct has been completed, it can be further manipulated, such as by deletion of the bacterial sequences, linearization, introducing a short deletion in the homologous sequence. After final manipulation, the construct can be introduced into the cell.

Techniques which can be used to allow the DNA construct entry into the host cell include calcium phosphate/DNA co-precipitation, microinjection of DNA into the nucleus, electroporation, bacterial protoplast fusion with intact cells, transfection, or any other technique known by one skilled in the art. The DNA can be single or double stranded, linear or circular, relaxed or supercoiled DNA. For various techniques for transfecting mammalian cells, see, for example, Keown et al., *Methods in Enzymology* Vol. 185, pp. 527-537 (1990).

The present invention further includes recombinant constructs comprising one or more of the sequences as broadly described above (for example in Tables 9-12). The constructs comprise a vector, such as a plasmid or viral vector, into which a sequence of the invention has been inserted, in a forward or reverse orientation. The construct can also include regulatory sequences, including, for example, a promoter, operably linked to the sequence. Large numbers of suitable vectors and promoters are known to those of skill in the art, and are commercially available. The following vectors are provided by way of example: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia). Also, any other plasmids and vectors can be used as long as they are replicable and viable in the host. Vectors known in the art and those commercially available (and variants or derivatives thereof) can in accordance with the invention be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors suitable for use in the invention include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Invitrogen) and variants or derivatives thereof. Viral vectors can also be used, such as lentiviral vectors (see, for example, WO 03/059923; Tiscomia et al. PNAS 100:1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEBVHis, pPIC9K, pPIC3.5K, pAO815, pPICZ, pPICZA, pPICZB, pPICZC, pGAPZA, pGAPZB, pGAPZC, pBlueBac4.5, pBlueBacHis2, pMelBac, pSinRep5, pSinHis, pIND, pIND(SP1), pVgRXR, pcDNA2.1, pYES2, pZErO11, pZErO-2.1, pCR-Blunt, pSE280, pSE380, pSE420, pVL1392, pVL1393, pCDM8, pcDNA1.1, pcDNA 1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λgt11, pTrc99A, pKK223-3, pGEX-1λT, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2 LIC, pT7Blue-2, λ SCREEN-1, λ BlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBAC-gus-1, pBAC4x-1, pBACgus4x-1, pBAC-3cp, pBACgus-2cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, p1 pβgal-Basic, pβgal-Control, pβgal-Promoter, pβgal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and λTriplEx from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT,pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Additional vectors include, for example, pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Also, any other plasmids and vectors known in the art can be used as long as they are replicable and viable in the host.

Selection of Homologously Recombined Cells

Cells that have been homologously recombined to knockout expression of the porcine CMP-Neu5Ac hydroxylase gene can then be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, cells can be identified in which homologous recombination has occurred to inactivate or otherwise modify the target gene.

The presence of the selectable marker gene inserted into the CMP-Neu5Ac hydroxylase gene establishes the integration of the target construct into the host genome. Those cells which show the desired phenotype can then be further analyzed by restriction analysis, electrophoresis, Southern analysis, polymerase chain reaction, monoclonal antibody assays, Fluorescent Activated Cell Sorter (FACS), or any other techniques or methods known in the art to analyze the DNA in order to establish whether homologous or non-homologous recombination occurred. This can be determined by employing probes for the insert and then sequencing the 5' and 3' regions flanking the insert for the presence of the CMP-Neu5Ac hydroxylase gene extending beyond the flanking regions of the construct or identifying the presence of a deletion, when such deletion is introduced. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is described, for example, in Kim and Smithies, *Nucleic Acids Res.* 16:8887-8903, 1988; and Joyner, et al., *Nature* 338:153-156, 1989.

An alternative method for screening homologous recombination events includes utilizing monoclonal or polyclonal antibodies specific for porcine CMP-Neu5Ac Hydroxylase and/or Neu5Gc, as described in, for example, Malykh, et al., *European Journal of Cell Biology* 80, 48-58 (2001), Malykh, et al., *Glycoconjugate J.* 15, 885-893 (1998).

Further characterization of porcine cells lacking expression of functional CMP-Neu5Ac Hydroxylase due to homologous recombination events include, but are not limited to, Southern Blot analysis, Northern Blot analysis, specific lectin binding assays, and/or sequence analysis, or by using anti-Neu5Gc or anti-CMP-Neu5Ac hydroxylase antibody assays as described, for example, in Y. Malykh, et. al. *Biochem J.* 370: 601-607 (2003); Y. Malykh, et al. *European Journal of Cell Biology* 80: 48-58 (2001); Y. Malykh et al. *Glycoconjugate J.* 15: 885-893 (1998). See generally, for example, A. Sharma, et al. *Transplantation* 75(4): 430-436 (2003).

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting of the remaining porcine CMP-Neu5Ac hydroxylase allele using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

VIII. Genetic Manipulation of Additional Genes to Overcome Immunologic Barriers of Xenotransplantation In one aspect of the invention, cells homozygous for the nonfunctional CMP-Neu5Ac hydroxylase gene can be subject to further genetic modification. For example, one can introduce additional genetic capability into the homozygotic hosts, where the endogenous CMP Neu5Ac hydroxylase alleles have been made nonfunctional, to substitute, replace or provide different genetic capability to the host. One can remove the marker gene after homogenotization. By introducing a construct comprising substantially the same homologous DNA, possibly with extended sequences, having the marker gene portion of the original construct deleted, one can be able to obtain homologous recombination with the target locus. By using a combination of marker genes for integration, one providing positive selection and the other negative selection, in the removal step, one can select against the cells retaining the marker genes.

In one embodiment, porcine cells are provided that lack the CMP-Neu5Ac hydroxylase gene and the $\alpha(1,3)$GT gene. Animals lacking functional CMP-Neu5Ac hydroxylase can be produced according to the present invention, and then cells from this animal can be used to knockout the $\alpha(1,3)$GT gene. Homozygous $\alpha(1,3)$GT negative porcine have recently been reported (Phelps et. al. Science 2003; WO 04/028243). Alternatively, cells from these $\alpha(1,3)$GT knockout animals can be used and further modified to inactivate the CMP-Neu5Ac hydroxylase gene.

In another embodiment, porcine cells are also provided that lack the porcine CMP-Neu5Ac hydroxylase gene and produce human complement inhibiting proteins. Animals lacking functional porcine CMP-Neu5Ac hydroxylase gene can be produced according to the present invention, and then cells from this animal can be further modified to express human complement inhibiting proteins, such as, but not limited to, CD59 (cDNA reported by Philbrick, W. M., et al. (1990) *Eur. J. Immunol.* 20:87-92), human decay accelerating factor (DAF)(cDNA reported by Medof, et al. (1987) *Proc. Natl. Acad. Sci. USA* 84: 2007), and human membrane cofactor protein (MCP) (cDNA reported by Lublin, D., et al. (1988) *J. Exp. Med.* 168: 181-194).

In an alternative embodiment, cells from transgenic pigs producing human complement inhibiting proteins can be used and further modified to inactivate the porcine CMP-Neu5Ac hydroxylase gene. Transgenic pigs producing human complement inhibiting proteins are known in the art (see, for example, U.S. Pat. No. 6,166,288).

In a further embodiment, porcine cells are provided that lack the porcine CMP-Neu5Ac hydroxylase gene and the porcine Forssman synthetase (FSM) gene. Animals lacking functional porcine CMP-Neu5Ac hydroxylase gene can be produced according to the present invention, and then cells from this animal can be further modified to knockout the porcine FSM synthetase gene, which is involved in the production of gal-$\alpha$-gal epitopes, and plays a role in xenotransplant rejection. The porcine FSM synthetase gene has recently been identified (see U.S. Application 60/568, 922). Alternatively, cells from these FSM synthetase gene knockout animals can be used and further modified to inactivate the porcine CMP-Neu5Ac hydroxylase gene.

In a still further embodiment, porcine cells are provided that lack the porcine CMP-Neu5Ac hydroxylase gene and the porcine isogloboside 3 synthase gene. Animals lacking functional porcine CMP-Neu5Ac hydroxylase gene can be produced according to the present invention, and then cells from this animal can be used to knockout the porcine iGb3 synthase gene. The porcine iGb3 synthase gene has recently been reported (U.S. Application No. 60/517,524). Alternatively, cells from these porcine iGb3 synthase gene knockout animals can be used and further modified to inactivate the porcine CMP-Neu5Ac hydroxylase gene.

In another embodiment, porcine cells are provided that lack the porcine CMP-Neu5Ac hydroxylase gene, the $\alpha(1, 3)$GT gene, the FSM synthetase gene, and the porcine iGb3 synthase gene. Animals lacking functional CMP-Neu5Ac hydroxylase gene can be produced according to the present invention, and then cells from this animal can be used to knockout the $\alpha(1,3)$GT gene, the FSM synthetase gene, and the porcine iGb3 synthase gene. Homozygous $\alpha(1,3)$GT-negative porcine have recently been reported (Phelps et al. supra, Science 2003; WO 04/028243) Alternatively, cells from these $\alpha(1,3)$GT knockout animals can be used and further modified to inactivate the porcine iGb3 synthase gene, the porcine FSM synthetase gene, and the CMP-Neu5Ac hydroxylase gene, and, in addition, express human complement inhibiting proteins, such as, but not limited to, CD59, human decay accelerating factor (DAF), and human membrane cofactor protein (MCP).

VIII. Production of Genetically Modified Animals

The present invention provides methods of producing a transgenic pig that lacks expression of CMP-Neu5Ac hydroxylase through the genetic modification of porcine totipotent embryonic cells. In one embodiment, the animals can be produced by: (a) identifying one or more target CMP-Neu5Ac hydroxylase nucleic acid genomic sequences in an animal; (b) preparing one or more homologous recombination vectors targeting the CMP-Neu5Ac hydroxylase nucleic acid genomic sequences; (c) inserting the one or more targeting vectors into the genomes of a plurality of totipotent cells of the animal, thereby producing a plurality of transgenic totipotent cells; (d) obtaining a tetraploid blastocyst of the animal; (e) inserting the plurality of totipotent cells into the tetraploid blastocyst, thereby producing a transgenic embryo; (f) transferring the embryo to a recipient female animal; and (g) allowing the embryo to develop to term in the female animal. The method of transgenic animal production described here by which to generate a transgenic pig is further generally described in U.S. Pat. No. 6,492,575.

In another embodiment, the totipotent cells can be embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang, et al., Nature 336:741-744 (1992). For example, after transforming embryonic stem cells with the targeting vector to alter the CMP-Neu5Ac hydroxylase gene, the cells can be plated onto a feeder layer in an appropriate medium, for example, such as fetal bovine serum enhanced DMEM. Cells containing the construct can be detected by employing a selective medium, and after sufficient time for colonies to grow, colonies can be picked and analyzed for the occurrence of homologous recombination. Polymerase chain reaction can be used, with primers within and without the construct sequence but at the target locus. Those colonies which show homologous recombination can then be used for embryo manipulating and blastocyst injection. Blastocysts can be obtained from superovulated females. The embryonic stem cells can then be trypsinized and the modified cells added to a droplet containing the blastocysts. At least one of the modified embryonic stem cells can be injected into the blastocoel of the blastocyst. After injection, at least one of the blastocysts can be returned to each uterine horn of pseudopregnant females. Females are then allowed to go to term and the resulting litters screened for mutant cells having the construct. The blastocysts are selected for different parentage from the transformed ES cells. By providing for a different phenotype of the blastocyst and the ES cells, chimeric progeny can be readily detected, and then genotyping can be conducted to probe for the presence of the modified CMP-Neu5Ac hydroxylase gene.

In a further embodiment of the invention, the totipotent cells can be embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui, et al., Cell 70:841-847 (1992); Resnick, et al., Nature 359:550-551 (1992)). The cultivation of EG cells can be carried out using methods known to one skilled in the art, such as described in Donovan et al., "Transgenic Animals, Generation and Use," Ed. L. M. Houdebine, Harwood Academic Publishers (1997).

Tetraploid blastocysts for use in the invention can be obtained by natural zygote production and development, or by known methods by electrofusion of two-cell embryos and subsequently cultured as described, for example, by James, et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art, for example, as described by Wang, et al., EMBO J. 10:2437-2450 (1991).

A "plurality" of totipotent cells can encompass any number of cells greater than one. For example, the number of totipotent cells for use in the present invention can be about 2 to about 30 cells, about 5 to about 20 cells, or about 5 to about 10 cells. In one embodiment, about 5-10 ES cells taken from a single cell suspension are injected into a blastocyst immobilized by a holding pipette in a micromanipulation apparatus. Then the embryos are incubated for at least 3 hours, possibly overnight, prior to introduction into a female recipient animal via methods known in the art (see for example Robertson, E. J. "Teratocarcinomas and Embryonic Stem Cells: A Practical Approach" IRL Press, Oxford, England (1987)). The embryo can then be allowed to develop to term in the female animal.

Somatic Cell Nuclear Transfer to Produce Cloned, Transgenic Offspring

The present invention provides a method for cloning a pig lacking a functional CMP-Neu5Ac hydroxylase gene via somatic cell nuclear transfer. In general, a wide variety of methods to accomplish mammalian cloning are currently being rapily developed and reported, any method that accomplishes the desired result can be used in the present invention. Nonlimiting examples of such methods are described below. For example, the pig can be produced by a nuclear transfer process comprising the following steps: obtaining desired differentiated pig cells to be used as a source of donor nuclei; obtaining oocytes from a pig; enucleating the oocytes; transferring the desired differentiated cell or cell nucleus into the enucleated oocyte, e.g., by fusion or injection, to form NT units; activating the resultant NT unit; and transferring said cultured NT unit to a host pig such that the NT unit develops into a fetus.

Nuclear transfer techniques or nuclear transplantation techniques are known in the art (Campbell et al, Theriogenology, 43:181 (1995); Collas, et al, Mol. Report Dev., 38:264-267 (1994); Keefer et al, Biol. Reprod., 50:935-939 (1994); Sims, et al, Proc. Natl. Acad. Sci., USA, 90:6143-6147 (1993); WO 94/26884; WO 94/24274, and WO 90/03432, U.S. Pat. Nos. 4,944,384 and 5,057,420). In one nonlimiting example, methods are provided such as those described in U.S. Patent Publication No. 2003/0046722 to Collas, et al., which describes methods for cloning mammals that allow the donor chromosomes or donor cells to be reprogrammed prior to insertion into an enucleated oocyte. The invention also describes methods of inserting or fusing chromosomes, nuclei or cells with oocytes.

A donor cell nucleus, which has been modified to alter the CMP-Neu5Ac hydroxylase gene, is transferred to a recipient porcine oocyte. The use of this method is not restricted to a particular donor cell type. The donor cell can be as described in Wilmut, et al., Nature 385 810 (1997); Campbell, et al., Nature 380 64-66 (1996); or Cibelli, et al., Science 280 1256-1258 (1998). All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell, et al., *Theriogenology* 43 181 (1995), Collas, et al., *Mol. Reprod Dev.* 38 264-267 (1994), Keefer, et al., *Biol. Reprod.* 50 935-939 (1994), Sims, et al., *Proc. Nat'l. Acad. Sci. USA* 90 6143-6147 (1993), WO-A-9426884, WO-A-9424274, WO-A-9807841, WO-A-9003432, U.S. Pat. Nos. 4,994,384 and 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell, et al. (*Nature*, 380:64-68, 1996) and Stice, et al (*Biol. Reprod.*, 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cadiac muscle cells, other muscle cells, granulose cells, cumulus cells, epidermal cells or endothelial cells. In another embodiment, the nuclear cell is an embryonic stem cell. In a preferred embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (GO, GI, G2, S, M) so as to ensure coordination with the acceptor cell. Any method known in the art may be used to manipulate the cell cycle phase. Methods to control the cell cycle phase include, but are not limited to, GO quiescence induced by contact inhibition of cultured cells, GO quiescence induced by removal of serum or other essential nutrient, GO quiescence induced by senescence, GO quiescence induced by addition of a specific growth factor; GO or GI quiescence induced by physical or chemical means such as heat shock, hyperbaric pressure or other treatment with a chemical, hormone, growth factor or other substance; S-phase control via treatment with a chemical agent which interferes with any. Point of the replication procedure; M-phase control via selection using fluorescence activated cell sorting, mitotic shake off, treatment with microtubule disrupting agents or any chemical which disrupts progression in mitosis (see also Freshney, R. I,. "Culture of Animal Cells: A Manual of Basic Technique," Alan R. Liss, Inc, New York (1983).

Methods for isolation of oocytes are well known in the art. Essentially, this can comprise isolating oocytes from the ovaries or reproductive tract of a pig. A readily available source of pig oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period".

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, which ranges from about 10 to 40 hours, and preferably about 16-18 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, preferably not more than 24 hours later, and more preferably 16-18 hours later.

Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, *Wister Inot. Symp. Monogr.*, 9, 19, 1969). Also, the nucleus can be injected directly into the oocyte rather than using electroporation fusion. See, for example, Collas and Barnes, *Mol. Reprod. Dev.*, 38:264-267 (1994). After fusion, the resultant fused NT units are then placed in a suitable medium until activation, for example, CR1aa medium. Typically activation can be effected shortly thereafter, for example less than 24 hours later, or about 4-9 hours later.

The NT unit can be activated by any method that accomplishes the desired result. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical pigs after nuclear transfer. Also, treatments such as electrical and chemical shock can be used to activate NT embryos after fusion. See, for example, U.S. Pat. No. 5,496,720, to Susko-Parrish, et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media.

Afterward, the cultured NT unit or units can be washed and then placed in a suitable media contained in well plates which preferably contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. Preferably, these NT units can be cultured until at least about 2 to 400 cells, more preferably about 4 to 128 cells, and most preferably at least about 50 cells.

Activated NT units can then be transferred (embryo transfers) to the oviduct of an female pigs. In one embodiment, the female pigs can be an estrus-synchronized recipient gilt. Crossbred gilts (large white/Duroc/Landrace) (280-400 lbs) can be used. The gilts can be synchronized as recipient animals by oral administration of 18-20 mg Regu-Mate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers of the can then be performed about 22-26 h after the hCG injection. In one embodiment, the pregnancy can be brought to term and result in the birth of live offspring. In another embodiment, the pregnancy can be terminated early and embryonic cells can be harvested.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. "Critical review of embryo transfer procedures with cattle" in *Fertilization and Embryonic Development in Vitro* (1981) L. Mastroianni, Jr. and J. D. Biggers, ed., Plenum Press, New York, N.Y., page 323.

VIII. Porcine Animals, Organs, Tissues, Cells and Cell Lines

The present invention provides viable porcine in which both alleles of the CMP-Neu5Ac hydroxylase gene have been inactivated. The invention also provides organs, tissues, and cells derived from such porcine, which are useful for xenotransplantation.

In one embodiment, the invention provides porcine organs, tissues and/or purified or substantially pure cells or cell lines obtained from pigs that lack any expression of functional CMP-Neu5Ac hydroxylase.

In one embodiment, the invention provides organs that are useful for xenotransplantation. Any porcine organ can be used, including, but not limited to: brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels.

In another embodiment, the invention provides tissues that are useful for xenotransplantation. Any porcine tissue can be used, including, but not limited to: epithelium, connective tissue, blood, bone, cartilage, muscle, nerve, adenoid, adipose, areolar, bone, brown adipose, cancellous, muscle, cartaginous, cavernous, chondroid, chromaffin, dartoic, elastic, epithelial, fatty, fibrohyaline, fibrous, Gaingee, gelatinous, granulation, gut-associated lymphoid, Haller's vascular, hard hemopoietic, indifferent, interstitial, investing, islet, lymphatic, lymphoid, mesenchymal, mesonephric, mucous connective, multilocular adipose, myeloid, nasion soft, nephrogenic, nodal, osseous, osteogenic, osteoid, periapical, reticular, retiform, rubber, skeletal muscle, smooth muscle, and subcutaneous tissue.

In a further embodiment, the invention provides cells and cell lines from porcine animals that lack expression of functional alpha1,3GT. In one embodiment, these cells or cell lines can be used for xenotransplantation. Cells from any porcine tissue or organ can be used, including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, ☐hosphate cells, cumulus cells, epidermal cells, endothelial cells, Islets of Langerhans cells, pancreatic insulin secreting cells, pancreatic alpha-2 cells, pancreatic beta cells, pancreatic alpha-1 cells, blood cells, blood precursor cells, bone cells, bone precursor cells, neuronal stem cells, primordial stem cells., hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopaminergic cells, squamous epithelial cells, osteocytes, osteoblasts, osteoclasts, embryonic stem cells, fibroblasts and fetal fibroblasts. In a specific embodiment, pancreatic cells, including, but not limited to, Islets of Langerhans cells, insulin secreting cells, 48 alpha-2 cells, beta cells, alpha-1 cells from pigs that lack expression of functional alpha-1,3-GT are provided.

Nonviable derivatives include tissues stripped of viable cells by enzymatic or chemical treatment these tissue derivatives can be further processed via crosslinking or other chemical treatments prior to use in transplantation. In a preferred embodiment, the derivatives include extracellular matrix derived from a variety of tissues, including skin, urinary, bladder or organ submucosal tissues. Also, tendons, joints and bones stripped of viable tissue to include heart valves and other nonviable tissues as medical devices are provided.

Therapeutic Uses

The cells can be administered into a host in order in a wide variety of ways. Preferred modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous, leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphonia; autoinimune diseases including rheumatoid arthritis, diabetes type 1, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome IIV, Chwachmann-Diamond syndrome, dihydrofolate reductase deficiencies, forinamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose ☐hosphate dehydrogenase) variants 1, 2, 3, pyruvate kinase deficiency, congenital erythropoietin sensitivity, deficiency, sickle cell disease and trait, thalassernia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myeloselerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha lantirypsin deficiency, etc.

Diseases or pathologies include neurodegenerative diseases, hepatodegenerative diseases, nephrodegenerative disease, spinal cord injury, head trauma or surgery, viral infections that result in tissue, organ, or gland degeneration, and the like. Such neurodegenerative diseases include but are 10 not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multisystem disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Parkinson's Disease, Wernicke-Korsakoff syndrome; chronic alcoholism; Creutzfeldt-Jakob disease; Subacute sclerosing panencephalitis hallefforden-Spatz disease; and Dementia pugilistica. See, e.g., Berkow et. al., (eds.) (1987), The Merck Manual, (15') ed.), Merck and Co., Rahway, N.J.

Industrial Farming Uses

The present invention provides viable porcine for purposes of farming applications in which one or both alleles of the CMP-Neu5Ac hydroxylase gene have been inactivated. Inactivation of one or both alleles of the CMP-Neu5Ac hydroxylase gene can reduce the susceptibility of porcine animals to zoonotic diseases and infections in pigs such as, for example, E. coli, pig rotavirus, and pig transmissible gastroenteritis coronavirus, and any other zoonotic or entertoxigenic organism that utilizes Neu5Gc in a host animal. The reduction in disease susceptibility allows greater economic realization of farming operations due to the ability to harvest more healthy animals, and the reduction of animal death due to enterotoxigenic organisms.

The following examples are offered by way of illustration and not by way of limitation.

EXAMPLES

Isolation of Nucleic Acids Combination strategy of PCR-based methods was employed to identify the porcine CMP-Neu5Ac hydroxylase gene. Such PCR methods are well known in the art and described, for example, in PCR Technology, H. A. Erlich, ed., Stockton Press, London, 1989; PCR Protocols: A Guide to Methods and Applications, M. A. Innis, D. H. Gelfand, J. J. Sninsky, and T. J. White, eds., Academic Pres, Inc., New York, 1990.

Total RNA was extracted from an adult porcine (Great Yorkshire) spleen using Trizol reagent (Gibco, Grand Island, N.Y.). After treatment with Dnase I (Ambion, Inc., Austin, Tex.), poly $A^+$ RNA was separated using the Dynabeads mRNA Purification Kit (Dynal, Oslo, Norway). To identify the 5'- or 3'-end of porcine CMP-Neu5Ac Hydroxylase gene, 5'- or 3'-RACE (rapid amplification of cDNA ends) procedures were performed using Marathon™ cDNA Amplification kit (Clontech). To identify exon-intron boundaries, or 5'- or 3'-flanking region of the transcripts, porcine GenomeWalker™ libraries were constructed using Universal GenomeWalker™ Library kit (Clontech). Gene-specific and nested primer pairs were designed from the partial cDNA sequence provided by GenBank Accession #A59058.

Determination of cDNA and Genomic CMP-Neu5Ac Hydroxylase Sequence

5'- or 3'-RACE analysis: To identify the 5' and 3' ends of porcine CMP-Neu5Ac hydroxylase gene transcripts, 5'-and 3'-RACE procedures were performed using the Marathon cDNA Amplification Kit (Clontech) with poly A+ RNA isolated from adult porcine spleen as a template. First strand cDNA synthesis from 1 ug of poly A+ RNA was accomplished using 20 U of AMV-RT and 1 pmol of the supplied cDNA Synthesis Primer by incubating at 48° C. for 2 hours. Second strand cDNA synthesis involved incubating th entire first strand reaction with a supplied enzyme cocktail composed of Rnase H, E. coli DNA polymerase I, and E. coli DNA polymerase I, and E. coli DNA ligase at 16° C. for 1.5 hr. After blunting of the double stranded cDNA ends by T4 DNA polymerase, the supplied Marathon cDNA Adapters were ligated to an aliquot of purified, double-stranded cDNA. Dilution of ht eadapter-ligated product in 10 mM ticme-KOH/0.1 mM EDTA buffer provided with the kit readied the cDNA for PCR amplification.

To obtain the 5'- and 3'- most sequences of the porcine CMP-Neu5Ac hydroxylase gene transcripts, provided Marathon cDNA Amplification primer sets were paired with gene-specific and nested gene-specific primers based on the sequence provided by GenBank accession number A59058. These primer sets are provided for in Table 13. By this method, oligonucleotide primers based on the sequence contained in Genbank accession number A59058 are oriented in the 3' and 5' directions and are used to generate overlapping PCR fragments. These overlapping 3' and 5' products are combined to produce an intact full-length cDNA. This method is described, for example, in Innis, et al., supra; and Frohman et al., Proc. Natl. Acad. Sci., 85:8998, 1988, and further described, for example, in U.S. Pat. No. 4,683,195.

Genome Walking analysis: To identify exon-intron boundaries, or 5'- or 3'-flanking region of the porcine CMP-Neu5Ac hydroxylase transcripts, porcine GenomeWalker™ libraries were constructed using the Universal GenomeWalker™ Library Kit (Clontech, Palo Alto, Calif.).

Briefly, five aliquots of porcine genomic DNA were separately digested with a single blunt-cutting restriction endonuclease (DraI, EcoRV, PvuII, ScaI, or StuI). After phenol-chloroform extraction, ethanol precipitation, and resuspension of the restricted fragments, a portion of each digested aliquot was used in separate ligation reaction with the GenomeWalker adapters provided with the kit. This process created five libraries for use in the PCR based cloning strategy. Primer pairs identified in Table 13 were used in a genome walking strategy. Either eLON-Gase or TaKaRa LA Taq (Takara Shuzo Co., Ltd., Shiga, Japan) enzyme was used for PCR in all GenomeWalker experiments as well as for direct long PCR of genomic DNA. The thermal cycling conditions recommended by the manufacturer were employed in all GenomeWalker-PCR experiments on a Perkin Elmer Gene Amp System 9600 or 9700 thermocycler.

TABLE 13

Primers Used in PCR Strategies

| Primer Set | PCR Strategy | Sequence |
|---|---|---|
| XA | 3'-RACE/Genome Walking | 5'-CATGGACCTCAAGCTGGGGGACAAGA-3' (SEQ ID NO: 51) |

TABLE 13-continued

Primers Used in PCR Strategies

| Primer Set | PCR Strategy | Sequence |
|---|---|---|
| XB | 3'-RACE/Genome Walking | 5'-GTGTTCGACCCTTGGTTAATCGGTCCTG-3' (SEQ ID NO: 52) |
| XM | 5'-RACE/Genome Walking | 5'-CAGGACCGATTAACCAAGGGTCGAACAC-3' (SEQ ID NO: 53) |
| SN | 5'-RACE/Genome Walking | 5'-TCTTGTCCCCCAGCTTGAGGTCCATG-3' (SEQ ID NO: 54) |

Subcloning and sequencing of amplified products: PCR products amplified from genomic DNA, GeneWalker-PCR (Clontech), and 5'-3'-RACE wre gel-purified using the Qiagen Gel Extraction Kit (Qiagen, Valencia, Calif.), if necessary, then subcloned into the pCRII vector provided with the Original TA Cloning Kit (Invitrogen, Carlsbad, Calif.). Plasmid DNA minipreps of pCRII-ligated inserts were prepared with the QIAprep Spin Miniprep Kit (Qiagen) as directed. Automated fluorescent sequencing of cloned inserts was performed using an ABI 377 Automated Sequence Analyzer (Applied Biosystems, Inc., Foster City, Calif.) with either the dRhodamine or BigDye Terminator Cycle Sequencing Kits (Applied Biosystems) primed with T7 and SP6 promoter primers or primers designed from internal insert sequences.

Primer Synthesis: All oligonucleotides used as primers in the various PCR-based methods were synthesized on an ABI 394 DNA Synthesizer (Applied Biosystems, Inc., Foster City Calif.) using solid phase synthesis and phosphoramidite nucleoside chemistry, unless otherwise stated.

Analysis of Transcription Factor Binding Sites

Analysis of possible transcription factors binding sites were performed using 228 bp of exon 1 sequence and 601 bp upstream of exon 1. The sequences were screened using "MatInspector" software available in www.genomatix.de. The sequences contain binding sites for the following transcription factors: MZF1, ETSF, SF1, CMYB, MEF2, NMP4, BRN2, AP1, GAT1, SATB1, ATF, USF, WHN, ZF5, NFκB, MOK2, NFY, MYCMAX, ZF5. See FIG. 4.

Construction of Porcine CMP-Neu5Ac Hydroxylase Homologous Recombination Targeting Vectors CMP-Neu5Ac hydroxylase knock-out target vector: A vector targeting Exon 6 of the porcine CMP-Neu5Ac Hyudroxylase gene for knockout can be constructed. In a first step, a portion of Intron 6 is amplified by PCR for use as a 3'-arm of the targeting vector utilizing primers such as pDH3 (5'-CTCCTGGAAGCTTCTGTCAAGACGAAC-3') (SEQ ID NO: 55) and pDH4 (5'-GCCTGATACACAGTGCTGTGCAATGGT-3') (SEQ ID NO: 56) (see FIG. 5). The amplified PCR product of approximately 3.7 kb can be inserted into the pCRII vector after restriction enzyme digestion utilizing EcoRI and ApaI. See FIG. 6.

Following the insertion of the 3'-arm, a portion of Intron 5 can be amplified by PCR for use as a 5'-arm in the targeting vector utilizing primers such as pDH1 (5'-ACCACCCAAGTCTGGAATCTTCTTACACT-3') (SEQ ID NO: 57) and pDH2 (5'GACTCTCATACAAAAGCTAAGCTGGGTAAG-3') (SEQ ID NO: 58) (see FIG. 5). Following this initial amplification, successive PCR amplifications can be performed to introduce an EcoNI restriction site into the 3' portion of the 5'-arm utilizing primers such s pDH1 in conjunction with primers such as pDH2a (5'-GACTCTCATACAAAACCTAAGCTGGGTAAG-3') (SEQ ID NO: 59), pDH2b (5'-GACTCTCATACAAAACCTAGGCTGGGTAAG-3') (SEQ ID NO: 60), and pDH2c (5'-GACTCTCATACAAAACCTAGGCTAGGTAAG-3') (SEQ ID NO: 61), respectively (see FIG. 5). The amplified PCR product of approximately 2.6 kb containing the engineered EcoNI site can be restriction enzyme digested using ApaI and EcoNI, and inserted into the pCRII vector containing the previously inserted 3'-arm (See FIG. 7), generating a targeting vector (pDHΔex6) containing an approximate 6.3 kb porcine CMP-Neu5Ac hydroxylase targeting sequence (see FIG. 8).

Figure 11:
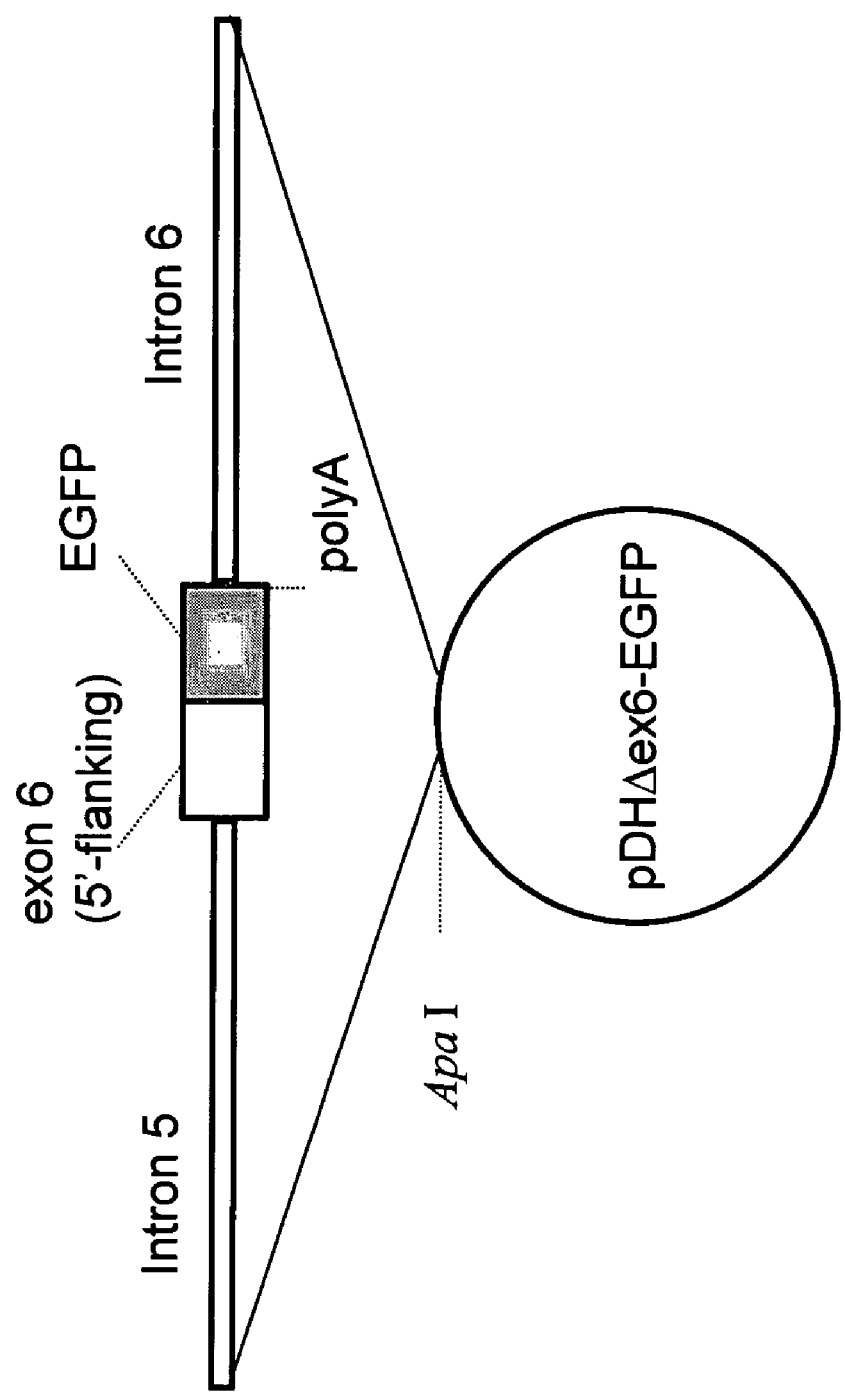
FIG. 11 is a schematic illustrating a knock-in vector for expression of eGFP.

EGFP knock-in target vector. pDHΔex6 can be further modified by an in-frame insertion of an enhanced green fluorescent protein sequence at the terminal 3' end of Exon 6 of the porcine CMP-Neu5Ac hydroxylase gene. In a first step, a portion of Intron 5 and a portion of Exon 6 of the porcine CMP-Neu5Ac hydroxylase gene can be amplified by PCR utilizing primers such as pDH5 (5'-CCTTATACTGGCCCCAATTGGATCTTAC-3') (SEQ ID NO: 62) and pDH6 (5'-CAGGAGGATTGATATCCTTCATGCTGCT-3) (SEQ ID NO: 67) (see FIG. 9), and inserted into a vector (pIRES-EGFP) containing the EGFP and a poly A tail following restriction enzyme digestion with MunI and EcoRv. Following insertion, PCR amplification can be performed on the pIRES-EGFP vector containing the insertion utilizing primer such as pDH7 (5'-CTTACCTAGCCTAGGTTTTGTATGAGAGTC-3') (SEQ ID NO: 64) and pDH8 (5'-GACAAACCACAATTGGAATGCACTCGAG-3') (SEQ ID NO: 65) (see FIG. 9). The PCR amplified product can be restriction enzyme digested using EcoNI and MunI and inserted into the previously constructed pDHΔex6 targeting vector (see FIG. 10). The resultant targeting vector (pDHΔex6-EGFP) is illustrated in FIG. 11.

Production of Porcine CMP-Neu5Ac Hydroxylase Deficient Fetal Fibroblast Cells

Fetal fibroblast cells are isolated from 10 fetuses of the same pregnancy at day 33 of gestation. After removing the head and viscera, fetuses are washed with Hanks' balanced salt solution (HBSS; Gibco-BRL, 15 Rockville, Md.), placed in 20 ml of HBSS, and diced with small surgical scissors. The tissue is pelleted and resuspended in 50-ml tubes with 40 ml of DMEM and 100 U/ml collagenase (Gibco-BRL) per fetus. Tubes are incubated for 40 min in a shaking water bath at 37C. The digested tissue is allowed to settle for 3-4 min and the cell-rich supernatant is transferred to a new 50-ml tube and pelleted. The cells are then resuspended in 40 ml of DMEM containing 10% fetal calf serum (FCS), 1× nonessential amino acids, 1 mM sodium pyruvate and 2 ng/ml bFGF, and seeded into 10 cm. dishes. For transfections, 10 µg of linearized pDHΔex6EGFP vector is introduced into 2 million cells using lipofectamine 2000 (Carlsbad, Calif.) following manufacturer's guidelines. Forty-eight hours after transfection, the transfected cells are seeded into 48-well plates at a density of 2,000 cells per well and grown to confluence. Following confluence, cells are sorted via Fluorescent Activated Cell Sorting (FACS) (FACSCalibur, Becton Dickenson, San Jose, Calif.), wherein only cells having undergone homologous recombination and expressing the EGFP are selected (see, for example, FIG. 13).

Selected cells are then reseeded, and grown to confluency. Once confluency is reached, several small aliquots are frozen back for future use, and the remainder are utilized for PCR and Southern Blot verification of homologous recombination. The putative targeted clones can be screened by PCR across the Exon 6/EGFP insert utilizing a primer complimentary to the EGFP sequence and a primer complimentary to a sequence outside the vector as the antisense primer. The PCR products can be analyzed by Southern Blotting using an EGFP probe to identify the positive clones by the presence of the expected band from the targeted allele.

Generation of Cloned Pigs Using Heterologous CMP-Neu5Ac Hydroxylase Deficient Fetal Fibroblasts as Nuclear Donors Preparation of cells for Nuclear Transfer: Donor cells are genetically manipulated to produce cells heterozygous for porcine CMP-Neu5Ac hydroxylase as described generally above. Nuclear transfer can be performed by methods that are well known in the art (see, e.g., Dai et al., Nature Biotechnology 20: 251255, 2002; and Polejaeva et al., Nature 407:86-90, 2000), using EGFP selected porcine fibroblasts as nuclear donors that are produced as described in detail hereinabove.

Oocytes can be isolated from synchronized super ovulated sexually mature Large-White X Landacre outcross gilts as described, for example, in I. Polejaeva et al. Nature 407: 505 (2000). Donor cells are synchronized in presumptive G0/G1 by serum starvation (0.5%) between 24 to 120 hours. Oocytes enucleation, nuclear transfer, electrofusion, and electroactivation can be performed as essentially described in, for example, A. C. Boquest et al., Biol. Reproduction 68: 1283 (2002). Reconstructed embryos can be cultured overnight and can be transferred to the oviducts of asynchronous (−1 day) recipients. Pregnancies can be confirmed and monitored by real-time ultrasound.

Breeding of heterozygous CMP-Neu5Ac hydroxylase single knockout (SKO) male and female pigs can be performed to establish a miniherd of double knockout (DKO) pigs.

Verification of CMP-Neu5Ac Hydroxylase Deficient Pigs

Following breeding of the single knockout male and female pigs, verification of double knockout pigs is performed. Fibroblasts from the offspring are incubated with 1 µg of anti-N-glycolyl GM2 monoclonal antibody MK2-34 (Seikagaku Kogyo, JP) on ice for 30 minutes. FITC conjugated goat-anti-mouse IgG is added to the cells and antibody binding indicating the presence or absence of Neu5GC, and thus, an indication of the presence or absence of active CMP-Neu5Ac hydroxylase, is detected by flow cytometry (FACSCalibur, Becton Dickenson, San Jose, Calif.).

I claim:

1. An isolated nucleotide comprising a nucleotide sequence of SEQ ID No 46.

2. A vector comprising a sequence of claim 1.

3. A nucleic acid construct comprising a sequence of claim 1.

4. A plasmid comprising a sequence of claim 1.

* * * * *